US010328157B2

(12) United States Patent
Zhao

(10) Patent No.: US 10,328,157 B2
(45) Date of Patent: Jun. 25, 2019

(54) ACETYLENEDICARBOXYL LINKERS AND THEIR USES IN SPECIFIC CONJUGATION OF A CELL-BINDING MOLECULE

(71) Applicant: SUZHOU M-CONJ BIOTECH CO., LTD., Suzhou (CN)

(72) Inventor: Robert Yongxin Zhao, Lexington, MA (US)

(73) Assignee: HANGZHOU DAC BIOTECH CO., LTD., Hangzhou (CN)

( * ) Notice: Subject to any disclaimer, the term of this patent is extended or adjusted under 35 U.S.C. 154(b) by 0 days.

(21) Appl. No.: 15/423,695

(22) Filed: Feb. 3, 2017

(65) Prior Publication Data

US 2017/0143845 A1 May 25, 2017

Related U.S. Application Data

(62) Division of application No. 14/799,666, filed on Jul. 15, 2015, now Pat. No. 9,839,687.

(51) Int. Cl.

| | |
|---|---|
| ***A61K 47/68*** | (2017.01) |
| ***C07K 16/28*** | (2006.01) |
| ***C07C 59/76*** | (2006.01) |
| ***C07D 417/14*** | (2006.01) |
| ***C07C 237/52*** | (2006.01) |
| ***A61K 39/395*** | (2006.01) |
| ***A61K 45/06*** | (2006.01) |
| ***C07D 207/46*** | (2006.01) |
| ***C07C 233/20*** | (2006.01) |
| ***C07D 413/14*** | (2006.01) |
| ***C07D 309/14*** | (2006.01) |
| ***C07D 403/14*** | (2006.01) |
| ***C07D 407/12*** | (2006.01) |
| ***C07D 407/14*** | (2006.01) |
| ***C07D 413/04*** | (2006.01) |
| ***C07D 417/12*** | (2006.01) |
| ***C07D 493/04*** | (2006.01) |
| ***C07D 498/14*** | (2006.01) |
| ***C07D 277/56*** | (2006.01) |
| ***C07D 519/00*** | (2006.01) |
| ***A61K 31/337*** | (2006.01) |
| ***A61K 31/404*** | (2006.01) |
| ***A61K 31/537*** | (2006.01) |
| ***A61K 31/5517*** | (2006.01) |
| ***G01N 33/50*** | (2006.01) |
| ***A61K 38/05*** | (2006.01) |
| ***C07K 16/32*** | (2006.01) |
| *A61K 39/00* | (2006.01) |

(52) U.S. Cl.

CPC ........ *A61K 47/6803* (2017.08); *A61K 31/337* (2013.01); *A61K 31/404* (2013.01); *A61K 31/537* (2013.01); *A61K 31/5517* (2013.01); *A61K 38/05* (2013.01); *A61K 39/395* (2013.01); *A61K 39/3955* (2013.01); *A61K 45/06* (2013.01); *A61K 47/6809* (2017.08); *A61K 47/6849* (2017.08); *A61K 47/6851* (2017.08); *A61K 47/6889* (2017.08); *C07C 59/76* (2013.01); *C07C 233/20* (2013.01); *C07C 237/52* (2013.01); *C07D 207/46* (2013.01); *C07D 277/56* (2013.01); *C07D 309/14* (2013.01); *C07D 403/14* (2013.01); *C07D 407/12* (2013.01); *C07D 407/14* (2013.01); *C07D 413/04* (2013.01); *C07D 413/14* (2013.01); *C07D 417/12* (2013.01); *C07D 417/14* (2013.01); *C07D 493/04* (2013.01); *C07D 498/14* (2013.01); *C07D 519/00* (2013.01); *C07K 16/28* (2013.01); *C07K 16/2863* (2013.01); *C07K 16/32* (2013.01); *G01N 33/5014* (2013.01); *A61K 2039/505* (2013.01); *C07K 2317/24* (2013.01); *Y02A 50/416* (2018.01); *Y02A 50/466* (2018.01); *Y02A 50/473* (2018.01)

(58) Field of Classification Search

CPC .................................................. A61K 47/6803

See application file for complete search history.

(56) References Cited

U.S. PATENT DOCUMENTS

| | | | |
|---|---|---|---|
| 4,000,304 | A | 12/1976 | Wu et al. |
| 4,169,888 | A | 10/1979 | Hanka et al. |
| 4,256,746 | A | 3/1981 | Miyashita et al. |
| 4,294,757 | A | 10/1981 | Asai |
| 4,307,016 | A | 12/1981 | Asai et al. |
| 4,313,946 | A | 2/1982 | Powell et al. |
| 4,315,929 | A | 2/1982 | Freedman et al. |
| 4,322,348 | A | 3/1982 | Asai et al. |
| 4,331,598 | A | 5/1982 | Hasegawa et al. |

(Continued)

FOREIGN PATENT DOCUMENTS

| | | | |
|---|---|---|---|
| CA | 2 710 693 | A1 | 1/2011 |
| CN | 101723961 | A | 6/2010 |

(Continued)

OTHER PUBLICATIONS

"Chromophore", http://goldbook.iupac.org/plain/C01076-plain.html, 1994 (Year: 1994).*

(Continued)

*Primary Examiner* — Noble E Jarrell

(74) *Attorney, Agent, or Firm* — Buchanan Ingersoll & Rooney PC

(57) ABSTRACT

Cell binding agent-drug conjugates comprising bridge linkers, and methods of using such linkers and conjugates are provided.

27 Claims, 11 Drawing Sheets

(56) References Cited

U.S. PATENT DOCUMENTS 4,341,761 A 7/1982 Ganfield et al.
4,361,650 A 11/1982 Asai et al.
4,362,663 A 12/1982 Kida et al.
4,364,866 A 12/1982 Asai et al.
4,371,533 A 2/1983 Akimoto et al.
4,391,904 A 7/1983 Litman et al.
4,399,121 A 8/1983 Albarella et al.
4,414,205 A 11/1983 Pettit
4,424,219 A 1/1984 Hashimoto et al.
4,427,587 A 1/1984 Kaneko et al.
4,427,783 A 1/1984 Newman et al.
4,444,887 A 4/1984 Hoffmann
4,450,254 A 5/1984 Isley et al.
4,451,570 A 5/1984 Royston et al.
4,464,467 A 8/1984 Hatori et al.
4,466,917 A 8/1984 Nussenzweig et al.
4,472,500 A 9/1984 Milstein et al.
4,491,632 A 1/1985 Wands et al.
4,493,795 A 1/1985 Nestor, Jr. et al.
4,493,890 A 1/1985 Morris
4,508,647 A 4/1985 Hatori et al.
4,663,453 A 5/1987 Glamkowski et al.
4,671,958 A 6/1987 Rodwell et al.
4,683,230 A 7/1987 Tsunakawa et al.
4,723,003 A 2/1988 Glamkowski et al.
4,723,007 A 2/1988 Glamkowski et al.
4,753,894 A 6/1988 Frankel et al.
4,761,412 A 8/1988 Glamkowski et al.
4,764,368 A 8/1988 Blattler et al.
4,764,616 A 8/1988 Glamkowski et al.
4,816,444 A 3/1989 Pettit et al.
4,816,567 A 3/1989 Cabilly et al.
4,879,278 A 11/1989 Pettit et al.
4,912,227 A 3/1990 Kelly et al.
4,923,990 A 5/1990 Nakano et al.
4,935,362 A 6/1990 Tsunakawa et al.
4,943,628 A 7/1990 Rosen et al.
4,952,394 A 8/1990 Senter
4,956,303 A 9/1990 Self
4,970,198 A 11/1990 Lee et al.
4,975,278 A 12/1990 Senter et al.
4,978,744 A 12/1990 Pettit et al.
4,978,757 A 12/1990 Kelly et al.
4,994,578 A 2/1991 Ohba et al.
5,037,993 A 8/1991 Ohba et al.
5,053,394 A 10/1991 Ellestad et al.
5,070,092 A 12/1991 Kanda et al.
5,084,468 A 1/1992 Saito et al.
5,101,038 A 3/1992 Nakano et al.
5,106,951 A 4/1992 Morgan, Jr. et al.
5,108,912 A 4/1992 Lee et al.
5,117,006 A 5/1992 Saito et al.
5,122,368 A 6/1992 Greenfield et al.
5,137,877 A 8/1992 Kaneko et al.
5,138,059 A 8/1992 Takahashi et al.
5,146,064 A 9/1992 Poirier
5,147,786 A 9/1992 Feng et al.
5,165,923 A 11/1992 Thorpe et al.
5,169,774 A 12/1992 Frankel et al.
5,177,016 A 1/1993 Balsari et al.
5,187,186 A 2/1993 Kanda et al.
5,208,020 A 5/1993 Chari et al.
5,208,323 A 5/1993 Page et al.
5,223,409 A 6/1993 Ladner et al.
5,225,539 A 7/1993 Winter
5,264,586 A 11/1993 Nicolaou et al.
5,286,637 A 2/1994 Veronese et al.
5,288,514 A 2/1994 Ellman
5,324,483 A 6/1994 Cody et al.
5,332,740 A 7/1994 Saito et al.
5,332,837 A 7/1994 Kelly et al.
5,334,528 A 8/1994 Stanker et al.
5,384,412 A 1/1995 Nicolaou et al.
5,403,484 A 4/1995 Ladner et al.
5,410,024 A 4/1995 Pettit et al.
5,416,064 A 5/1995 Chari et al.
5,427,908 A 6/1995 Dower et al.
5,436,149 A 7/1995 Barnes
5,475,011 A 12/1995 Ojima et al.
5,475,092 A 12/1995 Chari et al.
5,495,009 A 2/1996 Matteucci et al.
5,521,284 A 5/1996 Pettit et al.
5,530,097 A 6/1996 Pettit et al.
5,530,101 A 6/1996 Queen et al.
5,545,806 A 8/1996 Lonberg et al.
5,547,667 A 8/1996 Angelucci et al.
5,554,725 A 9/1996 Pettit
5,569,825 A 10/1996 Lonberg et al.
5,571,698 A 11/1996 Ladner et al.
5,573,922 A 11/1996 Hoess et al.
5,580,717 A 12/1996 Dower et al.
5,585,089 A 12/1996 Queen et al.
5,585,499 A 12/1996 Chari et al.
5,587,161 A 12/1996 Burke et al.
5,595,499 A 1/1997 Zander et al.
5,599,902 A 2/1997 Pettit et al.
5,606,017 A 2/1997 Willner et al.
5,606,040 A 2/1997 McGahren et al.
5,622,929 A 4/1997 Willner et al.
5,625,126 A 4/1997 Lonberg et al.
5,629,197 A 5/1997 Ring et al.
5,629,430 A 5/1997 Terashima et al.
5,633,425 A 5/1997 Lonberg et al.
5,635,483 A 6/1997 Pettit et al.
5,641,780 A 6/1997 Amishiro et al.
5,660,829 A 8/1997 Burke et al.
5,661,016 A 8/1997 Lonberg et al.
5,663,149 A 9/1997 Pettit et al.
5,665,860 A 9/1997 Pettit et al.
5,686,237 A 11/1997 Al-Bayati
5,693,762 A 12/1997 Queen et al.
5,703,080 A 12/1997 Nakakura et al.
5,708,146 A 1/1998 Willner et al.
5,712,374 A 1/1998 Kuntsmann et al.
5,714,586 A 2/1998 Kuntsmann et al.
5,728,849 A 3/1998 Bouchard et al.
5,739,116 A 4/1998 Hamann et al.
5,739,350 A 4/1998 Kelly et al.
5,741,892 A 4/1998 Barlozzari et al.
5,767,236 A 6/1998 Kim et al.
5,767,237 A 6/1998 Sakakibara et al.
5,770,429 A 6/1998 Lonberg et al.
5,770,701 A 6/1998 McGahren et al.
5,770,710 A 6/1998 McGahren et al.
5,773,001 A 6/1998 Hamann et al.
5,773,435 A 6/1998 Kadow et al.
5,780,588 A 7/1998 Pettit et al.
5,786,377 A 7/1998 García et al.
5,786,486 A 7/1998 Fukuda et al.
5,789,650 A 8/1998 Lonberg et al.
5,811,452 A 9/1998 Ojima et al.
5,814,318 A 9/1998 Lonberg et al.
5,821,337 A 10/1998 Carter et al.
5,824,805 A 10/1998 King et al.
5,840,699 A 11/1998 Sakakibara et al.
5,846,545 A 12/1998 Chari et al.
5,859,205 A 1/1999 Adair et al.
5,874,299 A 2/1999 Lonberg et al.
5,877,296 A 3/1999 Hamann et al.
5,877,397 A 3/1999 Lonberg et al.
5,880,122 A 3/1999 Trybulski et al.
5,885,793 A 3/1999 Griffiths et al.
5,922,545 A 7/1999 Mattheakis et al.
5,939,598 A 8/1999 Kucherlapati et al.
5,962,216 A 10/1999 Trouet et al.
5,965,537 A 10/1999 Ritter et al.
5,969,108 A 10/1999 McCafferty et al.
5,985,908 A 11/1999 Boger
6,004,934 A 12/1999 Sakakibara et al.
6,015,562 A 1/2000 Hinman et al.
6,033,876 A 3/2000 Lemke et al.
6,034,065 A 3/2000 Pettit et al.
6,048,720 A 4/2000 Dalborg et al.
6,054,297 A 4/2000 Carter et al.

(56) References Cited

U.S. PATENT DOCUMENTS

| | | | |
|---|---|---|---|
| 6,054,561 | A | 4/2000 | Ring |
| 6,060,608 | A | 5/2000 | Boger |
| 6,066,742 | A | 5/2000 | Fukuda et al. |
| 6,075,181 | A | 6/2000 | Kucherlapati et al. |
| 6,103,236 | A | 8/2000 | Suzawa et al. |
| 6,111,166 | A | 8/2000 | Van De Winkel |
| 6,114,598 | A | 9/2000 | Kucherlapati et al. |
| 6,124,310 | A | 9/2000 | Denny et al. |
| 6,124,431 | A | 9/2000 | Sakakibara et al. |
| 6,130,237 | A | 10/2000 | Denny et al. |
| 6,132,722 | A | 10/2000 | Siemers et al. |
| 6,143,721 | A | 11/2000 | Janssen et al. |
| 6,143,901 | A | 11/2000 | Dervan |
| 6,146,658 | A | 11/2000 | Bosslet et al. |
| 6,150,584 | A | 11/2000 | Kucherlapati et al. |
| 6,162,963 | A | 12/2000 | Kucherlapati et al. |
| 6,172,197 | B1 | 1/2001 | McCafferty et al. |
| 6,180,370 | B1 | 1/2001 | Queen et al. |
| 6,194,612 | B1 | 2/2001 | Boger et al. |
| 6,207,418 | B1 | 3/2001 | Hori et al. |
| 6,214,345 | B1 | 4/2001 | Firestone et al. |
| 6,239,104 | B1 | 5/2001 | Pettit et al. |
| 6,262,271 | B1 | 7/2001 | Boger |
| 6,281,354 | B1 | 8/2001 | Boger |
| 6,310,209 | B1 | 10/2001 | Boger |
| 6,323,315 | B1 | 11/2001 | Pettit et al. |
| 6,329,497 | B1 | 12/2001 | Boger |
| 6,333,410 | B1 | 12/2001 | Chari et al. |
| 6,340,701 | B1 | 1/2002 | Chari et al. |
| 6,342,219 | B1 | 1/2002 | Thorpe et al. |
| 6,342,221 | B1 | 1/2002 | Thorpe et al. |
| 6,342,480 | B1 | 1/2002 | Trouet et al. |
| 6,344,451 | B1 | 2/2002 | Steffan et al. |
| 6,372,738 | B2 | 4/2002 | Chari et al. |
| 6,391,913 | B1 | 5/2002 | Pagé et al. |
| 6,407,213 | B1 | 6/2002 | Carter et al. |
| 6,436,931 | B1 | 8/2002 | Chari et al. |
| 6,441,163 | B1 | 8/2002 | Chari et al. |
| 6,486,326 | B2 | 11/2002 | Boger |
| 6,512,101 | B1 | 1/2003 | King et al. |
| 6,521,404 | B1 | 2/2003 | Griffiths et al. |
| 6,534,660 | B1 | 3/2003 | Yongxin et al. |
| 6,544,731 | B1 | 4/2003 | Griffiths et al. |
| 6,548,530 | B1 | 4/2003 | Boger |
| 6,555,313 | B1 | 4/2003 | Griffiths et al. |
| 6,555,693 | B2 | 4/2003 | Ge et al. |
| 6,562,806 | B1 | 5/2003 | Thurston et al. |
| 6,566,336 | B1 | 5/2003 | Sugiyama et al. |
| 6,569,834 | B1 | 5/2003 | Pettit et al. |
| 6,586,618 | B1 | 7/2003 | Zhao et al. |
| 6,589,979 | B2 | 7/2003 | Bombardelli et al. |
| 6,593,081 | B1 | 7/2003 | Griffiths et al. |
| 6,596,541 | B2 | 7/2003 | Murphy et al. |
| 6,596,757 | B1 | 7/2003 | Chari et al. |
| 6,608,192 | B1 | 8/2003 | Thurston et al. |
| 6,620,911 | B1 | 9/2003 | Pettit et al. |
| 6,630,579 | B2 | 10/2003 | Chari et al. |
| 6,639,055 | B1 | 10/2003 | Carter et al. |
| 6,660,856 | B2 | 12/2003 | Wang |
| 6,706,708 | B2 | 3/2004 | Chari et al. |
| 6,716,821 | B2 | 4/2004 | Zhao et al. |
| 6,747,144 | B1 | 6/2004 | Thurston et al. |
| 6,756,397 | B2 | 6/2004 | Zhao et al. |
| 6,759,509 | B1 | 7/2004 | King et al. |
| 6,762,179 | B2 | 7/2004 | Cochran et al. |
| 6,797,492 | B2 | 9/2004 | Daugherty et al. |
| 6,800,622 | B1 | 10/2004 | Kamal et al. |
| 6,884,799 | B2 | 4/2005 | Kamal et al. |
| 6,884,869 | B2 | 4/2005 | Senter et al. |
| 6,897,034 | B2 | 5/2005 | Bebbington et al. |
| 6,909,006 | B1 | 6/2005 | Thurston et al. |
| 6,913,748 | B2 | 7/2005 | Widdison |
| 6,946,455 | B2 | 9/2005 | Sugiyama et al. |
| 6,951,853 | B1 | 10/2005 | Kamal et al. |
| 6,977,254 | B2 | 12/2005 | Failli et al. |
| 6,979,684 | B1 | 12/2005 | Kamal et al. |
| 7,008,942 | B2 | 3/2006 | Chari et al. |
| 7,015,215 | B2 | 3/2006 | Kamal et al. |
| 7,022,699 | B2 | 4/2006 | Failli et al. |
| 7,049,311 | B1 | 5/2006 | Thurston et al. |
| 7,049,316 | B2 | 5/2006 | Zhao et al. |
| 7,056,913 | B2 | 6/2006 | Kamal et al. |
| 7,064,120 | B2 | 6/2006 | Failli et al. |
| 7,067,511 | B2 | 6/2006 | Thurston et al. |
| 7,087,600 | B2 | 8/2006 | Ng et al. |
| 7,090,843 | B1 | 8/2006 | Francisco et al. |
| 7,091,186 | B2 | 8/2006 | Senter et al. |
| 7,097,840 | B2 | 8/2006 | Erickson et al. |
| 7,098,305 | B2 | 8/2006 | Deghenghi et al. |
| 7,098,308 | B2 | 8/2006 | Senter et al. |
| 7,109,193 | B2 | 9/2006 | Failli et al. |
| 7,115,573 | B2 | 10/2006 | Pickford et al. |
| 7,129,261 | B2 | 10/2006 | Ng et al. |
| 7,173,026 | B2 | 2/2007 | Kamal et al. |
| 7,186,851 | B2 | 3/2007 | Baloglu |
| 7,189,710 | B2 | 3/2007 | Kamal et al. |
| 7,202,239 | B2 | 4/2007 | Failli et al. |
| 7,214,663 | B2 | 5/2007 | Bebbington et al. |
| 7,217,819 | B2 | 5/2007 | Chari et al. |
| 7,223,837 | B2 | 5/2007 | De Groot et al. |
| 7,265,105 | B2 | 9/2007 | Thurston et al. |
| 7,276,497 | B2 | 10/2007 | Chari et al. |
| 7,276,499 | B2 | 10/2007 | Chari et al. |
| 7,301,019 | B2 | 11/2007 | Widdison et al. |
| 7,303,749 | B1 | 12/2007 | Chari |
| 7,304,032 | B2 | 12/2007 | Bebbington et al. |
| 7,312,210 | B2 | 12/2007 | Kamal et al. |
| 7,326,700 | B2 | 2/2008 | Failli et al. |
| 7,329,507 | B2 | 2/2008 | Pickford et al. |
| 7,329,760 | B2 | 2/2008 | Zhao et al. |
| 7,332,571 | B2 | 2/2008 | Miao et al. |
| 7,368,565 | B2 | 5/2008 | Chari et al. |
| 7,375,078 | B2 | 5/2008 | Feng |
| 7,388,026 | B2 | 6/2008 | Zhao et al. |
| 7,407,951 | B2 | 8/2008 | Thurston et al. |
| 7,411,063 | B2 | 8/2008 | Widdison et al. |
| 7,429,658 | B2 | 9/2008 | Howard et al. |
| 7,462,352 | B2 | 12/2008 | Hansen et al. |
| 7,498,298 | B2 | 3/2009 | Doronina et al. |
| 7,511,032 | B2 | 3/2009 | Liu et al. |
| 7,521,541 | B2 | 4/2009 | Eigenbrot et al. |
| 7,528,126 | B2 | 5/2009 | Howard et al. |
| 7,528,128 | B2 | 5/2009 | Ahmed et al. |
| 7,553,816 | B2 | 6/2009 | Senter et al. |
| 7,557,099 | B2 | 7/2009 | Howard et al. |
| 7,569,358 | B2 | 8/2009 | Salamone et al. |
| 7,598,290 | B2 | 10/2009 | Miller et al. |
| 7,608,615 | B2 | 10/2009 | Ahmed et al. |
| 7,612,062 | B2 | 11/2009 | Gregson et al. |
| 7,632,492 | B2 | 12/2009 | Grabstein et al. |
| 7,638,299 | B2 | 12/2009 | Cho et al. |
| 7,655,660 | B2 | 2/2010 | Zhao et al. |
| 7,655,661 | B2 | 2/2010 | Zhao et al. |
| 7,659,241 | B2 | 2/2010 | Senter et al. |
| 7,662,387 | B2 | 2/2010 | Law et al. |
| 7,667,054 | B2 | 2/2010 | Miller et al. |
| 7,678,787 | B2 | 3/2010 | Failli et al. |
| 7,691,848 | B2 | 4/2010 | Failli et al. |
| 7,691,962 | B2 | 4/2010 | Boyd et al. |
| 7,696,312 | B2 | 4/2010 | Miao et al. |
| 7,704,924 | B2 | 4/2010 | Thurston et al. |
| 7,723,485 | B2 | 5/2010 | Junutula et al. |
| 7,741,319 | B2 | 6/2010 | Howard et al. |
| 7,745,394 | B2 | 6/2010 | Doronina et al. |
| 7,754,681 | B2 | 7/2010 | Feng |
| 7,803,903 | B2 | 9/2010 | Kratz |
| 7,829,531 | B2 | 11/2010 | Senter et al. |
| 7,829,659 | B2 | 11/2010 | Grabstein et al. |
| 7,834,005 | B2 | 11/2010 | Liu et al. |
| 7,837,980 | B2 | 11/2010 | Alley et al. |
| 7,837,995 | B2 | 11/2010 | Goldenberg |
| 7,851,432 | B2 | 12/2010 | Chari et al. |
| 7,851,437 | B2 | 12/2010 | Senter et al. |
| 7,855,275 | B2 | 12/2010 | Eigenbrot et al. |

(56) References Cited

U.S. PATENT DOCUMENTS

| | | |
|---|---|---|
| 7,893,019 B2 | 2/2011 | Tonon et al. |
| 7,902,338 B2 | 3/2011 | Hansen et al. |
| 7,906,545 B2 | 3/2011 | Zhao et al. |
| 7,964,566 B2 | 6/2011 | Doronina et al. |
| 7,964,567 B2 | 6/2011 | Doronina et al. |
| 7,985,783 B2 | 7/2011 | Carrico et al. |
| 7,994,135 B2 | 8/2011 | Doronina et al. |
| 8,012,978 B2 | 9/2011 | Zhao et al. |
| 8,034,808 B2 | 10/2011 | Delavault et al. |
| 8,053,205 B2 | 11/2011 | Salamone et al. |
| 8,097,701 B2 | 1/2012 | Carrico et al. |
| 8,153,627 B2 | 4/2012 | Kamal et al. |
| 8,153,768 B2 | 4/2012 | Kunz et al. |
| 8,163,736 B2 | 4/2012 | Gauzy et al. |
| 8,163,888 B2 | 4/2012 | Steeves et al. |
| 8,309,300 B2 | 11/2012 | Junutula et al. |
| 8,349,910 B2 | 1/2013 | Carrico et al. |
| 8,778,631 B2 | 7/2014 | Voloshin et al. |
| 8,871,908 B2 | 10/2014 | Liu et al. |
| 8,916,159 B2 | 12/2014 | Rader et al. |
| 9,839,687 B2 | 12/2017 | Zhao |
| 2003/0195196 A1 | 10/2003 | Thurston et al. |
| 2004/0249130 A1 | 12/2004 | Stanton et al. |
| 2005/0009751 A1 | 1/2005 | Senter et al. |
| 2005/0239713 A1 | 10/2005 | Domling et al. |
| 2005/0249740 A1 | 11/2005 | Domling et al. |
| 2006/0022925 A1 | 2/2006 | Hara et al. |
| 2006/0074008 A1 | 4/2006 | Senter et al. |
| 2006/0128754 A1 | 6/2006 | Hoefle et al. |
| 2006/0217360 A1 | 9/2006 | Hoefle et al. |
| 2007/0041901 A1 | 2/2007 | Diener et al. |
| 2010/0184135 A1 | 7/2010 | Voloshin et al. |
| 2010/0203007 A1 | 8/2010 | Li et al. |
| 2010/0210543 A1 | 8/2010 | Rabuka et al. |
| 2010/0316656 A1 | 12/2010 | Bouchard et al. |
| 2011/0021568 A1 | 1/2011 | Ellman et al. |
| 2011/0027274 A1 | 2/2011 | Cheng et al. |
| 2011/0263650 A1 | 10/2011 | Ellman et al. |
| 2012/0129779 A1 | 5/2012 | Richter |
| 2013/0189287 A1 | 7/2013 | Bregeon et al. |
| 2014/0141025 A1 | 5/2014 | Kudirka et al. |
| 2015/0105539 A1 | 4/2015 | Miao et al. |
| 2016/0015832 A1 | 1/2016 | An et al. |

FOREIGN PATENT DOCUMENTS

| | | | |
|---|---|---|---|
| CN | 20091020073 | * 6/2010 | ........... C07D 519/06 |
| DE | 196 38 870 A1 | 3/1998 | |
| DE | 100 08 089 A1 | 10/2001 | |
| DE | 102 41 152 A1 | 3/2004 | |
| DE | 102 54 439 A1 | 6/2004 | |
| DE | 10 2004 030 227 A1 | 1/2006 | |
| EP | 2 174 947 A1 | 4/2010 | |
| WO | 01/38318 A1 | 5/2001 | |
| WO | 02/077036 A | 10/2002 | |
| WO | 2004/005269 A1 | 1/2004 | |
| WO | 2004/005326 A2 | 1/2004 | |
| WO | 2004/005327 A1 | 1/2004 | |
| WO | 2005/058367 A2 | 6/2005 | |
| WO | 2006/033913 A2 | 3/2006 | |
| WO | 2006/056464 A2 | 6/2006 | |
| WO | 2006/069246 A2 | 6/2006 | |
| WO | 2006/096754 A2 | 9/2006 | |
| WO | 2007/059312 A2 | 5/2007 | |
| WO | 2007/130453 A2 | 11/2007 | |
| WO | 2008/076333 A2 | 6/2008 | |
| WO | 2008/112873 A2 | 9/2008 | |
| WO | 2008/125116 A2 | 10/2008 | |
| WO | 2008/138561 A1 | 11/2008 | |
| WO | 2008/141044 A2 | 11/2008 | |
| WO | 2009/002993 A1 | 12/2008 | |
| WO | 2009/012958 A2 | 1/2009 | |
| WO | 2009/026177 A1 | 2/2009 | |
| WO | 2009/055562 A1 | 4/2009 | |
| WO | 2009/095447 A1 | 8/2009 | |
| WO | 2009/134279 A1 | 11/2009 | |
| WO | 2010/033733 A1 | 3/2010 | |
| WO | 2010/034724 A1 | 4/2010 | |
| WO | 2010/081110 A1 | 7/2010 | |
| WO | 2013/190272 A1 | 12/2013 | |
| WO | 2014/009774 A1 | 1/2014 | |
| WO | 2014/064424 A1 | 5/2014 | |
| WO | 2014/114207 A1 | 7/2014 | |

OTHER PUBLICATIONS

Levi, Chemical Society Reviews, 2016, 45, 2825-2846 (Year: 2016).*
Boger. Proceedings of the National Academy of Science, 1995, 92, 3642-49 (Year: 1995).*
CSUK. Bioorganic and Medicinal Chemistry, 2010, 18, 7252-59 (Year: 2010).*
Adams et al., "Generating Improved Single-Chain Fv Molecules for Tumor Targeting," Journal of Immunological Methods, (Dec. 10, 1999), vol. 231, Issue 1-2, pp. 249-260.
Adem et al., "Auristatin Antibody Drug Conjugate Physical Instability and the Role of Drug Payload," Bioconjugate Chemistry, (2014), vol. 25, No. 4, pp. 656-664.
Afar et al., "Preclinical validation of anti-TMEFF2-auristatin E-conjugated antibodies in the treatment of prostate cancer," Molecular Cancer Therapeutics, (Aug. 2004), vol. 3, No. 8, pp. 921-932.
Almagro et al., "Humanization of antibodies," Frontiers in Bioscience, (Jan. 1, 2008), vol. 13, pp. 1619-1633.
Almutairi et al., "Biodegradable dendritic positron-emitting nanoprobes for the noninvasive imaging of angiogenesis," Proceedings of the National Academy of Sciences of the United States of America, (Jan. 20, 2009), vol. 106, No. 3, pp. 685-690.
Axup et al., "Synthesis of site-specific antibody-drug conjugates using unnatural amino acids," Proceedings of the National Academy of Sciences of the United States of America, (Oct. 2, 2012), vol. 109, No. 40, pp. 16101-16106.
Badescu et al., "Bridging Disulfides for Stable and Defined Antibody Drug Conjugates," Bioconjugate Chemistry, (2014), vol. 25, pp. 1124-1136.
Balasubramanian et al., "Total Synthesis and Biological Evaluation of Tubulysin U, Tubulysin V, and Their Analogues," Journal of Medicinal Chemistry, (2009), vol. 52, No. 2, pp. 238-240.
Boger et al., "Parallel Synthesis and Evaluation of 132 (+)-1,2,9,9a-Tetrahydrocycloproa[c]benz[e]indol-4-one (CBI) Analogues of CC-1065 and the Duocarmycins Definig the Contribution of the DNA-Binding Domain," (Sep. 13, 2001), vol. 66, No. 20, pp. 6654-6661.
Boylan et al., "Conjugation Site Heterogeneity Causes Variable Electrostatic Properties in Fc Conjugates," Bioconjugate Chemistry, (2013) vol. 24, pp. 1008-1016.
Brannigan et al., "Protein engineering 20 years on," Nature Publishing Group, (Dec. 2002), vol. 3, pp. 964-970.
Brich et al., "Preparation and characterization of a water soluble dextran immunoconjugate of doxorubicin and the monoclonal antibody," Journal of Controlled Release, (1992), vol. 19, pp. 245-258.
Burgess, Antony W., "The complex mediators of cell growth and differentiation," Immunology Today, (Jun. 1984), vol. 5, No. 6, pp. 155-158.
Chai et al., "Discovery of 23 Natural Tubulysins from *Angiococcus disciformis* An d48 and Cystobacter SBCb004," Chemistry & Biology, (Mar. 26, 2010), No. 17, pp. 296-309.
Chandrasekhar et al., "Toward Tubulsin: Gram-Scale Synthesis of Tubuvaline-Tubuphenylalanine Fragment," The Journal of Organic Chemistry, (2009), vol. 74, No. 24, pp. 9531-9534.
Chari, Ravi V.J., "Targeted Cancer Therapy: Conferring Specificity to Cytotoxin Drugs," Accounts of Chemical Research, (Jan. 2008), vol. 41, No. 1, pp. 98-107.
Chari et al., "Antibody-Drug Conjugates: An Emerging Concept in Cancer Therapy," Angewandte Chemie International Edition, (2014), vol. 53, pp. 3796-3827.
Chen et al., "Synthesis of Doxorubicin Conjugates Through Hydrazone Bonds to Melanotransferrin P97," Synthetic Communications: An International Journal for Rapid Communications of Synthetic Organic Chemistry, (Aug. 20, 2006), vol. 33, No. 14, pp. 2377-2390.

(56) References Cited

OTHER PUBLICATIONS

Clackson et al., "Making antibody fragments using phage display libraries," Letters to Nature, (Aug. 15, 1991), vol. 352, pp. 624-628.
Dennler et al., "Transglutaminase-Based Chemo-Enzymatic Conjugation Approach Yields Homogeneous Antibody-Drug Conjugates," Bioconjugate Chemistry, vol. 25, pp. 569-578.
Dente et al., "Monoclonal antibodies that recognise filamentous phage: tools for phage display technology," Gene, (Oct. 11, 1994), vol. 148, No. 1, pp. 7-13.
Dhar et aL, "Targeted delivery of cisplatin to prostate cancer cells by aptamer functionalized Pt(IV) prodrug-PLGA-PEG nanoparticles," Proceedings of the National Academy of Sciences of the United States of America, (Nov. 11, 2008), vol. 105, No. 45, pp. 17356-17361.
Dömling et al., "Total Synthesis of Tubulysin U and V," Angewandte Chemie International Edition, (2006) vol. 45, pp. 7235-7239.
Drake et al., "Aldehyde Tag Coupled with HIPS Chemistry Enables the Production of ADCs Conjugated Site-Specifically to Different Antibody Regions with Distinct in Vivo Efficacy and PK Outcomes," Bioconjugate Chemistry, (2014), vol. 25, pp. 1331-1341.
Edelman et al., "The Covalent Structure of an Entire γG Immunoglobulin Molecule," Proceedings of the National Academy of Sciences of the United States of America, (1969), vol. 63, pp. 78-85.
Elsadek et al., "Impact of albumin on drug delivery—New applications on the horizon," Journal of Controlled Release, (Jan. 10, 2012) vol. 157, No. 1, pp. 4-28.
Epenetos et al., "Limitations of Radiolabeled Monoclonal Antibodies for Localization of Human Neoplasms," Cancer Research, (Jun. 1986), vol. 46, No. 6, pp. 3183-3191.
Flenniken et al., "A Library of Protein Cage Architectures as Nanomaterials," Viruses and Nanotechnology, Current Topics in Microbiology and Immunology, vol. 327, pp. 71-93.
Frangione et al., "Intrachain Disulphide Bridges in Immunoglobulin G Heavy Chains. The Fc fragment," Biochemical Journal, (Jan. 1968), vol. 106, No. 15, pp. 15-21.
Frangione et al., "Variations in the S—S bridges of immunoglobins G: Interchain disulphide bridges of γG3 myeloma proteins," Journal of Molecular Biology, (May 14, 1968), vol. 33, No. 3, pp. 893-906.
Frangione et al., "Structural Studies of Immunoglobulin G," Nature, (Jan. 11, 1969), vol. 221, No. 5176, pp. 145-148.
Frankel et al., "Cell Surface Receptor—Targeted Therapy of Acute Myeloid Leukemia: A Review," Cancer Biotherapy & Radiopharmaceuticals, (2000), vol. 15, No. 5. pp. 459-476.
Friestad et al., "Stereoselective Mn-Mediated Coupling of Functionalized Iodides and Hydrazones: A Synthetic Entry to the Tubulysin γ-Amino Acids," Organic Letters, (2004), vol. 6, No. 19, pp. 3249-3252.
Friestad et al., "Synthesis of γ-Amino Esters via Mn-Mediated Radical Addition to Chiral γ-Hydrazonoesters," Organic Letters, (2009), vol. 11, No. 5, pp. 1095-1098.
Gerber et al., "Antibody drug-conjugates targeting the tumor vasculature," mAbs, (May/Jun. 2009), vol. 1, No. 3, pp. 247-253.
Geysen et al., "Small peptides induce antibodies with a sequence and structural requirement for binding antigen comparable to antibodies raised against the native protein," Proceedings of the National Academy of Sciences of the United States of America, (Jan. 1985), vol. 82, No. 1, pp. 178-182.
Hamblett et al., "Effects of Drug Loading on the Antitumor Activity of a Monoclonal Antibody Drug Conjugate," Clinical Cancer Research, (Oct. 15, 2004), vol. 10, pp. 7063-7070.
Harlow et al., "Antibodies: A Laboratory Manual," Cold Spring Harbor Laboratory, (1988). (105 pages).
Hinman et al., "Preparation and Characterization of Monoclonal Antibody Conjugates of the Calicheamicins: A Novel and Potent Family of Antitumor Antibiotics," Cancer Research, (Jul. 15, 1993), vol. 53, pp. 3336-3342.
Hofer et al., "Molecularly Defined Antibody Conjugation through a Selenocysteine Interface," Biochemistry, (2009), vol. 48, pp. 12047-12057.
Houdebine, Louis-Marie, "Antibody manufacture in transgenic animals and comparisons with other systems," Current Opinion in Biotechnology, (2002), vol. 13, No. 6, pp. 625-629.
Hurwitz et al., "The Covalent Binding of Daunomycin and Adriamycin to Antibodies, with Retention of Both Drug and Antibody Activities," Cancer Research, (May 1975), vol. 35, pp. 1175-1181.
Huse et al., "Generation of a Large Combinatorial Library of the Immunoglobulin Repertoire in Phage Lambda," Science, (Dec. 1989), vol. 246, No. 4935, pp. 1275-1281.
Javier et al., "Aptamer-Targeted Gold Nanoparticles As Molecular-Specific Contrast Agents for Reflectance Imaging," Bioconjugate Chemistry, (Jun. 2008), vol. 19, No. 6, pp. 1309-1312.
Junutula et al., "Site-specific conjugation of a cytotoxic drug to an antibody improves the therapeutic index," Nature Biotechnology, (Aug. 2008), vol. 26, No. 8, pp. 925-932.
Junutula et al., "Engineered Thio-Trastuzumab-DM1 Conjugate with an Improved Therapeutic Index to Target Human Epidermal Growth Factor Receptor 2-Positive Breast Cancer," Clinical Cancer Research, (2010), vol. 16, No. 19, pp. 4769-4778.
Kim et al., "C-2 Modified Taxol Analogs with Improved Aqueous Solubility," Bulletin of the Korean Chemical Society, (1999), vol. 20, No. 12, pp. 1389-1390.
King et al., "Monoclonal Antibody Conjugates of Doxorubicin Prepared with Branched Linkers: A Novel Method for Increasing the Potency of Doxorubicin Immunoconjugates," Bioconjugate Chemistry, (Mar.-Apr. 1999), vol. 10, No. 2, pp. 279-288.
King et al., "Monoclonal Antibody Conjugates of Doxorubicin Prepared with Branched Peptide Linkers: Inhibition of Aggregation by Methoxytriethyleneglycol Chains," Journal of Medicinal Chemistry, (2002), vol. 45, No. 19, pp. 4336-4343.
Kipriyanov et al., "Generation and Production of Engineered Antibodies," Molecular Biotechnology, (2004), vol. 26, pp. 39-60.
"Chromophore," http://goldbook.iupac.org/plain/C01076-plain.html, 1994. (1 page).
Levi et al., "Multicomponent syntheses of functional chromophores," Chemical Society Reviews, (May 21, 2016), vol. 45, No. 10, pp. 2825-2846.
Office Action dated Aug. 6, 2018, by the U.S. Patent and Trademark Office in U.S. Appl. No. 15/448,639. (9 pages).
Köhler et al., "Continuous cultures of fused cells secreting antibody of predefined specificity," Nature, (Aug. 7, 1975), vol. 256, pp. 495-497.
Kratz et al., "Preparation, Characterization and in Vitro Efficacy of Albumin Conjugates of Doxorubicin," Biological & Pharmaceutical Bulletin, (Jan. 1998), vol. 21, No. 1, pp. 56-61.
Kratz et al., "Probing the Cysteine-34 Position of Endogenous Serum Albumin with Thiol-Binding Doxorubicin Derivatives. Improved Efficacy of an Acid-Sensitive Doxorubicin Derivative with Specific Albumin-Binding Properties Compared to That of the Parent Compound," Journal of Medicinal Chemistry, (2002), vol. 45, No. 25, pp. 5523-5533.
Kubicek et al., "The Tubulin-Bound Structure of the Antimitotic Drug Tubulysin," Angewandte Chemie International Edition, (2010), vol. 49, Issue. 28, pp. 4809-4812.
Laguzza et al., "New Antitumor Monoclonal Antibody-Vinca Conjugates LY203725 and Related Compounds: Design, Preparation, and Representative in Vivo Activity," Journal of Medicinal Chemistry, (1989), vol. 32, No. 3, pp. 548-555.
Lau et al., "Novel Doxorubicin-Monoclonal Anti-carcinoembryonic Antigen Antibody Immunoconjugate Activity in Vitro," Bioorganic & Medicinal Chemistry, (1995), vol. 3, No. 10, pp. 1305-1312.
Lazar et al., "A molecular immunology approach to antibody humanization and functional optimization," Molecular Immunology, (2007), vol. 44, pp. 1986-1998.
Lee et al., "Designing dendrimers for biological applications," Nature Biotechnology, (Dec. 2005), vol. 23, No. 12, pp. 1517-1526.
Lei et al., "Binding of Monoclonal Antibodies against the Carboxyl Terminal Segment of the Nicotinic Receptor δ Subunit Suggests an Unusual Transmembrane Disposition of This Sequence Region," Biochemistry, (1995), vol. 34, No. 20, pp. 6675-6688.
Li et al., "Human antibodies for immunotherapy development generated via a human B cell hybridoma technology," Proceedings

(56) References Cited

OTHER PUBLICATIONS of the National Academy of Sciences of the United States of America, (Mar. 7, 2006), vol. 103, No. 10, pp. 3557-3562.
Liong et al., "Multifunctional Inorganic Nanoparticles for Imaging, Targeting, and Drug Delivery," ACS Nano, (2008), vol. 2, No. 5, pp. 889-896.
Little et al., "Surface Display of Antibodies," Biotechnology Advances, (1994), vol. 12, No. 3, pp. 539-555.
Liu et al., "Ranking the Susceptibility of Disulfide Bonds in Human IgG1 Antibodies by Reduction, Differential Alkylation, and LC—MS Analysis," Analytical Chemistry, (Jun. 15, 2010), vol. 82, No. 12, pp. 5219-5226.
Liu et al., "Disulfide bond structures of IgG molecules," mAbs, (Jan./Feb. 2012), vol. 4, No. 1, pp. 17-23.
Liu et al., "Engineering therapeutic monoclonal antibodies," Immunological Reviews, (2008), vol. 222, No. 1, pp. 9-27.
Liu et al., "Targeting Cell Surface Alpha(v)beta(3) Integrin Increases Therepeutic Efficacies of a Legumain Protease-Activated Aunstatin Prodrug," Molecular Pharmaceutics, (2012), vol. 9, pp. 168-175.
Lundholm et al., "Plaque Production by the Polyoma Virus," Letters to the Editors (1959) pp. 396-397.
Lutz et al., "Efficient construction of therapeutics, bioconjugates, biomaterials and bioactive surfaces using azide-alkyne "click" chemistry," Advanced Drug Delivery Reviews, (2008), vol. 60, pp. 958-970.
McBride, Gordon E., "Cytokinesis in Green Alga Fritschiella," Nature, (Dec. 2, 1967), vol. 216, p. 939.
Medarova et al., "In vivo imaging of siRNA delivery and silencing in tumors," Nature Medicine, (Mar. 2007), vol. 13, No. 3, pp. 372-377.
Medina et al., "Targeted Liposomal Drug Delivery in Cancer," Current Pharmaceutical Design, (2004), vol. 10, No. 24, pp. 2981-2989.
Mehrling, Thomas, "Chemotherapy is getting "smarter,"" Future Oncology, (2015), vol. 11, No. 4, pp. 549-552.
Miller et al., "Design, Construction, and In Vitro Analyses of Multivalent Antibodies," The Journal of Immunology, (2003), vol. 170, pp. 4854-4861.
Miller et al., "Synthesis of Taxoids with Improved Cytotoxicity and Solubility for Use in Tumor-Specific Delivery," Journal of Medicinal Chemistry, (2004), vol. 47, No. 20, pp. 4802-4805.
Milstein, C., "The Disulphide Bridges of Immunoglobulin x-Chains," Biochemical Journal, (1966), vol. 101, pp. 338-351.
Mohammad et al., "A new tubulin polymerization inhibitor, auristatin PE, induces tumor regression in a human Waldenstrom's macroglobulinemia xenograft model," International Journal of Oncology, (1999), vol. 15, pp. 367-372.
Nicolaou et al., "Chemistry and biology of natural and designed enediynes," Proceedings of the National Academy of Sciences of the United States of America, (Jul. 1993), vol. 90, pp. 5881-5888.
Nicolaou et al., "Calicheamicin θ: A Rationally Designed Molecule with Extremely Potent and Selective DNA Cleaving Properties and Apoptosis Inducing Activity," Angewandte Chemie International Edition, (1994), vol. 33, No. 2, pp. 183-186.
Nicolaou et al., "Chemical Synthesis and Biological Evaluation of C-2 Taxoids," The Journal of the American Chemical Society, (1995), vol. 117, No. 9, pp. 2409-2420.
Niman et al., "Generation of protein-reactive antibodies by short peptides is an event of high frequency: Implications for the structural basis of immune recognition," Proceedings of the National Academy of Sciences of the United States of America, (Aug. 1983), vol. 80, pp. 4949-4953.
Novellino et al., "A listing of human tumor antigens recognized by T cells: Mar. 2004 update," Cancer Immunology, Immunotherapy, (Mar. 2005), vol. 54, No. 3, pp. 187-207.
Ojima et al., "A common pharmacophore for cytotoxic natural products that stabilize microtubules," Proceedings of the National Academy of Sciences of the United States of America, (Apr. 1999), vol. 96, pp. 4256-4261.
Ojima et al., "Tumor-Specific Novel Taxoid-Monoclonal Antibody Conjugates," Journal of Medicinal Chemistry, (2002), vol. 45, No. 26, pp. 5620-5623.
O'Keefe et al., "Characterization of a Transferrin-Diphtheria Toxin Conjugate," The Journal of Biological Chemistry, (Jan. 25, 1985), vol. 260. No. 2, pp. 932-937.
Okeley et al., "Metabolic Engineering of Monoclonal Antibody Carbohydrates for Antibody-Drug Conjugation," Bioconjugate Chemistry, (2013), vol. 24, pp. 1650-1655.
Pando et al., "First Total Synthesis of Tubulysin B," Organic Letters, (2009), vol. 11, No. 24, pp. 5567-5569.
Pando et al., "The Multiple Multicomponent Approach to Natural Product Mimics: Tubugis, N-Substituted Anticancer Peptides with Picomolar Activity," Journal of the American Chemical Society, (2011), vol. 133, pp. 7692-7695.
Panowski et al., "Site-specific antibody drug conjugates for cancer therapy," mAbs, (Jan./Feb. 2014), vol. 6, No. 1, pp. 34-45.
Parham, P., "On the fragmentation of monoclonal IgG1, IgG2a, and IgG2b from BALB/c mice," The Journal of Immunology, (Dec. 1983), vol. 131, No. 6, pp. 2895-2902.
Patterson et al., "Expedient Synthesis of N-Methyl Tubulysin Analogues with High Cytotoxicity," Journal of Organic Chemistry, (2008), vol. 73, No. 12, pp. 4362-4369.
Peltier et al., "The Total Synthesis of Tubulysin D," Journal of the American Chemical Society, (2006), vol. 128, No. 50, pp. 16018-16019.
Pietersz et al., "Immunochemotherapy of a Murine Thymoma with the Use of Idarubicin Monoclonal Antibody Conjugates," Cancer Research (Feb. 15, 1988), vol. 48, pp. 926-931.
Pink et al., "Inter Heavy-Light Chain Disulphide Bridge in Immune Globulins," Nature, (Apr. 1, 1967), vol. 214, pp. 92-94.
Pink et al., "Disulphide Bridges of a Human Immunoglobulin G Protein," Nature, (Dec. 2, 1967), vol. 216, pp. 941-942.
Rabuka et al., "Site-specific chemical protein conjugation using genetically encoded aldehyde tags," Nature Protocols, (2012), vol. 7, No. 6, pp. 1052-1067.
Raghavan et al., "Cytotoxic Simplified Tubulysin Analogues," Journal of Medicinal Chemistry, (2008), vol. 51, No. 6, pp. 1530-1533.
Reddy et al., "In Vivo Structural Activity and Optimization Studies of Folate-Tubulysin Conjugates," Molecular Pharmaceutics, (2009), vol. 6, No. 5, pp. 1518-1525.
Sani et al., "Total Synthesis of Tubulysins U and V," Angewandte Chemie International Edition, (2007), vol. 46, No. 19, pp. 3526-3529.
Schumacher et al., "Next generation maleimides enable the controlled assembly of antibody-drug conjugates via native disulfide bond bridging," Organic & Biomolecualr Chemistry, (2014), vol 12, pp. 7261-7269.
Scott et al., "Synthesis of Reagents for the One Step Incorporation of Hydrazide Functionality onto the Lysine Residues of Proteins, and their use as Linkers for Carbonyl Containing Molecules," Bioorganic & Medicinal Chemistry Letters, (1996), vol. 6, No. 13, pp. 1491-1496.
Office Action dated Sep. 20, 2018, by the U.S. Patent and Trademark Office in U.S. Appl. No. 15/448,634. (7 pages).
Aly et al., "Thieno[2,3-d]pyrimidines in the Synthesis of New Fused Heterocyclic Compounds of Prospective Antitumon and Antioxidant Agents (Part II)," Journal of Heterocyclic Chemistry, (Sep. 2012), vol. 49, pp. 1009-1018.
Bemis et al., "The Properties of Known Drugs. 1. Molecular Frameworks," Journal of Medicinal Chemistry, (1996), vol. 39, No. 15, pp. 2887-2893.
Bode, "Emerging methods in amide- and peptide-bond formation," Current Opinion in Drug Discovery & Development, (2006), vol. 9, No. 6, pp. 765-775.
"Imine synthesis," https://www.organic-chemistry.org/synthesis/C2N/imines.shtm. accessed Sep. 12, 2018, attached as a PDF (Year 2018). (4 pages).
Sievers et al., "Antibody-Drug Conjugates in Cancer Therapy," Annual Review of Medicine, (2013), vol. 64, pp. 15-29.

(56) References Cited

OTHER PUBLICATIONS

Sletten et al., "From Mechanism to Mouse: A Tale of Two Bioorthogonal Reactions," Accounts of Chemical Research, (2011) vol. 44, No. 9, pp. 666-676.
Smith et al., "The Enediyne Antibiotics," Journal of Medicinal Chemistry, (May 24, 1996), vol. 39, No. 11, pp. 2103-2117.
Spiegelberg et al., "Human Myeloma IgG Half-Molecules. Structural and Antigenic Analyses," Biochemistry, (1975), vol. 14, No. 10, pp. 2157-2163.
Strop et al., "Location Matters: Site of Conjugation Modulates Stability and Pharmacokinetics of Antibody Drug Conjugates," Chemistry & Biology, (Feb. 21, 2013), vol. 20, pp. 161-167.
Strop, P., "Versatility of Microbial Transglutaminase," Bioconjugate Chemistry, (2014), vol. 25, pp. 855-862.
Szardenings, "Phage Display of Random Peptide Libraries: Applications, Limits, and Potential," Journal of Receptors and Signal Transduction, (2003), vol. 23, No. 4, pp. 307-349.
Teicher et al., "Antibody Conjugate Therapeutics: Challenges and Potential," Clinical Cancer Research, (Oct. 15, 2011), vol. 17, No. 20, pp. 6389-3698.
Tian et al., "A general approach to site-specific antibody drug conjugates," Proceedings of the National Academy of Sciences of the United States of America, (Feb. 4, 2014), vol. 111, No. 5, pp. 1766-1771.
Trail et al., "Effect of Linker Variation on the Stability, Potency, and Efficacy of Carcinoma-reactive BR64-Doxorubicin Immunoconjugates," Cancer Research, (Jan. 1, 1997), vol. 57, No. 1, pp. 100-105.
Trouet et al., "A Covalent Linkage between Daunorubicin and Proteins that is Stable in Serum and Reversible by Lysosomal Hydrolases, as Required for a Lysosomotropic Drug-Carrier Conjugate: In Vitro and in Vivo Studies," Proceedings of the National Academy of Sciences of the United States of America, (Jan. 1982), vol. 79, No. 2, pp. 626-629.
Ullrich et al., "Pretubulysin, a Potent and Chemically Accessible Tubulysin Precursor from *Angiococcus disciformis*," Angewandte Chemie International Edition, (2009), vol. 48, No. 24, pp. 4422-4425.
Wakankar et al., "Analytical methods for physicochemical characterization of antibody drug conjugates," mAbs, (Mar./Apr. 2011), vol. 3, No. 2, pp. 161-172.
Wang et al., "Structural characterization of the maytansinoid-monoclonal antibody immunoconjugate, huN901-DM1, by mass spectrometry," Protein Science, (2005), vol. 14, pp. 2436-2446.
Warpehoski et al., "Stereoelectronic Factors Influencing the Biological Activity and DNA Interaction of Synthetic Antitumor Agents Modeled on CC-1065," Journal of Medicinal Chemistry, (1988), vol. 31, No. 3, pp. 590-603.
Watanabe et al., "Measurement of Cross-Reactive Properties of Adriamycin Derivatives by the Inhibition Enzyme-Linked Immunosorbent Assay for Adriamycin," Tokai Journal of Experimental and Clinical Medicine, (1990), vol. 15, No. 4, pp. 327-334.
Wipf et al., "Synthesis of the Tubuvaline-Tubuphenylalanine (Tuv-Tup) Fragment of Tubulysin," Organic Letters, (2004), vol. 6, No. 22, pp. 4057-4060.
Wipf et al., "Total Synthesis of N14-Desacetoxytubulysin H," Organic Letters, (2007), vol. 9, No. 8, pp. 1605-1607.
Wu et al., "Arming antibodies: prospects and challenges for immunoconjugates," Nature Biotechnology, (Sep. 2005), vol. 23, No. 9, pp. 1137-1146.
Wu et al., "Site-specific chemical modification of recombinant proteins produced in mammalian cells by using the genetically encoded aldehyde tag," Proceedings of the National Academy of Sciences of the United States of America, (Mar. 3, 2009), vol. 106, No. 9, pp. 3000-3005.
Yang et al., "Doxorubicin conjugated with a monoclonal antibody directed to a human melanoma-associated proteoglycan suppresses the growth of established tumor xenografts in nude mice," Proceedings of the National Academy of Sciences of the United States of America, (Feb. 1988), vol. 85, pp. 1189-1193.
Zhao et al., "Synthesis and Evaluation of Hydrophilic Linkers for Antibody-Maytansinoid Conjugates," Journal of Medicinal Chemistry, (2011), vol. 54, No. 10, pp. 3606-3623.
Zhou et al., "Site-Specific Antibody-Drug Conjugation through Glycoengineering," Bioconjugate Chemistry, (2014), vol. 25, pp. 510-520.
Zhou et al., "Cell-Specific Delivery of a Chemotherapeutic to Lung Cancer Cells," Journal of the American Chemical Society, (2004), vol. 126, No. 48, pp. 15656-15657.
Zimmerman et al., "Production of Site-Specific Antibody-Drug Conjugates Using Optimized Non-Natural Amino Acids in a Cell-Free Expression System," Bioconjugate Chemistry, (2014), vol. 25, pp. 351-361.
Heyl et al., "Facile Direct Synthesis of Acetylenedicarbonamides," (Mar. 2014), vol. 46, No. 11, pp. 1463-1468.
Office Action dated May 10, 2017, by the U.S. Patent and Trademark Office in copending U.S. Appl. No. 14/799,666. (9 pages).
Office Action dated Nov. 29, 2018, by the U.S. Patent and Trademark Office in U.S. Appl. No. 15/448,639. (5 pages).
Notice of Allowance dated Dec. 21, 2018, by the U.S. Patent and Trademark Office in U.S. Appl. No. 15/448,639. (9 pages).
Notice of Allowance dated Sep. 15, 2017, by the U.S. Patent and Trademark Office in copending U.S. Appl. No. 14/799,666. (12 pages).

* cited by examiner 13
14
15
13
16
15
17
18
15
19
20
21
22

42

50

51

52

53

ACETYLENEDICARBOXYL LINKERS AND THEIR USES IN SPECIFIC CONJUGATION OF A CELL-BINDING MOLECULE

CROSS REFERENCE TO RELATED APPLICATIONS

This application is a division of U.S. application Ser. No. 14/799,666, filed on Jul. 15, 2015, entitled "ACETYLENEDICARBOXYL LINKERS AND THEIR USES IN SPECIFIC CONJUGATION OF A CELL-BINDING MOLECULE." The content of the prior application is hereby incorporated by reference in its entirety.

FIELD OF THE INVENTION

The present invention relates to the preparation of novel linkers used for the specific conjugation of compounds, in particular, cytotoxic agents to a biological molecule. The present invention also relates to methods of making cell-binding agent-drug (cytotoxic agent) conjugates in a specific manner comprising either modification of drugs with these linkers first, followed by reaction with prepared cell-binding agents; or modification of cell-binding agents with these linkers first, followed by reaction with drugs.

BACKGROUND OF THE INVENTION

Proteins, specifically antibodies have been extensively used in therapeutic applications, in vitro assays as research reagents and in vivo as diagnostic tools or as therapeutic drugs (Gad, S. C. Drug discovery handbook, published by Wiley-Interscience, 2005). For many applications the protein needs to be modified with an interesting group, such as a cytotoxic drug, a radio label element or a chromophore molecule for use in therapy or a detection agent when used in diagnostics (Teicher, B. A. et al. Clin. Cancer Res. 2011, 17, 6389-97; Elsadek, B. et al., J. Control Release, 2012, 157, 4~28). One of these applications, called antibody-drug conjugates (ADCs), which is the exquisite targeting ability of antibodies in combination with the cytotoxic action of anticancer agents, enables to target and deliver drugs to cancer cells leaving normal cells largely unaffected, has been intensely exploitation in the last two decades. In particular, since US FDA approvals of Adcetris (brentuximab vedotin) in 2011 and Kadcyla (ado-trastuzumab emtansine) in 2013, the applications of antibody-drug conjugate (ADC) as a promise targeted treatment of cancers have been exploded and almost every major pharmaceutical and biotech company has adopted this approach (Chari, R. et al, Angew. Chem., Int. Ed. 2014, 53, 3796-3827; Sievers, E. L. et al. Annu Rev Med. 2013, 64, 15-29; Mehrling, T. Future Oncol, 2015, 11, 549). Currently there are more than 50 ADC drugs in the clinic trials according to www.clinictrails.gov.

The first-generation ADCs, including Kadcyla and Adcetris, are produced through nonselective conjugation of native lysine amines or interchain cysteine thiols on an antibody respectively to a cytotoxic drug. Since there are over 50 surface-exposed lysines and 8 hinge cysteine residues in IgG1 antibodies, this nonselective conjugation results in randomly crosslinkage of cytotoxic drugs to practically all areas of the antibody molecule, particularly having a diverse population of ADCs with a wide distribution of drugs per antibody (DAR) (Wang, L., et al. 2005 Protein Sci. 14, 2436; Hamblett, K. J., et al. 2004 Clin. Cancer Res. 10, 7063). Thus some of the undesired ADC subpopulation could lead to shorter circulation halflife, lower efficacy, potentially increased off-target toxicity and a wide range of in vivo pharmacokinetic (PK) properties (Hamblett, K. J. et al, Clin. Cancer Res. 2004, 10, 7063-7070; Adem, Y. T. et al, Bioconjugate Chem. 2014, 25, 656-664; Boylan, N. J. Bioconjugate Chem., 2013, 24, 1008-1016; Strop, P., et al2013 Chem. Biol. 20, 161-167). In addition, with this classical conjugation, the batch-to-batch consistency in ADC production can be challenging and may require diligent manufacturing capabilities (Wakankar, A. mAbs, 2011, 3, 161-172).

Therefore, biotechnology companies and academic institutions are highly focusing on establishing novel reliable methods for site-specific ADC conjugation. So far, there are several approaches developed in recent years for site selective ADC preparation (Panowski, S, 2014, mAbs 6, 34). They include incorporation of unpaired cysteines, e.g. engineered reactive cysteine residues, called THIOMAB from Genentech (Junutula, J. R., et al2010 Clin. Cancer Res. 16, 4769; Junutula, J. R., et al 2008 Nat Biotechnol. 26, 925-32; U.S. Pat. Nos. 8,309,300; 7,855,275; 7,521,541; 7,723,485, WO2008/141044), genetically introduced glutamine tag with Streptoverticillium mobaraense transglutaminase (mTG) (Strop, P., Bioconjugate Chem., 2014, 25, 855-862; Strop, P., et al., 2013, Chem. Biol. 20, 161-167; U.S. Pat. No. 8,871,908 for Rinat-Pfizer) or with Microbial transglutaminase (MTGase) (Dennler, P., et al, 2014, Bioconjug. Chem. 25, 569-578. US pat appl 20130189287 for Innate Pharma; U.S. Pat. No. 7,893,019 for Bio-Ker S.r.l. (IT)), incorporation of thiolfucose (Dennler, P., et al, 2014 Bioconjugate Chemistry 25, 569; Okeley, N. M., et al 2013 Bioconjugate Chem. 24, 1650), incorporation of unnatural amino acids through mutagenesis (Axup, J. Y., et al., 2012, Proc. Natl. Acad. Sci. 109, 16101-16106; Zimmerman, E. S., et al., 2014, Bioconjug. Chem. 25, 351-361; Wu, P., et al, 2009 Proc. Natl. Acad. Sci. 106, 3000-3005; Rabuka, D., et al, 2012 Nat. Protoc. 7, 1052-67; U.S. Pat. No. 8,778,631 and US Pat Appl. 20100184135, WO2010/081110 for Sutro Biopharma; WO2006/069246, 2007/059312, U.S. Pat. Nos. 7,332,571, 7,696,312, and 7,638,299 for Ambrx; WO2007/130453, U.S. Pat. Nos. 7,632,492 and 7,829,659 for Allozyne), Incorporation of selenocysteine into antibodies (Hofer, T., et al 2009, Biochemistry 48, 12047-12057; U.S. Pat. No. 8,916,159 for US National Cancer Institute), Convertion of cysteines located in the CXPXR consensus sequence to formylglycine (FGly) with formylglycine generating enzyme (FGE) (Drake, P. M., et al., 2014, Bioconjug. Chem. 25, 1331-1341. Carrico; Isaac S. et al U.S. Pat. Nos. 7,985,783; 8,097,701; 8,349,910, and US Pat Appl 20140141025, 20100210543 for Redwood Bioscience), and through glycoengineeringly introduction of sialic acid with the use of galactosyl- and sialytransferases (Zhou, Q., et al 2014, Bioconjug. Chem., 25, 510-520, US Pat Appl 20140294867 for Sanofi-Genzyme). These above methods have produced nearly homogeneous product profiles, but they are required antibody-engineering processes and reoptimization of cell culture conditions. Moreover, expression yields for genetic encoding of an unnatural amino acid were typically not promisingly high enough (Tian, F., et al, 2014, Proc. Natl. Acad. Sci. U.S.A 111, 1766-71) which has a significant impact on the cost of goods of the ADC. In addition, it has been known that ADCs obtained by conjugation to cysteine side chains often display limited stability in circulation, leading to premature disconnection of the cytotoxic payload before the tumor site is reached (Junutula, J. R., et al 2008, Nat. Biotechnol. 26, 925-32).

The disulfide bond structures of the four subclasses of IgG antibodies were known in the 1960s (Milstein C. Biochem J 1966, 101:338-351; Pink J R, Milstein C. Nature 1967, 214:92-94; Frangione B, Milstein C. Nature 1967, 216:939-941; Pink J R, Milstein C. Nature 1967, 216:941-942; Frangione B, et al. Biochem J 1968, 106, 15-21; Frangione B, Milstein C. J Mol Biol 1968; 33:893-906; Edelman G M, et al. Proc Natl Acad Sci USA 1969; 63:78-85; Frangione B, et al. Nature 196, 221:145-148, Spiegelberg, H. L. et al Biochemistry, 1975, 10, 2157-63). Disulfide bond structure is critical for the structure, stability, and biological functions of IgG molecules. Among the four subclasses of IgG antibodies, $IgG_1$, $IgG_2$, $IgG_3$ and $IgG_4$, each IgG contains a total of 12 intra-chain disulfide bonds; each disulfide bond is associated with an individual IgG domain. The two heavy chains are connected in the hinge region by a variable number of disulfide bonds: 2 for $IgG_1$ and $IgG_4$, 4 for $IgG_2$ and 11 for $IgG_3$. The light chain of the $IgG_1$ is connected to the heavy chain by a disulfide bond between the last cysteine residue of the light chain and the fifth cysteine residue of the heavy chain. But, for $IgG_2$, $IgG_3$ and $IgG_4$, the light chain is linked to the heavy chain by a disulfide bond between the last cysteine residue of the light chain and the third cysteine residue of the heavy chain (Liu, H. and May, K., 2012, mAbs 4, 17-23). On the ranks of the susceptibility of disulfide bonds in human IgG1 antibodies by experimental reduction, differential alkylation, and LC-MS analysis (Liu, H, et al Anal. Chem., 2010, 82, 5219-5226), inter chain disulfide bonds are more susceptible to reduction than intra chain disulfide bonds, and the disulfide bonds between the light chain and heavy chain were more susceptible than disulfide bonds between the two heavy chains. The upper disulfide bond of the two inter heavy chain disulfide bonds was more susceptible than the lower one. Furthermore, disulfide bonds in the CH2 domain were the most susceptible to reduction. Disulfide bonds in VL, CL, VH, and CH1 domains had similar and moderate susceptibility, while disulfide bonds in the CH3 domain were the least susceptible to reduction (Liu, H, et al Anal. Chem., 2010, 82, 5219-5226).

Based on the more susceptibility of inter chain disulfide bonds in human IgG1 antibodies, several institutions and companies adopted the chemically specific conjugation strategy through rebridging reduced interchain disulfide bonds of a native antibody, such as, using bromo or dibromo-maleimides, called next generation maleimides (NGMs) (Schumacher, F. F., et al 2014, Org. Biomol. Chem. 12, 7261-7269; UCL Cancer Institute), applying bis-alkylating reagents via a three-carbon bridge (Badescu, G., et al., 2014, Bioconjug. Chem. 25, 1124-1136., WO2013/190272, WO2014/064424 for PolyTherics Ltd), with di-substituted heteroaryl bridge (US Pat Appl. 2015/0105539 for Concortis Biosystem), or through dimaleimide as a bridge (WO2014/114207). We have also used bromo maleimide and dibromomaleimide linkers to conjugate both drugs and antibodies for a quite while (WO2014/009774, PCT/IB2012/053554). However, these above bridge linkers were designed in the way to conjugate only one cytotoxic agents to a pair of disulfide bonds, and therefore at most of time they only produced ADCs at DAR less than 2 (drugs per antibody), due to limited numbers (about two pairs) of reduced disulfide bonds are more accessible for conjugation.

As one of the major issues for ADCs is the limited numbers or amount of cytotoxic compound that ultimately reaches the tumor, and the favorable DAR over 3 is much important factor for improvement of ADC therapeutical index (Epenetos, A. A. et al, Cancer Res., 1986, 46, 3183-3191; Chari, R. V. Acc. Chem. Res., 2008, 41, 98-107, Zhao, R. Y. et al, 2011, J. Med. Chem. 54, 3606-3623), we therefore disclose novel acetylenedicarboxyl linkers of this invention that not only are able to conjugate two or more drugs per linker for achieving higher DARs (≥4), but also can selectively rebridge pairs of reduced inter chain disulfide bonds on surface of antibody due to the nature of stretch-out triple bond of the acetylenedicarboxyl group, particularly when two cytotoxic agents are linked at both ends of the stretch-out bridge linker, forming a quite large size (>20 Å) of molecule which in turn hardly accesses to the other disulfide bond sites, such as reduced intra chain disulfide bonds beneath the antibodies. The acetylenedicarboxyl linkers of this invention therefore can be used for selective bridging the pairs of free thiols on the inter chain of antibody, which are generated by overloaded TCEP or DTT, and for producing an ADC having DAR (drugs per antibody) over four. And the over reduced pairs of thiol groups that are inaccessibly reached by the bridge linkers, particularly by the stretch-out acetylenedicarboxyl linkers containing two cytotoxic agents, can be recoupled (regenerated) by an oxide, e.g. dehydroascorbic acid (DHAA) or Cu(II), to form back disulfide bonds at the end of conjugation. In a word, these bridge linkers of the invention can make homogeneous production of specific ADCs in a simple manner.

SUMMARY OF THE INVENTION

The present invention provides linkers containing an acetylenedicarboxylic group to link two drugs to a cell-binding agent (e.g., an antibody). The preferred formula of the cell-binding molecule-linker-drug conjugates can be represented as:

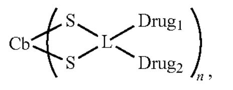

wherein Cb is a cell-binding agent, L is a acetylenedicarboxyl linker, Drug1 and Drug2 are a drug molecule, n is an integer from 1 to 20, and two S (sulfur) elements from Cb bridgely link to L, which covalently connects two or more drugs (per bridge linker L). The advantages in applying the linker in the cell molecule-drug conjugate are: a). Retaining the stability of the conjugates by covalently cross-linking (re-bridging) the pairs of reduced disulfur atoms of the cell-binding agents, particularly of antibodies; b). Enabling conjugation of the cytotoxic agents/drugs to specific sites of a cell-binding molecule, e.g. the inter chain disulfide bond sites of IgG antibodies, resulting in homogeneous production of ADC.

In one aspect of the present invention, the linker is represented by Formula (I)

(I)

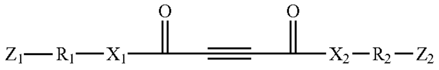

Wherein the acetylenedicarboxyl group on the linker is capable of reacting with a pair of sulfur atoms of the cell-binding agent. The sulfur atoms are preferred pairs of thiols reduced from the interchain disulfide bonds of the cell-binding agent by a reducing agent, such as DTT and/or TCEP;

$Z_1$ and $Z_2$ are the same or different a function group that enables to react with a cytotoxic drug, to form a disulfide, ether, ester, thioether, thioester, peptide, hydrazone, carbamate, carbonate, amine (secondary, tertiary, or quartary), imine, cycloheteroalkyane, heteroaromatic, alkoxime or amide bond;

$R_1$ and $R_2$ are the same or different, and are absent, linear alkyl having from 1-6 carbon atoms, branched or cyclic alkyl having from 3 to 6 carbon atoms, linear, branched or cyclic alkenyl or alkynyl, or 1~6 carbon atoms of esters, ether, amide, or polyethyleneoxy unit of formula $(OCH_2CH_2)_p$, wherein p is an integer from 0 to about 1000, or combination thereof.

Additionally $R_1$ and $R_2$ are respectively a chain of atoms selected from C, N, O, S, Si, and P, preferably having 0~500 atoms, which covalently connects to $X_1$ or $X_2$ and $Z_1$ or $Z_2$. The atoms used in forming the $R_1$ and $R_2$ may be combined in all chemically relevant ways, such as forming alkylene, alkenylene, and alkynylene, ethers, polyoxyalkylene, esters, amines, imines, polyamines, hydrazines, hydrazones, amides, ureas, semicarbazides, carbazides, alkoxyamines, alkoxylamines, urethanes, amino acids, peptides, acyloxylamines, hydroxamic acids, or combination thereof.

$X_1$ and $X_2$ are independently selected from NH, $N(R_3)$, O, S or $CH_2$; $R_3$ is H, linear alkyl having from 1-6 carbon atoms, branched or cyclic alkyl having from 3 to 6 carbon atoms, linear, branched or cyclic alkenyl or alkynyl, or 1~6 carbon atoms of esters, ether, amide, or polyethyleneoxy unit of formula $(OCH_2CH_2)_p$, wherein p is an integer from 0 to about 1000, or combination thereof.

In another aspect, this invention provides a cell-binding agent-drug conjugate of Formula (II), in which the cell-binding agent, Cb, and the drug, Drug1 and Drug2, have reacted at the ends of the bridge linker:

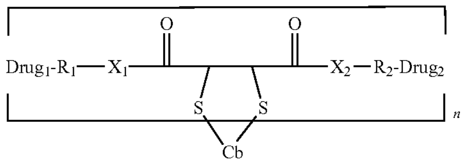

(II)

wherein:

Cb represents a cell-binding agent, preferred an antibody;

Inside the bracket (parentheses) are the linker-drug components that are conjugated to pairs of sulfur atoms of the cell-binding molecule. The sulfur atoms are preferred pairs of thiols reduced from the interchain disulfide bonds of the cell-binding agent by a reduction agent, such as DTT and/or TCEP;

$Drug_1$ and $Drug_2$ represent the same or different cytotoxic agents, which linked to the cell-binding agent via the bridge linker by a disulfide, thioether, thioester, peptide, hydrazone, ether, ester, carbamate, carbonate, cycloheteroalkyane, heteroaromatic, alkoxime or amide bond;

n is 1~20; $R_1$, $R_2$, $X_1$ and $X_2$ are described the same previously in Formula (I).

In a further aspect, the present invention provides a modified cell-binding agent of Formula (III), in which the cell-binding agent, Cb, through its pair of thiols generated with reduction of disulfide bonds, has reacted with the bridge linker, which has $Z_1$ and $Z_2$, the function groups capable of reacting with a drug:

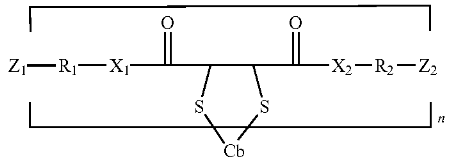

(III)

Wherein Cb, $Z_1$, $Z_2$, n, $R_1$, $R_2$, $X_1$, and $X_2$ are defined the same as in Formula (I) and (II).

In an even further aspect, the present invention provides a modified drug of Formula (IV), in which the drug, $Drug_1$ and $Drug_2$, have reacted with the linker of Formula (I), which still has the acetylenedicarboxyl group capable of reacting with a pair of sulfur atoms of the cell-binding agent:

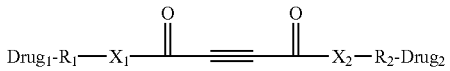

(IV)

Wherein $Drug_1$, $Drug_2$, $R_1$, $R_2$, $X_1$, and $X_2$ are defined the same as in Formula (I) and (II).

The present invention further relates to a method of making a cell-binding molecule-drug conjugate of Formula (II), wherein the drugs, $Drug_1$ and $Drug_2$ are linked to a cell-binding agent via the bridge linker.

The present invention also relates to a method of making a modified cell-binding molecule of Formula (III), wherein the cell-binding molecule is reacted with the bridge linker of Formula (I).

The present invention also relates to a method of making a modified drug of formula (IV), wherein the drug is reacted with the bridge linker of Formula (I).

DETAILED DESCRIPTION OF THE INVENTION

Definitions

Figure 1:
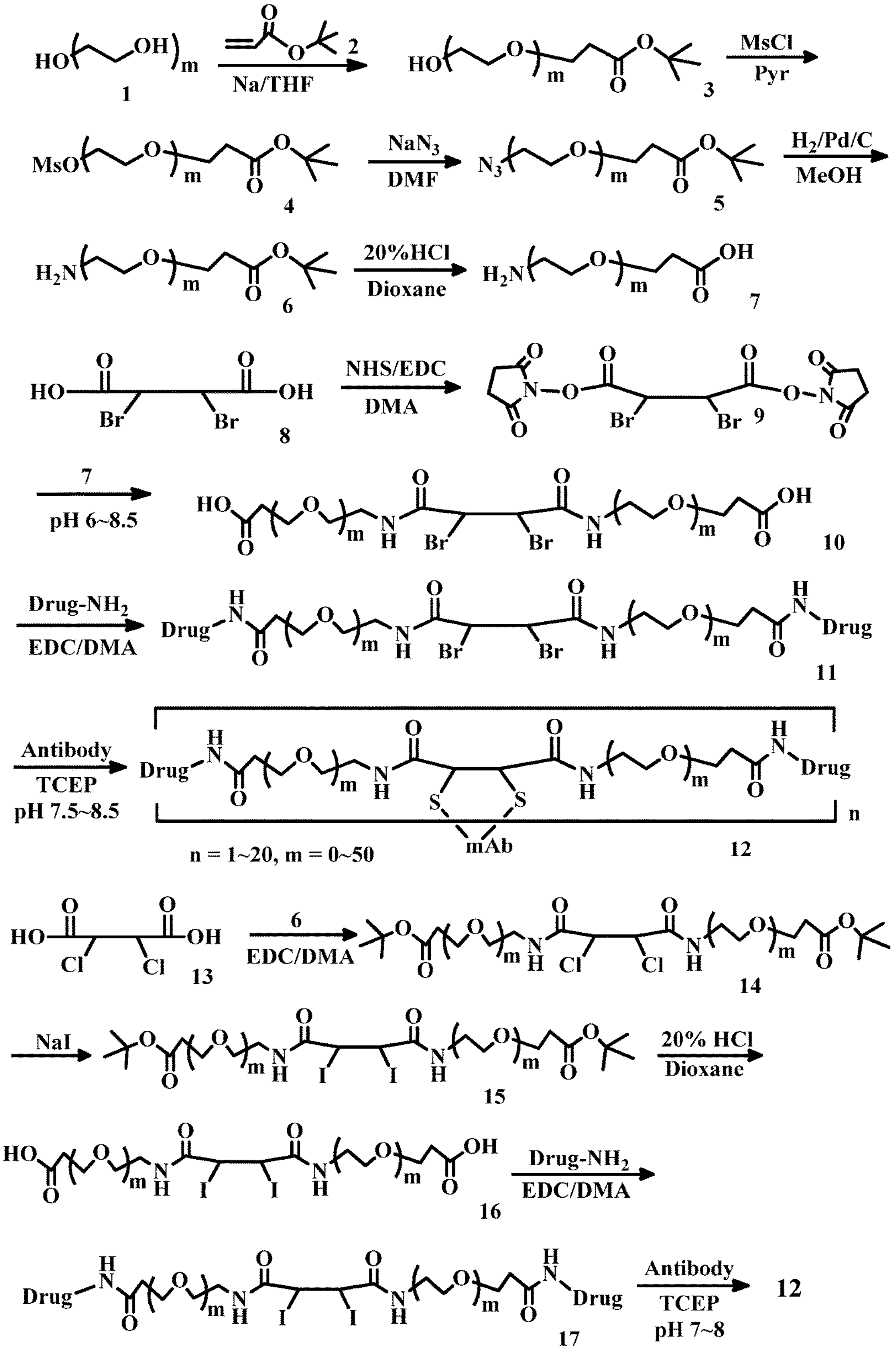
FIG. 1 shows the synthesis of a bridge linker containing polyethylene glycol groups and the application of this linker in the conjugation of an antibody with drugs.
Figure 2:
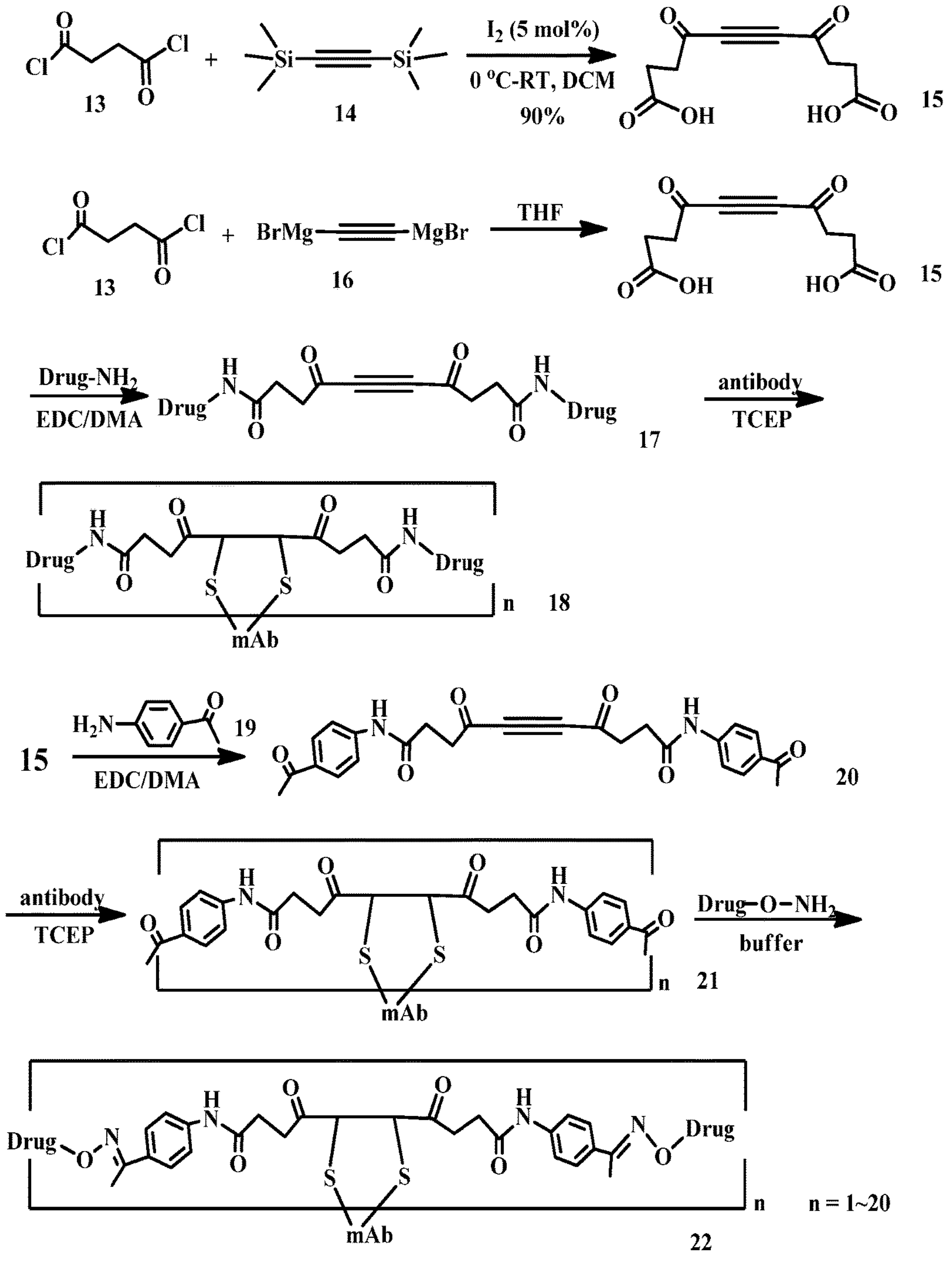
FIG. 2 shows the synthesis of a bridge linker and the application of this linker in the conjugation of drugs to an antibody via oxime linkage.
Figure 3:
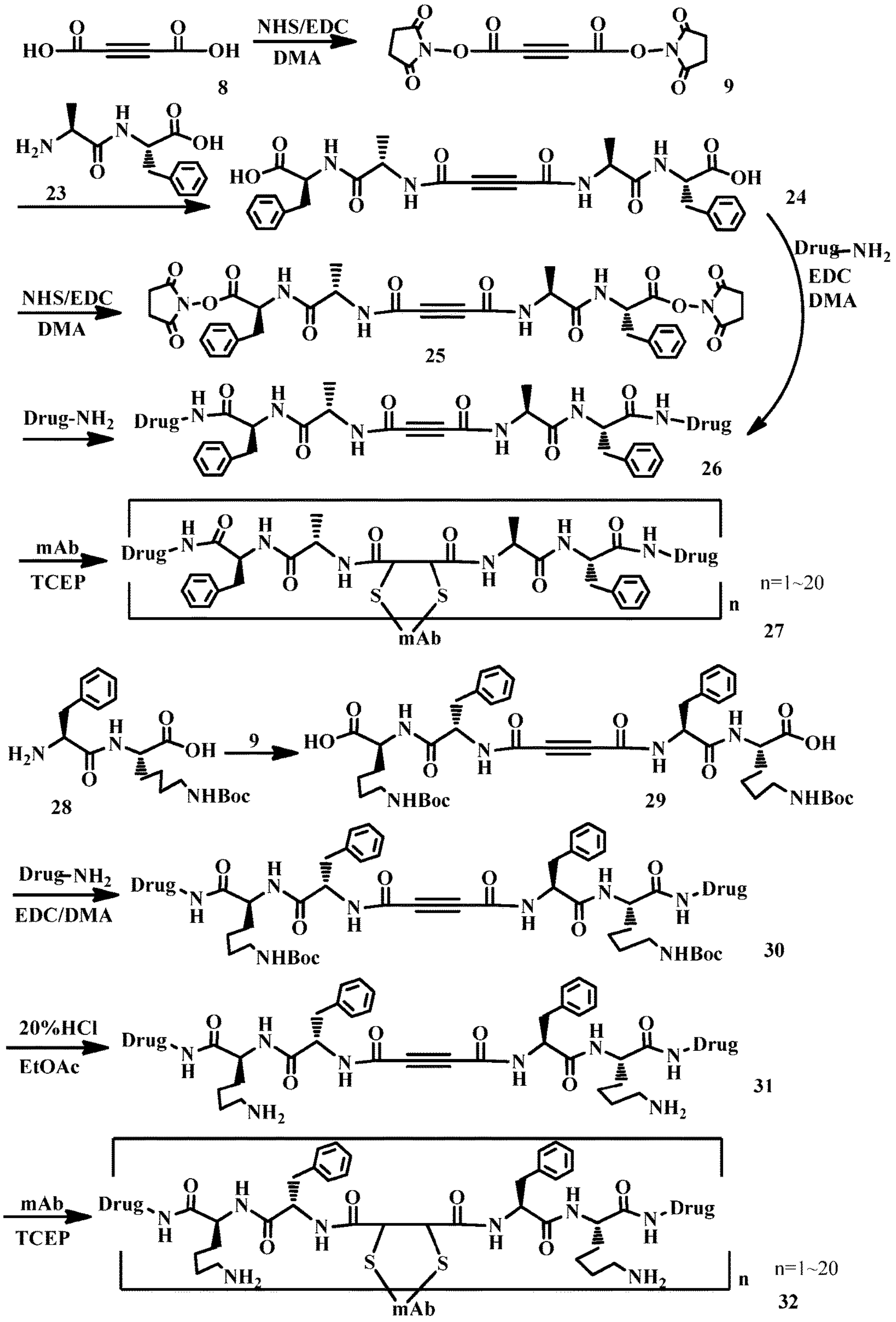
FIG. 3 shows the synthesis of a bridge linker containing a peptide and the application of this linker in the conjugation of drugs to an antibody via amide linkage.
Figure 4:
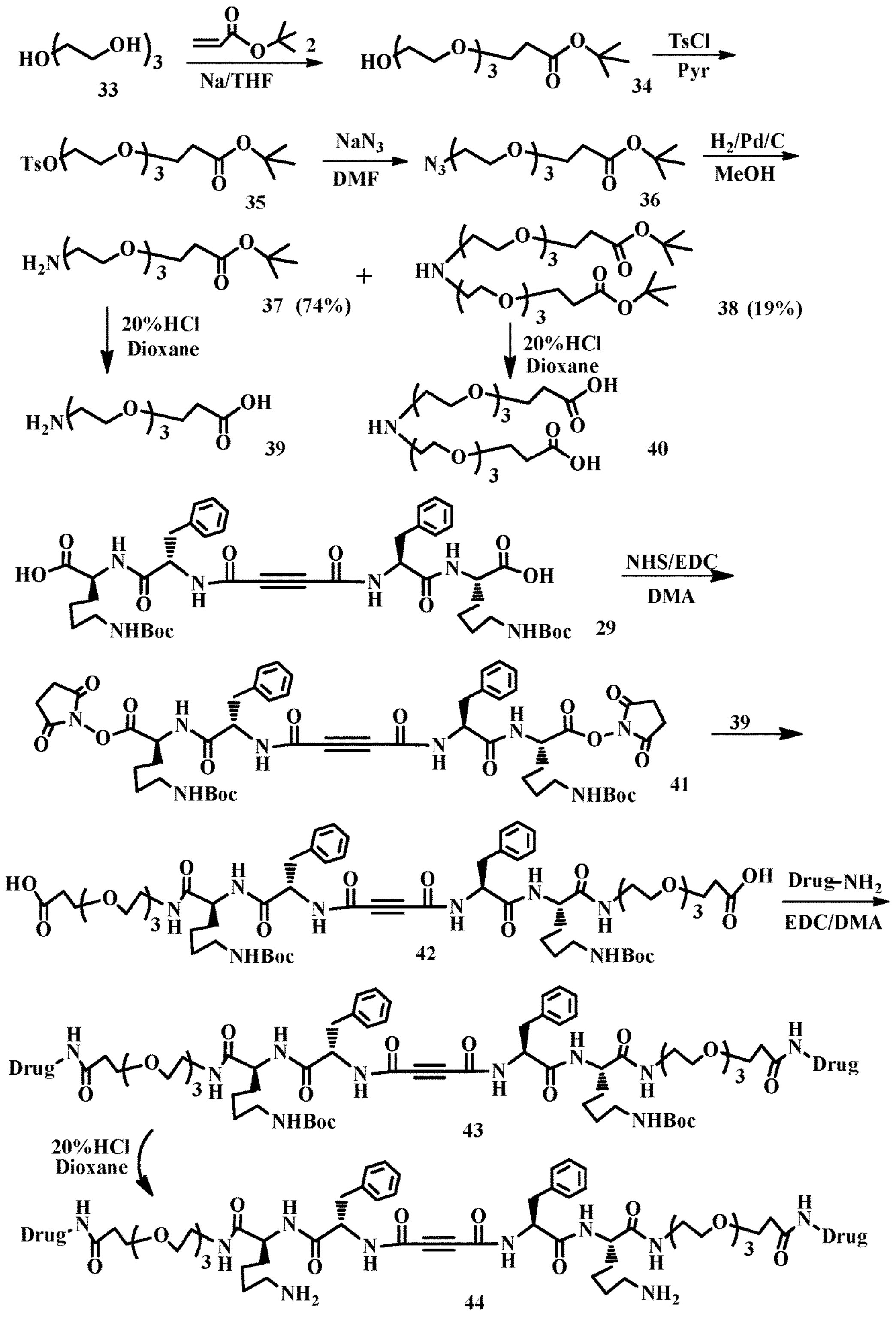
FIG. 4 shows the synthesis of a bridge linker containing peptides, polyethylene glycol.
Figure 5:
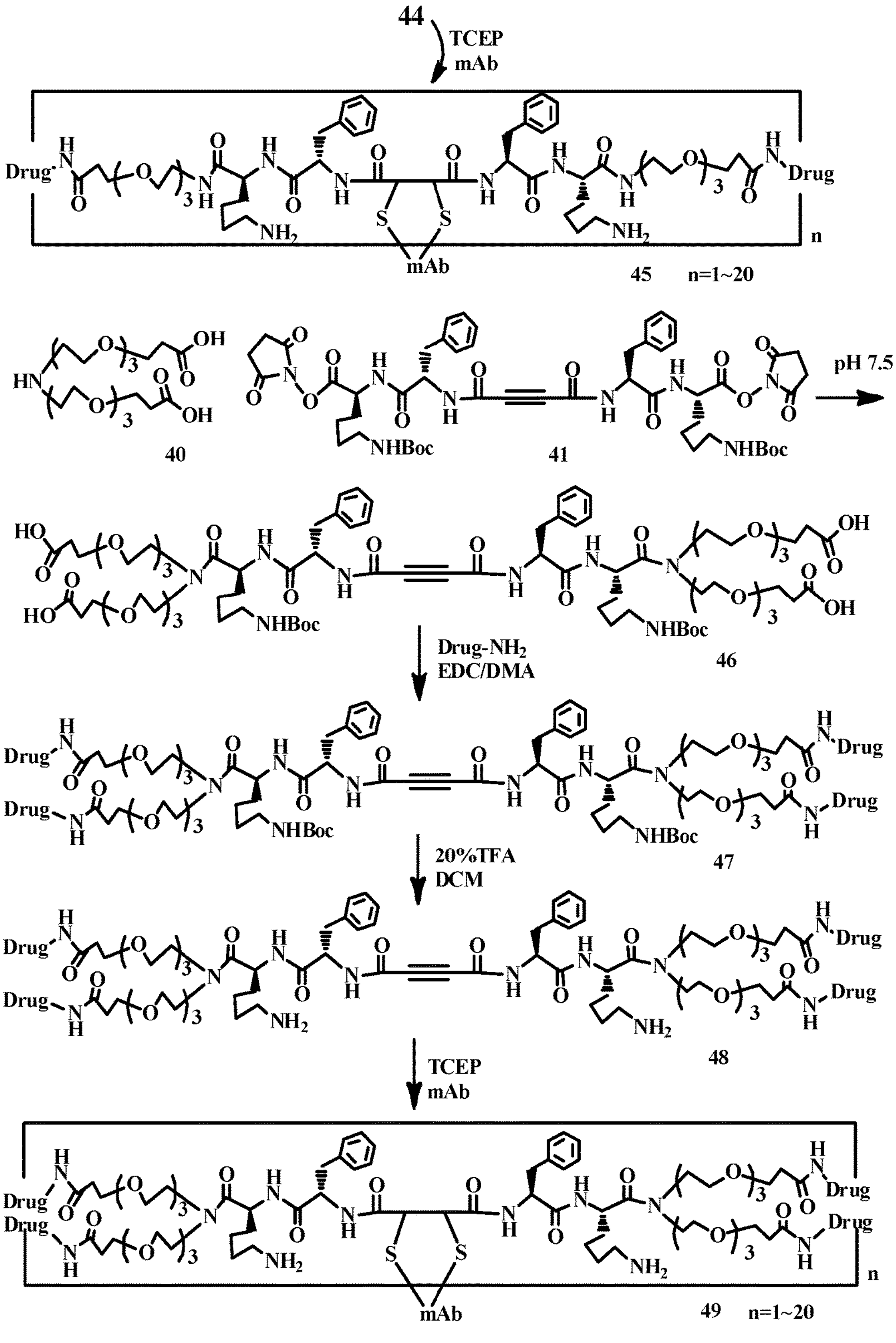
FIG. 5 shows the synthesis of a bridge linker containing peptides and polyethylene glycols, and the application in the conjugation of two or four drugs per linker to an antibody via amide linkage.
Figure 6:
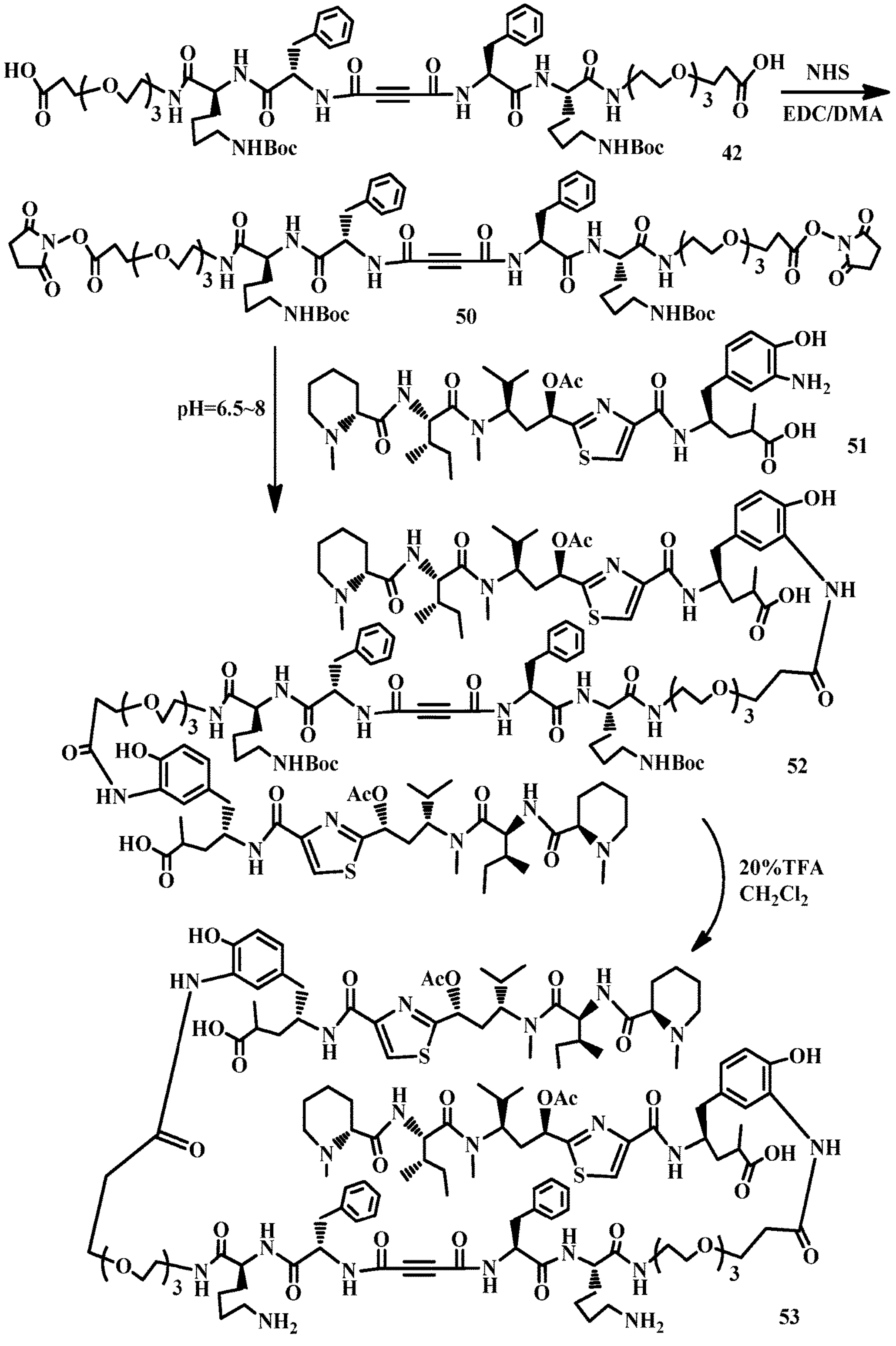
FIG. 6 shows the synthesis of tubulysin analogs which are modified with the bridge-linker containing peptides and polyethylene glycols.
Figure 7:
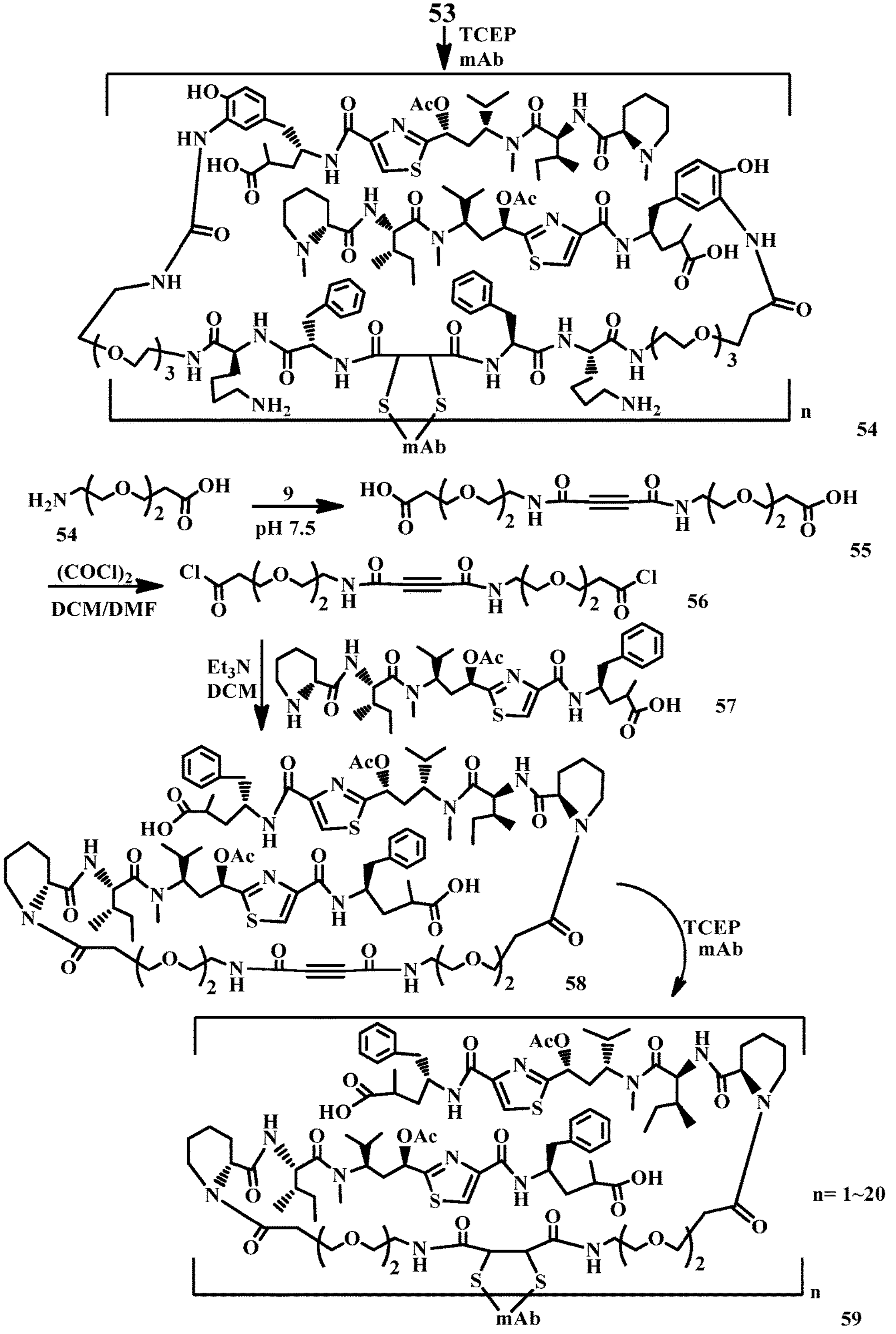
FIG. 7 shows the synthesis of the conjugates of cell-binding molecule-tubulysin analogs via the bridge-linker containing polyethylene glycols.
Figure 8:
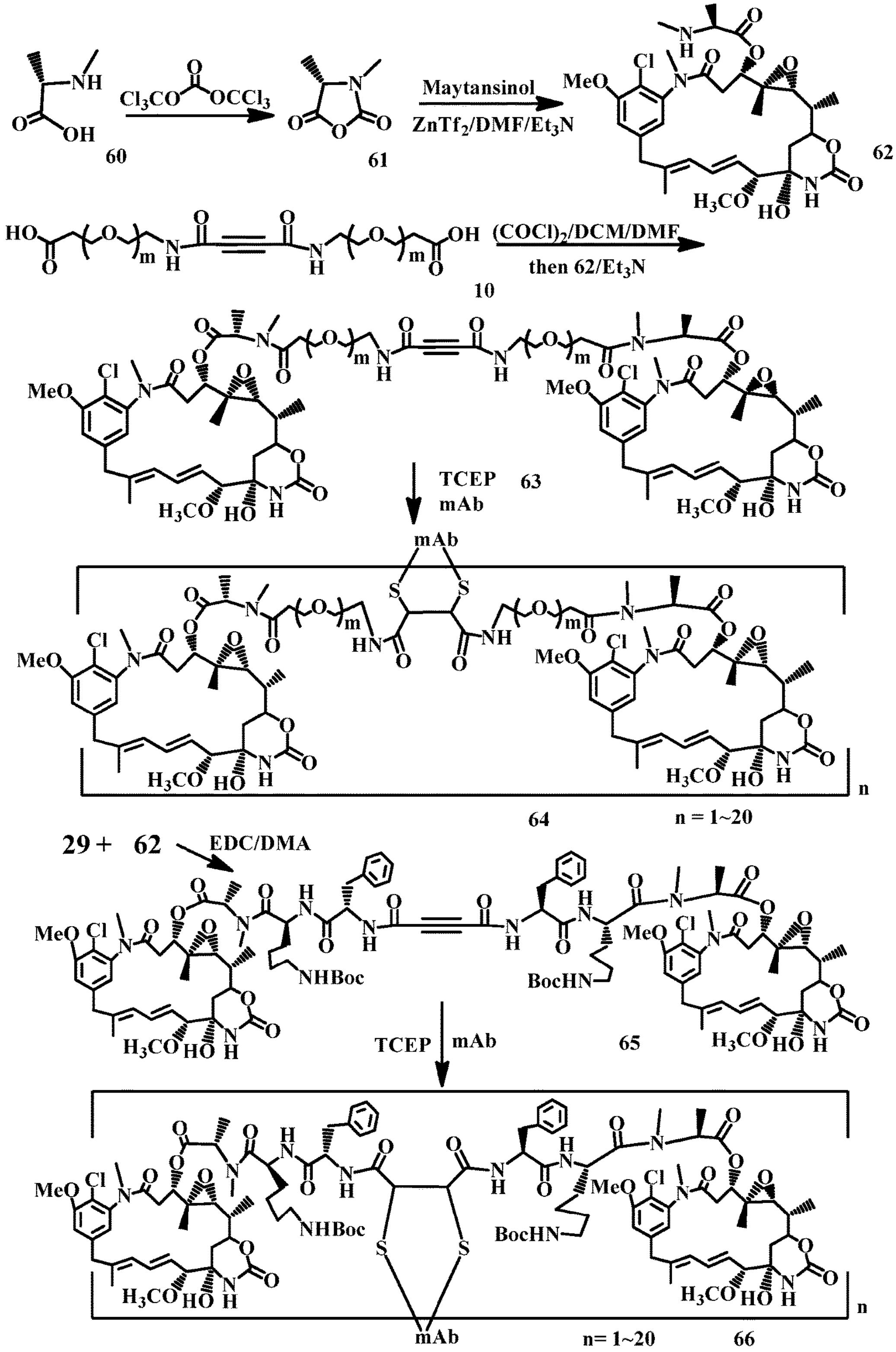
FIG. 8 shows the synthesis of the conjugates of cell-binding molecule-maytansinoids via the bridge-linker.
Figure 9:
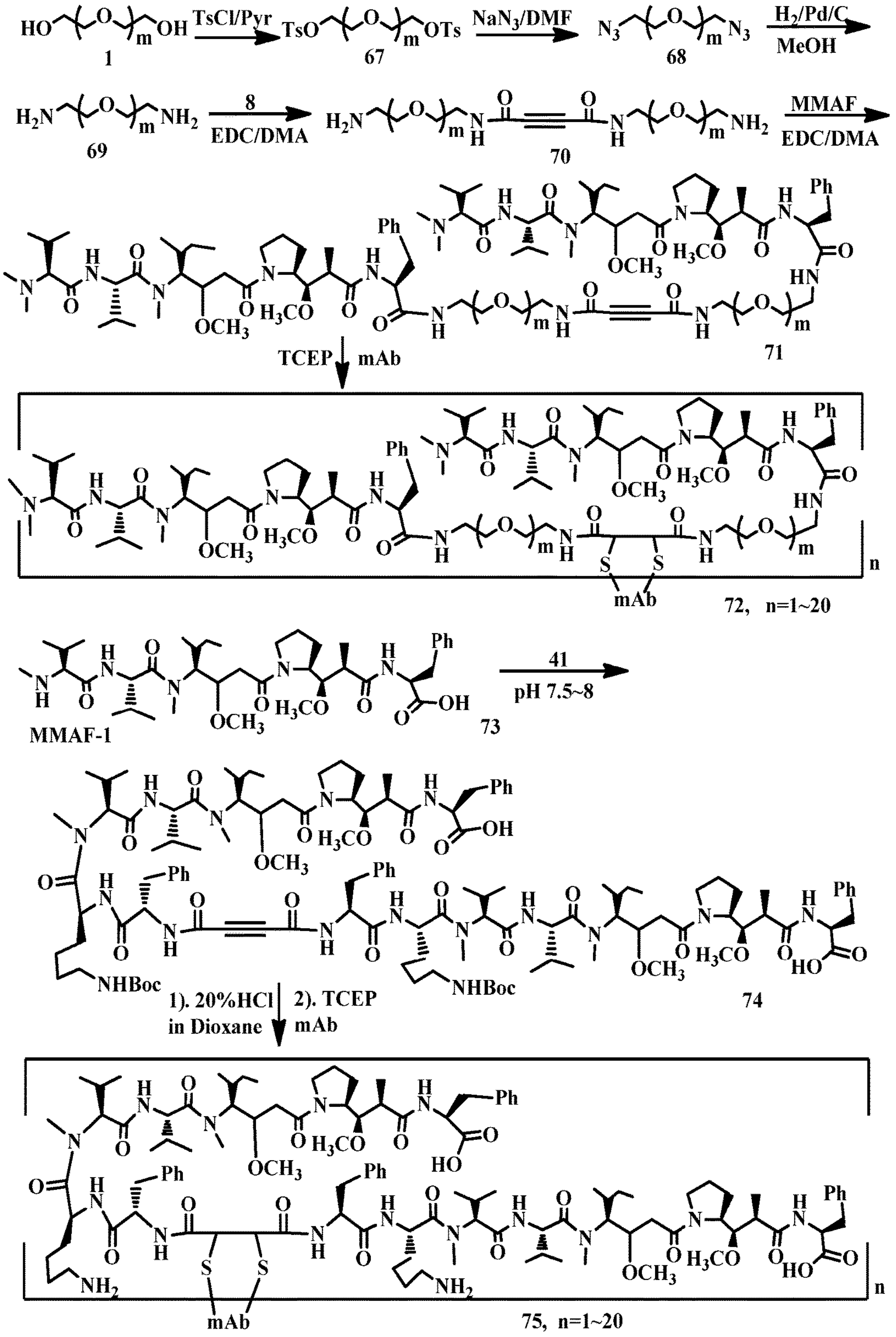
FIG. 9 shows the synthesis of the conjugates of cell-binding molecule-MMAF analogs via the bridge-linker.
Figure 10:
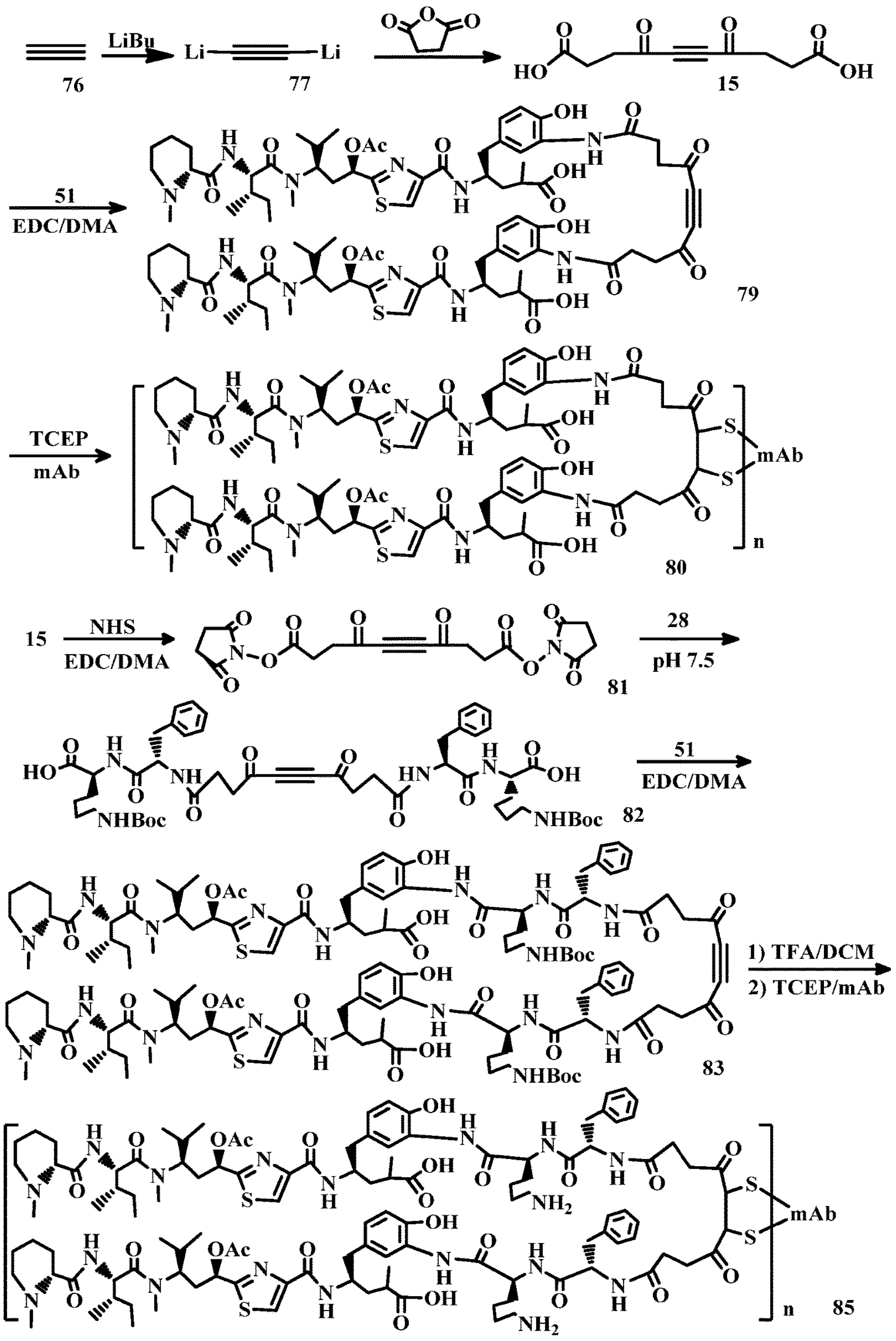
FIG. 10 shows the synthesis of the conjugates of cell-binding molecule-tubulysin analogs via the bridge-linker.

"Alkyl" refers to an aliphatic hydrocarbon group which may be straight or branched having 1 to 8 carbon atoms in the chain. "Branched" means that one or more lower C numbers of alkyl groups such as methyl, ethyl or propyl are attached to a linear alkyl chain. Exemplary alkyl groups include methyl, ethyl, n-propyl, i-propyl, n-butyl, t-butyl, n-pentyl, 3-pentyl, octyl, nonyl, decyl, cyclopentyl, cyclohexyl, 2,2-dimethylbutyl, 2,3-dimethylbutyl, 2,2-dimethylpentyl, 2,3-dimethylpentyl, 3,3-dimethylpentyl, 2,3,4-trimethylpentyl, 3-methylhexyl, 2,2-dimethylhexyl, 2,4-dimethylhexyl, 2,5-dimethylhexyl, 3,5-dimethylhexyl, 2,4-dimethylpentyl, 2-methylheptyl, 3-methylheptyl, n-heptyl, isoheptyl, n-octyl, and isooctyl. A $C_1$-$C_8$ alkyl group can be unsubstituted or substituted with one or more groups including, but not limited to, —$C_1$-$C_8$ alkyl, —O—($C_1$-$C_8$ alkyl), -aryl, —C(O)R', —OC(O)R', —C(O)OR', —C(O)$NH_2$, —C(O)NHR', —C(O)N$(R')_2$, —NHC(O)R', —SR', —$S(O)_2$R', —S(O)R', —OH, -halogen, —$N_3$, —$NH_2$, —NH(R'), —N$(R')_2$ and —CN; where each R' is independently selected from —$C_1$-$C_8$ alkyl and aryl. "Halogen" refers to fluorine, chlorine, bromine or iodine atom; preferably fluorine and chlorine atom.

"Heteroalkyl" refers to $C_2$-$C_8$ alkyl in which one to four carbon atoms are independently replaced with a heteroatom from the group consisting of O, S and N.

"Carbocycle" refers to a saturated or unsaturated ring having 3 to 8 carbon atoms as a monocycle or 7 to 13 carbon atoms as a bicycle. Monocyclic carbocycles have 3 to 6 ring atoms, more typically 5 or 6 ring atoms. Bicyclic carbocycles have 7 to 12 ring atoms, arranged as a bicycle [4,5], [5,5], [5,6] or [6,6] system, or 9 or 10 ring atoms arranged as a bicycle [5,6] or [6,6] system. Representative $C_3$-$C_8$ carbocycles include, but are not limited to, -cyclopropyl, -cyclobutyl, -cyclopentyl, -cyclopentadienyl, -cyclohexyl, -cyclohexenyl, -1,3-cyclohexadienyl, -1,4-cyclohexadienyl, -cycloheptyl, -1,3-cycloheptadienyl, -1,3,5-cycloheptatrienyl, -cyclooctyl, and -cyclooctadienyl.

A "$C_3$-$C_8$ carbocycle" refers to a 3-, 4-, 5-, 6-, 7- or 8-membered saturated or unsaturated nonaromatic carbocyclic ring. A $C_3$-$C_8$ carbocycle group can be unsubstituted or substituted with one or more groups including, but not limited to, —$C_1$-$C_8$ alkyl, —O—($C_1$-$C_8$ alkyl), -aryl, —C(O)R', —OC(O)R', —C(O)OR', —C(O)$NH_2$, —C(O) NHR', —C(O)N$(R')_2$, —NHC(O)R', —SR', —S(O)R', —$S(O)_2$R', —OH, -halogen, —$N_3$, —$NH_2$, —NH(R'), —N$(R')_2$ and —CN; where each R' is independently selected from —$C_1$-$C_8$ alkyl and aryl.

"Alkenyl" refers to an aliphatic hydrocarbon group containing a carbon-carbon double bond which may be straight or branched having 2 to 8 carbon atoms in the chain. Exemplary alkenyl groups include ethenyl, propenyl, n-butenyl, i-butenyl, 3-methylbut-2-enyl, n-pentenyl, hexylenyl, heptenyl, octenyl.

"Alkynyl" refers to an aliphatic hydrocarbon group containing a carbon-carbon triple bond which may be straight or branched having 2 to 8 carbon atoms in the chain. Exemplary alkynyl groups include ethynyl, propynyl, n-butynyl, 2-butynyl, 3-methylbutynyl, 5-pentynyl, n-pentynyl, hexylynyl, heptynyl, and octynyl.

"Alkylene" refers to a saturated, branched or straight chain or cyclic hydrocarbon radical of 1-18 carbon atoms, and having two monovalent radical centers derived by the removal of two hydrogen atoms from the same or two different carbon atoms of a parent alkane. Typical alkylene radicals include, but are not limited to: methylene (—$CH_2$—), 1,2-ethyl (—$CH_2CH_2$—), 1,3-propyl (—$CH_2CH_2CH_2$—), 1,4-butyl (—$CH_2CH_2CH_2CH_2$—), and the like.

"Alkenylene" refers to an unsaturated, branched or straight chain or cyclic hydrocarbon radical of 2-18 carbon atoms, and having two monovalent radical centers derived by the removal of two hydrogen atoms from the same or two different carbon atoms of a parent alkene. Typical alkenylene radicals include, but are not limited to: 1,2-ethylene (—CH═CH—).

"Alkynylene" refers to an unsaturated, branched or straight chain or cyclic hydrocarbon radical of 2-18 carbon atoms, and having two monovalent radical centers derived by the removal of two hydrogen atoms from the same or two different carbon atoms of a parent alkyne. Typical alkynylene radicals include, but are not limited to: acetylene, propargyl and 4-pentynyl.

"Aryl" or Ar refers to an aromatic or hetero aromatic group, composed of one or several rings, comprising three to fourteen carbon atoms, preferentially six to ten carbon atoms. The term of "hetero aromatic group" refers one or several carbon on aromatic group, preferentially one, two, three or four carbon atoms are replaced by O, N, Si, Se, P or S, preferentially by O, S, and N. The term aryl or Ar also refers to an aromatic group, wherein one or several H atoms are replaced independently by —R', -halogen, —OR', or —SR', —NR'R", —N═NR', —N═R', —NR'R", —$NO_2$, —S(O)R', —$S(O)_2$R', —$S(O)_2$OR', —OS$(O)_2$OR', —PR'R", —P(O)R'R", —P(OR')(OR"), —P(O)(OR')(OR") or —OP(O)(OR')(OR") wherein R', R" are independently H, alkyl, alkenyl, alkynyl, heteroalkyl, aryl, arylalkyl, carbonyl, or pharmaceutical salts.

"Heterocycle" refers to a ring system in which one to four of the ring carbon atoms are independently replaced with a heteroatom from the group of O, N, S, Se, B, Si and P. Preferable heteroatoms are O, N and S. Heterocycles are also described in The Handbook of Chemistry and Physics, 78th Edition, CRC Press, Inc., 1997-1998, p. 225 to 226, the disclosure of which is hereby incorporated by reference. Preferred nonaromatic heterocyclic include, but are not limited to epoxy, aziridinyl, thiiranyl, pyrrolidinyl, pyrazolidinyl, imidazolidinyl, oxiranyl, tetrahydrofuranyl, dioxolanyl, tetrahydropyranyl, dioxanyl, dioxolanyl, piperidyl, piperazinyl, morpholinyl, pyranyl, imidazolinyl, pyrrolinyl, pyrazolinyl, thiazolidinyl, tetrahydrothiopyranyl, dithianyl, thiomorpholinyl, dihydropyranyl, tetrahydropyranyl, dihydropyranyl, tetrahydropyridyl, dihydropyridyl, tetrahydropyrimidinyl, dihydrothiopyranyl, azepanyl, as well as the fused systems resulting from the condensation with a phenyl group.

The term "heteroaryl" or aromatic heterocycles refers to a 5 to 14, preferably 5 to 10 membered aromatic hetero, mono-, bi- or multicyclic ring. Examples include pyrrolyl, pyridyl, pyrazolyl, thienyl, pyrimidinyl, pyrazinyl, tetrazolyl, indolyl, quinolinyl, purinyl, imidazolyl, thienyl, thiazolyl, benzothiazolyl, furanyl, benzofuranyl, 1,2,4-thiadiazolyl, isothiazolyl, triazoyl, tetrazolyl, isoquinolyl, benzothienyl, isobenzofuryl, pyrazolyl, carbazolyl, benzimidazolyl, isoxazolyl, pyridyl-N-oxide, as well as the fused systems resulting from the condensation with a phenyl group.

"Alkyl", "cycloalkyl", "alkenyl", "alkynyl", "aryl", "heteroaryl", "heterocyclic" and the like refer also to the corresponding "alkylene", "cycloalkylene", "alkenylene", "alkynylene", "arylene", "heteroarylene", "heterocyclene" and the likes which are formed by the removal of two hydrogen atoms.

"Arylalkyl" refers to an acyclic alkyl radical in which one of the hydrogen atoms bonded to a carbon atom, typically a terminal or $sp^3$ carbon atom, is replaced with an aryl radical. Typical arylalkyl groups include, but are not limited to, benzyl, 2-phenylethan-1-yl, 2-phenylethen-1-yl, naphthylmethyl, 2-naphthylethan-1-yl, 2-naphthylethen-1-yl, naphthobenzyl, 2-naphthophenylethan-1-yl and the like.

"Heteroarylalkyl" refers to an acyclic alkyl radical in which one of the hydrogen atoms bonded to a carbon atom, typically a terminal or $sp^3$ carbon atom, is replaced with a heteroaryl radical. Typical heteroarylalkyl groups include, but are not limited to, 2-benzimidazolylmethyl, 2-furylethyl and the like.

Examples of a "hydroxyl protecting group" include, but are not limited to, methoxymethyl ether, 2-methoxyethoxymethyl ether, tetrahydropyranyl ether, benzyl ether, p-methoxybenzyl ether, trimethylsilyl ether, triethylsilyl ether, triisopropylsilyl ether, t-butyldimethylsilyl ether, triphenylmethylsilyl ether, acetate ester, substituted acetate esters, pivaloate, benzoate, methanesulfonate and p-toluenesulfonate.

"Leaving group" refers to a functional group that can be substituted by another functional group. Such leaving groups are well known in the art, and examples include, but are not limited to, a halide (e.g., chloride, bromide, and iodide), methanesulfonyl (mesyl), p-toluenesulfonyl (tosyl), trifluoromethylsulfonyl (triflate), and trifluoromethylsulfonate.

The following abbreviations may be used herein and have the indicated definitions: Boc, tert-butoxy carbonyl; BroP, bromotrispyrrolidinophosphonium hexafluorophosphate; CDI, 1,1'-carbonyldiimidazole; DCC, dicyclohexylcarbodiimide; DCE, dichloroethane; DCM, dichloromethane; DIAD, diisopropylazodicarboxylate; DIBAL-H, diisobutylaluminium hydride; DIPEA, diisopropylethylamine; DEPC, diethyl phosphorocyanidate; DMA, N,N-dimethyl acetamide; DMAP, 4-(N, N-dimethylamino)pyridine; DMF, N,N-dimethylformamide; DMSO, dimethylsulfoxide; DTT, dithiothreitol; EDC, 1-(3-dimethylaminopropyl)-3-ethylcarbodiimide hydrochloride; ESI-MS, electrospray mass spectrometry; HATU, O-(7-azabenzotriazol-1-yl)-N, N, N', N'-tetramethyluronium hexafluorophosphate; HOBt, 1-hydroxybenzotriazole; HPLC, high pressure liquid chromatography; NHS, N-Hydroxysuccinimide; MMP, 4-methylmorpholine; PAB, p-aminobenzyl; PBS, phosphate-buffered saline (pH 7.0~7.5); PEG, polyethylene glycol; SEC, size-exclusion chromatography; TCEP, tris(2-carboxyethyl) phosphine; TFA, trifluoroacetic acid; THF, tetrahydrofuran; Val, valine.

"Pharmaceutically" or "pharmaceutically acceptable" refer to molecular entities and compositions that do not produce an adverse, allergic or other untoward reaction when administered to an animal, or a human, as appropriate.

"Pharmaceutically acceptable solvate" or "solvate" refer to an association of one or more solvent molecules and a disclosed compound. Examples of solvents that form pharmaceutically acceptable solvates include, but are not limited to, water, isopropanol, ethanol, methanol, DMSO, ethyl acetate, acetic acid and ethanolamine.

"Pharmaceutically acceptable excipient" includes any carriers, diluents, adjuvants, or vehicles, such as preserving or antioxidant agents, fillers, disintegrating agents, wetting agents, emulsifying agents, suspending agents, solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions as suitable therapeutic combinations.

As used herein, "pharmaceutical salts" refer to derivatives of the disclosed compounds wherein the parent compound is modified by making acid or base salts thereof. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, tartaric, citric, methanesulfonic, benzenesulfonic, glucuronic, glutamic, benzoic, salicylic, toluenesulfonic, oxalic, fumaric, maleic, lactic and the like. Further addition salts include ammonium salts such as tromethamine, meglumine, epolamine, etc., metal salts such as sodium, potassium, calcium, zinc or magnesium.

The pharmaceutical salts of the present invention can be synthesized from the parent compound which contains a basic or acidic moiety by conventional chemical methods. Generally, such salts can be prepared via reaction the free acidic or basic forms of these compounds with a stoichiometric amount of the appropriate base or acid in water or in an organic solvent, or in a mixture of the two. Generally, non-aqueous media like ether, ethyl acetate, ethanol, isopropanol, or acetonitrile are preferred. Lists of suitable salts are found in Remington's Pharmaceutical Sciences, $17^{th}$ ed., Mack Publishing Company, Easton, Pa., 1985, p. 1418, the disclosure of which is hereby incorporated by reference.

The novel conjugates disclosed herein use the bridge linkers. Examples of some suitable linkers and their synthesis are shown in FIGS. 1 to 10.

The Bridge Linkers

The synthetic routes to produce bridge linkers as well as the preparation of the conjugates of drugs to a cell binding molecules of the present invention are shown in FIGS. 1-9. The bridge linkers possess two elements: a) A Substituent that is acetylenedicarboxyl group that can react to a pair of thiols to form covalent thioether bonds, and b) A group, such as but not limited to, a disulfide, maleimide, haloacetyl, aldehyde, ketone, azide, amine, alkoxyamine and hydrazide, capable of reaction with a drug. The bridge substituents of acetylenedicarboxyl can be introduced by direct condensation of acetylenedicarboxylic acid with an amine, an alcohol, or a thiol group to form amide, ester or thioester bonds at both the ends of acetylenedicarboxyl sites. The synthesis of these bridge linkers is exampled in the FIGS. 1, 3, 4, 5, 6, 7, 8 and 9. The bridge substituents of acetylenedicarboxyl can be introduced by condensation of acetylene with acid halides or acid anhydrides to form carbon-carbon bonds at both the ends of acetylenedicarboxyl sites. The synthesis of these bridge linkers is exampled in the FIGS. 2 and 10.

Preferably, the bridge linkers are compounds of the Formula (I) below:

(I)

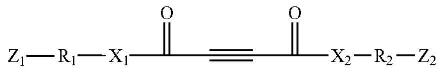

Wherein the acetylenedicarboxyl group on the linker is capable of reacting with a pair of sulfur atoms of the cell-binding agent; The sulfur atoms are preferred pairs of thiols reduced from the interchain disulfide bonds of the cell-binding agent by a reducing agent, such as DTT and/or TCEP;

$Z_1$ and $Z_2$ are the same or different a function group that enables to react with a cytotoxic drug, to form a disulfide, thioether, thioester, peptide, hydrazone, ether, ester, carbamate, carbonate, amine (secondary, tertiary, or quarter), imine, cycloheteroalkyane, heteroaromatic, alkoxime or amide bond;

$R_1$ and $R_2$ are the same or different, and are absent, linear alkyl having from 1-6 carbon atoms, branched or cyclic alkyl having from 3 to 6 carbon atoms, linear, branched or cyclic alkenyl or alkynyl, or 1~6 carbon atoms of esters, ether, amide, or polyethyleneoxy unit of formula $(OCH_2CH_2)_p$, or polypropyleneoxy unit of formula $(OCH_2(CH_3)CH_2)_p$ wherein p is an integer from 0 to about 1000, or combination thereof.

Additionally $R_1$ and $R_2$ are respectively a chain of atoms selected from C, N, O, S, Si, and P, preferably having 0~500 atoms, which covalently connects to $X_1$ or $X_2$ and $Z_1$ or $Z_2$. The atoms used in forming the $R_1$ and $R_2$ may be combined in all chemically relevant ways, such as forming alkylene, alkenylene, and alkynylene, ethers, polyoxyalkylene, esters, amines, imines, polyamines, hydrazines, hydrazones, amides, ureas, semicarbazides, carbazides, alkoxyamines, alkoxylamines, urethanes, amino acids, peptides, acyloxylamines, hydroxamic acids, or combination thereof.

$X_1$ and $X_2$ are independently selected from $N(R_3)$, O, S or $CH_2$; Wherein $R_3$ is H, linear alkyl having from 1-6 carbon atoms, branched or cyclic alkyl having from 3 to 6 carbon atoms, linear, branched or cyclic alkenyl or alkynyl, or 1~6 carbon atoms of esters, ether, amide, or polyethyleneoxy unit of formula $(OCH_2CH_2)_p$, wherein p is an integer from 0 to about 1000, or combination thereof.

In another embodiment, $R_1$, $R_2$, and $R_3$, can be respectively a chain of atoms selected from C, N, O, S, Si, and P which covalently connects the cell-surface binding molecule and/or the conjugated drug. The atoms used in forming the bridge linker may be combined in all chemically relevant ways, such as forming alkylene, alkenylene, and alkynylene, ethers, polyoxyalkylene, esters, amines, imines, polyamines, hydrazines, hydrazones, amides, ureas, semicarbazides, carbazides, alkoxyamines, alkoxylamines, urethanes, amino acids, acyloxylamines, hydroxamic acids, and many others. In addition, it is to be understood that the atoms forming the linker (L) may be either saturated or unsaturated, or may be radicals, or may be cyclized upon each other to form divalent cyclic structures, including cyclo alkanes, cyclic ethers, cyclic amines, arylenes, heteroarylenes, and the like in the linker.

Examples of the functional groups, $Z_1$ and $Z_2$, which enable linkage of a cytotoxic drug, include groups that enable linkage via a disulfide, thioether, thioester, peptide, hydrazone, ester, carbamate, carbonate, alkoxime or an amide bond. Such functional groups include, but are not limited to, thiol, disulfide, amino, carboxy, aldehydes, ketone, maleimido, haloacetyl, hydrazines, alkoxyamino, and/or hydroxy.

Examples of the functional groups, $Z_1$ and $Z_2$, that enable reaction with the terminal of amine of a drug/cytotoxic agent can be, but not limited to, N-hydroxysuccinimide esters, p-nitrophenyl esters, dinitrophenyl esters, pentafluorophenyl esters, carboxylic acid chlorides or carboxylic acid anhydride; With the terminal of thiol can be, as but not limited to, p-yridyldisulfides, nitropyridyldisulfides, maleimides, haloacetates, methylsulfone phenyloxadiazole (ODA), carboxylic acid chlorides and carboxylic acid anhydride; With the terminal of ketone or aldehyde can be, as but not limited to, amines, alkoxyamines, hydrazines, acyloxylamine, or hydrazide; With the terminal of azide can be, as but not limited to, alkyne. Examples of these function groups are displayed below:

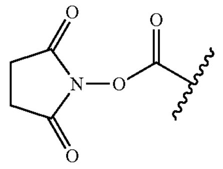 [SMILES: *C(=O)ON1C(=O)CCC1=O]

N-hydroxysuccinimide ester;

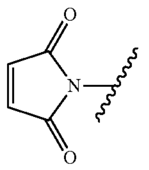 [SMILES: *N1C(=O)C=CC1=O]

maleimide;

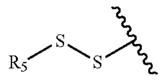

disulfide;

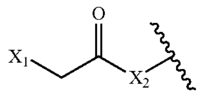

haloacetyl;

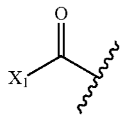

acyl halide (acid halide),
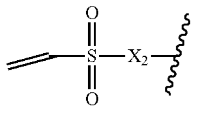
ethenesulfonyl;
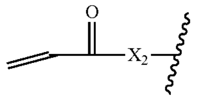
acryl (acryloyl);
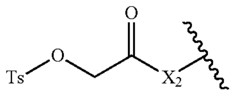
2-(tosyloxy)acetyl;
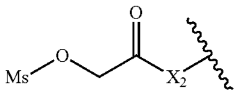
2-(mesyloxy)acetyl;
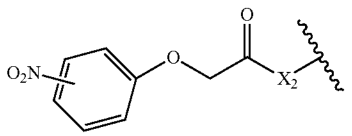
2-(nitrophenoxy)acetyl;
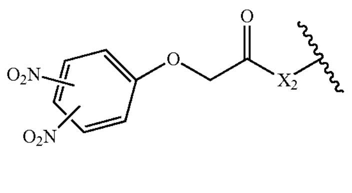
(dinitrophenoxy)acetyl;
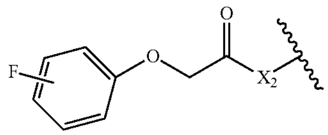
2-(fluorophenoxy)-acetyl;
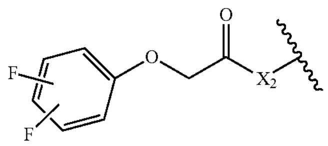
2-(difluorophenoxy)-acetyl;
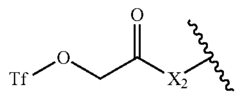
2-(((trifluoromethyl)-sulfonyl)oxy)acetyl;
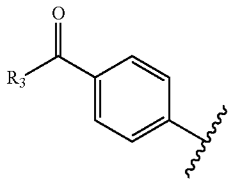
ketone, or aldehyde,
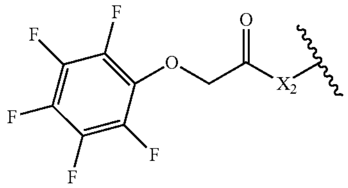
2-(pentafluorophenoxy)acetyl;
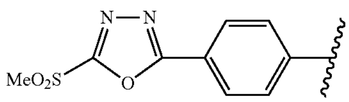
,
methylsulfone phenyloxadiazole (ODA);
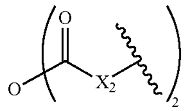
,
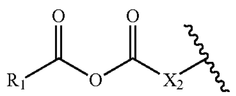
acid anhydride,
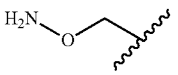

alkyloxyamino;

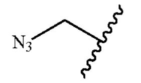

azido,

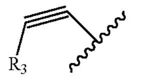

alkynyl, or

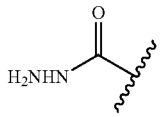

hydrazide. Wherein $X_1$ is F, Cl, Br, I or Lv; $X_2$ is O, NH, $N(R_1)$, or $CH_2$; $R_5$ and $R_3$ are H, $R_1$, aromatic, heteroaromatic, or aromatic group wherein one or several H atoms are replaced independently by —$R_1$, -halogen, —$OR_1$, —$SR_1$, —$NR_1R_2$, —$NO_2$, —$S(O)R_1$, —$S(O)_2R_1$, or —$COOR_1$; Lv is a leaving group selected from nitrophenol; N-hydroxysuccinimide (NETS); phenol; dinitrophenol; pentafluorophenol; tetrafluorophenol; difluorophenol; monofluorophenol; pentachlorophenol; triflate; imidazole; dichlorophenol; tetrachlorophenol; 1-hydroxybenzotriazole; tosylate; mesylate; 2-ethyl-5-phenylisoxazolium-3'-sulfonate, anhydrides formed its self, or formed with the other anhydride, e.g. acetyl anhydride, formyl anhydride; or a intermediate molecule generated with a condensation reagent for peptide coupling reactions, or for Mitsunobu reactions.

In preferred embodiments, $R_1$, $R_2$, and $R_3$, are linear alkyl having from 1-6 carbon atoms, or polyethyleneoxy unit of formula $(OCH_2CH_2)_p$, p=1~100.

The key step of synthesis of the bridge linker containing acetylenedicarboxyl groups is the condensation of the acetylenedicarboxylic acid, or its acid derivatives, with the other components containing an amine (1° or 2° amines), alcohol, or thiol on their terminal, as shown in the following scheme (Ia):

(Ia)

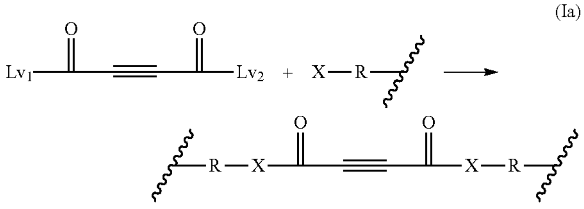

Wherein X is $X_1$ or $X_2$ described in Formula (I) as NH, $N(R_3)$, O, or S; R is $R_1$ and/or $R_2$ that described in Formula (I); $R_3$ is the same defined in Formula (I).

$Lv_1$ and $Lv_2$ are the same or independently OH; F; Cl; Br; I; nitrophenol; N-hydroxysuccinimide (NHS); phenol; dinitrophenol; pentafluorophenol; tetrafluorophenol; difluorophenol; monofluorophenol; pentachlorophenol; triflate; imidazole; dichlorophenol; tetrachlorophenol; 1-hydroxybenzotriazole; tosylate; mesylate; 2-ethyl-5-phenylisoxazolium-3'-sulfonate, anhydrides formed its self, or formed with the other anhydride, e.g. acetyl anhydride, formyl anhydride; or a intermediate molecule generated with a condensation reagent for peptide coupling reactions, or for Mitsunobu reactions, e.g. condensation reagents are: EDC (N-(3-Dimethylaminopropyl)-N'-ethylcarbodiimide), DCC (Dicyclohexyl-carbodiimide), N,N'-Diisopropylcarbodiimide (DIC), N-Cyclohexyl-N'-(2-morpholinoethyl)carbodiimide metho-p-toluenesulfonate (CMC, or CME-CDI), 1,1'-Carbonyldiimidazole (CDI), TBTU (O-(Benzotriazol-1-yl)-N,N,N',N'-tetramethyluronium tetrafluoroborate), N,N,N',N'-Tetramethyl-O-(1H-benzotriazol-1-yl)uronium hexafluorophosphate (HBTU), (Benzotriazol-1-yloxy)tris(dimethylamino)phosphonium hexafluorophosphate (BOP), (Benzotriazol-1-yloxy)tripyrrolidinophosphonium hexafluorophosphate (PyBOP), Diethyl cyanophosphonate (DEPC), Chloro-N,N,N',N'-tetramethylformamidinium hexafluorophosphate, 1-[Bis(dimethylamino)methylene]-1H-1,2,3-triazolo[4,5-b]pyridinium 3-oxid hexafluorophosphate (HATU), 1-[(Dimethylami-no)(morpholino) methylene]-1H-[1,2,3]triazolo[4,5-b]pyridine-1-ium 3-oxide hexafluorophosphate (HDMA), 2-Chloro-1,3-dimethylimidazolidinium hexafluorophosphate (CIP), Chlorotripyrrolidinophosphonium hexafluorophosphate (PyCloP), Fluoro-N,N,N',N'-bis(tetramethylene)formamidinium hexafluorophosphate (BTFFH), N,N,N',N'-Tetramethyl-S-(1-oxido-2-pyridyl)thiuronium hexafluorophosphate, O-(2-Oxo-1(2H)pyridyl)-N,N,N',N'-tetramethyluronium tetrafluoroborate (TPTU), S-(1-Oxido-2-pyridyl)-N,N,N',N'-tetramethylthiuronium tetrafluoroborate, O-[(Ethoxycarbonyl) cyano-methylenamino]-N,N,N',N'-tetramethyluronium hexafluorophosphate (HOTU), (1-Cyano-2-ethoxy-2-oxoethylidenaminooxy) dimethylamino-morpholino-carbenium hexafluorophosphate (COMU), O-(Benzotriazol-1-yl)-N,N,N',N'-bis(tetramethylene) uronium hexafluorophosphate (HBPyU), N-Benzyl-N'-cyclohexylcarbodiimide (with, or without polymer-bound), Dipyrrolidino(Nsuccinimidyloxy)carbenium hexafluorophosphate (HSPyU), Chlorodipyrrolidinocarbenium hexafluorophosphate (PyClU), 2-Chloro-1,3-dimethylimidazolidinium tetrafluoroborate (CIB), (Benzotriazol-1-yloxy) dipiperidinocarbenium hexafluorophosphate (HBPipU), O-(6-Chlorobenzotriazol-1-yl)-N,N,N',N'-tetramethyluronium tetrafluoroborate (TCTU), Bromotris(dimethylamino)-phosphonium hexafluorophosphate (BroP), Propylphosphonic anhydride (PPACA, T3P®), 2-Morpholinoethyl isocyanide (MEI), N,N,N',N'-Tetramethyl-O-(N-succinimidyl)uronium hexafluorophosphate (HSTU), 2-Bromo-1-ethyl-pyridinium tetrafluoroborate (BEP), O-[(Ethoxycarbonyl)cyanomethylenamino]-N,N,N',N'-tetramethyluronium tetrafluoroborate (TOTU), 4-(4,6-Dimethoxy-1,3,5-triazin-2-yl)-4-methylmorpholinium chloride (MMTM, DMTMM), N,N,N',N'-Tetramethyl-O-(N-succinimidyl)uronium tetrafluoroborate (TSTU), 0-(3,4-Dihydro-4-oxo-1,2,3-benzotriazin-3-yl)-N,N,N',N'-tetramethyluronium tetrafluoro-borate (TDBTU), 1,1'-(Azodicarbonyl)dipiperidine (ADD), Di-(4-chlorobenzyl) azodicar-boxylate (DCAD), Di-tert-butyl azodicarboxylate (DBAD), Diisopropyl azodicarboxylate (DIAD), Diethyl azodicarboxylate (DEAD).

When X is $CH_2$, wherein the acetylenedicarboxyl group on the bridge linker connects to the other components of linker through C—C bonds, then the key step of synthesis of the bridge linker containing acetylenedicarboxyl groups is the condensation of bis(trimethylsilyl)acetylene, or acetylene bis-magnesiums (Grignard reagent), or acetylene bislithiums (dilithioacetylene) or other di-metal acetylide with acid halides or acid anhydrides, depicted as following reaction equations (Ib), (Ic), (Id), (Ie), (If), (Ig) and (Ih):

(Ib)

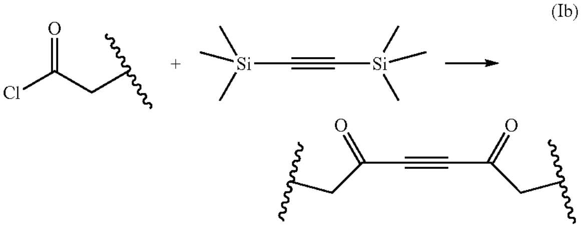

(Ic)

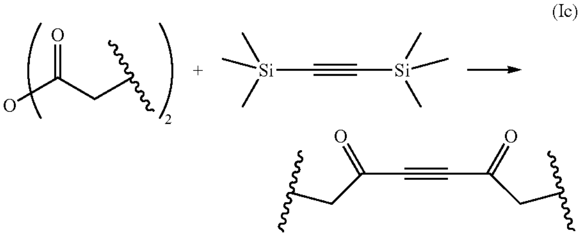

(Ie)

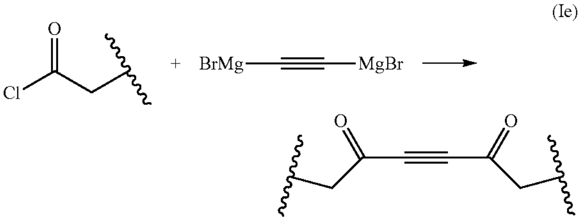

(If)

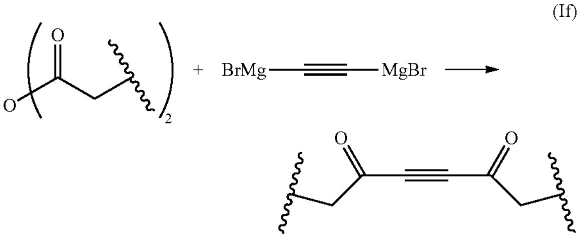

(Ig)

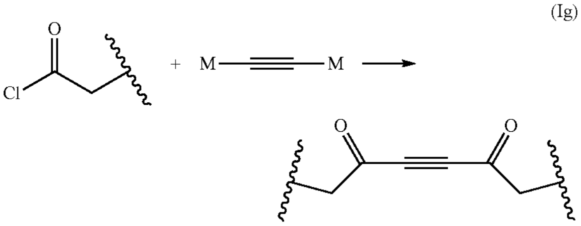

(Ih)

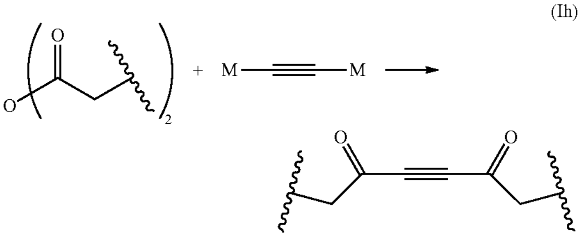

Wherein M is Na, K, Li, Cu, CuLi, Sn, Ti, Ca, Mg or Zn.

The detail examples of the synthesis of the bridge linkers are shown in the FIGS. 1~10. Normally the bridge substituents of acetylenedicarboxyl can be condensated with linker components containing function groups capable to react to drugs of desired conjugation.

Cell-Binding Agent-Drug Conjugates

The conjugates of the present invention can be represented by the following formula,

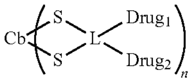, wherein Cb is a cell-binding agent, L is the acetylenedicarboxyl bridge linker, $Drug_1$ and $Drug_2$ are a drug molecule, n is an integer from 1 to 20, and two S (sulfur) elements from Cb bridgely link to L, which covalently connects two or more drugs (per bridge linker L).

The bridge linker L may be composed of one or more linker components. Exemplary linker components include 6-maleimidocaproyl ("MC"), maleimidopropanoyl ("MP"), valine-citrulline ("val-cit" or "vc"), alanine-phenylalanine ("ala-phe" or "af"), p-aminobenzyloxycarbonyl ("PAB"), 4-thiopentanoate ("SPP"), 4-(N-maleimidomethyl)cyclohexane-1 carboxylate ("MCC"), (4-acetyl)aminobenzoate ("SIAB"), 4-thio-butyrate (SPDB), 4-thio-2-hydroxysulfonyl-butyrate (2-Sulfo-SPDB), ethyleneoxy —$CH_2CH_2O$— as one or more repeating units ("EO" or "PEO"). Additional linker components are known in the art and some are described herein.

Example structures of these components containing linkers are:

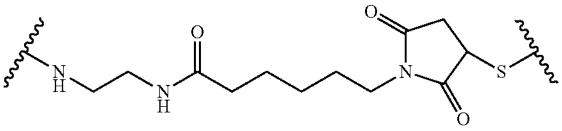;

(MC, 6-maleimidocaproyl containing)

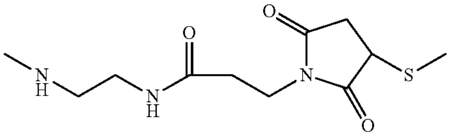

(MP, maleimidopropanoyl containing)

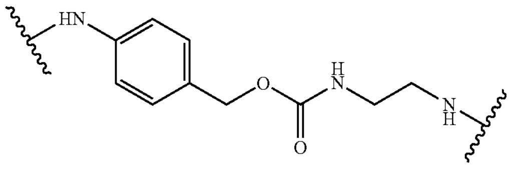, (PAB, p-aminobenzyloxycarbonyl containing)

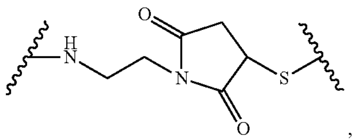,

-continued

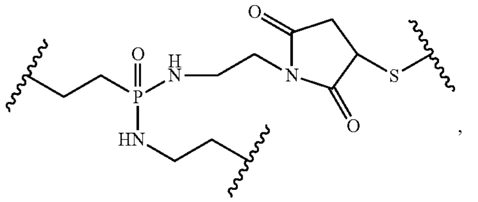

,

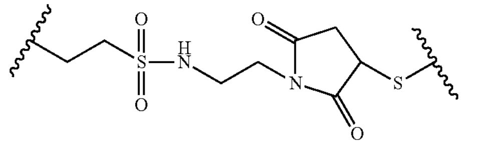

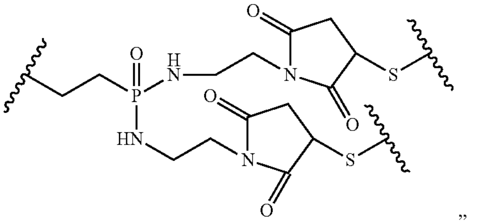

,,

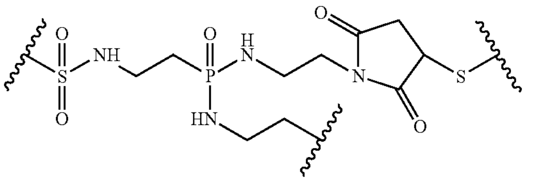

(ME, maleimidoethyl containing).

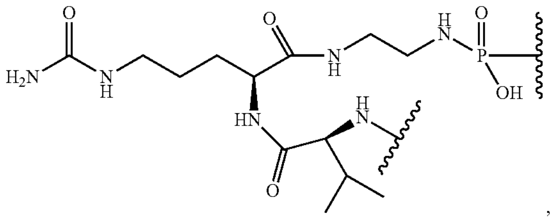

,

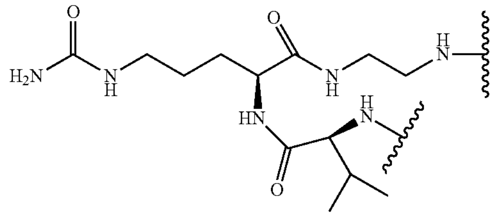

(valine-citrulline containing)

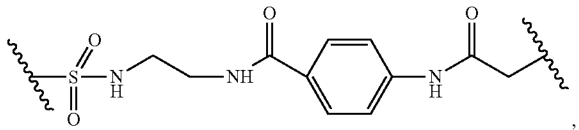

,

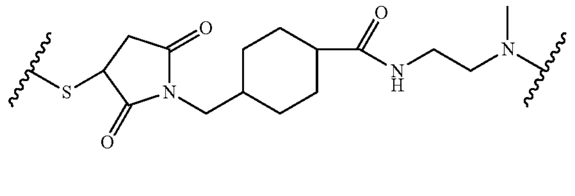

(MCC, 4-(N-maleimidomethyl)cyclohexane-1 carboxylate)

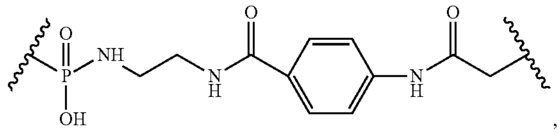

,

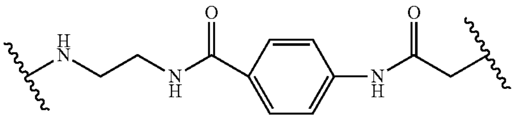

((4-acetyl)aminobenzoate containing)

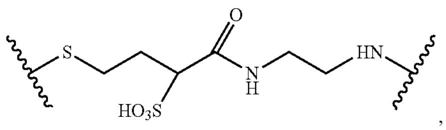

,

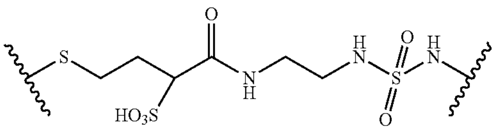

(4-thio-2-hydroxysulfonyl-butyrate, 2-sulfo-SPDB)

Preferably, the conjugates have the following Formula (II):

(II)

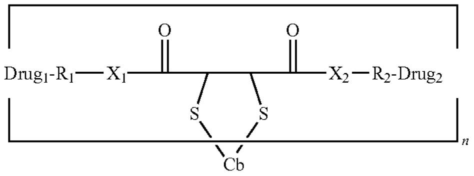

wherein:

Cb represents a cell-binding agent, preferably an antibody, which conjugates to $Drug_1$ and $Drug_2$ via a pair of sulfur atoms (thiols). The conjugatable thiol groups can generally be generated from TCEP or DTT reduction of pairs of disulfide bonds on the surface of cell-binding molecule.

$Drug_1$ and $Drug_2$ represent the same or different cytotoxic agents, linked to the cell-binding agent via the bridge linker through an alkyl, alkylene, alkenylene, alkynylene, ether, polyoxyalkylene, ester, amine, imine, polyamine, hydrazine, hydrazone, amide, urea, semicarbazide, carbazide, alkoxyamine, urethanes, amino acid, peptide, acyloxylamine, hydroxamic acid, disulfide, thioether, thioester, carbamate, carbonate, heterocyclic ring, heteroalkyl, heteroaromatic, or alkoxime bond, or combination thereof.

n is 1~20; $R_1$, $R_2$, $X_1$ and $X_2$ are described the same previously in Formula (I).

As described in more detail below, $Drug_1$ and $Drug_2$ can be any of many small molecule drugs, including, but not limited to, tubulysins, calicheamicins, auristatins, maytansinoids, CC-1065 analogs, morpholinos doxorubicins, taxanes, cryptophycins, epothilones, and benzodiazepine dimers (e.g., dimmers of pyrrolobenzodiazepine (PBD) or tomaymycin), indolinobenzodiazepines, imidazobenzothiadiazepines, or oxazolidinobenzodiazepines).

To synthesize the conjugate, the cell-binding agent can be first modified with the bridge linkers of the present invention through reduction of disulfide bonds of the cell-binding molecule. The yielded a pair of free thiols can react to the bridge linker of Formula (I) at pH 5~9 aqueous media with or without addition of 0~30% of water mixable (miscible) organic solvents, such as DMA, DMF, ethanol, methanol, acetone, acetonitrile, THF, isopropanol, dioxane, propylene glycol, or ethylene diol, to introduce the reactive groups of $Z_1$ and $Z_2$ containing disulfide, maleimido, haloacetyl, azide, 1-yne, ketone, aldehyde, alkoxyamino, or hydrazide groups. Then a reactive group of a cytotoxic agent reacts to the modified cell-binding molecule accordingly. For example, synthesis of the cell-binding agent-drug conjugates linked via disulfide bonds is achieved by a disulfide exchange between the disulfide bond in the modified cell-binding agent and a drug containing a free thiol group. Synthesis of the cell-binding agent-drug conjugates linked via thioether is achieved by reaction of the maleimido or haloacetyl or ethylsulfonyl modified cell-binding agent and a drug containing a free thiol group. Synthesis of conjugates bearing an acid labile hydrazone can be achieved by reaction of a carbonyl group with the hydrazide moiety in the linker, by methods known in the art (see, for example, P. Hamann et al., Hinman, L. M., et al, Cancer Res. 53, 3336-334, 1993; B. Laguzza et al., J. Med. Chem., 32; 548-555, 1959; P. Trail et al., Cancer Res., 57; 100-105, 1997). Synthesis of conjugates bearing triazole linkage can be achieved by reaction of a 1-yne group of the drug with the azido moiety in the linker, through the click chemistry (Huisgen cycloaddition) (Lutz, J-F. et al, 2008, Adv. Drug Del. Rev. 60, 958-970; Sletten, E. M. et al 2011, Acc Chem. Research 44, 666-676).

Alternatively, the drug can react with the bridge linkers of the present invention that have conjugated to a cell-binding molecule to give a modified cell-binding molecule linker of Formula (III) bearing functionalities. For example, a thiol-containing drug can be reached with the modified cell-binding molecule bridge linker of Formula (III) bearing a maleimdo, or a haloacetyl, or an ethylsulfonyl substituent at pH 5.5~9.0 in aqueous buffer to give a cell-binding molecule-drug conjugate via a thioether linkage. A thiol-containing drug can undergo disulfide exchange with a modified bridge linker of Formula (III) bearing a pyridyldithio moiety to give a conjugate a disulfide bond linkage. A drug bearing a hydroxyl group or a thiol group can be reacted with a modified bridge linker of Formula (III) bearing a halogen, particularly the alpha halide of carboxylates, in the presence of a mild base, e.g. pH 8.0~9.5, to give a modified drug bearing an ether or thiol ether link. A hydroxyl group containing drug can be condensed with a bridge cross linker of Formula (I) bearing a carboxyl group, in the presence of a dehydrating agent, such as EDC or DCC, to give ester linkage, then the subject drug modified bridge linker undergoes the conjugation with a cell-binding molecule. A drug containing an amino group can condensate with a carboxyl ester of NHS, imidazole, nitrophenol; N-hydroxysuccinimide (NETS); phenol; dinitrophenol; pentafluorophenol; tetrafluorophenol; difluorophenol; monofluorophenol; pentachlorophenol; triflate; imidazole; dichlorophenol; tetrachlorophenol; 1-hydroxybenzotriazole; tosylate; mesylate; 2-ethyl-5-phenylisoxazolium-3'-sulfonate on the cell-binding molecule-bridge linker of Formula (III) to give a conjugate via amide bond linkage.

The conjugate may be purified by standard biochemical means, such as gel filtration on a Sephadex G25 or Sephacryl S300 column, adsorption chromatography, and ion exchange or by dialysis. In some cases, a small molecule as a cell-binding agent (e.g. folic acid, melanocyte stimulating hormone, EGF etc) conjugated with a small molecular drugs can be purified by chromatography such as by HPLC, medium pressure column chromatography or ion exchange chromatography.

Modified Cell-Binding Agents/Molecules

The cell-binding agent modified by reaction with linkers of the present invention are preferably represented by the Formula (III)

(III)

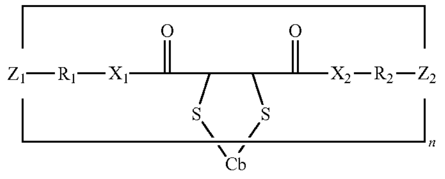

Wherein Cb, $Z_1$, $Z_2$, n, $R_1$, $R_2$, $X_1$, and $X_2$ are defined the same as in Formula (I) and (II).

In preferred embodiments, $Z_1$ and $Z_2$ are a disulfide substituent, maleimido, haloacetyl, alkoxyamine, azido, ketone, aldehyde, hydrazine, alkyne, an N-hydroxysuccinimide ester, or a carboxyl ester formed with phenol; dinitrophenol; pentafluorophenol; tetrafluorophenol; difluorophenol; monofluorophenol; pentachlorophenol; triflate; imidazole; dichlorophenol; tetrachlorophenol; 1-hydroxybenzotriazole; tosylate; mesylate; 2-ethyl-5-phenylisoxa-zolium-3'-sulfonate. $Z_1$ and $Z_2$ can then react with a cytotoxic agent through disulfide, thioether, hydrazone, amide, alkoxime, carbamate, ester, ether bond or heteroaromatic ring. The modified cell-binding agent can be prepared via a reaction of the cell-binding agent with the bridge linkers of Formula (I) as described in Formula (II) above.

In order to achieve a higher conjugation yield of the alkyne group on the bridge linkers with a pair of free thiols on the cell-binding molecule, preferably on an antibody, a small percentage of organic co-solvent may be required to add to the reaction mixture, as well in the solution after the reaction to maintain solubility of the Formula (III) in aqueous solution. To modify the cell-binding agents, the cross-linking reagent (bridge linker) of Formula (I) can be first dissolved in a polar organic solvent that is miscible with water, for example different alcohols, such as methanol, ethanol, and propanol, acetone, acetonitrile, tetrahydrofuran (THF), 1,4-dioxane, dimethyl formamide (DMF), dimethyl acetamide (DMA), or dimethylsulfoxide (DMSO) at a high concentration, for example 1-500 mM. Meanwhile, the cell-binding molecule, such as antibody dissolved in an aqueous buffer pH 5~9.5, preferably pH 6~8.5, at 1~35 mg/ml concentration was treated with 1~20 equivalent of TCEP or DTT for 20 min to 12 hour. After the reduction, DTT can be removed by SEC chromatographic purification. TCEP can be optionally removed by SEC chromatography too, or staying in the reaction mixture for the next step reaction without purification. Furthermore, the reduction of antibodies or the other cell-binding agents with TCEP can be performed with a bridge linker of Formula (I), for which the cross-linking conjugation for the cell-binding molecules can be achieved simultaneously along with the TCEP reduction.

The aqueous solutions for the modification of cell-binding agents are buffered between pH 6 and 9, preferably between 6.5 and 7.5 and can contain any non-nucleophilic buffer salts useful for these pH ranges. Typical buffers include phosphate, triethanolamine HCl, HEPES, and MOPS buffers, which can contain additional components, such as cyclodextrins, sucrose and salts, for examples, NaCl and KCl. After the addition of the bridge linker of Formula (I) into the solution containing the reduced cell-binding molecules, the reaction mixture is incubated at a temperature of from 4° C. to 45° C., preferably at ambient temperature. The progress of the reaction can be monitored by measuring the decrease in the absorption at 254 nm, or increase in the absorption at 280 nm, or the other appropriate wavelength. After the reaction is complete, isolation of the modified cell-binding agent can be performed in a routine way, using for example gel filtration chromatography, or adsorptive chromatography.

The extent of modification can be assessed by measuring the absorbance of the nitropyridine thione, dinitropyridine dithione, pyridine thione, carboxamidopyridine dithione and dicarboxamidopyridine dithione group released via UV spectra. For the conjugation without a chromophore group, the modification or conjugation reaction can be monitored by LC-MS, preferably by UPLC-QTOF mass spectrometry, or Capillary electrophoresis-mass spectrometry (CE-MS). The bridge cross-linkers described herein have diverse functional groups that can react with any drugs, preferably cytotoxic agents that possess a suitable substituent. For examples, the modified cell-binding molecules bearing an amino or hydroxyl substituent can react with drugs bearing an N-hydroxysuccinimide (NHS) ester, the modified cell-binding molecules bearing a thiol substituent can react with drugs bearing a maleimido or haloacetyl group. Additionally, the modified cell-binding molecules bearing a carbonyl (ketone or aldehyde) substituent can react with drugs bearing a hydrazide or an alkoxyamine. One skilled in the art can readily determine which linker to use based on the known reactivity of the available functional group on the linkers.

Modified Cytotoxic Drugs

The cytotoxic drugs modified by reaction with cross-linkers of the present invention are preferably represented by the Formula (IV):

(IV)

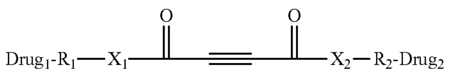

Wherein $Drug_1$, $Drug_2$, $Z_1$, $Z_2$, n, $R_1$, $R_2$, $X_1$, and $X_2$ are defined the same as in Formula (I) and (II).

The modified drugs can be prepared via reaction of the drug with the linkers of the Formula (I) to give a modified drug of Formula (IV) bearing functionality of an acetylenedicarboxyl group capable of reacting with a pair of thiol groups of a cell-binding agent. The acetylenedicarboxyl group is synthesized through condensation with acetylene via the methods described in reaction equation (Ia), (Ib), (Ic), (Id), (Ie), (If), (Ig) and (Ih). But for drugs containing a thiol, or the drugs undergoing to link a cell-binding molecule via the bridge linkers through thioether, thioester or disulfide bond, it is therefore preferred that the $Drug_1$ or $Drug_2$ may be synthesized to connect to $R_1$, or $R_2$ in a piece of components via the linkage of thioether, thioester or disulfide bond first. Then the synthesized $R_1$-$Drug_1$ or $R_2$-$Drug_2$ component is assembled to an acetylenedicarboxyl group to form the bridge linker modified drugs of Formula (IV).

For examples of the synthesis, a thiol-containing drug can be reacted with the linker of components $R_1$ or $R_2$ bearing a maleimdo substituent at neutral pH in aqueous buffer to give a $R_1$-$Drug_1$ or $R_2$-$Drug_2$ compartment bearing thioether linkage, and following by condensation with a compartment of acetylenedicarboxyl group to give a modified drug of Formula (IV) bearing thioether linkage. A drug bearing a hydroxyl group can be reacted with a linker component $R_1$ or $R_2$ bearing a halogen, or a tosylate, or a mesylate, in the presence of a mild base, to give a $R_1$-$Drug_1$ or $R_2$-$Drug_2$ compartment bearing ether linkage, and following by condensation with a compartment of acetylenedicarboxyl group to give a modified drug of Formula (IV) bearing thioether linkage. A hydroxyl group containing drug can be condensed with a linker of Formula (I) bearing a carboxyl group, in the presence of a dehydrating agent, such as EDC or dicyclohexylcarbodiimide (DCC), to give a modified drug of Formula (IV) via ester linkage. A drug bearing a thiol group can also react the linker of components $R_1$ or $R_2$ bearing a maleimido or a vinylsulfonyl, or a haloacetyl group, give a $R_1$-$Drug_1$ or $R_2$-$Drug_2$ compartment bearing thioether linkage, and following by condensation with a compartment of acetylenedicarboxyl group to give a modified drug of Formula (IV) bearing thioether linkage. An amino group containing drug can similarly undergo condensation with a carboxyl group on the bridge linker of Formula (I) to give a modified drug of Formula (IV) bearing amide bonds. The modified drug can be purified by standard methods such as column chromatography over silica gel or alumina, crystallization, preparatory thin layer chromatography, ion exchange chromatography, or HPLC.

Cell-Binding Agents

The cell-binding molecule that comprises the conjugates and the modified cell-binding agents of the present invention may be of any kind presently known, or that become known, molecule that binds to, complexes with, or reacts with a moiety of a cell population sought to be therapeutically or otherwise biologically modified.

The cell binding agents include, but are not limited to, large molecular weight proteins such as, for example, full-length antibodies (polyclonal antibodies, monoclonal antibodies, dimers, multimers, multispecific antibodies (e.g., bispecific antibodies); single chain antibodies; fragments of antibodies such as Fab, Fab', $F(ab')_2$, $F_v$, [Parham, J. Immunol. 131, 2895-2902 (1983)], fragments produced by a Fab expression library, anti-idiotypic (anti-Id) antibodies, CDR's, diabody, triabody, and epitope-binding fragments of any of the above which immuno-specifically bind to cancer cell antigens, viral antigens, microbial antigens or a protein generated by the immune system that is capable of recognizing, binding to a specific antigen or exhibiting the desired biological activity (Miller et al (2003) J. of Immunology 170:4854-4861); interferons (such as type I, II, III); peptides; lymphokines such as IL-2, IL-3, IL-4, IL-5, IL-6, IL-10, GM-CSF, interferon-gamma (IFN-γ); hormones such as insulin, TRH (thyrotropin releasing hormones), MSH (melanocyte-stimulating hormone), steroid hormones, such as androgens and estrogens, melanocyte-stimulating hormone (MSH); growth factors and colony-stimulating factors such as epidermal growth factors (EGF), granulocyte-macrophage colony-stimulating factor (GM-CSF), transforming growth factors (TGF), such as TGFα, TGFβ, insulin and insulin like growth factors (IGF-I, IGF-II) G-CSF, M-CSF and GM-CSF [Burgess, Immunology Today, 5, 155-158 (1984)]; vaccinia growth factors (VGF); fibroblast growth factors (FGFs); smaller molecular weight proteins, polypeptide, peptides and peptide hormones, such as bombesin, gastrin, gastrin-releasing peptide; platelet-derived growth factors; interleukin and cytokines, such as interleukin-2 (IL-2), interleukin-6 (IL-6), leukemia inhibitory factors, granulocyte-macrophage colony-stimulating factor (GM- CSF); vitamins, such as folate; apoproteins and glycoproteins, such as transferrin [O'Keefe et al, 260 J. Biol. Chem. 932-937 (1985)]; sugar-binding proteins or lipoproteins, such as lectins; cell nutrient-transport molecules; and small molecular inhibitors, such as prostate-specific membrane antigen (PSMA) inhibitors and small molecular tyrosine kinase inhibitors (TKI), non-peptides or any other cell binding molecule or substance, such as bioactive polymers (Dhar, et al, Proc. Natl. Acad. Sci. 2008, 105, 17356-61); bioactive dendrimers (Lee, et al, Nat. Biotechnol. 2005, 23, 1517-26; Almutairi, et al; Proc. Natl. Acad. Sci. 2009, 106, 685-90); nanoparticles (Liong, et al, ACS Nano, 2008, 19, 1309-12; Medarova, et al, Nat. Med. 2007, 13, 372-7; Javier, et al, Bioconjugate Chem. 2008, 19, 1309-12); liposomes (Medinai, et al, Curr. Phar. Des. 2004, 10, 2981-9); viral capsides (Flenniken, et al, Viruses Nanotechnol. 2009, 327, 71-93).

In general, a monoclonal antibody is preferred as a cell-surface binding agent if an appropriate one is available. And the antibody may be murine, human, humanized, chimeric, or derived from other species.

Production of antibodies used in the present invention involves in vivo or in vitro procedures or combinations thereof. Methods for producing polyclonal anti-receptor peptide antibodies are well-known in the art, such as in U.S. Pat. No. 4,493,795 (to Nestor et al). A monoclonal antibody is typically made by fusing myeloma cells with the spleen cells from a mouse that has been immunized with the desired antigen (Köhler, G.; Milstein, C. (1975). *Nature* 256: 495-497). The detailed procedures are described in "Antibodies—A Laboratory Manual", Harlow and Lane, eds., Cold Spring Harbor Laboratory Press, New York (1988), which is incorporated herein by reference. Particularly monoclonal antibodies are produced by immunizing mice, rats, hamsters or any other mammal with the antigen of interest such as the intact target cell, antigens isolated from the target cell, whole virus, attenuated whole virus, and viral proteins. Splenocytes are typically fused with myeloma cells using polyethylene glycol (PEG) 6000. Fused hybrids are selected by their sensitivity to HAT (hypoxanthine-aminopterin-thymine). Hybridomas producing a monoclonal antibody useful in practicing this invention are identified by their ability to immunoreact specified receptors or inhibit receptor activity on target cells.

A monoclonal antibody used in the present invention can be produced by initiating a monoclonal hybridoma culture comprising a nutrient medium containing a hybridoma that secretes antibody molecules of the appropriate antigen specificity. The culture is maintained under conditions and for a time period sufficient for the hybridoma to secrete the antibody molecules into the medium. The antibody-containing medium is then collected. The antibody molecules can then be further isolated by well-known techniques, such as using protein-A affinity chromatography; anion, cation, hydrophobic, or size exclusive chromatographies (particularly by affinity for the specific antigen after protein A, and sizing column chromatography); centrifugation, differential solubility, or by any other standard technique for the purification of proteins.

Media useful for the preparation of these compositions are both well-known in the art and commercially available and include synthetic culture media. An exemplary synthetic medium is Dulbecco's minimal essential medium (DMEM; Dulbecco et al., Virol. 8, 396 (1959)) supplemented with 4.5 gm/l glucose, 0~20 mM glutamine, 0~20% fetal calf serum, several ppm amount of heavy metals, such as Cu, Mn, Fe, or Zn, etc, or/and the heavy metals added in their salt forms, and with an anti-foaming agent, such as polyoxyethylene-polyoxypropylene block copolymer.

In addition, antibody-producing cell lines can also be created by techniques other than fusion, such as direct transformation of B lymphocytes with oncogenic DNA, or transfection with an oncovirus, such as Epstein-Barr virus (EBV, also called human herpesvirus 4 (HHV-4)) or Kaposi's sarcoma-associated herpesvirus (KSHV). See, U.S. Pat. Nos. 4,341,761; 4,399,121; 4,427,783; 4,444,887; 4,451,570; 4,466,917; 4,472,500; 4,491,632; 4,493,890. A monoclonal antibody may also be produced via an anti-receptor peptide or peptides containing the carboxyl terminal as described well-known in the art. See Niman et al., Proc. Natl. Acad. Sci. USA, 80: 4949-4953 (1983); Geysen et al., Proc. Natl. Acad. Sci. USA, 82: 178-182 (1985); Lei et al. Biochemistry 34(20): 6675-6688, (1995). Typically, the anti-receptor peptide or a peptide analog is used either alone or conjugated to an immunogenic carrier, as the immunogen for producing anti-receptor peptide monoclonal antibodies.

There are also a number of other well-known techniques for making monoclonal antibodies as binding molecules in this invention. Particularly useful are methods of making fully human antibodies. One method is phage display technology which can be used to select a range of human antibodies binding specifically to the antigen using methods of affinity enrichment. Phage display has been thoroughly described in the literature and the construction and screening of phage display libraries are well known in the art, see, e.g., Dente et al, Gene. 148(1):7-13 (1994); Little et al, Biotechnol Adv. 12(3):539-55 (1994); Clackson et al., Nature 352: 264-628 (1991); Huse et al., Science 246:1275-1281 (1989).

Monoclonal antibodies derived by hybridoma technique from another species than human, such as mouse, can be humanized to avoid human anti-mouse antibodies when infused into humans. Among the more common methods of humanization of antibodies are complementarity-determining region grafting and resurfacing. These methods have been extensively described, see e.g. U.S. Pat. Nos. 5,859,205 and 6,797,492; Liu et al, Immunol Rev. 222:9-27 (2008); Almagro et al, Front Biosci. 13: 1619-33 (2008); Lazar et al, Mol Immunol. 44(8):1986-98 (2007); Li et al, Proc. Natl. Acad. Sci. USA. 103(10):3557-62 (2006) each incorporated herein by reference. Fully human antibodies can also be prepared by immunizing transgenic mice, rabbits, monkeys, or other mammals, carrying large portions of the human immunoglobulin heavy and light chains, with an immunogen. Examples of such mice are: the Xenomouse. (Abgenix/Amgen), the HuMAb-Mouse (Medarex/BMS), the VelociMouse (Regeneron), see also U.S. Pat. Nos. 6,596,541, 6,207,418, No. 6,150,584, No. 6,111,166, No. 6,075,181, No. 5,922,545, Nos. 5,661,016, 5,545,806, 5,436,149 and 5,569,825. In human therapy, murine variable regions and human constant regions can also be fused to construct called "chimeric antibodies" that are considerably less immunogenic in man than murine mAbs (Kipriyanov et al, Mol Biotechnol. 26:39-60 (2004); Houdebine, Curr Opin Biotechnol. 13:625-9 (2002) each incorporated herein by reference). In addition, site-directed mutagenesis in the variable region of an antibody can result in an antibody with higher affinity and specificity for its antigen (Brannigan et al, Nat Rev Mol Cell Biol. 3:964-70, (2002)); Adams et al, J Immunol Methods. 231:249-60 (1999)) and exchanging constant regions of a mAb can improve its ability to mediate effector functions of binding and cytotoxicity.

Antibodies immunospecific for a malignant cell antigen can also be obtained commercially or produced by any method known to one of skill in the art such as, e.g., chemical synthesis or recombinant expression techniques. The nucleotide sequence encoding antibodies immunospecific for a malignant cell antigen can be obtained commercially, e.g., from the GenBank database or a database like it, the literature publications, or by routine cloning and sequencing.

Apart from an antibody, a peptide or protein that bind/block/target or in some other way interact with the epitopes or corresponding receptors on a targeted cell can be used as a binding molecule. These peptides or proteins could be any random peptide or proteins that have an affinity for the epitopes or corresponding receptors and they don't necessarily have to be of the immunoglobulin family. These peptides can be isolated by similar techniques as for phage display antibodies (Szardenings, J Recept Signal Transduct Res. 2003; 23(4):307-49). The use of peptides from such random peptide libraries can be similar to antibodies and antibody fragments. The binding molecules of peptides or proteins may be conjugated on or linked to a large molecules or materials, such as, but is not limited, an albumin, a polymer, a liposome, a nano particle, a dendrimer, as long as such attachment permits the peptide or protein to retain its antigen binding specificity.

Examples of antibodies used for conjugation of drugs via the bridge linkers of this prevention for treating cancer, autoimmune disease, and/or infectious disease include, but are not limited to, 3F8 (anti-GD2), Abagovomab (anti CA-125), Abciximab (anti CD41 (integrin alpha-IIb), Adalimumab (anti-TNF-α), Adecatumumab (anti-EpCAM, CD326), Afelimomab (anti-TNF-α); Afutuzumab (anti-CD20), Alacizumab pegol (anti-VEGFR2), ALD518 (anti-IL-6), Alemtuzumab (Campath, MabCampath, anti-CD52), Altumomab (anti-CEA), Anatumomab (anti-TAG-72), Anrukinzumab (IMA-638, anti-IL-13), Apolizumab (anti-HLA-DR), Arcitumomab (anti-CEA), Aselizumab (anti-L-selectin (CD62L), Atlizumab (tocilizumab, Actemra, RoActemra, anti-IL-6 receptor), Atorolimumab (anti-Rhesus factor), Bapineuzumab (anti-beta amyloid), Basiliximab (Simulect, antiCD25 (α chain of IL-2 receptor), Bavituximab (anti-phosphatidylserine), Bectumomab (LymphoScan, anti-CD22), Belimumab (Benlysta, LymphoStat-B, anti-BAFF), Benralizumab (anti-CD125), Bertilimumab (anti-CCL11 (eotaxin-1)), Besilesomab (Scintimun, anti-CEA-related antigen), Bevacizumab (Avastin, anti-VEGF-A), Biciromab (FibriScint, anti-fibrin II beta chain), Bivatuzumab (anti-CD44 v6), Blinatumomab (BiTE, anti-CD19), Brentuximab (cAC10, anti-CD30 TNFRSF8), Briakinumab (anti-IL-12, IL-23) Canakinumab (Ilaris, anti-IL-1), Cantuzumab (C242, anti-CanAg), Capromab, Catumaxomab (Removab, anti-EpCAM, anti-CD3), CC49 (anti-TAG-72), Cedelizumab (anti-CD4), Certolizumab pegol (Cimzia anti-TNF-α), Cetuximab (Erbitux, IMC-C225, anti-EGFR), Citatuzumab bogatox (anti-EpCAM), Cixutumumab (anti-IGF-1), Clenoliximab (anti-CD4), Clivatuzumab (anti-MUC1), Conatumumab (anti-TRAIL-R2), CR6261 (anti-Influenza A hemagglutinin), Dacetuzumab (anti-CD40), Daclizumab (Zenapax, anti-CD25 (α chain of IL-2 receptor)), Daratumumab (anti-CD38 (cyclic ADP ribose hydrolase), Denosumab (Prolia, anti-RANKL), Detumomab (anti-B-lymphoma cell), Dorlimomab, Dorlixizumab, Ecromeximab (anti-GD3 ganglioside), Eculizumab (Soliris, anti-05), Edobacomab (anti-endotoxin), Edrecolomab (Panorex, MAb17-1A, anti-EpCAM), Efalizumab (Raptiva, anti-LFA-1 (CD11a), Efungumab (Mycograb, anti-Hsp90), Elotuzumab (anti-SLAMF7), Elsilimomab (anti-IL-6), Enlimomab pegol (anti-ICAM-1 (CD54)), Epitumomab (anti-episialin), Epratuzumab (anti-CD22), Erlizumab (anti-ITGB2 (CD18)), Ertumaxomab (Rexomun, anti-HER2/neu, CD3), Etaracizumab (Abegrin, anti-integrin $\alpha_v\beta_3$), Exbivirumab (anti-hepatitis B surface antigen), Fanolesomab (NeutroSpec, anti-CD15), Faralimomab (anti-interferon receptor), Farletuzumab (anti-folate receptor 1), Felvizumab (anti-respiratory syncytial virus), Fezakinumab (anti-IL-22), Figitumumab (anti-IGF-1 receptor), Fontolizumab (anti-IFN-γ), Foravirumab (anti-rabies virus glycoprotein), Fresolimumab (anti-TGF-β), Galiximab (anti-CD80), Gantenerumab (anti-beta amyloid), Gavilimomab (anti-CD147 (basigin)), Gemtuzumab (anti-CD33), Girentuximab (anti-carbonic anhydrase 9), Glembatumumab (CR011, anti-GPNMB), Golimumab (Simponi, anti-TNF-α), Gomiliximab (anti-CD23 (IgE receptor)), Ibalizumab (anti-CD4), Ibritumomab (anti-CD20), Igovomab (Indimacis-125, anti-CA-125), Imciromab (Myoscint, anti-cardiac myosin), Infliximab (Remicade, anti-TNF-α), Intetumumab (anti-CD51), Inolimomab (anti-CD25 (a chain of IL-2 receptor)), Inotuzumab (anti-CD22), Ipilimumab (anti-CD152), Iratumumab (anti-CD30 (TNFRSF8)), Keliximab (anti-CD4), Labetuzumab (CEA-Cide, anti-CEA), Lebrikizumab (anti-IL-13), Lemalesomab (anti-NCA-90 (granulocyte antigen)), Lerdelimumab (anti-TGF beta 2), Lexatumumab (anti-TRAIL-R2), Libivirumab (anti-hepatitis B surface antigen), Lintuzumab (anti-CD33), Lucatumumab (anti-CD40), Lumiliximab (anti-CD23 (IgE receptor), Mapatumumab (anti-TRAIL-R1), Maslimomab (anti-T-cell receptor), Matuzumab (anti-EGFR), Mepolizumab (Bosatria, anti-IL-5), Metelimumab (anti-TGF beta 1), Milatuzumab (anti-CD74), Minretumomab (anti-TAG-72), Mitumomab (BEC-2, anti-GD3 ganglioside), Morolimumab (anti-Rhesus factor), Motavizumab (Numax, anti-respiratory syncytial virus), Muromonab-CD3 (Orthoclone OKT3, anti-CD3), Nacolomab (anti-C242), Naptumomab (anti-5T4), Natalizumab (Tysabri, anti-integrin $\alpha_4$), Nebacumab (anti-endotoxin), Necitumumab (anti-EGFR), Nerelimomab (anti-TNF-α), Nimotuzumab (Theracim, Theraloc, anti-EGFR), Nofetumomab, Ocrelizumab (anti-CD20), Odulimomab (Afolimomab, anti-LFA-1 (CD11a)), Ofatumumab (Arzerra, anti-CD20), Olaratumab (anti-PDGF-R α), Omalizumab (Xolair, anti-IgE Fc region), Oportuzumab (anti-EpCAM), Oregovomab (OvaRex, anti-CA-125), Otelixizumab (anti-CD3), Pagibaximab (anti-lipoteichoic acid), Palivizumab (Synagis, Abbosynagis, anti-respiratory syncytial virus), Panitumumab (Vectibix, ABX-EGF, anti-EGFR), Panobacumab (anti-*Pseudomonas aeruginosa*), Pascolizumab (anti-IL-4), Pemtumomab (Theragyn, anti-MUC1), Pertuzumab (Omnitarg, 2C4, anti-HER2/neu), Pexelizumab (anti-C5), Pintumomab (anti-adenocarcinoma antigen), Priliximab (anti-CD4), Pritumumab (anti-vimentin), PRO 140 (anti-CCR5), Racotumomab (1E10, anti-(N-glycolylneuraminic acid (NeuGc, NGNA)-gangliosides GM3)), Rafivirumab (anti-rabies virus glycoprotein), Ramucirumab (anti-VEGFR2), Ranibizumab (Lucentis, anti-VEGF-A), Raxibacumab (anti-anthrax toxin, protective antigen), Regavirumab (anti-cytomegalovirus glycoprotein B), Reslizumab (anti-IL-5), Rilotumumab (anti-HGF), Rituximab (MabThera, Rituxanmab, anti-CD20), Robatumumab (anti-IGF-1 receptor), Rontalizumab (anti-IFN-α), Rovelizumab (LeukArrest, anti-CD11, CD18), Ruplizumab (Antova, anti-CD154 (CD40L)), Satumomab (anti-TAG-72), Sevirumab (anti-cytomegalovirus), Sibrotuzumab (anti-FAP), Sifalimumab (anti-IFN-α), Siltuximab (anti-IL-6), Siplizumab (anti-CD2), (Smart) MI95 (anti-CD33), Solanezumab (anti-beta amyloid), Sonepcizumab (anti-sphingosine-1-phosphate), Sontuzumab (anti-episialin), Stamulumab (anti-myostatin), Sulesomab (LeukoScan, (anti-NCA-90

(granulocyte antigen), Tacatuzumab (anti-alpha-fetoprotein), Tadocizumab (anti-integrin $\alpha_{IIb}\beta_3$), Talizumab (anti-IgE), Tanezumab (anti-NGF), Taplitumomab (anti-CD19), Tefibazumab (Aurexis, (anti-clumping factor A), Telimomab, Tenatumomab (anti-tenascin C), Teneliximab (anti-CD40), Teplizumab (anti-CD3), TGN1412 (anti-CD28), Ticilimumab (Tremelimumab, (anti-CTLA-4), Tigatuzumab (anti-TRAIL-R2), TNX-650 (anti-IL-13), Tocilizumab (Atlizumab, Actemra, RoActemra, (anti-IL-6 receptor), Toralizumab (anti-CD154 (CD40L)), Tositumomab (anti-CD20), Trastuzumab (Herceptin, (anti-HER2/neu), Tremelimumab (anti-CTLA-4), Tucotuzumab celmoleukin (anti-EpCAM), Tuvirumab (anti-hepatitis B virus), Urtoxazumab (anti-*Escherichia coli*), Ustekinumab (Stelara, anti-IL-12, IL-23), Vapaliximab (anti-AOC3 (VAP-1)), Vedolizumab, (anti-integrin $\alpha_4\beta_7$), Veltuzumab (anti-CD20), Vepalimomab (anti-AOC3 (VAP-1), Visilizumab (Nuvion, anti-CD3), Vitaxin (anti-vascular integrin avb3), Volociximab (anti-integrin $\alpha_5\beta_1$), Votumumab (HumaSPECT, anti-tumor antigen CTAA16.88), Zalutumumab (HuMax-EGFr, (anti-EGFR), Zanolimumab (HuMax-CD4, anti-CD4), Ziralimumab (anti-CD147 (basigin)), Zolimomab (anti-CD5), Etanercept (Enbrel®), Alefacept (Amewive®), Abatacept (Orencia®), Rilonacept (Arcalyst), 14F7 [anti-IRP-2 (Iron Regulatory Protein 2)], 14G2a (anti-GD2 ganglioside, from Nat. Cancer Inst. for melanoma and solid tumors), J591 (anti-PSMA, Weill Cornell Medical School for prostate cancers), 225.285 [anti-HMW-MAA (High molecular weight-melanoma-associated antigen), Sorin Radiofarmaci S.R.L. (Milan, Italy) for melanoma], COL-1 (anti-CEACAM3, CGM1, from Nat. Cancer Inst. USA for colorectal and gastric cancers), CYT-356 (Oncoltad®, for prostate cancers), HNK20 (OraVax Inc. for respiratory syncytial virus), ImmuRAIT (from Immunomedics for NHL), Lym-1 (anti-HLA-DR10, Peregrine Pharm. for Cancers), MAK-195F [anti-TNF (tumor necrosis factor; TNFA, TNF-alpha; TNFSF2), from Abbott/Knoll for Sepsis toxic shock], MEDI-500 [T10B9, anti-CD3, TRαβ (T cell receptor alpha/beta), complex, from MedImmune Inc for Graft-versus-host disease], RING SCAN [anti-TAG 72 (tumour associated glycoprotein 72), from Neoprobe Corp. for Breast, Colon and Rectal cancers], Avicidin (anti-EPCAM (epithelial cell adhesion molecule), anti-TACSTD1 (Tumor-associated calcium signal transducer 1), anti-GA733-2 (gastrointestinal tumor-associated protein 2), anti-EGP-2 (epithelial glycoprotein 2); anti-KSA; KS1/4 antigen; M4S; tumor antigen 17-1A; CD326, from NeoRx Corp. for Colon, Ovarian, Prostate cancers and NHL]; LymphoCide (Immunomedics, NJ), Smart ID10 (Protein Design Labs), Oncolym (Techniclone Inc, CA), Allomune (BioTransplant, CA), anti-VEGF (Genentech, CA); CEAcide (Immunomedics, NJ), IMC-1C11 (ImClone Systems, NJ) and Cetuximab (ImClone, NJ).

Other antibodies as cell binding molecules/ligands include, but are not limited to, are antibodies against the following antigens: Aminopeptidase N (CD13), Annexin A1, B7-H3 (CD276, various cancers), CA125 (ovarian), CA15-3 (carcinomas), CA19-9 (carcinomas), L6 (carcinomas), Lewis Y (carcinomas), Lewis X (carcinomas), alpha fetoprotein (carcinomas), CA242 (colorectal), placental alkaline phosphatase (carcinomas), prostate specific antigen (prostate), prostatic acid phosphatase (prostate), epidermal growth factor (carcinomas), CD2 (Hodgkin's disease, NHL lymphoma, multiple myeloma), CD3 epsilon (T cell lymphoma, lung, breast, gastric, ovarian cancers, autoimmune diseases, malignant ascites), CD19 (B cell malignancies), CD20 (non-Hodgkin's lymphoma), CD22 (leukemia, lymphoma, multiple myeloma, SLE), CD30 (Hodgkin's lymphoma), CD33 (leukemia, autoimmune diseases), CD38 (multiple myeloma), CD40 (lymphoma, multiple myeloma, leukemia (CLL)), CD51 (Metastatic melanoma, sarcoma), CD52 (leukemia), CD56 (small cell lung cancers, ovarian cancer, Merkel cell carcinoma, and the liquid tumor, multiple myeloma), CD66e (cancers), CD70 (metastatic renal cell carcinoma and non-Hodgkin lymphoma), CD74 (multiple myeloma), CD80 (lymphoma), CD98 (cancers), mucin (carcinomas), CD221 (solid tumors), CD227 (breast, ovarian cancers), CD262 (NSCLC and other cancers), CD309 (ovarian cancers), CD326 (solid tumors), CEACAM3 (colorectal, gastric cancers), CEACAM5 (carcinoembryonic antigen; CEA, CD66e) (breast, colorectal and lung cancers), DLL4 (delta-like-4), EGFR (Epidermal Growth Factor Receptor, various cancers), CTLA4 (melanoma), CXCR4 (CD184, Heme-oncology, solid tumors), Endoglin (CD105, solid tumors), EPCAM (epithelial cell adhesion molecule, bladder, head, neck, colon, NHL prostate, and ovarian cancers), ERBB2 (Epidermal Growth Factor Receptor 2; lung, breast, prostate cancers), FCGR1 (autoimmune diseases), FOLR (folate receptor, ovarian cancers), GD2 ganglioside (cancers), G-28 (a cell surface antigen glyvolipid, melanoma), GD3 idiotype (cancers), Heat shock proteins (cancers), HER1 (lung, stomach cancers), HER2 (breast, lung and ovarian cancers), HLA-DR10 (NHL), HLA-DRB (NHL, B cell leukemia), human chorionic gonadotropin (carcinoma), IGF1R (insulin-like growth factor 1 receptor, solid tumors, blood cancers), IL-2 receptor (interleukin 2 receptor, T-cell leukemia and lymphomas), IL-6R (interleukin 6 receptor, multiple myeloma, RA, Castleman's disease, IL6 dependent tumors), Integrins (αvβ3, α5β1, α6β4, αllβ3, α5β5, αvβ5, for various cancers), MAGE-1 (carcinomas), MAGE-2 (carcinomas), MAGE-3 (carcinomas), MAGE 4 (carcinomas), anti-transferrin receptor (carcinomas), p97 (melanoma), MS4A1 (membrane-spanning 4-domains subfamily A member 1, Non-Hodgkin's B cell lymphoma, leukemia), MUC1 or MUC1-KLH (breast, ovarian, cervix, bronchus and gastrointestinal cancer), MUC16 (CA125) (Ovarian cancers), CEA (colorectal), gp100 (melanoma), MART1 (melanoma), MPG (melanoma), MS4A1 (membrane-spanning 4-domains subfamily A, small cell lung cancers, NHL), Nucleolin, Neu oncogene product (carcinomas), P21 (carcinomas), Paratope of anti-(N-glycolylneuraminic acid, Breast, Melanoma cancers), PLAP-like testicular alkaline phosphatase (ovarian, testicular cancers), PSMA (prostate tumors), PSA (prostate), ROBO4, TAG 72 (tumour associated glycoprotein 72, AML, gastric, colorectal, ovarian cancers), T cell transmembrane protein (cancers), Tie (CD202b), TNFRSF10B (tumor necrosis factor receptor superfamily member 10B, cancers), TNFRSF13B (tumor necrosis factor receptor superfamily member 13B, multiple myeloma, NHL, other cancers, RA and SLE), TPBG (trophoblast glycoprotein, Renal cell carcinoma), TRAIL-R1 (Tumor necrosis apoprosis Inducing ligand Receptor 1,lymphoma, NHL, colorectal, lung cancers), VCAM-1 (CD106, Melanoma), VEGF, VEGF-A, VEGF-2 (CD309) (various cancers). Some other tumor associated antigens recognized by antibodies have been reviewed (Gerber, et al, mAbs 1:3, 247-253 (2009); Novellino et al, Cancer Immunol Immunother. 54(3), 187-207 (2005). Franke, et al, Cancer Biother Radiopharm. 2000, 15, 459-76).

The cell-binding agents, more preferred antibodies, can be any agents that are able to against tumor cells, virus infected cells, microorganism infected cells, parasite infected cells, autoimmune cells, activated cells, myeloid cells, activated T-cells, B cells, or melanocytes. More specifically the cell binding agents can be any agent/molecule that is able to against any one of the following antigens or receptors: CD3, CD4, CD5, CD6, CD7, CD8, CD9, CD10, CD11a, CD11b, CD11c, CD12w, CD14, CD15, CD16, CDw17, CD18, CD19, CD20, CD21, CD22, CD23, CD24, CD25, CD26, CD27, CD28, CD29, CD30, CD31, CD32, CD33, CD34, CD35, CD36, CD37, CD38, CD39, CD40, CD41, CD42, CD43, CD44, CD45, CD46, CD47, CD48, CD49b, CD49c, CD51, CD52, CD53, CD54, CD55, CD56, CD58, CD59, CD61, CD62E, CD62L, CD62P, CD63, CD66, CD68, CD69, CD70, CD72, CD74, CD79, CD79a, CD79b, CD80, CD81, CD82, CD83, CD86, CD87, CD88, CD89, CD90, CD91, CD95, CD96, CD98, CD100, CD103, CD105, CD106, CD109, CD117, CD120, CD125, CD126, CD127, CD133, CD134, CD135, CD138, CD141, CD142, CD143, CD144, CD147, CD151, CD147, CD152, CD154, CD156, CD158, CD163, CD166, .CD168, CD174, CD180, CD184, CDw186, CD194, CD195, CD200, CD200a, CD200b, CD209, CD221, CD227, CD235a, CD240, CD262, CD271, CD274, CD276 (B7-H3), CD303, CD304, CD309, CD326, 4-1BB, 5AC, 5T4 (Trophoblast glycoprotein, TPBG, 5T4, Wnt-Activated Inhibitory Factor 1 or WAIF1), Adenocarcinoma antigen, AGS-5, AGS-22M6, Activin receptor-like kinase 1, AFP, AKAP-4, ALK, Alpha intergrin, Alpha v beta6, Amino-peptidase N, Amyloid beta, Androgen receptor, Angiopoietin 2, Angiopoietin 3, Annexin A1, Anthrax toxin protective antigen, Anti-transferrin receptor, AOC3 (VAP-1), B7-H3, *Bacillus anthracis* anthrax, BAFF (B-cell activating factor), B-lymphoma cell, bcr-abl, Bombesin, BORIS, C5, C242 antigen, CA125 (carbohydrate antigen 125, MUC16), CA-IX (or CAIX, carbonic anhydrase 9), CALLA, CanAg, *Canis lupus familiaris* IL31, Carbonic anhydrase IX, Cardiac myosin, CCL11 (C—C motif chemokine 11), CCR4 (C—C chemokine receptor type 4, CD194), CCR5, CD3E (epsilon), CEA (Carcinoembryonic antigen), CEACAM3, CEACAM5 (carcinoembryonic antigen), CFD (Factor D), Ch4D5, Cholecystokinin 2 (CCK2R), CLDN18 (Claudin-18), Clumping factor A, CRIPTO, FCSF1R (Colony stimulating factor 1 receptor, CD115), CSF2 (colony stimulating factor 2, Granulocyte-macrophage colony-stimulating factor (GM-CSF)), CTLA4 (cytotoxic T-lymphocyte-associated protein 4), CTAA16.88 tumor antigen, CXCR4 (CD184), C-X-C chemokine receptor type 4, cyclic ADP ribose hydrolase, Cyclin B1, CYP1B1, Cytomegalovirus, Cytomegalovirus glycoprotein B, Dabigatran, DLL4 (delta-like-ligand 4), DPP4 (Dipeptidyl-peptidase 4), DR5 (Death receptor 5), *E. coli* shiga toxin type-1, *E. coli* shiga toxin type-2, ED-B, EGFL7 (EGF-like domain-containing protein 7), EGFR, EGFRII, EGFRvIII, Endoglin (CD105), Endothelin B receptor, Endotoxin, EpCAM (epithelial cell adhesion molecule), EphA2, Episialin, ERBB2 (Epidermal Growth Factor Receptor 2), ERBB3, ERG (TMPRSS2 ETS fusion gene), *Escherichia coli*, ETV6-AML, FAP (Fibroblast activation protein alpha), FCGR1, alpha-Fetoprotein, Fibrin II, beta chain, Fibronectin extra domain-B, FOLR (folate receptor), Folate receptor alpha, Folate hydrolase, Fos-related antigen 1.F protein of respiratory syncytial virus, Frizzled receptor, Fucosyl GM1, GD2 ganglioside, G-28 (a cell surface antigen glyvolipid), GD3 idiotype, GloboH, Glypican 3, N-glycolylneuraminic acid, GM3, GMCSF receptor α-chain, Growth differentiation factor 8, GP100, GPNMB (Transmembrane glycoprotein NMB), GUCY2C (Guanylate cyclase 2C, guanylyl cyclase C(GC-C), intestinal Guanylate cyclase, Guanylate cyclase-C receptor, Heat-stable enterotoxin receptor (hSTAR)), Heat shock proteins, Hemagglutinin, Hepatitis B surface antigen, Hepatitis B virus, HER1 (human epidermal growth factor receptor 1), HER2, HER2/neu, HER3 (ERBB-3), IgG4, HGF/SF (Hepatocyte growth factor/scatter factor), HHGFR, HIV-1, Histone complex, HLA-DR (human leukocyte antigen), HLA-DR10, HLA-DRB, HMWMAA, Human chorionic gonadotropin, HNGF, Human scatter factor receptor kinase, HPV E6/E7, Hsp90, hTERT, ICAM-1 (Intercellular Adhesion Molecule 1), Idiotype, IGF1R (IGF-1, insulin-like growth factor 1 receptor), IGHE, IFN-γ, Influeza hemag-glutinin, IgE, IgE Fc region, IGHE, IL-1, IL-2 receptor (interleukin 2 receptor), IL-4, IL-5, IL-6, IL-6R (interleukin 6 receptor), IL-9, IL-10, IL-12, IL-13, IL-17, IL-17A, IL-20, IL-22, IL-23, IL31RA, ILGF2 (Insulin-like growth factor 2), Integrins (α4, $\alpha_{IIb}\beta_3$, αvβ3, $\alpha_4\beta_7$, α5β1, α6β4, α7β7, αllβ3, α5β5, αvβ5), Interferon gamma-induced protein, ITGA2, ITGB2, KIR2D, LCK, Le, Legumain, Lewis-Y antigen, LFA-1 (Lymphocyte function-associated antigen 1, CD11a), LHRH, LINGO-1, Lipoteichoic acid, LIV1A, LMP2, LTA, MAD-CT-1, MAD-CT-2, MAGE-1, MAGE-2, MAGE-3, MAGE A1, MAGE A3, MAGE 4, MART1, MCP-1, MIF (Macrophage migration inhibitory factor, or glycosylation-inhibiting factor (GIF)), MS4A1 (membrane-spanning 4-domains subfamily A member 1), MSLN (mesothelin), MUC1 (Mucin 1, cell surface associated (MUC1) or polymorphic epithelial mucin (PEM)), MUC1-KLH, MUC16 (CA125), MCP1 (monocyte chemotactic protein 1), MelanA/MART1, ML-IAP, MPG, MS4A1 (membrane-spanning 4-domains subfamily A), MYCN, Myelin-associated glycoprotein, Myostatin, NA17, NARP-1, NCA-90 (granulocyte antigen), Nectin-4 (ASG-22ME), NGF, Neural apoptosis-regulated proteinase 1, NOGO-A, Notch receptor, Nucleolin, Neu oncogene product, NY-BR-1, NY-ESO-1, OX-40, OxLDL (Oxidized low-density lipoprotein), OY-TES1, P21, p53 nonmutant, P97, Page4, PAP, Paratope of anti-(N-glycolylneuraminic acid), PAX3, PAX5, PCSK9, PDCD1 (PD-1, Programmed cell death protein 1,CD279), PDGF-Rα (Alpha-type platelet-derived growth factor receptor), PDGFR-β, PDL-1, PLAC1, PLAP-like testicular alkaline phosphatase, Platelet-derived growth factor receptor beta, Phosphate-sodium co-transporter, PMEL 17, Polysialic acid, Proteinase3 (PR1), Prostatic carcinoma, PS (Phosphatidylserine), Prostatic carcinoma cells, *Pseudomonas aeruginosa*, PSMA, PSA, PSCA, Rabies virus glycoprotein, RHD (Rh polypeptide 1 (RhPI), CD240), Rhesus factor, RANKL, RhoC, Ras mutant, RGS5, ROBO4, Respiratory syncytial virus, RON, Sarcoma translocation breakpoints, SART3, Sclerostin, SLAMF7 (SLAM family member 7), Selectin P, SDC1 (Syndecan 1), sLe(a), Somatomedin C, SIP (Sphingosine-1-phosphate), Somatostatin, Sperm protein 17, SSX2, STEAP1 (six-transmembrane epithelial antigen of the prostate 1), STEAP2, STn, TAG-72 (tumor associated glycoprotein 72), Survivin, T-cell receptor, T cell transmembrane protein, TEM1 (Tumor endothelial marker 1), TENB2, Tenascin C (TN-C), TGF-α, TGF-β (Transforming growth factor beta), TGF-β1, TGF-β2 (Transforming growth factor-beta 2), Tie (CD202b), Tie2, TIM-1 (CDX-014), Tn, TNF, TNF-α, TNFRSF8, TNFRSF10B (tumor necrosis factor receptor superfamily member 10B), TNFRSF13B (tumor necrosis factor receptor superfamily member 13B), TPBG (trophoblast glycoprotein), TRAIL-R1 (Tumor necrosis apoprosis Inducing ligand Receptor 1), TRAILR2 (Death receptor 5 (DR5)), tumor-associated calcium signal transducer 2, tumor specific glycosylation of MUC1, TWEAK receptor, TYRP1 (glycoprotein 75), TRP-2, Tyrosinase, VCAM-1 (CD106), VEGF, VEGF-A, VEGF-2 (CD309), VEGFR-1, VEGFR2, or vimentin, WT1, XAGE 1, or cells expressing any insulin growth factor receptors, or any epidermal growth factor receptors.

In another specific embodiment, the cell-binding ligand-drug conjugates via the bridge linkers of this invention are used for the targeted treatment of cancers. The targeted cancers include, but are not limited, Adrenocortical Carcinoma, Anal Cancer, Bladder Cancer, Brain Tumor (Adult, Brain Stem Glioma, Childhood, Cerebellar Astrocytoma, Cerebral Astrocytoma, Ependymoma, Medulloblastoma, Supratentorial Primitive Neuroectodermal and Pineal Tumors, Visual Pathway and Hypothalamic Glioma), Breast Cancer, Carcinoid Tumor, Gastrointestinal, Carcinoma of Unknown Primary, Cervical Cancer, Colon Cancer, Endometrial Cancer, Esophageal Cancer, Extrahepatic Bile Duct Cancer, Ewings Family of Tumors (PNET), Extracranial Germ Cell Tumor, Eye Cancer, Intraocular Melanoma, Gallbladder Cancer, Gastric Cancer (Stomach), Germ Cell Tumor, Extragonadal, Gestational Trophoblastic Tumor, Head and Neck Cancer, Hypopharyngeal Cancer, Islet Cell Carcinoma, Kidney Cancer (renal cell cancer), Laryngeal Cancer, Leukemia (Acute Lymphoblastic, Acute Myeloid, Chronic Lymphocytic, Chronic Myelogenous, Hairy Cell), Lip and Oral Cavity Cancer, Liver Cancer, Lung Cancer (Non-Small Cell, Small Cell, Lymphoma (AIDS-Related, Central Nervous System, Cutaneous T-Cell, Hodgkin's Disease, Non-Hodgkin's Disease, Malignant Mesothelioma, Melanoma, Merkel Cell Carcinoma, Metasatic Squamous Neck Cancer with Occult Primary, Multiple Myeloma, and Other Plasma Cell Neoplasms, Mycosis Fungoides, Myelodysplastic Syndrome, Myeloproli-ferative Disorders, Nasopharyngeal Cancer, Neuroblastoma, Oral Cancer, Oropharyngeal Cancer, Osteosarcoma, Ovarian Cancer (Epithelial, Germ Cell Tumor, Low Malignant Potential Tumor), Pancreatic Cancer (Exocrine, Islet Cell Carcinoma), Paranasal Sinus and Nasal Cavity Cancer, Parathyroid Cancer, Penile Cancer, Pheochromocytoma Cancer, Pituitary Cancer, Plasma Cell Neoplasm, Prostate Cancer Rhabdomyosarcoma, Rectal Cancer, Renal Cell Cancer (kidney cancer), Renal Pelvis and Ureter (Transitional Cell), Salivary Gland Cancer, Sezary Syndrome, Skin Cancer, Skin Cancer (Cutaneous T-Cell Lymphoma, Kaposi's Sarcoma, Melanoma), Small Intestine Cancer, Soft Tissue Sarcoma, Stomach Cancer, Testicular Cancer, Thymoma (Malignant), Thyroid Cancer, Urethral Cancer, Uterine Cancer (Sarcoma), Unusual Cancer of Childhood, Vaginal Cancer, Vulvar Cancer, Wilms' Tumor.

In another specific embodiment, the cell-binding-drug conjugates via the bridge likers of this invention are used in accordance with the compositions and methods for the treatment or prevention of an autoimmune disease. The autoimmune diseases include, but are not limited, Achlorhydra Autoimmune Active Chronic Hepatitis, Acute Disseminated Encephalomyelitis, Acute hemorrhagic leukoencephalitis, Addison's Disease, Agammaglobulinemia, Alopecia areata, Amyotrophic Lateral Sclerosis, Ankylosing Spondylitis, Anti-GBM/TBM Nephritis, Antiphospholipid syndrome, Antisynthetase syndrome, Arthritis, Atopic allergy, Atopic Dermatitis, Autoimmune Aplastic Anemia, Autoimmune cardiomyopathy, Autoimmune hemolytic anemia, Autoimmune hepatitis, Autoimmune inner ear disease, Autoimmune lymphoproliferative syndrome, Autoimmune peripheral neuropathy, Autoimmune pancreatitis, Autoimmune polyendocrine syndrome Types I, II, & III, Autoimmune progesterone dermatitis, Autoimmune thrombocytopenic purpura, Autoimmune uveitis, Balo disease/Balo concentric sclerosis, Bechets Syndrome, Berger's disease, Bickerstaffs encephalitis, Blau syndrome, Bullous Pemphigoid, Castleman's disease, Chagas disease, Chronic Fatigue Immune Dysfunction Syndrome, Chronic inflammatory demyelinating polyneuropathy, Chronic recurrent multifocal ostomyelitis, Chronic lyme disease, Chronic obstructive pulmonary disease, Churg-Strauss syndrome, Cicatricial Pemphigoid, Coeliac Disease, Cogan syndrome, Cold agglutinin disease, Complement component 2 deficiency, Cranial arteritis, CREST syndrome, Crohns Disease (a type of idiopathic inflammatory bowel diseases), Cushing's Syndrome, Cutaneous leukocytoclastic angiitis, Dego's disease, Dercum's disease, Dermatitis herpetiformis, Dermatomyositis, Diabetes mellitus type 1, Diffuse cutaneous systemic sclerosis, Dressler's syndrome, Discoid lupus erythematosus, Eczema, Endometriosis, Enthesitis-related arthritis, Eosinophilic fasciitis, Epidermolysis bullosa acquisita, Erythema nodosum, Essential mixed cryoglobulinemia, Evan's syndrome, Fibrodysplasia ossificans progressiva, Fibromyalgia, Fibromyositis, Fibrosing aveolitis, Gastritis, Gastrointestinal pemphigoid, Giant cell arteritis, Glomerulonephritis, Goodpasture's syndrome, Graves' disease, Guillain-Barré syndrome, Hashimoto's encephalitis, Hashimoto's thyroiditis, Haemolytic anaemia, Henoch-Schonlein purpura, Herpes gestationis, Hidradenitis suppurativa, Hughes syndrome (See Antiphospholipid syndrome), Hypogammaglobulinemia, Idiopathic Inflammatory Demyelinating Diseases, Idiopathic pulmonary fibrosis, Idiopathic thrombocytopenic purpura (See Autoimmune thrombocytopenic purpura), IgA nephropathy (Also Berger's disease), Inclusion body myositis, Inflammatory demyelinating polyneuopathy, Interstitial cystitis, Irritable Bowel Syndrome, Juvenile idiopathic arthritis, Juvenile rheumatoid arthritis, Kawasaki's Disease, Lambert-Eaton myasthenic syndrome, Leukocytoclastic vasculitis, Lichen planus, Lichen sclerosus, Linear IgA disease (LAD), Lou Gehrig's Disease (Also Amyotrophic lateral sclerosis), Lupoid hepatitis, Lupus erythematosus, Majeed syndrome, Ménière's disease, Microscopic polyangiitis, Miller-Fisher syndrome, Mixed Connective Tissue Disease, Morphea, Mucha-Habermann disease, Muckle-Wells syndrome, Multiple Myeloma, Multiple Sclerosis, Myasthenia gravis, Myositis, Narcolepsy, Neuromyelitis optica (Devic's Disease), Neuromyotonia, Occular cicatricial pemphigoid, Opsoclonus myoclonus syndrome, Ord thyroiditis, Palindromic rheumatism, PANDAS (Pediatric Autoimmune Neuropsychiatric Disorders Associated with *Streptococcus*), Paraneoplastic cerebellar degeneration, Paroxysmal nocturnal hemoglobinuria, Parry Romberg syndrome, Parsonnage-Turner syndrome, Pars planitis, Pemphigus, Pemphigus vulgaris, Pernicious anaemia, Perivenous encephalomyelitis, POEMS syndrome, Polyarteritis nodosa, Polymyalgia rheumatica, Polymyositis, Primary biliary cirrhosis, Primary sclerosing cholangitis, Progressive inflammatory neuropathy, Psoriasis, Psoriatic Arthritis, Pyoderma gangrenosum, Pure red cell aplasia, Rasmussen's encephalitis, Raynaud phenomenon, Relapsing polychondritis, Reiter's syndrome, Restless leg syndrome, Retroperitoneal fibrosis, Rheumatoid arthritis, Rheumatoid fever, Sarcoidosis, Schizophrenia, Schmidt syndrome, Schnitzler syndrome, Scleritis, Scleroderma, Sjögren's syndrome, Spondyloarthropathy, Sticky blood syndrome, Still's Disease, Stiff person syndrome, Subacute bacterial endocarditis, Susac's syndrome, Sweet syndrome, Sydenham Chorea, Sympathetic ophthalmia, Takayasu's arteritis, Temporal arteritis (giant cell arteritis), Tolosa-Hunt syndrome, Transverse Myelitis, Ulcerative Colitis (a type of idiopathic inflammatory bowel diseases), Undifferentiated connective tissue disease, Undifferentiated spondyloarthropathy, Vasculitis, Vitiligo, Wegener's granulomatosis, Wilson's syndrome, Wiskott-Aldrich syndrome In another specific embodiment, a binding molecule used for the conjugate via the bridge linkers of this invention for the treatment or prevention of an autoimmune disease can be, but are not limited to, anti-elastin antibody; Abys against epithelial cells antibody; Anti-Basement Membrane Collagen Type IV Protein antibody; Anti-Nuclear Antibody; Anti ds DNA; Anti ss DNA, Anti Cardiolipin Antibody IgM, IgG; anti-celiac antibody; Anti Phospholipid Antibody IgK, IgG; Anti SM Antibody; Anti Mitochondrial Antibody; Thyroid Antibody; Microsomal Antibody, T-cells antibody; Thyroglobulin Antibody, Anti SCL-70; Anti-Jo; Anti-U.sub.1RNP; Anti-La/SSB; Anti SSA; Anti SSB; Anti Perital Cells Antibody; Anti Histones; Anti RNP; C-ANCA; P-ANCA; Anti centromere; Anti-Fibrillarin, and Anti GBM Antibody, Anti-ganglioside antibody; Anti-Desmogein 3 antibody; Anti-p62 antibody; Anti-sp100 antibody; Anti-Mitochondrial(M2) antibody; Rheumatoid factor antibody; Anti-MCV antibody; Anti-topoisomerase antibody; Anti-neutrophil cytoplasmic (cANCA) antibody.

In certain preferred embodiments, the binding molecule for the conjugate in the present invention, can bind to both a receptor and a receptor complex expressed on an activated lymphocyte which is associated with an autoimmune disease. The receptor or receptor complex can comprise an immunoglobulin gene superfamily member (e.g. CD2, CD3, CD4, CD8, CD19, CD20, CD22, CD28, CD30, CD33, CD37, CD38, CD56, CD70, CD79, CD79b, CD90, CD125, CD147, CD152/CTLA-4, PD-1, or ICOS), a TNF receptor superfamily member (e.g. CD27, CD40, CD95/Fas, CD134/OX40, CD137/4-1BB, INF-R1, TNFR-2, RANK, TACI, BCMA, osteoprotegerin, Apo2/TRAIL-R1, TRAIL-R2, TRAIL-R3, TRAIL-R4, and APO-3), an integrin, a cytokine receptor, a chemokine receptor, a major histocompatibility protein, a lectin (C-type, S-type, or I-type), or a complement control protein.

In another specific embodiment, useful cell binding ligands that are immunospecific for a viral or a microbial antigen are humanized or human monoclonal antibodies. As used herein, the term "viral antigen" includes, but is not limited to, any viral peptide, polypeptide protein (e.g. HIV gp120, HIV nef, RSV F glycoprotein, influenza virus neuramimi-dase, influenza virus hemagglutinin, HTLV tax, herpes simplex virus glycoprotein (e.g. gB, gC, gD, and gE) and hepatitis B surface antigen) that is capable of eliciting an immune response. As used herein, the term "microbial antigen" includes, but is not limited to, any microbial peptide, polypeptide, protein, saccharide, polysaccharide, or lipid molecule (e.g., a bacteria, fungi, pathogenic protozoa, or yeast polypeptides including, e.g., LPS and capsular polysaccharide 5/8) that is capable of eliciting an immune response. Examples of antibodies available 1 for the viral or microbial infection include, but are not limited to, Palivizumab which is a humanized anti-respiratory syncytial virus monoclonal antibody for the treatment of RSV infection; PRO542 which is a CD4 fusion antibody for the treatment of HIV infection; Ostavir which is a human antibody for the treatment of hepatitis B virus; PROTVIR which is a humanized IgG.sub.1 antibody for the treatment of cytomegalovirus; and anti-LPS antibodies.

The cell binding molecules-drug conjugates via the bridge linkers of this invention can be used in the treatment of infectious diseases. These infectious diseases include, but are not limited to, *Acinetobacter* infections, Actinomycosis, African sleeping sickness (African trypanosomiasis), AIDS (Acquired immune deficiency syndrome), Amebiasis, Anaplasmosis, Anthrax, *Arcanobacterium haemolyticum* infection, Argentine hemorrhagic fever, Ascariasis, Aspergillosis, Astrovirus infection, Babesiosis, *Bacillus cereus* infection, Bacterial pneumonia, Bacterial vaginosis, *Bacteroides* infection, Balantidiasis, *Baylisascaris* infection, BK virus infection, Black *piedra, Blastocystis hominis* infection, Blastomycosis, Bolivian hemorrhagic fever, *Borrelia* infection, Botulism (and Infant botulism), Brazilian hemorrhagic fever, Brucellosis, *Burkholderia* infection, Buruli ulcer, Calicivirus infection (Norovirus and Sapovirus), Campylobacteriosis, Candidiasis (Moniliasis; Thrush), Cat-scratch disease, Cellulitis, Chagas Disease (American trypanosomiasis), Chancroid, Chickenpox, *Chlamydia, Chlamydophila pneumoniae* infection, Cholera, Chromoblastomycosis, Clonorchiasis, *Clostridium difficile* infection, Coccidioidomycosis, Colorado tick fever, Common cold (Acute viral rhinopharyngitis; Acute coryza), Creutzfeldt-Jakob disease, Crimean-Congo hemorrhagic fever, Cryptococcosis, Cryptosporidiosis, Cutaneous larva migrans, Cyclosporiasis, Cysticercosis, Cytomegalovirus infection, Dengue fever, Dientamoebiasis, Diphtheria, Diphyllobothriasis, Dracunculiasis, Ebola hemorrhagic fever, Echinococcosis, Ehrlichiosis, Enterobiasis (Pinworm infection), *Enterococcus* infection, *Enterovirus* infection, Epidemic typhus, Erythema infectiosum (Fifth disease), Exanthem subitum, Fasciolopsiasis, Fasciolosis, Fatal familial insomnia, Filariasis, Food poisoning by *Clostridium perfringens*, Free-living amebic infection, *Fusobacterium* infection, Gas gangrene (Clostridial myonecrosis), Geotrichosis, Gerstmann-Sträussler-cheinker syndrome, Giardiasis, Glanders, Gnathosto-miasis, Gonorrhea, Granuloma inguinale (Donovanosis), Group A streptococcal infection, Group B streptococcal infection, *Haemophilus influenzae* infection, Hand, foot and mouth disease (HFMD), Hantavirus Pulmonary Syndrome, *Helicobacter pylori* infection, Hemolytic-uremic syndrome, Hemorrhagic fever with renal syndrome, Hepatitis A, Hepatitis B, Hepatitis C, Hepatitis D, Hepatitis E, Herpes simplex, Histoplasmosis, Hookworm infection, Human bocavirus infection, Human ewingii ehrlichiosis, Human granulocytic anaplasmosis, Human metapneumovirus infection, Human monocytic ehrlichiosis, Human papillomavirus infection, Human parainfluenza virus infection, Hymenolepiasis, Epstein-Barr Virus Infectious Mononucleosis (Mono), Influenza, Isosporiasis, Kawasaki disease, Keratitis, Kingella kingae infection, Kuru, Lassa fever, Legionellosis (Legionnaires' disease), Legionellosis (Pontiac fever), Leishmaniasis, Leprosy, Leptospirosis, Listeriosis, Lyme disease (Lyme borreliosis), Lymphatic filariasis (Elephantiasis), Lymphocytic choriomeningitis, Malaria, Marburg hemorrhagic fever, Measles, Melioidosis (Whitmore's disease), Meningitis, Meningococcal disease, Metagonimiasis, Microsporidiosis, Molluscum contagiosum, Mumps, Murine typhus (Endemic typhus), *Mycoplasma* pneumonia, Mycetoma, Myiasis, Neonatal conjunctivitis (Ophthalmia neonatorum), (New) Variant Creutzfeldt-Jakob disease (vCJD, nvCJD), Nocardiosis, Onchocerciasis (River blindness), Paracoccidioidomycosis (South American blastomycosis), Paragonimiasis, Pasteurellosis, Pediculosis capitis (Head lice), Pediculosis corporis (Body lice), Pediculosis pubis (Pubic lice, Crab lice), Pelvic inflammatory disease, Pertussis (Whooping cough), Plague, Pneumococcal infection, *Pneumocystis* pneumonia, Pneumonia, Poliomyelitis, *Prevotella* infection, Primary amoebic meningoencephalitis, Progressive multifocal leukoencephalopathy, Psittacosis, Q fever, Rabies, Rat-bite fever, Respiratory syncytial virus infection, Rhinosporidiosis, Rhinovirus infection, Rickettsial infection, Rickettsial-pox, Rift Valley fever, Rocky mountain spotted fever, Rotavirus infection, Rubella, *Salmonellosis*, SARS (Severe Acute Respiratory Syndrome), Scabies, Schistosomiasis, Sepsis, Shigellosis (Bacillary dysentery), Shingles (Herpes zoster), Smallpox (Variola), Sporotrichosis, Staphylococcal food poisoning, Staphylococcal infection, Strongyloidiasis, Syphilis, Taeniasis, Tetanus (Lockjaw), Tinea barbae (Barber's itch), Tinea capitis (Ringworm of the Scalp), Tinea corporis (Ringworm of the Body), Tinea cruris (Jock itch), Tinea manuum (Ringworm of the Hand), Tinea nigra, Tinea pedis (Athlete's foot), Tinea unguium (Onychomycosis), Tinea versicolor (*Pityriasis versicolor*), Toxocariasis (Ocular Larva Migrans), Toxocariasis (Visceral Larva Migrans), Toxoplasmosis, Trichinellosis, Trichomoniasis, Trichuriasis (Whipworm infection), Tuberculosis, Tularemia, *Ureaplasma urealyticum* infection, Venezuelan equine encephalitis, Venezuelan hemorrhagic fever, Viral pneumonia, West Nile Fever, White piedra (Tinea blanca), *Yersinia* pseudotuberculosis infection, Yersiniosis, Yellow fever, Zygomycosis.

The cell binding molecule, which is more preferred to be an antibody described in this patent that are against pathogenic strains include, but are not limit, *Acinetobacter baumannii, Actinomyces israelii, Actinomyces gerencseriae* and *Propionibacterium propionicus, Trypanosoma brucei*, HIV (Human immunodeficiency virus), *Entamoeba histolytica, Anaplasma genus, Bacillus anthracis, Arcanobacterium haemolyticum, Junin virus, Ascaris lumbricoides, Aspergillus* genus, Astroviridae family, *Babesia* genus, *Bacillus cereus*, multiple bacteria, *Bacteroides* genus, *Balantidium coli, Baylisascaris* genus, BK virus, Piedraia hortae, *Blastocystis hominis, Blastomyces dermatitides*, Machupo virus, *Borrelia* genus, *Clostridium botulinum, Sabia, Brucella* genus, usually *Burkholderia cepacia* and other *Burkholderia* species, *Mycobacterium ulcerans*, Caliciviridae family, *Campylobacter* genus, usually *Candida albicans* and other *Candida* species, *Bartonella henselae*, Group A *Streptococcus* and *Staphylococcus, Trypanosoma cruzi, Haemophilus ducreyi*, Varicella zoster virus (VZV), *Chlamydia trachomatis, Chlamydophila pneumoniae, Vibrio cholerae, Fonsecaea pedrosoi, Clonorchis sinensis, Clostridium difficile, Coccidioides immitis* and *Coccidioides posadasii*, Colorado tick fever virus, rhinoviruses, coronaviruses, CJD prion, Crimean-Congo hemorrhagic fever virus, *Cryptococcus neoformans, Cryptosporidium genus, Ancylostoma braziliense*; multiple parasites, *Cyclospora cayetanensis, Taenia solium*, Cytomegalovirus, Dengue viruses (DEN-1, DEN-2, DEN-3 and DEN-4)-Flaviviruses, *Dientamoeba fragilis, Corynebacterium diphtheriae, Diphyllobothrium, Dracunculus medinensis*, Ebolavirus, *Echinococcus* genus, *Ehrlichia* genus, *Enterobius vermicularis, Enterococcus* genus, *Enterovirus* genus, *Rickettsia prowazekii*, Parvovirus B19, Human herpesvirus 6 and Human herpesvirus 7, *Fasciolopsis buski, Fasciola hepatica* and *Fasciola gigantica*, FFI prion, Filarioidea superfamily, *Clostridium perfringens, Fusobacterium genus, Clostridium perfringens*; other *Clostridium* species, *Geotrichum candidum*, GSS prion, *Giardia intestinalis, Burkholderia mallei, Gnathostoma spinigerum* and *Gnathostoma hispidum, Neisseria gonorrhoeae, Klebsiella granulomatis, Streptococcus pyogenes, Streptococcus agalactiae, Haemophilus influenzae*, Enteroviruses, mainly Coxsackie A virus and *Enterovirus* 71, Sin Nombre virus, *Helicobacter pylori, Escherichia coli* O157: H7, Bunyaviridae family, Hepatitis A Virus, Hepatitis B Virus, Hepatitis C Virus, Hepatitis D Virus, Hepatitis E Virus, Herpes simplex virus 1, Herpes simplex virus 2, *Histoplasma capsulatum, Ancylostoma duodenale* and *Necator americanus, Hemophilus influenzae, Human bocavirus, Ehrlichia ewingii, Anaplasma phagocytophilum, Human metapneumovirus, Ehrlichia chaffeensis*, Human papillomavirus, Human parainfluenza viruses, *Hymenolepis nana* and *Hymenolepis diminuta*, Epstein-Barr Virus, Orthomy-xoviridae family, *Isospora belli, Kingella kingae, Klebsiella pneumoniae, Klebsiella ozaenas, Klebsiella rhinoscleromotis*, Kuru prion, Lassa virus, *Legionella pneumophila, Legionella pneumophila, Leishmania* genus, *Mycobacterium leprae* and *Mycobacterium lepromatosis, Leptospira* genus, *Listeria monocytogenes, Borrelia burgdorferi* and other *Borrelia* species, *Wuchereria bancrofti* and *Brugia malayi*, Lymphocytic choriomeningitis virus (LCMV), *Plasmodium* genus, Marburg virus, Measles virus, *Burkholderia pseudomallei, Neisseria meningitides, Metagonimus yokagawai*, Microsporidia phylum, Molluscum contagiosum virus (MCV), Mumps virus, *Rickettsia typhi, Mycoplasma pneumoniae*, numerous species of bacteria (Actinomycetoma) and fungi (Eumycetoma), parasitic dipterous fly larvae, *Chlamydia trachomatis* and *Neisseria gonorrhoeae*, vCJD prion, *Nocardia asteroides* and other *Nocardia* species, *Onchocerca volvulus, Paracoccidioides brasiliensis, Paragonimus westermani* and other *Paragonimus* species, *Pasteurella* genus, *Pediculus humanus* capitis, *Pediculus humanus* corporis, *Phthirus pubis, Bordetella pertussis, Yersinia pestis, Streptococcus pneumoniae, Pneumocystis jirovecii*, Poliovirus, *Prevotella* genus, *Naegleria fowleri*, JC virus, *Chlamydophila psittaci, Coxiella burnetii, Rabies virus, Streptobacillus moniliformis* and Spirillum minus, Respiratory syncytial virus, *Rhinosporidium seeberi*, Rhinovirus, *Rickettsia* genus, *Rickettsia akari*, Rift Valley fever virus, *Rickettsia rickettsii*, Rotavirus, Rubella virus, *Salmonella* genus, SARS coronavirus, *Sarcoptes scabiei, Schistosoma genus, Shigella* genus, Varicella zoster virus, Variola major or Variola minor, *Sporothrix schenckii, Staphylococcus genus, Staphylococcus* genus, *Staphylococcus aureus, Streptococcus pyogenes, Strongyloides stercoralis, Treponema pallidum, Taenia* genus, *Clostridium tetani, Trichophyton* genus, *Trichophyton tonsurans, Trichophyton* genus, *Epidermophyton floccosum, Trichophyton rubrum*, and *Trichophyton mentagrophytes, Trichophyton rubrum, Hortaea werneckii, Trichophyton* genus, *Malassezia genus, Toxocara canis* or *Toxocara cati, Toxoplasma gondii, Trichinella spiralis, Trichomonas vaginalis, Trichuris trichiura, Mycobacterium tuberculosis, Francisella tularensis, Ureaplasma urealyticum*, Venezuelan equine encephalitis virus, *Vibrio* colerae, Guanarito virus, West Nile virus, *Trichosporon beigelii, Yersinia pseudotuberculosis, Yersinia enterocolitica*, Yellow fever virus, Mucorales order (Mucormycosis) and Entomophthorales order (*Entomophthoramycosis*), *Pseudomonas aeruginosa, Campylobacter* (*Vibrio*) fetus, *Aeromonas hydrophila, Edwardsiella tarda, Yersinia pestis, Shigella dysenteriae, Shigella flexneri, Shigella sonnei, Salmonella typhimurium, Treponema pertenue, Treponema carateneum, Borrelia vincentii, Borrelia burgdorferi, Leptospira icterohemorrhagiae, Pneumocystis carinii, Brucella abortus, Brucella suis, Brucella melitensis, Mycoplasma* spp., *Rickettsia prowazeki, Rickettsia tsutsugumushi, Clamydia* spp.; pathogenic fungi (*Aspergillus fumigatus, Candida albicans, Histoplasma capsulatum*); protozoa (Entomoeba *histolytica, Trichomonas tenas, Trichomonas hominis, Tryoanosoma gambiense, Trypanosoma rhodesiense, Leishmania donovani, Leishmania tropica, Leishmania braziliensis, Pneumocystis pneumonia, Plasmodium vivax, Plasmodium falciparum, Plasmodium malaria*); or Helminiths (*Schistosoma japonicum, Schistosoma mansoni, Schistosoma haematobium*, and hookworms).

Other antibodies as cell binding ligands used in this invention for treatment of viral disease include, but are not limited to, antibodies against antigens of pathogenic viruses, including as examples and not by limitation: Poxyiridae, Herpesviridae, Adenoviridae, Papovaviridae, Enteroviridae, Picornaviridae, Parvoviridae, Reoviridae, Retroviridae, influenza viruses, parainfluenza viruses, mumps, measles, respiratory syncytial virus, rubella, Arboviridae, Rhabdoviridae, Arenaviridae, Non-A/Non-B Hepatitis virus, Rhinoviridae, Coronaviridae, Rotoviridae, Oncovirus [such as, HBV (Hepatocellular carcinoma), HPV (Cervical cancer, Anal cancer), Kaposi's sarcoma-associated herpesvirus (Kaposi's sarcoma), Epstein-Barr virus (Nasopharyngeal carcinoma, Burkitt's lymphoma, Primary central nervous system lymphoma), MCPyV (Merkel cell cancer), SV40 (Simian virus 40), HCV (Hepatocellular carcinoma), HTLV-I (Adult T-cell leukemia/lymphoma)], Immune disorders caused virus: [such as Human Immunodeficiency Virus (AIDS)]; Central nervous system virus: [such as, JCV (Progressive multifocal leukoencephalopathy), MeV (Subacute sclerosing panencephalitis), LCV (Lymphocytic choriomeningitis), Arbovirus encephalitis, Orthomyxoviridae (probable) (Encephalitis lethargica), RV (Rabies), Chandipura virus, Herpesviral meningitis, Ramsay Hunt syndrome type II; Poliovirus (Poliomyelitis, Post-polio syndrome), HTLV-I (Tropical spastic paraparesis)]; Cytomegalovirus (Cytomegalovirus retinitis, HSV (Herpetic keratitis)); Cardiovascular virus [such as CBV (Pericarditis, Myocarditis)]; Respiratory system/acute viral nasopharyngitis/viral pneumonia: [Epstein-Barr virus (EBV infection/Infectious mononucleosis), Cytomegalovirus; SARS coronavirus (Severe acute respiratory syndrome) Orthomyxoviridae: Influenzavirus A/B/C (Influenza/Avian influenza), Paramyxovirus: Human parainfluenza viruses (Parainfluenza), RSV (Human respiratory syncytial virus), hMPV]; Digestive system virus [MuV (Mumps), Cytomegalovirus (Cytomegalovirus esophagitis); Adenovirus (Adenovirus infection); Rotavirus, Norovirus, Astrovirus, Coronavirus; HBV (Hepatitis B virus), CBV, HAV (Hepatitis A virus), HCV (Hepatitis C virus), HDV (Hepatitis D virus), HEV (Hepatitis E virus), HGV (Hepatitis G virus)]; Urogenital virus [such as, BK virus, MuV (Mumps)].

According to a further object, the present invention also concerns pharmaceutical compositions comprising the conjugate via the bridge linkers of the invention together with a pharmaceutically acceptable carrier, diluent, or excipient for treatment of cancers, infections or autoimmune disorders. The method for treatment of cancers, infections and autoimmune disorders can be practiced in vitro, in vivo, or ex vivo. Examples of in vitro uses include treatments of cell cultures in order to kill all cells except for desired variants that do not express the target antigen; or to kill variants that express undesired antigen. Examples of ex vivo uses include treatments of hematopoietic stem cells (HSC) prior to the performance of the transplantation (HSCT) into the same patient in order to kill diseased or malignant cells. For instance, clinical ex vivo treatment to remove tumour cells or lymphoid cells from bone marrow prior to autologous transplantation in cancer treatment or in treatment of autoimmune disease, or to remove T cells and other lymphoid cells from allogeneic bone marrow or tissue prior to transplant in order to prevent graft-versus-host disease, can be carried out as follows. Bone marrow is harvested from the patient or other individual and then incubated in medium containing serum to which is added the conjugate of the invention, concentrations range from about 1 pM to 0.1 mM, for about 30 minutes to about 48 hours at about 37° C. The exact conditions of concentration and time of incubation (=dose) are readily determined by the skilled clinicians. After incubation, the bone marrow cells are washed with medium containing serum and returned to the patient by i.v. infusion according to known methods. In circumstances where the patient receives other treatment such as a course of ablative chemotherapy or total-body irradiation between the time of harvest of the marrow and reinfusion of the treated cells, the treated marrow cells are stored frozen in liquid nitrogen using standard medical equipment.

For clinical in vivo use, the conjugate via the linkers of the invention will be supplied as solutions or as a lyophilized solid that can be redissolved in sterile water for injection. Examples of suitable protocols of conjugate administration are as follows. Conjugates are given weekly for 8~20 weeks as an i.v. bolus. Bolus doses are given in 50 to 500 ml of normal saline to which human serum albumin (e.g. 0.5 to 1 mL of a concentrated solution of human serum albumin, 100 mg/mL) can be added. Dosages will be about 50 μg to 20 mg/kg of body weight per week, i.v. (range of 10 μg to 200 mg/kg per injection). 4~20 weeks after treatment, the patient may receive a second course of treatment. Specific clinical protocols with regard to route of administration, excipients, diluents, dosages, times, etc., can be determined by the skilled clinicians.

Examples of medical conditions that can be treated according to the in vivo or ex vivo methods of killing selected cell populations include malignancy of any types of cancer, autoimmune diseases, graft rejections, and infections (viral, bacterial or parasite).

The amount of a conjugate which is required to achieve the desired biological effect, will vary depending upon a number of factors, including the chemical characteristics, the potency, and the bioavailability of the conjugates, the type of disease, the species to which the patient belongs, the diseased state of the patient, the route of administration, all factors which dictate the required dose amounts, delivery and regimen to be administered.

In general terms, the conjugates via the linkers of this invention may be provided in an aqueous physiological buffer solution containing 0.1 to 10% w/v conjugates for parenteral administration. Typical dose ranges are from 1 μg/kg to 0.1 g/kg of body weight per day; a preferred dose range is from 0.01 mg/kg to 20 mg/kg of body weight per day, or per week, or an equivalent dose in a human child. The preferred dosage of drug to be administered is likely to depend on such variables as the type and extent of progression of the disease or disorder, the overall health status of the particular patient, the relative biological efficacy of the compound selected, the formulation of the compound, the route of administration (intravenous, intramuscular, or other), the pharmacokinetic properties of the conjugates by the chosen delivery route, and the speed (bolus or continuous infusion) and schedule of administrations (number of repetitions in a given period of time).

The conjugates via the linkers of the present invention are also capable of being administered in unit dose forms, wherein the term "unit dose" means a single dose which is capable of being administered to a patient, and which can be readily handled and packaged, remaining as a physically and chemically stable unit dose comprising either the active conjugate itself, or as a pharmaceutically acceptable composition, as described hereinafter. As such, typical total daily/weekly/biweekly/monthly dose ranges are from 0.01 to 100 mg/kg of body weight. By way of general guidance, unit doses for humans range from 1 mg to 3000 mg per day, or per week, per two week or per month. Preferably the unit dose range is from 1 to 500 mg administered one to four times a week, and even more preferably from 1 mg to 100 mg, once a week. Conjugates provided herein can be formulated into pharmaceutical compositions by admixture with one or more pharmaceutically acceptable excipients. Such unit dose compositions may be prepared for use by oral administration, particularly in the form of tablets, simple capsules or soft gel capsules; or intranasal, particularly in the form of powders, nasal drops, or aerosols; or dermally, for example, topically in ointments, creams, lotions, gels or sprays, or via transdermal patches.

Drugs/Cytotoxic Agents

Drugs that can be conjugated to a cell-binding molecule in the present invention are small molecule drugs including cytotoxic agents, which can be linked to or after they are modified for linkage to the cell-binding agent. A "small molecule drug" is broadly used herein to refer to an organic, inorganic, or organometallic compound that may have a molecular weight of for example 100 to 1800, more suitably from 120 to 1400. Small molecule drugs are well characterized in the art, such as in WO05058367A2, and in U.S. Pat. No. 4,956,303, among others and are incorporated in their entirety by reference. The drugs include known drugs and those that may become known drugs.

Drugs that are known include, but not limited to,

1). Chemotherapeutic agents: a). Alkylating agents: such as Nitrogen mustards: chlorambucil, chlornaphazine, cyclophosphamide, dacarbazine, estramustine, ifosfamide, mechlorethamine, mechlorethamine oxide hydrochloride, mannomustine, mitobronitol, melphalan, mitolactol, pipobroman, novembichin, phenesterine, prednimustine, thiotepa, trofosfamide, uracil mustard; CC-1065 (including its adozelesin, carzelesin and bizelesin synthetic analogues); Duocarmycin (including the synthetic analogues, KW-2189 and CBI-TMI); Benzodiazepine dimers (e.g., dimmers of pyrrolobenzodiazepine (PBD) or tomaymycin, indolinobenzodiazepines, imidazobenzothiadiazepines, or oxazolidinobenzodiazepines); Nitrosoureas: (carmustine, lomustine, chlorozotocin, fotemustine, nimustine, ranimustine); Alkylsulphonates: (busulfan, treosulfan, improsulfan and piposulfan); Triazenes: (dacarbazine); Platinum containing compounds: (carboplatin, cisplatin, oxaliplatin); aziridines, such as benzodopa, carboquone, meturedopa, and uredopa; ethylenimines and methylamelamines including altretamine, triethylenemel-amine, trietylenephosphoramide, triethylenethiophosphaoramide and trimethylolomel-amine]; b). Plant Alkaloids: such as Vinca alkaloids: (vincristine, vinblastine, vindesine, vinorelbine, navelbin); Taxoids: (paclitaxel, docetaxol) and their analogs, Maytansinoids (DM1, DM2, DM3, DM4, maytansine and ansamitocins) and their analogs, cryptophycins (particularly cryptophycin 1 and cryptophycin 8); epothilones, eleutherobin, discodermolide, bryostatins, dolostatins, auristatins, tubulysins, cephalostatins; pancratistatin; a sarcodictyin; spongistatin; c). DNA Topoisomerase Inhibitors: such as [Epipodophyllins: (9-aminocamptothecin, camptothecin, crisnatol, daunomycin, etoposide, etoposide phosphate, irinotecan, mitoxantrone, novantrone, retinoic acids (retinols), teniposide, topotecan, 9-nitrocamptothecin (RFS 2000)); mitomycins: (mitomycin C)]; d). Anti-metabolites: such as {[Anti-folate: DHFR inhibitors: (methotrexate, trimetrexate, denopterin, pteropterin, aminopterin (4-aminopteroic acid) or the other folic acid analogues); IMP dehydrogenase Inhibitors: (mycophenolic acid, tiazofurin, ribavirin, EICAR); Ribonucleotide reductase Inhibitors: (hydroxyurea, deferoxamine)]; [Pyrimidine analogs: Uracil analogs: (ancitabine, azacitidine, 6-azauridine, capecitabine (Xeloda), carmofur, cytarabine, dideoxyuridine, doxifluridine, enocitabine, 5-Fluorouracil, floxuridine, ratitrexed (Tomudex)); Cytosine analogs: (cytarabine, cytosine arabinoside, fludarabine); Purine analogs: (azathioprine, fludarabine, mercaptopurine, thiamiprine, thioguanine)]; folic acid replenisher, such as frolinic acid}; e). Hormonal therapies: such as {Receptor antagonists: [Anti-estrogen: (megestrol, raloxifene, tamoxifen); LHRH agonists: (goscrclin, leuprolide acetate); Anti-androgens: (bicalutamide, flutamide, calusterone, dromostanolone propionate, epitiostanol, goserelin, leuprolide, mepitiostane, nilutamide, testolactone, trilostane and other androgens inhibitors)]; Retinoids/Deltoids: [Vitamin D3 analogs: (CB 1093, EB 1089 KH 1060, cholecalciferol, ergocalciferol); Photodynamic therapies: (verteporfin, phthalocyanine, photosensitizer Pc4, demethoxy-hypocrellin A); Cytokines: (Interferon-alpha, Interferon-gamma, tumor necrosis factor (TNFs), human proteins containing a TNF domain)]}; f). Kinase inhibitors, such as BIBW 2992 (anti-EGFR/Erb2), imatinib, gefitinib, pegaptanib, sorafenib, dasatinib, sunitinib, erlotinib, nilotinib, lapatinib, axitinib, pazopanib. vandetanib, E7080 (anti-VEGFR2), mubritinib, ponatinib (AP24534), bafetinib (INNO-406), bosutinib (SKI-606), cabozantinib, vismodegib, iniparib, ruxolitinib, CYT387, axitinib, tivozanib, sorafenib, bevacizumab, cetuximab, Trastuzumab, Ranibizumab, Panitumumab, ispinesib; g). antibiotics, such as the enediyne antibiotics (e.g. calicheamicins, especially calicheamicin $\gamma 1$, $\delta 1$, $\alpha 1$ and $\beta 1$, see, e.g., J. Med. Chem., 39 (11), 2103-2117 (1996), Angew Chem Intl. Ed. Engl. 33:183-186 (1994); dynemicin, including dynemicin A and deoxydynemicin; esperamicin, kedarcidin, C-1027, maduropeptin, as well as neocarzinostatin chromophore and related chromoprotein enediyne antiobiotic chromomophores), aclacinomysins, actinomycin, authramycin, azaserine, bleomycins, cactinomycin, carabicin, carminomycin, carzinophilin; chromomycins, dactinomycin, daunorubicin, detorubicin, 6-diazo-5-oxo-L-norleucine, doxorubicin, morpholino-doxorubicin, cyanomorpholino-doxorubicin, 2-pyrrolino-doxorubicin and deoxydoxorubicin, epirubicin, esorubicin, idarubicin, marcellomycin, nitomycins, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; f). Others: such as Polyketides (acetogenins), especially bullatacin and bullatacinone; gemcitabine, epoxomicins (e. g. carfilzomib), bortezomib, thalidomide, lenalidomide, pomalidomide, tosedostat, zybrestat, PLX4032, STA-9090, Stimuvax, allovectin-7, Xegeva, Provenge, Yervoy, Isoprenylation inhibitors (such as Lovastatin), Dopaminergic neurotoxins (such as 1-methyl-4-phenylpyridinium ion), Cell cycle inhibitors (such as staurosporine), Actinomycins (such as Actinomycin D, dactinomycin), Bleomycins (such as bleomycin A2, bleomycin B2, peplomycin), Anthracyclines (such as daunorubicin, doxorubicin (adriamycin), idarubicin, epirubicin, pirarubicin, zorubicin, mtoxantrone, MDR inhibitors (such as verapamil), $Ca^{2+}$ ATPase inhibitors (such as thapsigargin), Histone deacetylase inhibitors (Vorinostat, Romidepsin, Panobinostat, Valproic acid, Mocetinostat (MGCD0103), Belinostat, PCI-24781, Entinostat, SB939, Resminostat, Givinostat, AR-42, CUDC-101, sulforaphane, Trichostatin A); Thapsigargin, Celecoxib, glitazones, epigallocatechin gallate, Disulfiram, Salinosporamide A.; Anti-adrenals, such as aminoglutethimide, mitotane, trilostane; aceglatone; aldophosphamide glycoside; aminolevulinic acid; amsacrine; arabinoside, bestrabucil; bisantrene; edatraxate; defofamine; demecolcine; diaziquone; eflornithine (DFMO), elfomithine; elliptinium acetate, etoglucid; gallium nitrate; gacytosine, hydroxyurea; ibandronate, lentinan; lonidamine; mitoguazone; mitoxantrone; mopidamol; nitracrine; pentostatin; phenamet; pirarubicin; podophyllinic acid; 2-ethylhydrazide; procarbazine; PSK®; razoxane; rhizoxin; sizofiran; spirogermanium; tenuazonic acid; triaziquone; 2, 2',2"-trichlorotriethylamine; trichothecenes (especially T-2 toxin, verrucarin A, roridin A and anguidine); urethane, siRNA, antisense drugs, and a nucleolytic enzyme.

2). An anti-autoimmune disease agent includes, but is not limited to, cyclosporine, cyclosporine A, aminocaproic acid, azathioprine, bromocriptine, chlorambucil, chloroquine, cyclophosphamide, corticosteroids (e.g. amcinonide, betamethasone, budesonide, hydrocortisone, flunisolide, fluticasone propionate, fluocortolone danazol, dexamethasone, Triamcinolone acetonide, beclometasone dipropionate), DHEA, enanercept, hydroxychloroquine, infliximab, meloxicam, methotrexate, mofetil, mycophenylate, prednisone, sirolimus, tacrolimus.

3). An anti-infectious disease agent includes, but is not limited to, a). Aminoglycosides: amikacin, astromicin, gentamicin (netilmicin, sisomicin, isepamicin), hygromycin B, kanamycin (amikacin, arbekacin, bekanamycin, dibekacin, tobramycin), neomycin (framycetin, paromomycin, ribostamycin), netilmicin, spectinomycin, streptomycin, tobramycin, verdamicin; b). Amphenicols: azidamfenicol, chloramphenicol, florfenicol, thiamphenicol; c). Ansamycins: geldanamycin, herbimycin; d). Carbapenems: biapenem, doripenem, ertapenem, imipenem/cilastatin, meropenem, panipenem; e). Cephems: carbacephem (loracarbef), cefacetrile, cefaclor, cefradine, cefadroxil, cefalonium, cefaloridine, cefalotin or cefalothin, cefalexin, cefaloglycin, cefamandole, cefapirin, cefatrizine, cefazaflur, cefazedone, cefazolin, cefbuperazone, cefcapene, cefdaloxime, cefepime, cefminox, cefoxitin, cefprozil, cefroxadine, ceftezole, cefuroxime, cefixime, cefdinir, cefditoren, cefepime, cefetamet, cefmenoxime, cefodizime, cefonicid, cefoperazone, ceforanide, cefotaxime, cefotiam, cefozopran, cephalexin, cefpimizole, cefpiramide, cefpirome, cefpodoxime, cefprozil, cefquinome, cefsulodin, ceftazidime, cefteram, ceftibuten, ceftiolene, ceftizoxime, ceftobiprole, ceftriaxone, cefuroxime, cefuzonam, cephamycin (cefoxitin, cefotetan, cefmetazole), oxacephem (flomoxef, latamoxef); f). Glycopeptides: bleomycin, vancomycin (oritavancin, telavancin), teicoplanin (dalbavancin), ramoplanin; g). Glycylcyclines: e. g. tigecycline; g). β-Lactamase inhibitors: penam (sulbactam, tazobactam), clavam (clavulanic acid); i). Lincosamides: clindamycin, lincomycin; j). Lipopeptides: daptomycin, A54145, calcium-dependent antibiotics (CDA); k). Macrolides: azithromycin, cethromycin, clarithromycin, dirithromycin, erythromycin, flurithromycin, josamycin, ketolide (telithromycin, cethromycin), midecamycin, miocamycin, oleandomycin, rifamycins (rifampicin, rifampin, rifabutin, rifapentine), rokitamycin, roxithromycin, spectinomycin, spiramycin, tacrolimus (FK506), troleandomycin, telithromycin; 1). Monobactams: aztreonam, tigemonam; m). Oxazolidinones: linezolid; n). Penicillins: amoxicillin, ampicillin (pivampicillin, hetacillin, bacampicillin, metampicillin, talampicillin), azidocillin, azlocillin, benzylpenicillin, benzathine benzylpenicillin, benzathine phenoxymethylpenicillin, clometocillin, procaine benzylpenicillin, carbenicillin (carindacillin), cloxacillin, dicloxacillin, epicillin, flucloxacillin, mecillinam (pivmecillinam), mezlocillin, meticillin, nafcillin, oxacillin, penamecillin, penicillin, pheneticillin, phenoxymethylpenicillin, piperacillin, propicillin, sulbenicillin, temocillin, ticarcillin; o). Polypeptides: bacitracin, colistin, polymyxin B; p). Quinolones: alatrofloxacin, balofloxacin, ciprofloxacin, clinafloxacin, danofloxacin, difloxacin, enoxacin, enrofloxacin, floxin, garenoxacin, gatifloxacin, gemifloxacin, grepafloxacin, kano trovafloxacin, levofloxacin, lomefloxacin, marbofloxacin, moxifloxacin, nadifloxacin, norfloxacin, orbifloxacin, ofloxacin, pefloxacin, trovafloxacin, grepafloxacin, sitafloxacin, sparfloxacin, temafloxacin, tosufloxacin, trovafloxacin; q). Streptogramins: pristinamycin, quinupristin/dalfopristin); r). Sulfonamides: mafenide, prontosil, sulfacetamide, sulfamethizole, sulfanilimide, sulfasalazine, sulfisoxazole, trimethoprim, trimethoprimsulfamethoxazole (co-trimoxazole); s). Steroid antibacterials: e.g. fusidic acid; t). Tetracyclines: doxycycline, chlortetracycline, clomocycline, demeclocycline, lymecycline, meclocydine, metacycline, minocycline, oxytetracycline, penimepicycline, rolitetracycline, tetracydine, glycylcyclines (e.g. tigecycline); u). Other types of antibiotics: annonacin, arsphenamine, bactoprenol inhibitors (Bacitracin), DADAL/AR inhibitors (cycloserine), dictyostatin, discodermolide, eleutherobin, epothilone, ethambutol, etoposide, faropenem, fusidic acid, furazolidone, isoniazid, laulimalide, metronidazole, mupirocin, mycolactone, NAM synthesis inhibitors (e. g. fosfomycin), nitrofurantoin, paclitaxel, platensimycin, pyrazinamide, quinupristin/dalfopristin, rifampicin (rifampin), tazobactam tinidazole, uvaricin;

4). Anti-viral drugs: a). Entry/fusion inhibitors: aplaviroc, maraviroc, vicriviroc, gp41 (enfuvirtide), PRO 140, CD4 (ibalizumab); b). Integrase inhibitors: raltegravir, elvitegravir, globoidnan A; c). Maturation inhibitors: bevirimat, vivecon; d). Neuraminidase inhibitors: oseltamivir, zanamivir, peramivir; e). Nucleosides & nucleotides: abacavir, aciclovir, adefovir, amdoxovir, apricitabine, brivudine, cidofovir, clevudine, dexelvucitabine, didanosine (ddI), elvucitabine, emtricitabine (FTC), entecavir, famciclovir, fluorouracil (5-FU), 3'-fluoro-substituted 2', 3'-dideoxynucleoside analogues (e.g. 3'-fluoro-2',3'-dideoxythymidine (FLT) and 3'-fluoro-2',3'-dideoxyguanosine (FLG), fomivirsen, ganciclovir, idoxuridine, lamivudine (3TC), 1-nucleosides (e.g. β-1-thymidine and β-1-2'-deoxycytidine), penciclovir, racivir, ribavirin, stampidine, stavudine (d4T), taribavirin (viramidine), telbivudine, tenofovir, trifluridine valaciclovir, valganciclovir, zalcitabine (ddC), zidovudine (AZT); f). Non-nucleosides: amantadine, ateviridine, capravirine, diarylpyrimidines (etravirine, rilpivirine), delavirdine, docosanol, emivirine, efavirenz, foscarnet (phosphonoformic acid), imiquimod, interferon alfa, loviride, lodenosine, methisazone, nevirapine, NOV-205, peginterferon alfa, podophyllotoxin, rifampicin, rimantadine, resiquimod (R-848), tromantadine; g). Protease inhibitors: amprenavir, atazanavir, boceprevir, darunavir, fosamprenavir, indinavir, lopinavir, nelfinavir, pleconaril, ritonavir, saquinavir, telaprevir (VX-950), tipranavir; h). Other types of anti-virus drugs: abzyme, arbidol, calanolide a, ceragenin, cyanovirin-n, diarylpyrimidines, epigallocatechin gallate (EGCG), foscarnet, griffithsin, taribavirin (viramidine), hydroxyurea, KP-1461, miltefosine, pleconaril, portmanteau inhibitors, ribavirin, seliciclib.

5). The drugs used for conjugates via a bridge linker of the present invention also include radioisotopes. Examples of radioisotopes (radionuclides) are $^{3}H$, $^{11}C$, $^{14}C$, $^{18}F$, $^{32}P$, $^{35}S$, $^{64}Cu$, $^{68}Ga$, $^{86}Y$, $^{99}Tc$, $^{111}In$, $^{123}I$, $^{124}I$, $^{125}I$, $^{131}I$, $^{133}Xe$, $^{177}Lu$, $^{211}At$, or $^{213}Bi$. Radioisotope labeled antibodies are useful in receptor targeted imaging experiments or can be for targeted treatment such as with the antibody-drug conjugates of the invention (Wu et al (2005) Nature Biotechnology 23(9): 1137-1146). The cell binding molecules, e.g. an antibody can be labeled with ligand reagents through the bridge linkers of the present patent that bind, chelate or otherwise complex a radioisotope metal, using the techniques described in Current Protocols in Immunology, Volumes 1 and 2, Coligen et al, Ed. Wiley-Interscience, New York, N.Y., Pubs. (1991). Chelating ligands which may complex a metal ion include DOTA, DOTP, DOTMA, DTPA and TETA (Macrocyclics, Dallas, Tex. USA).

6). The pharmaceutically acceptable salts, acids or derivatives of any of the above drugs.

In another embodiment, the drug in the Formula (II) and (IV) can a chromophore molecule, for which the conjugate can be used for detection, monitoring, or study the interaction of the cell binding molecule with a target cell. Chromophore molecules are a compound that have the ability to absorb a kind of light, such as UV light, florescent light, IR light, near IR light, visual light; A chromatophore molecule includes a class or subclass of xanthophores, erythrophores, iridophores, leucophores, melanophores, and cyanophores; a class or subclass of fluorophore molecules which are fluorescent chemical compounds re-emitting light upon light; a class or subclass of visual phototransduction molecules; a class or subclass of photophore molecules; a class or subclass of luminescence molecules; and a class or subclass of luciferin compounds.

The chromophore molecule can be selected from, but not limited, Non-protein organic fluorophores, such as: Xanthene derivatives (fluorescein, rhodamine, Oregon green, eosin, and Texas red); Cyanine derivatives: (cyanine, indocarbocyanine, oxacarbocyanine, thiacarbocyanine, and merocyanine); Squaraine derivatives and ring-substituted squaraines, including Seta, SeTau, and Square dyes; Naphthalene derivatives (dansyl and prodan derivatives); Coumarin derivatives; Oxadiazole derivatives (pyridyloxazole, nitrobenzoxadiazole and benzoxadiazole); Anthracene derivatives (anthraquinones, including DRAQ5, DRAQ7 and CyTRAK Orange); Pyrene derivatives (cascade blue, etc); Oxazine derivatives (Nile red, Nile blue, cresyl violet, oxazine 170 etc). Acridine derivatives (proflavin, acridine orange, acridine yellow etc). Arylmethine derivatives (auramine, crystal violet, malachite green). Tetrapyrrole derivatives (porphin, phthalocyanine, bilirubin).

Or a chromophore molecule can be selected from any analogs and derivatives of the following fluorophore compounds: CF dye (Biotium), DRAQ and CyTRAK probes (BioStatus), BODIPY (Invitrogen), Alexa Fluor (Invitrogen), DyLight Fluor (Thermo Scientific, Pierce), Atto and Tracy (Sigma Aldrich), FluoProbes (Interchim), Abberior Dyes (Abberior), DY and MegaStokes Dyes (Dyomics), Sulfo Cy dyes (Cyandye), HiLyte Fluor (AnaSpec), Seta, SeTau and Square Dyes (SETA BioMedicals), Quasar and Cal Fluor dyes (Biosearch Technologies), SureLight Dyes (APC, RPEPerCP, Phycobilisomes)(Columbia Biosciences), APC, APCXL, RPE, BPE (Phyco-Biotech);

Examples of the widely used fluorophore compounds which are reactive or conjugatable with the linkers of the invention are: Allophycocyanin (APC), Aminocou-marin, APC-Cy7 conjugates, BODIPY-FL, Cascade Blue, Cy2, Cy3, Cy3.5, Cy3B, Cy5, Cy5.5, Cy7, Fluorescein, FluorX, Hydroxycoumarin, Lissamine Rhodamine B, Lucifer yellow, Methoxycoumarin, NBD, Pacific Blue, Pacific Orange, PE-Cy5 conjugates, PE-Cy7 conjugates, PerCP, R-Phycoerythrin(PE), Red 613, Seta-555-Azide, Seta-555-DBCO, Seta-555-NHS, Seta-580-NHS, Seta-680-NHS, Seta-780-NHS, Seta-APC-780, Seta-PerCP-680, Seta-R-PE-670, SeTau-380-NHS, SeTau-405-Maleimide, SeTau-405-NHS, SeTau-425-NHS, SeTau-647-NHS, Texas Red, TRITC, TruRed, X-Rhodamine.

The fluorophore compounds that can be linked to the linkers of the invention for study of nucleic acids or proteins are selected from the following compounds or their derivatives: 7-AAD (7-aminoactinomycin D, CG-selective), Acridine Orange, Chromomycin A3, CyTRAK Orange (Biostatus, red excitation dark), DAPI, DRAQ5, DRAQ7, Ethidium Bromide, Hoechst33258, Hoechst33342, LDS 751, Mithramycin, Propidiumlodide (PI), SYTOX Blue, SYTOX Green, SYTOX Orange, Thiazole Orange, TO-PRO: Cyanine Monomer, TOTO-1, TO-PRO-1, TOTO-3, TO-PRO-3, YOSeta-1, YOYO-1. The fluorophore compounds that can be linked to the linkers of the invention for study cells are selected from the following compounds or their derivatives: DCFH (2'7'Dichorodihydro-fluorescein, oxidized form), DHR (Dihydrorhodamine 123, oxidized form, light catalyzes oxidation), Fluo-3 (AM ester. pH>6), Fluo-4 (AM ester. pH 7.2), Indo-1 (AM ester, low/high calcium (Ca2+)), SNARF (pH 6/9). The preferred fluorophore compounds that can be linked to the linkers of the invention for study proteins/antibodies are selected from the following compounds or their derivatives: Allophycocyanin (APC), AmCyan1 (tetramer, Clontech), AsRed2 (tetramer, Clontech), Azami Green (monomer, MBL), Azurite, B-phycoerythrin (BPE), Cerulean, CyPet, DsRed monomer (Clontech), DsRed2 ("RFP", Clontech), EBFP, EBFP2, ECFP, EGFP (weak dimer, Clontech), Emerald (weak dimer, Invitrogen), EYFP (weak dimer, Clontech), GFP (S65A mutation), GFP (S65C mutation), GFP (S65L mutation), GFP (S65T mutation), GFP (Y66F mutation), GFP (Y66H mutation), GFP (Y66W mutation), GFPuv, HcRedl, J-Red, Katusha, Kusabira Orange (monomer, MBL), mCFP, mCherry, mCitrine, Midoriishi Cyan (dimer, MBL), mKate (TagFP635, monomer, Evrogen), mKeima-Red (monomer, MBL), mKO, mOrange, mPlum, mRaspberry, mRFP1 (monomer, Tsien lab), mStrawberry, mTFP1, mTurquoise2, P3 (phycobilisome complex), Peridinin Chlorophyll (PerCP), R-phycoerythrin (RPE), T-Sapphire, TagCFP (dimer, Evrogen), TagGFP (dimer, Evrogen), TagRFP (dimer, Evrogen), TagYFP (dimer, Evrogen), tdTomato (tandem dimer), Topaz, TurboFP602 (dimer, Evrogen), TurboFP635 (dimer, Evrogen), TurboGFP (dimer, Evrogen), TurboRFP (dimer, Evrogen), TurboYFP (dimer, Evrogen), Venus, Wild Type GFP, YPet, ZsGreen1 (tetramer, Clontech), ZsYellow1 (tetramer, Clontech).

In yet another embodiment, the preferred cytotoxic agents that conjugated to a cell-binding molecule via a bridge linker of this patent are tubulysins, maytansinoids, taxanoids (taxanes), CC-1065 analogs, daunorubicin and doxorubicin compounds, benzodiazepine dimers (e.g., dimers of pyrrolobenzodiazepine (PBD), tomaymycin, anthramycin, indolinobenzodiazepines, imidazobenzothiadiazepines, or oxazolidino-benzodiazepines), calicheamicins and the enediyne antibiotics, actinomycin, azaserines, bleomycins, epirubicin, tamoxifen, idarubicin, dolastatins, auristatins (e.g. monomethyl auristatin E, MMAE, MMAF, auristatin PYE, auristatin TP, Auristatins 2-AQ, 6-AQ, EB (AEB), and EFP (AEFP)), duocarmycins, thiotepa, vincristines, hemiasterlins, nazumamides, microginins, radiosumins, alterobactins, microsclerodermins, theonellamides, esperamicins, PNU-159682, and their analogues and derivatives above thereof.

Tubulysins that are preferred for conjugation in the present invention are well known in the art and can be isolated from natural sources according to known methods or prepared synthetically according to known methods (e. g. Balasubramanian, R.; et al. J. Med. Chem., 2009, 52, 238-240. Wipf, P.; et al. Org. Lett., 2004, 6, 4057-4060. Pando, O.; et al. J. Am. Chem. Soc., 2011, 133, 7692-7695. Reddy, J. A.; et al. Mol. Pharmaceutics, 2009, 6, 1518-1525. Raghavan, B.; et al. J. Med. Chem., 2008, 51, 1530-1533. Patterson, A. W.; et al. J. Org. Chem., 2008, 73, 4362-4369. Pando, O.; et al. Org. Lett., 2009, 11 (24), pp 5567-5569. Wipf, P.; et al. Org. Lett., 2007, 9 (8), 1605-1607. Friestad, G. K.; Org. Lett., 2004, 6, pp 3249-3252. Hillary M. Peltier, H. M.; et al. J. Am. Chem. Soc., 2006, 128, 16018-16019. Chandrasekhar, S.; et al. J. Org. Chem., 2009, 74, 9531-9534. Liu, Y.; et al. Mol. Pharmaceutics, 2012, 9, 168-175. Friestad, G. K.; et al. Org. Lett., 2009, 11, 1095-1098. Kubicek, K.; et al., Angew Chem Int Ed Engl, 2010. 49: p. 4809-12. Chai, Y.; et al., Chem Biol, 2010, 17: 296-309. Ullrich, A.; et al., Angew Chem Int Ed Engl, 2009, 48, 4422-5. Sani, M.; et al. Angew Chem Int Ed Engl, 2007, 46, 3526-9. Domling, A.; et al., Angew Chem Int Ed Engl, 2006. 45, 7235-9. Patent applications: Zanda, M.; et al, Can. Pat. Appl. CA 2710693 (2011). Chai, Y.; et al. Eur. Pat. Appl. 2174947 (2010), PCT WO 2010034724. Leamon, C.; et al, PCT WO 2010033733, WO 2009002993. Ellman, J.; et al, PCT WO 2009134279; PCT WO 2009012958, US appl. 20110263650, 20110021568, Matschiner, G.; et al, PCT WO 2009095447.Vlahov, I.; et al, PCT WO 2009055562, WO 2008112873. Low, P.; et al, PCT WO 2009026177. Richter, W., PCT WO 2008138561. Kjems, J.; et al, PCT WO 2008125116. Davis, M.; et al, PCT WO 2008076333. Diener, J.; et al, U.S. Pat. Appl. 20070041901, WO 2006096754. Matschiner, G.; et al, PCT WO 2006056464. Vaghefi, F.; et al, 5 PCT WO 2006033913. Doemling, A., Ger. Offen. DE 102004030227; PCT WO 2004005327; WO 2004005326; WO2004005269. Stanton, M.; et al, U.S. Pat. Appl. Publ. 20040249130. Hoefle, G.; et al, Ger. Offen. DE 10254439; DE 10241152; DE 10008089. Leung, D.; et al, WO 2002077036. Reichenbach, H.; et al, Ger. Offen. DE 19638870; Wolfgang, R.; US 20120129779, Chen, H., US appl. 20110027274. The preferred structure of tubulysins for conjugation of cell binding molecules are described in the patent application of PCT/IB32012/053554.

Examples of the structures of the conjugates of the antibody-tubulysin analogs via the bridge linker are T01, T02, T03, T04, T05, T06 and T07 as following:

T01

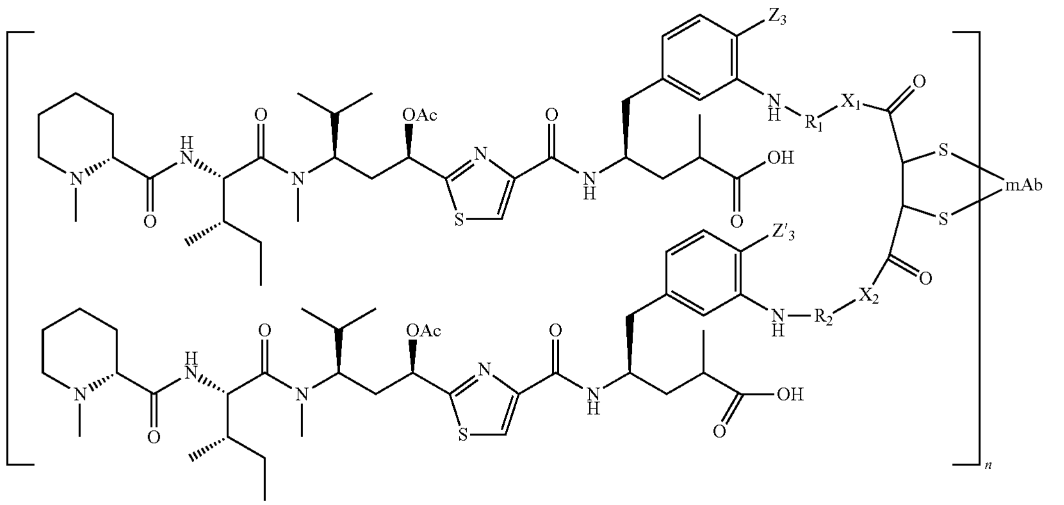

T02

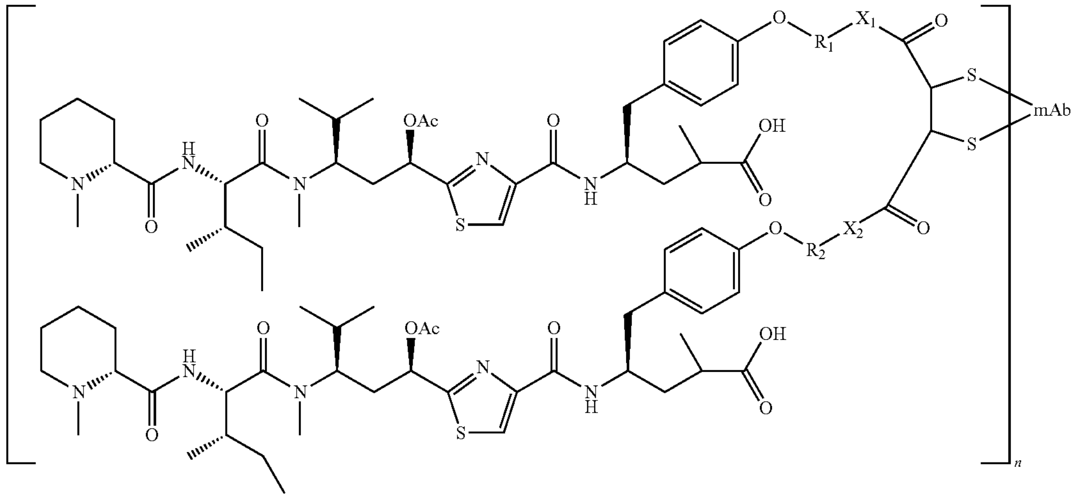

-continued
T03
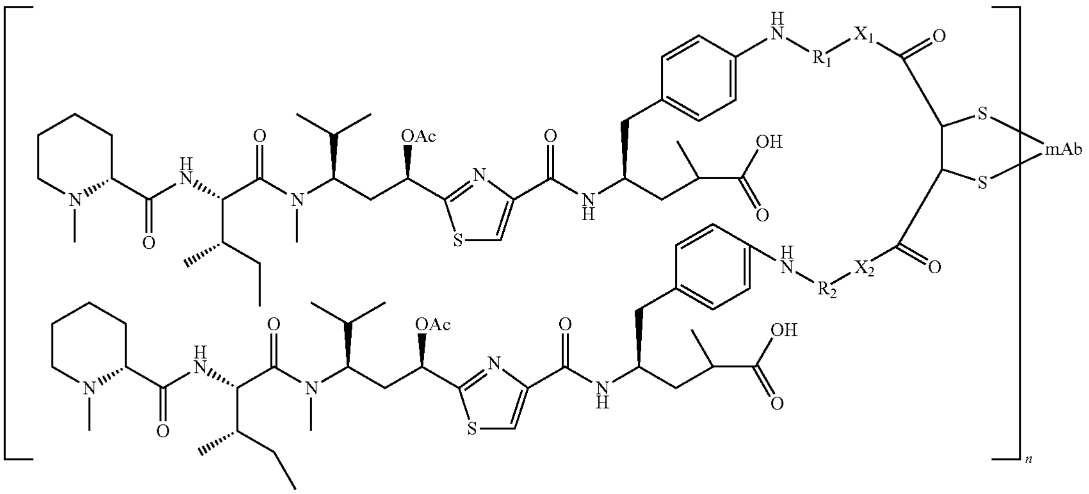
T04
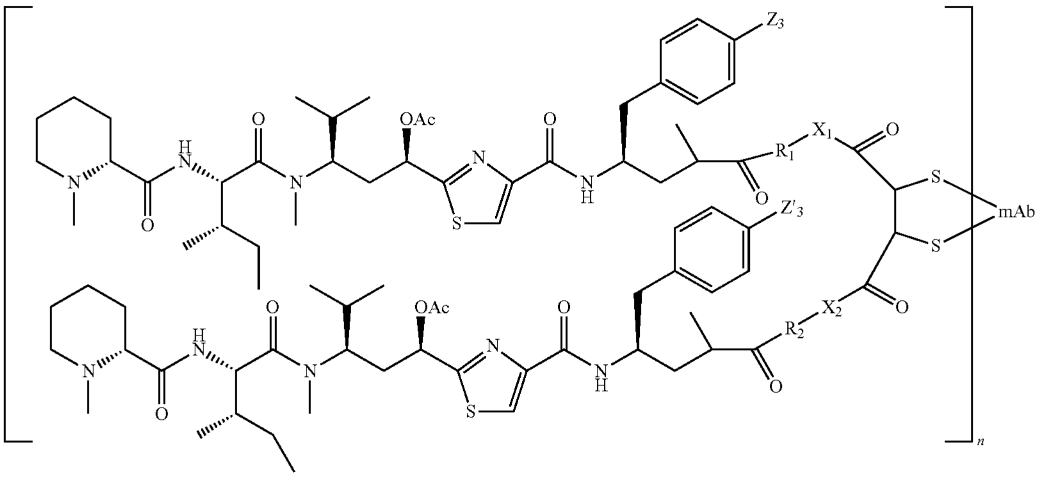
T05
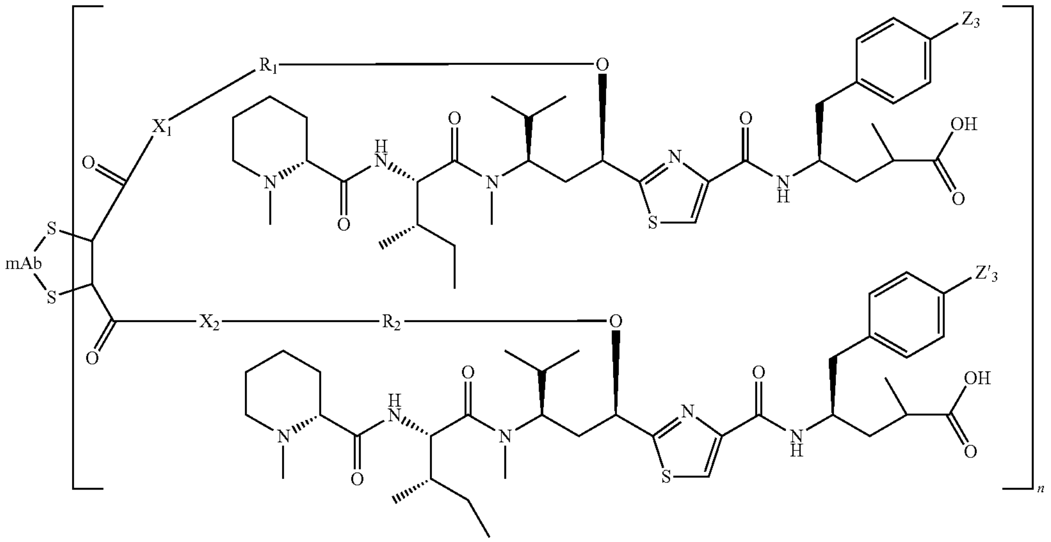

-continued

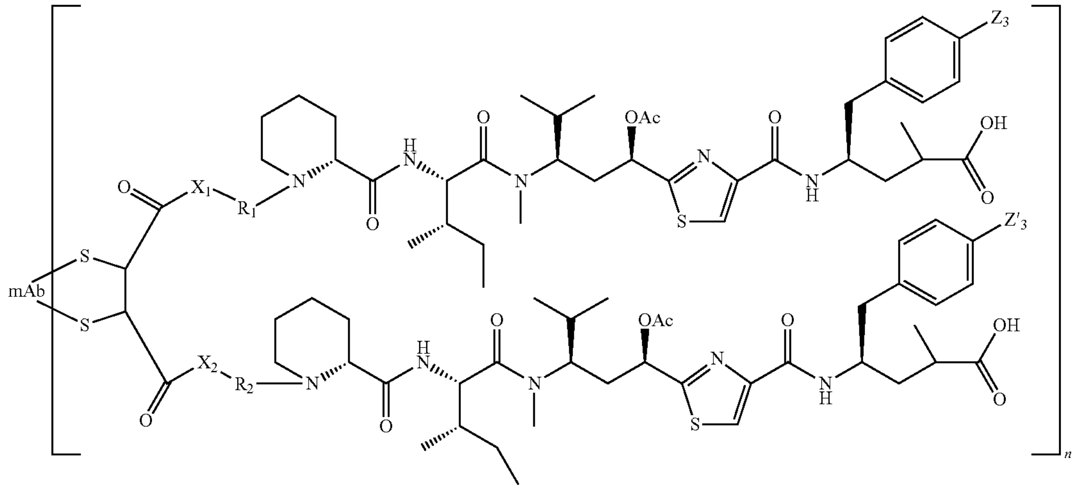

T06

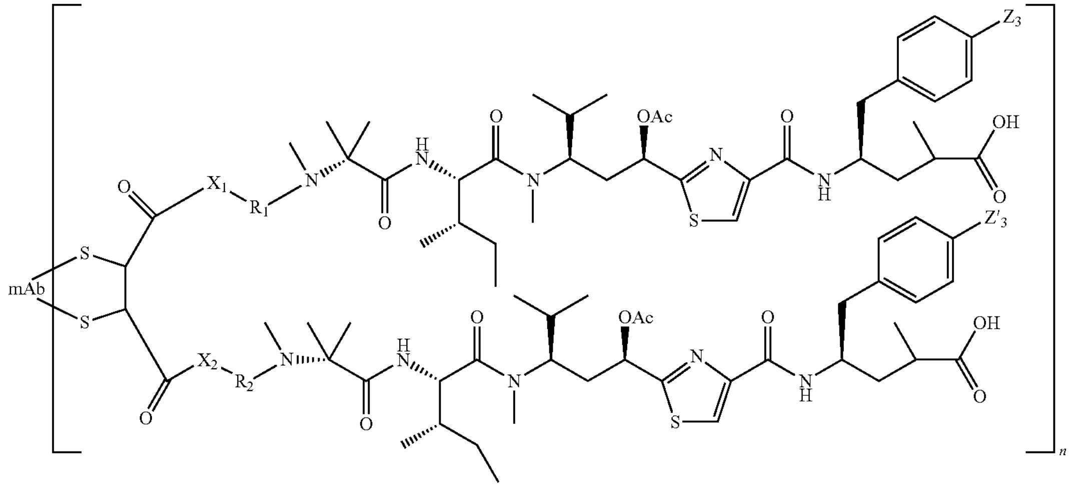

T07

Wherein mAb is an antibody; $Z_3$ and $Z'_3$ are independently H, $OP(O)(OM_1)(OM_2)$, $OCH_2OP(O)(OM_1)(OM_2)$, $OSO_3M_1$, $R_1$, or O-glycoside (glucoside, galactoside, mannoside, glucuronoside, alloside, fructoside, etc), NH-glycoside, S-glycoside or $CH_2$-glycoside; $M_1$ and $M_2$ are independently H, Na, K, Ca, Mg, $NH_4$, $NR_1R_2R_3$; n is 1~20; $X_1$, $X_2$, $R_1$, $R_2$ and $R_3$ are the same defined in Formula (I).

Calicheamicins and their related enediyne antibiotics that are preferred for cell-binding molecule-drug conjugates of this patent are described in: Nicolaou, K. C. et al, Science 1992, 256, 1172-1178; Proc. Natl. Acad. Sci USA. 1993, 90, 5881-5888), U.S. Pat. Nos. 4,970,198; 5,053,394; 5,108,912; 5,264,586; 5,384,412; 5,606,040; 5,712,374; 5,714,586; 5,739,116; 5,770,701; 5,770,710; 5,773,001; 5,877,296; 6,015,562; 6,124,310; 8,153,768. An Example of the structure of the conjugate of the antibody-Calicheamicin analog via the bridge linker is C01 as the following:

C01

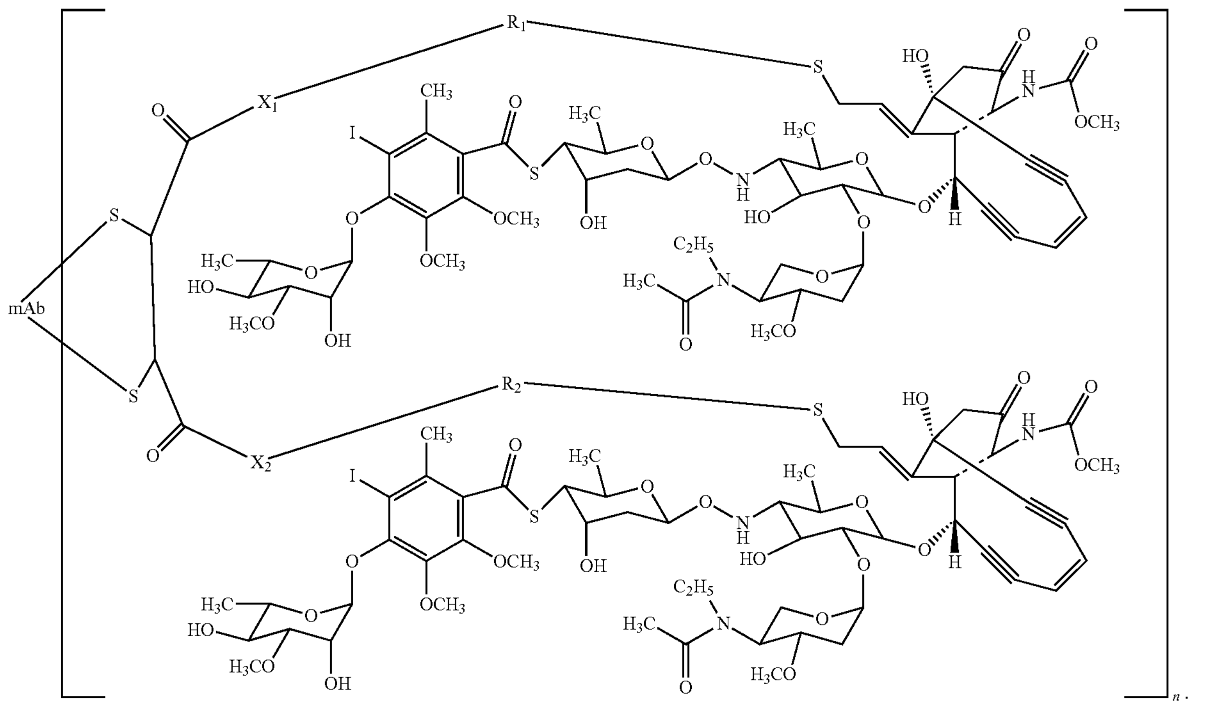

Wherein mAb is an antibody; n is 1~20; $X_1$, $X_2$, $R_1$, $R_2$ and $R_3$ are the same defined in Formula (I).

conjugate of the antibody-Maytansinoids via the bridge linker is as the following M01:

M01

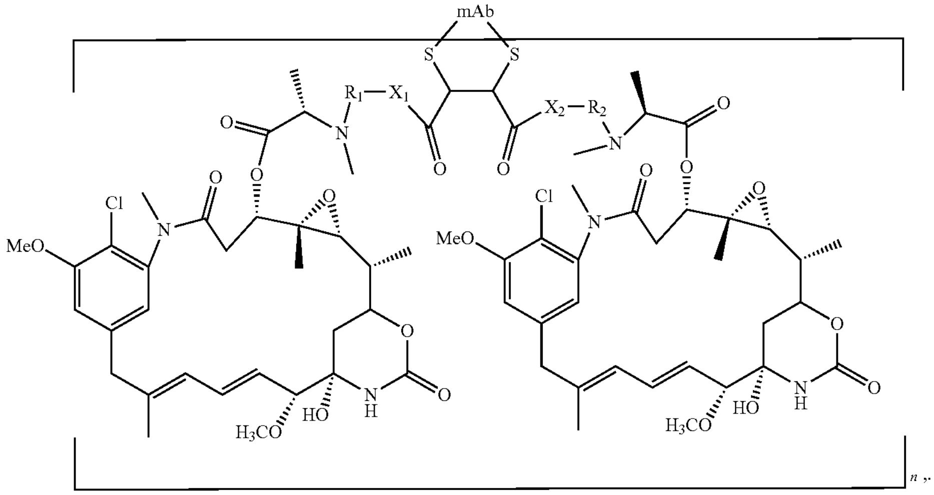

Wherein mAb is an antibody; n is 1~20; $X_1$, $X_2$, $R_1$, $R_2$ and $R_3$ are the same defined in Formula (I).

Maytansinoids that are preferred to be used in the present invention including maytansinol and its analogues are described in U.S. Pat. Nos. 4,256,746, 4,361,650, 4,307,016, 4,294,757, 4,294,757, 4,371,533, 4,424,219, 4,331,598, 4,450,254, 4,364,866, 4,313,946, 4,315,929 4,362,663, 4,322,348, 4,371,533, 4,424,219, 5,208,020, 5,416,064, 5,208,020; 5,416,064; 6,333.410; 6,441,163; 6,716,821, 7,276,497, 7,301,019, 7,303,749, 7,368,565, 7,411,063, 7,851,432, and 8,163,888. An example of the structure of the Taxanes, which includes Paclitaxel (Taxol), a cytotoxic natural product, and docetaxel (Taxotere), a semi-synthetic derivative, and their analogs which are preferred for conjugation via the bridge linkers of the present patent are exampled in: K C. Nicolaou et al., J. Am. Chem. Soc. 117, 2409-2420, (1995); Ojima et al, J. Med. Chem. 39:3889-3896 (1996); 40:267-278 (1997); 45, 5620-5623 (2002);

Ojima et al., Proc. Natl. Acad. Sci., 96:4256-4261 (1999; Kim et al., Bull. Korean Chem. Soc., 20, 1389-1390 (1999); Miller, et al. J. Med. Chem., 47, 4802-4805(2004); U.S. Pat. No. 5,475,011 5,728,849, 5,811,452; 6,340,701; 6,372,738; 6,391,913, 6,436,931; 6,589,979; 6,596,757; 6,706,708; 7,008,942; 7,186,851; 7,217,819; 7,276,499; 7,598,290; and 7,667,054.
Examples of the structures of the conjugate of the antibody-taxanes via the bridge linker are as the following Tx01, Tx02 and Tx03.
Tx01
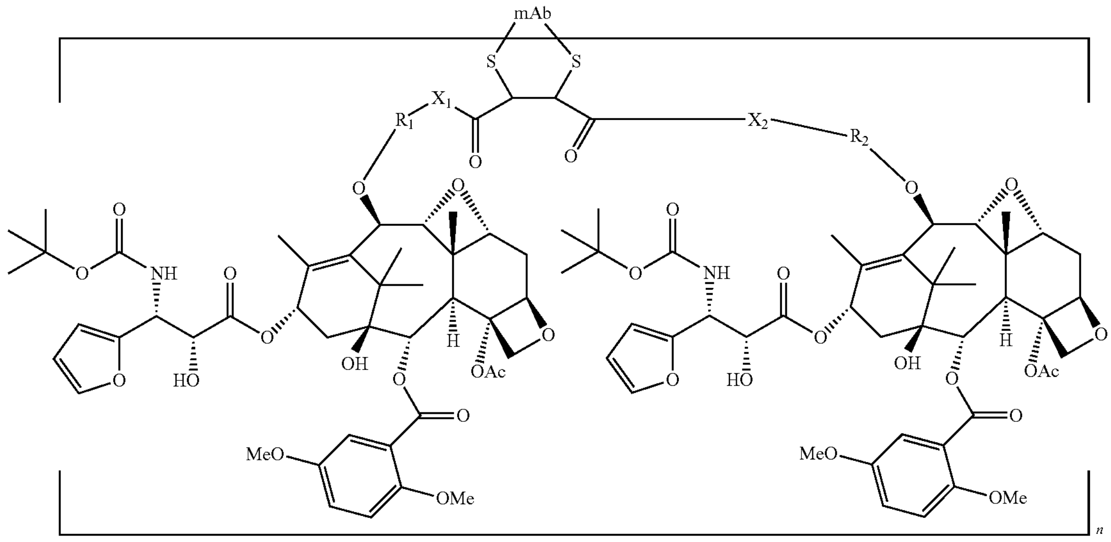
Tx02
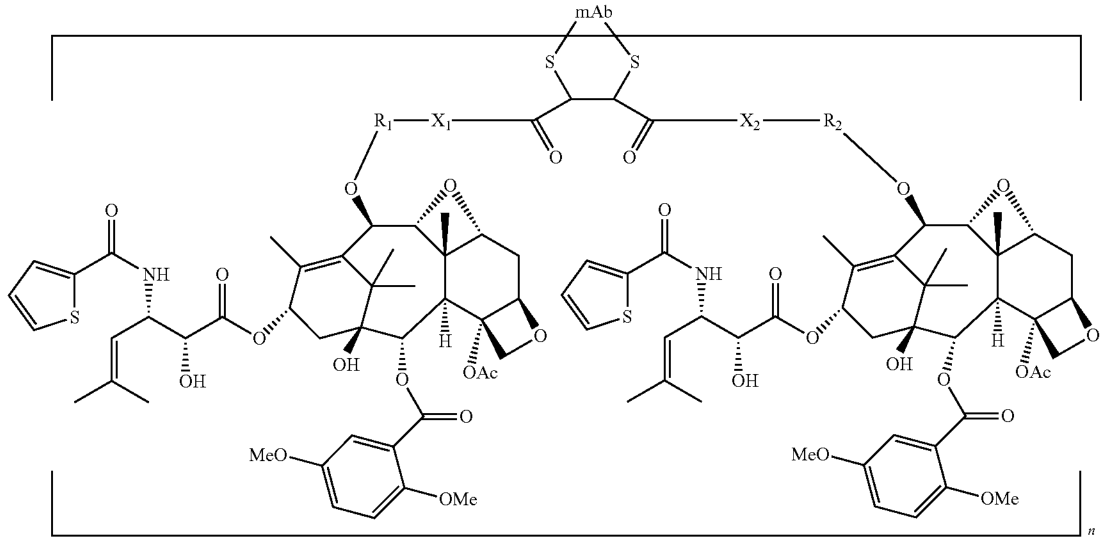

-continued

Tx03

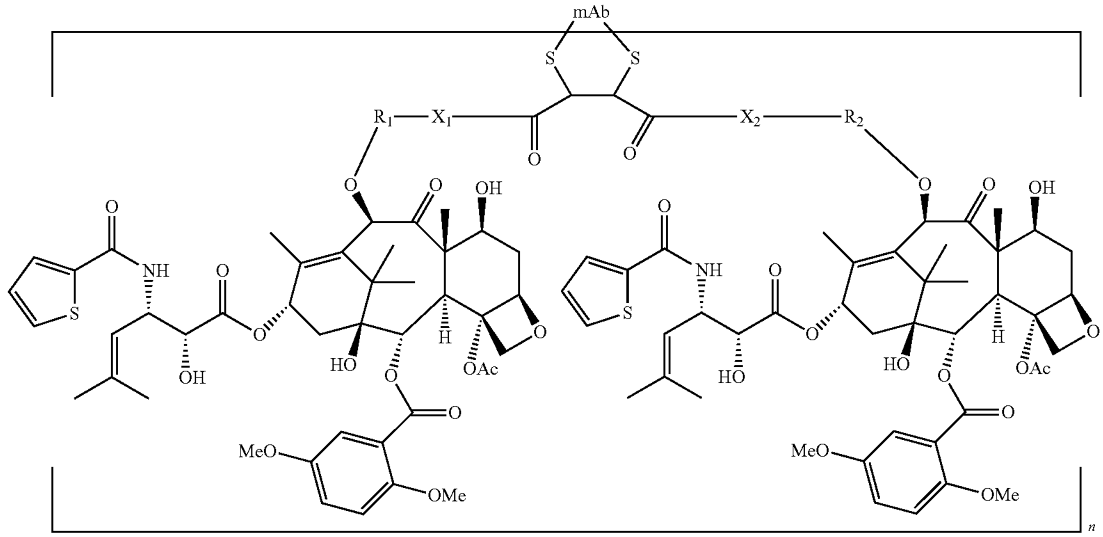

Wherein mAb is an antibody; n is 1~20; $X_1$, $X_2$, $R_1$ and $R_2$ are the same defined in Formula (I).

CC-1065 analogues and duocarmycin analogs are also preferred to be used for a conjugate with the bridge linkers of the present patent. The examples of the CC-1065 analogues and doucarmycin analogs as well as their synthesis are described in: e.g. Warpehoski, et al, J. Med. Chem. 31:590-603 (1988), D. Boger et al., J. Org. Chem; 66; 6654-6661, 2001; U.S. Pat. Nos. 4,169,888, 4,391,904, 4,671,958, 4,816,567, 4,912,227, 4,923,990, 4,952,394, 4,975,278, 4,978,757, 4,994,578, 5,037,993, 5,070,092, 5,084,468, 5,101,038, 5,117,006, 5,137,877, 5,138,059, 5,147,786, 5,187,186, 5,223,409, 5,225,539, 5,288,514, 5,324,483, 5,332,740, 5,332,837, 5,334,528, 5,403,484, 5,427,908, 5,475,092, 5,495,009, 5,530,101, 5,545,806, 5,547,667, 5,569,825, 5,571,698, 5,573,922, 5,580,717, 5,585,089, 5,585,499, 5,587,161, 5,595,499, 5,606,017, 5,622,929, 5,625,126, 5,629,430, 5,633,425, 5,641,780, 5,660,829, 5,661,016, 5,686,237, 5,693,762, 5,703,080, 5,712,374, 5,714,586, 5,739,116, 5,739,350, 5,770,429, 5,773,001, 5,773,435, 5,786,377, 5,786,486, 5,789,650, 5,814,318, 5,846,545, 5,874,299, 5,877,296, 5,877,397, 5,885,793, 5,939,598, 5,962,216, 5,969,108, 5,985,908, 6,060,608, 6,066,742, 6,075,181, 6,103,236, 6,114,598, 6,130,237, 6,132,722, 6,143,901, 6,150,584, 6,162,963, 6,172,197, 6,180,370, 6,194,612, 6,214,345, 6,262,271, 6,281,354, 6,310,209, 6,329,497, 6,342,480, 6,486,326, 6,512,101, 6,521,404, 6,534,660, 6,544,731, 6,548,530, 6,555,313, 6,555,693, 6,566,336, 6,586,618, 6,593,081, 6,630,579, 6,756,397, 6,759,509, 6,762,179, 6,884,869, 6,897,034, 6,946,455, 7,049,316, 7,087,600, 7,091,186, 7,115,573, 7,129,261, 7,214,663, 7,223,837, 7,304,032, 7,329,507, 7,329,760, 7,388,026, 7,655,660, 7,655,661, 7,906,545, and 8,012,978. Examples of the structures of the conjugate of the antibody-CC-1065 analogs via the bridge linker are as the following CC01, CC02, and CC03.

CC01

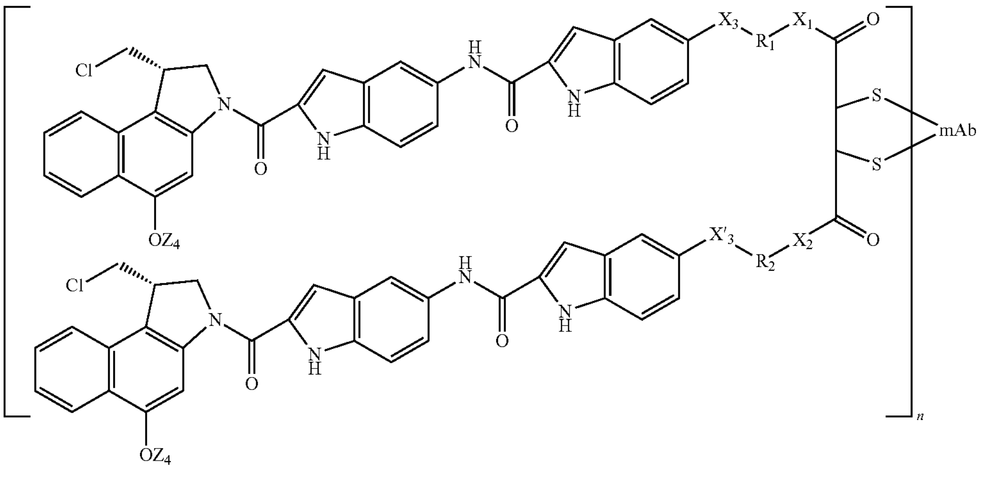

-continued

CC02

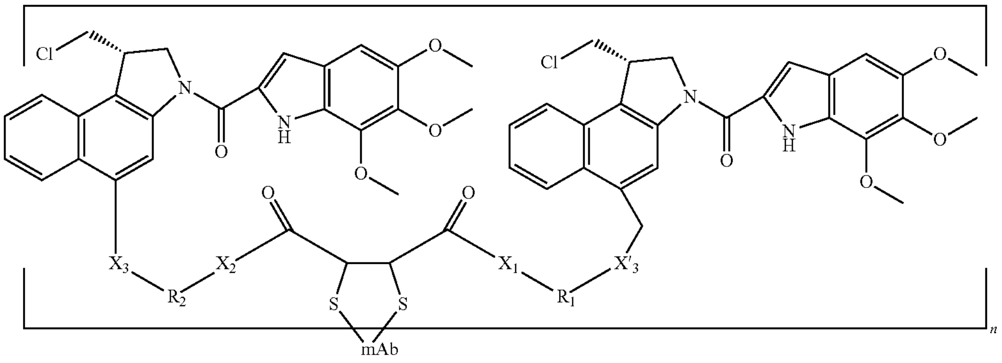

CC03

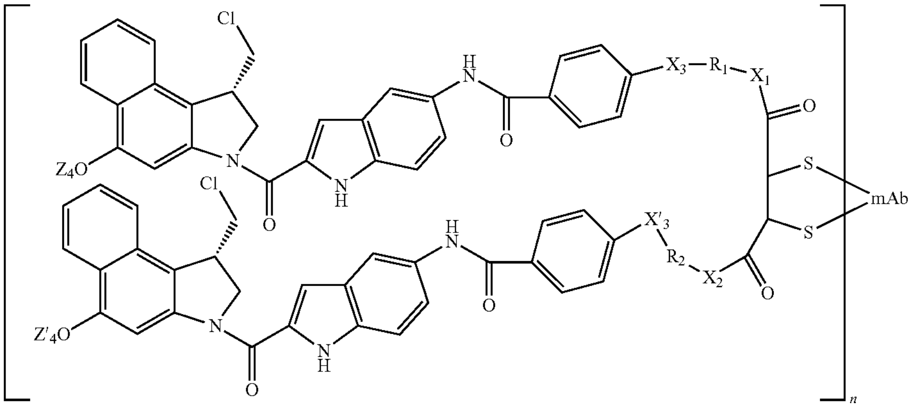

Wherein mAb is an antibody; n is 1~20; $Z_4$ and $Z'_4$ are independently H, $PO(OM_1)(OM_2)$, $CH_2PO(OM_1)(OM_2)$, $SO_3M_1$, $CH_3N(CH_2CH_2)_2NC(O)$—, $O(CH_2CH_2)_2NC(O)$—, $R_1$, or glycoside; $X_3$ and $X'_3$ are independently O, NH, NHC(O), OC(O), —C(O)O, $R_1$, or absent; $X_1$, $X_2$, $R_1$, $R_2$, $M_1$, and $M_2$ are the same defined in Formula (I).

Daunorubicin/Doxorubicin Analogues are also preferred for conjugation via the bridge linkers of the present patent. The preferred structures and their synthesis are exampled in: Hurwitz, E., et al., Cancer Res. 35, 1175-1181 (1975). Yang, H. M., and Reisfeld, R. A., Proc. Natl. Acad. Sci. 85, 1189-1193 (1988); Pietersz, C. A., E., et al., E., et al., "Cancer Res. 48, 926-9311 (1988); Trouet, et al., 79, 626-629 (1982); Z. Brich et al., J. Controlled Release, 19, 245-258 (1992); Chen et al., Syn. Comm., 33, 2377-2390, 2003; King et al., Bioconj. Chem., 10, 279-288, 1999; King et al., J. Med. Chem., 45, 4336-4343, 2002; Kratz et al., J Med Chem. 45, 5523-33. 2002; Kratz et al., Biol Pharm Bull. January 21, 56-61, 1998; Lau et al., Bioorg. Med. Chem. 3, 1305-1312, 1995; Scott et al., Bioorg. Med.l Chem. Lett. 6, 1491-1496; 1996; Watanabe et al., Tokai J. Experimental Clin. Med. 15, 327-334, 1990; Zhou et al., J. Am. Chem. Soc. 126, 15656-7, 2004; WO 01/38318; U.S. Pat. Nos. 5,106,951; 5,122,368; 5,146,064; 5,177,016; 5,208,323; 5,824,805; 6,146,658; 6,214,345; 7,569,358; 7,803,903; 8,084,586; 8,053,205. Examples of the structures of the conjugate of the antibody-CC-1065 analogs via the bridge linker are as the following Da01, Da02, Da03 and Da04.

Da01
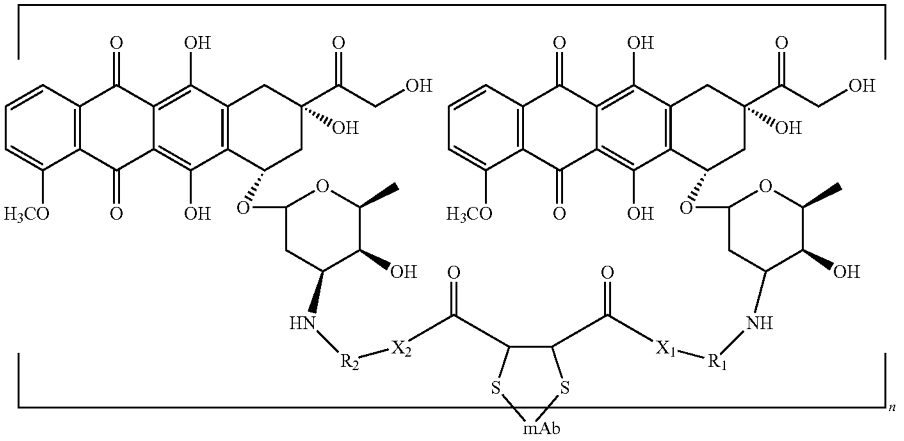
Da02
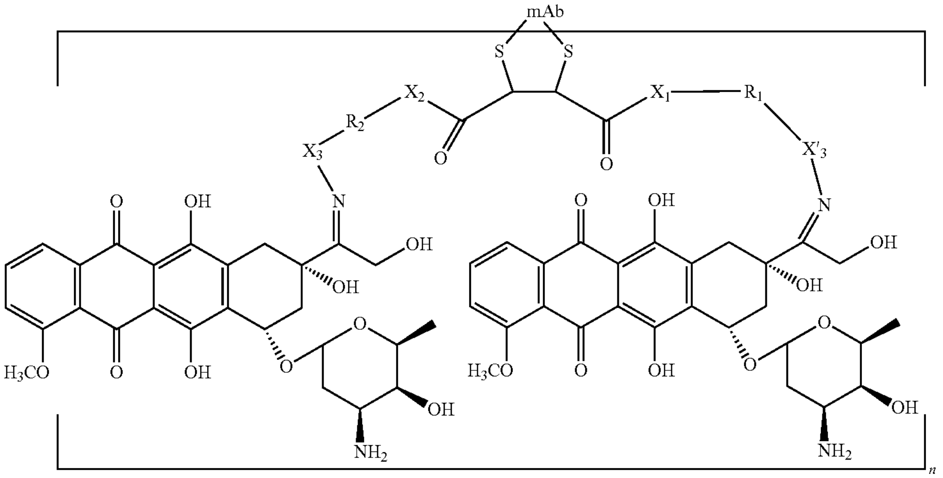
Da03
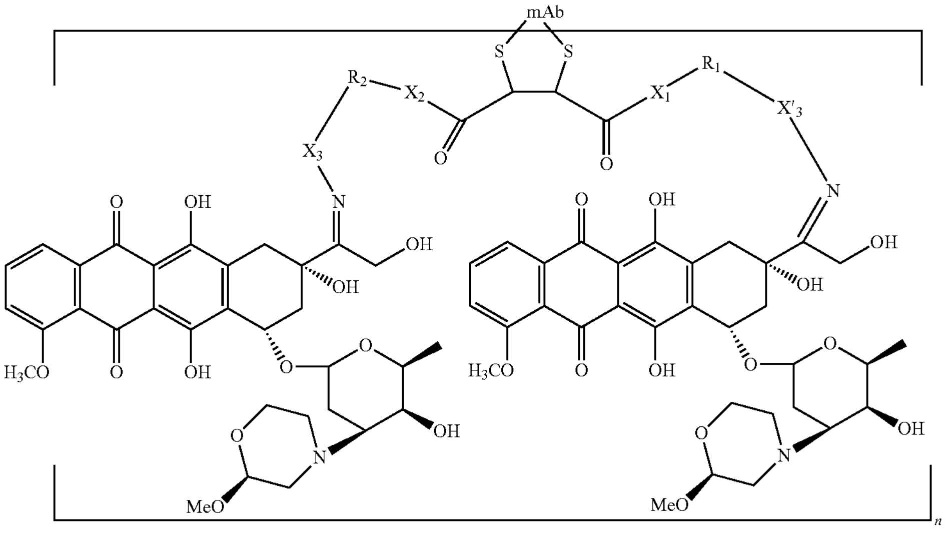

-continued

Da04

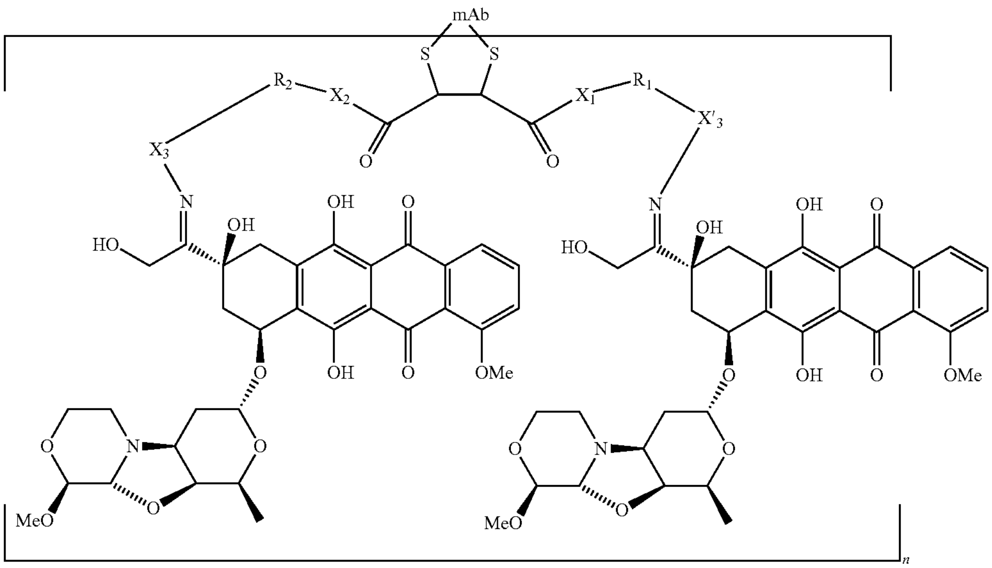

Wherein mAb is an antibody; n is 1~20; $X_3$ and $X'_3$ are independently H, O, NH, NHC(O), NHC(O)NH, C(O), $R_1$, or OC(O); $X_1$, $X_2$, $R_1$, and $R_2$ are the same defined in Formula (I).

Auristatins and dolastatins are preferred in conjugation via the bridge linkers of this patent. The auristatins (e. g. auristatin E (AE) auristatin EB (AEB), auristatin EFP (AEFP), monomethyl auristatin E (MMAE), Monomethylauristatin (MMAF), Auristatin F phenylene diamine (AFP) and a phenylalanine variant of MMAE) which are synthetic analogs of dolastatins, are described in Int. J. Oncol. 15:367-72 (1999); Molecular Cancer Therapeutics, vol. 3, No. 8, pp. 921-932 (2004); U.S. Application Nos. 11134826, 20060074008, 2006022925. U.S. Pat. Nos. 4,414,205, 4,753,894, 4,764,368, 4,816,444, 4,879,278, 4,943,628, 4,978,744, 5,122,368, 5,165,923, 5,169,774, 5,286,637, 5,410,024, 5,521,284, 5,530,097, 5,554,725, 5,585,089, 5,599,902, 5,629,197, 5,635,483, 5,654,399, 5,663,149, 5,665,860, 5,708,146, 5,714,586, 5,741,892, 5,767,236, 5,767,237, 5,780,588, 5,821,337, 5,840,699, 5,965,537, 6,004,934, 6,033,876, 6,034,065, 6,048,720, 6,054,297, 6,054,561, 6,124,431, 6,143,721, 6,162,930, 6,214,345, 6,239,104, 6,323,315, 6,342,219, 6,342,221, 6,407,213, 6,569,834, 6,620,911, 6,639,055, 6,884,869, 6,913,748, 7,090,843, 7,091,186, 7,097,840, 7,098,305, 7,098,308, 7,498,298, 7,375,078, 7,462,352, 7,553,816, 7,659,241, 7,662,387, 7,745,394, 7,754,681, 7,829,531, 7,837,980, 7,837,995, 7,902,338, 7,964,566, 7,964,567, 7,851,437, 7,994,135. Examples of the structures of the conjugate of the antibody-auristatins via the bridge linker are as the following Au01, Au02, Au03, Au04, and Au05.

Au01

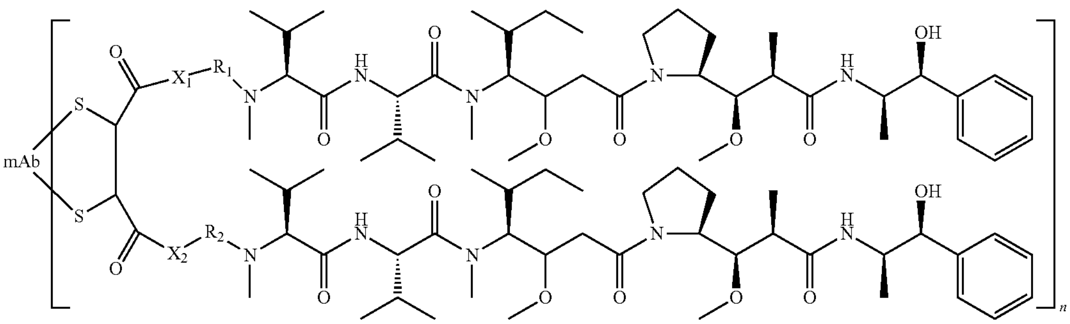

-continued

Au02

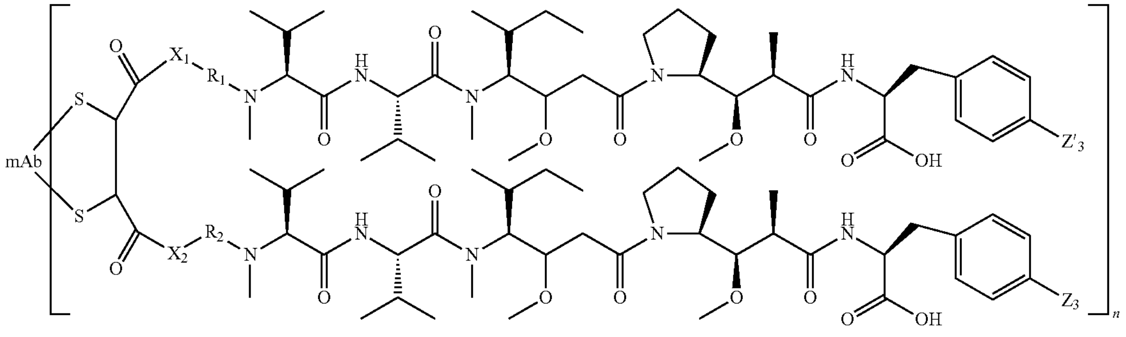

Au03

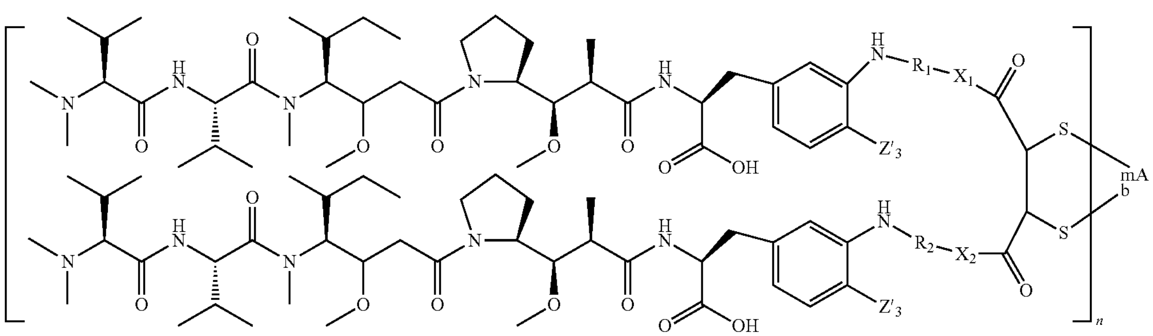

Au04

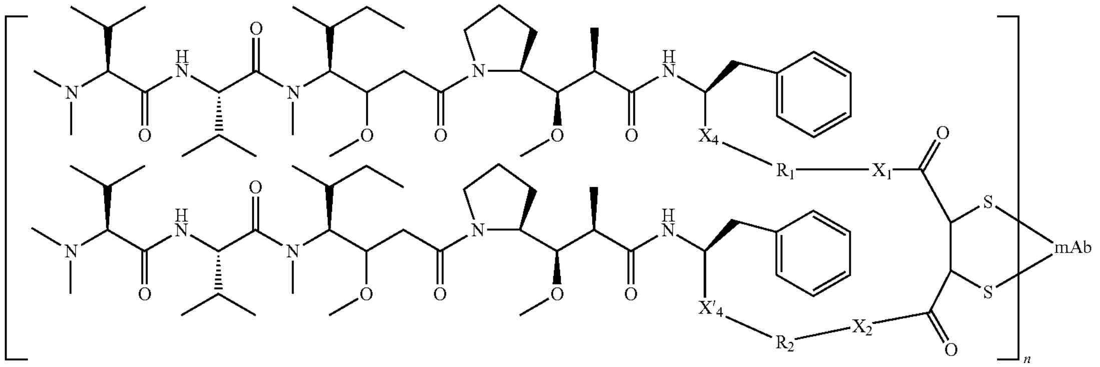

Au05

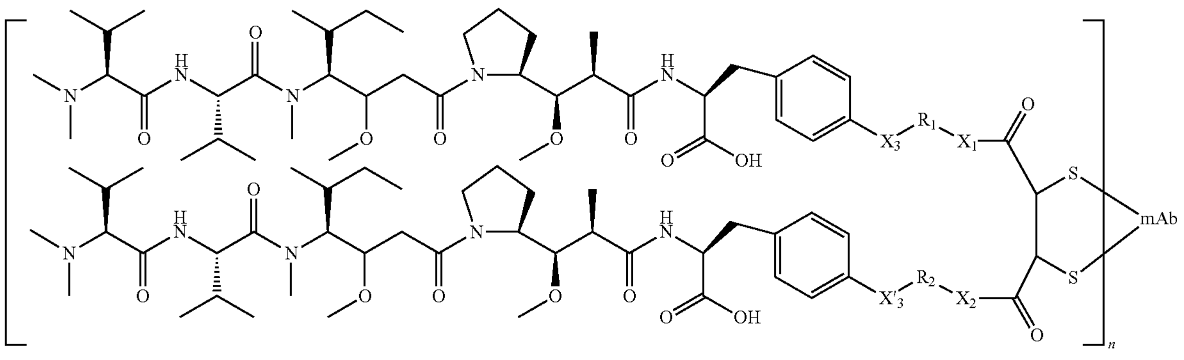

Wherein mAb is an antibody; n is 1~20; $X_3$ and $X'_3$ are independently $CH_2$, O, NH, NHC(O), NHC(O)NH, C(O), OC(O) $R_1$, or absent; $X_4$ and $X'_4$ are independently $CH_2$, C(O), C(O)NH, $C(O)N(R_1)$, $R_1$, $NHR_1$, $NR_1$, $C(O)R_1$ or C(O)O; $Z_3$ and $Z'_3$ are independently H, $R_1$, $OP(O)(OM_1)(OM_2)$, $NHR_1$, $OCH_2OP(O)(OM_1)(OM_2)$, $OSO_3M_1$, or O-glycoside (glucoside, galactoside, mannoside, glucuronoside, alloside, fructoside), NH-glycoside, S-glycoside, or $CH_2$-glycoside; $X_1$, $X_2$, $R_1$, $R_2$, and $R_3$ are the same defined in Formula (I).

The benzodiazepine dimers (e. g. dimmers of pyrrolobenzodiazepine (PBD) or (tomaymycin), indolinobenzodiazepines, imidazobenzothiadiazepines, or oxazolidinobenzodiazepines) which are preferred cytotoxic agents according to the present invention are exampled in the art: U.S. Pat. Nos. 8,163,736; 8,153,627; 8,034,808; 7,834,005; 7,741,319; 7,704,924; 7,691,848; 7,678,787; 7,612,062; 7,608,615; 7,557,099; 7,528,128; 7,528,126; 7,511,032; 7,429,658; 7,407,951; 7,326,700; 7,312,210; 7,265,105; 7,202,239; 7,189,710; 7,173,026; 7,109,193; 7,067,511; 7,064,120; 7,056,913; 7,049,311; 7,022,699; 7,015,215; 6,979,684; 6,951,853; 6,884,799; 6,800,622; 6,747,144; 6,660,856; 6,608,192; 6,562,806; 6,977,254; 6,951,853; 6,909,006; 6,344,451; 5,880,122; 4,935,362; 4,764,616; 4,761,412; 4,723,007; 4,723,003; 4,683,230; 4,663,453; 4,508,647; 4,464,467; 4,427,587; 4,000,304; US patent appl. 20100203007, 20100316656, 20030195196. Examples of the structures of the conjugate of the antibody-benzodiazepine dimers via the bridge linker are as the following PB01, PB02, PB03, PB04, PB05, PB06, PB07, PB08, PB09, PB10 and PB11.
PB01
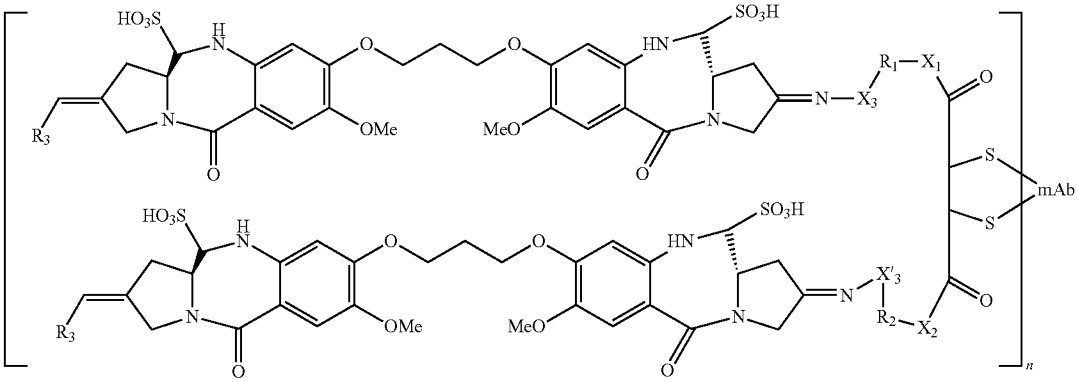
PB02
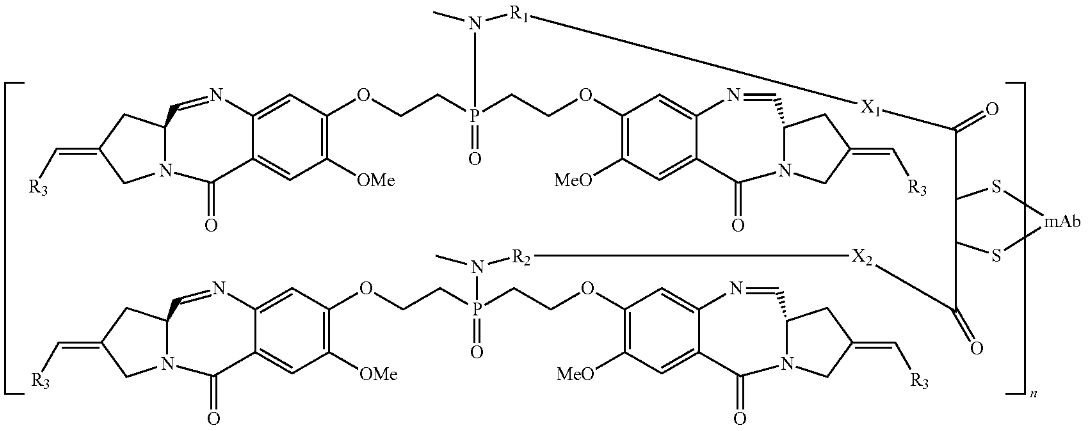
PB03
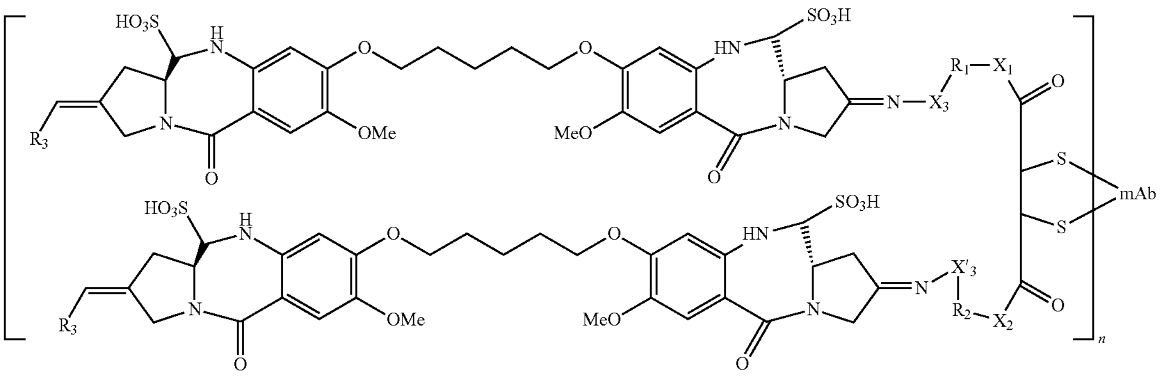

-continued
PB04
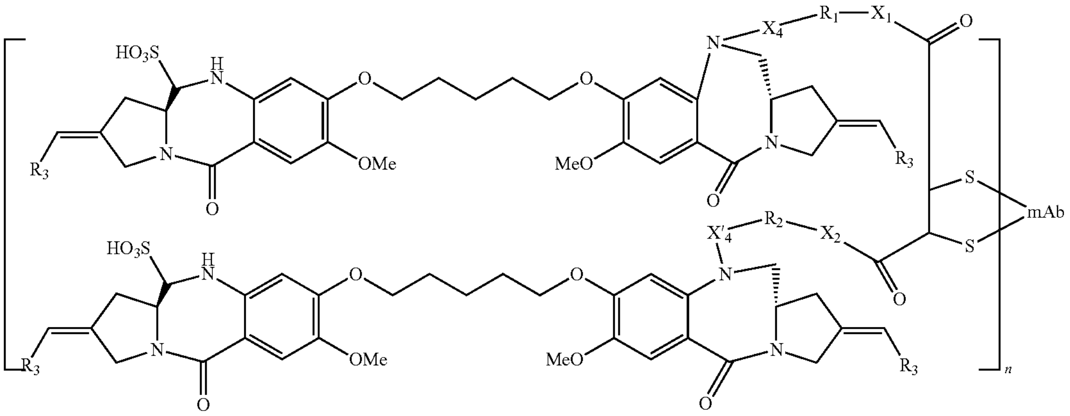
PB05
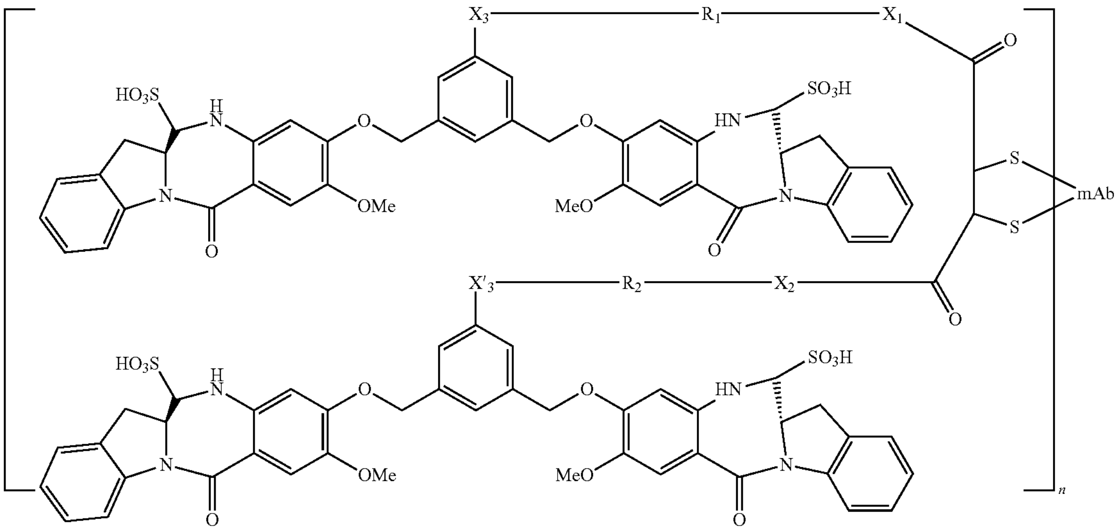
PB06
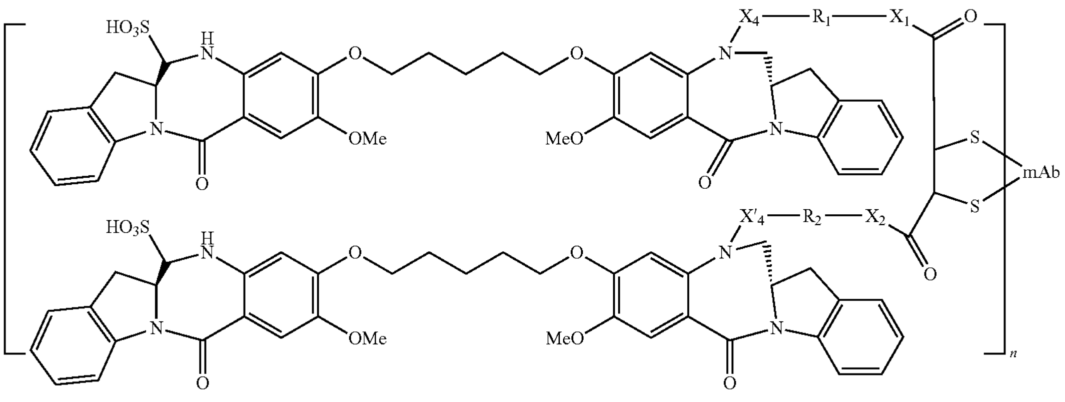

-continued
PB07
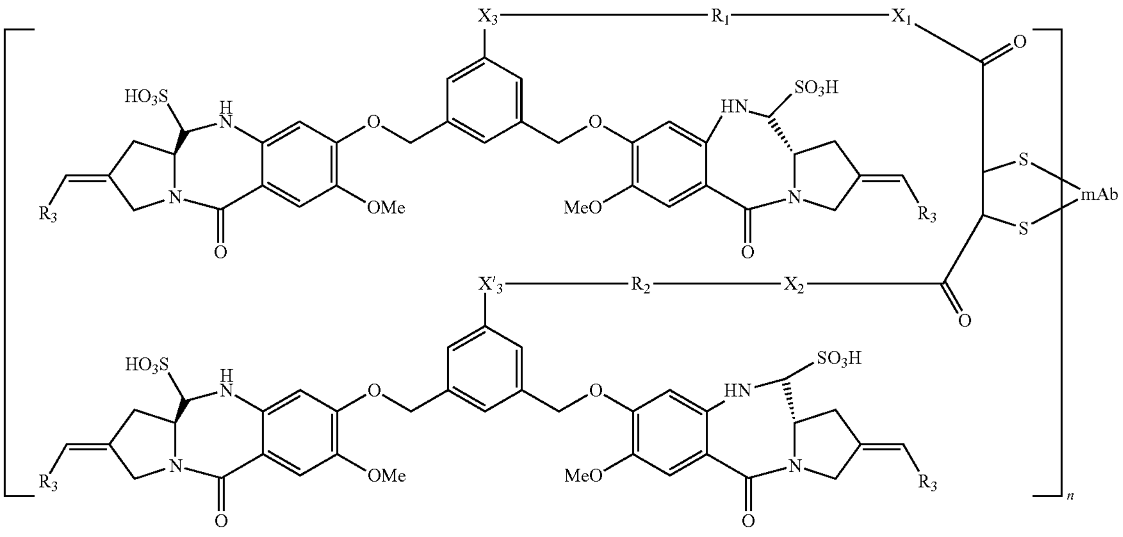
PB08
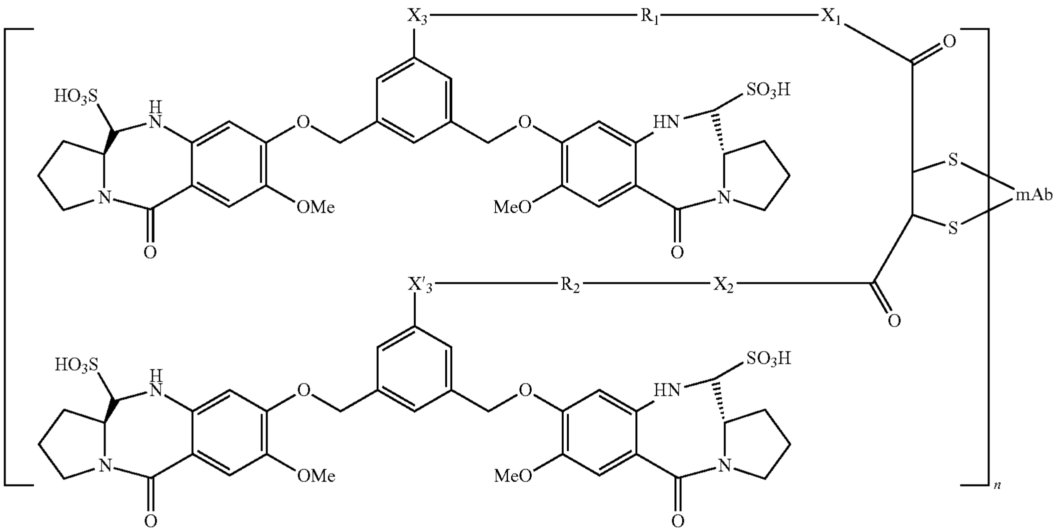
PB09
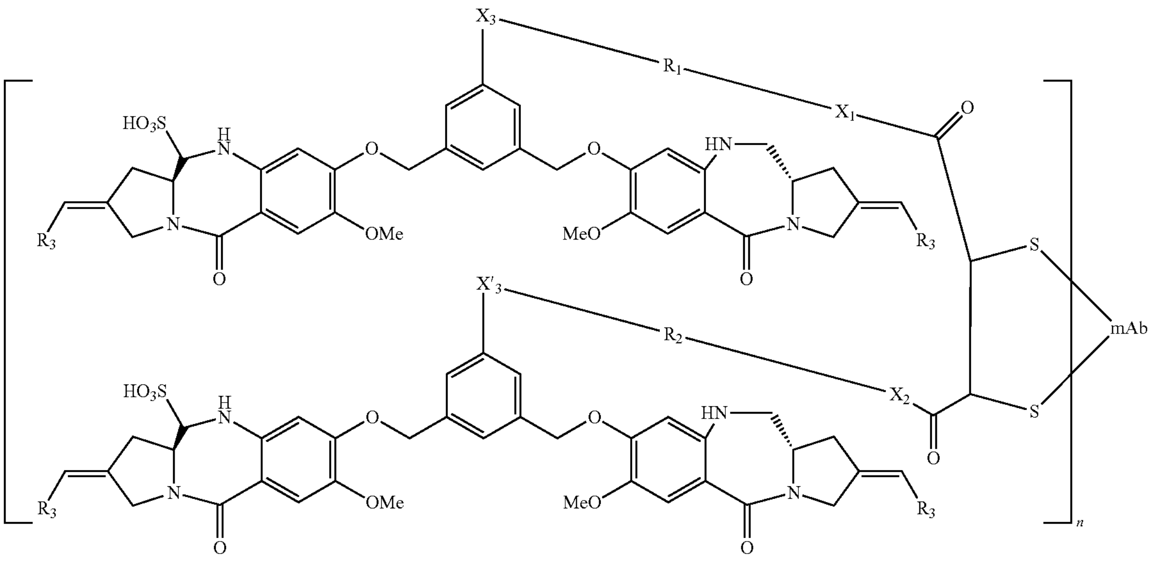

-continued

PB10

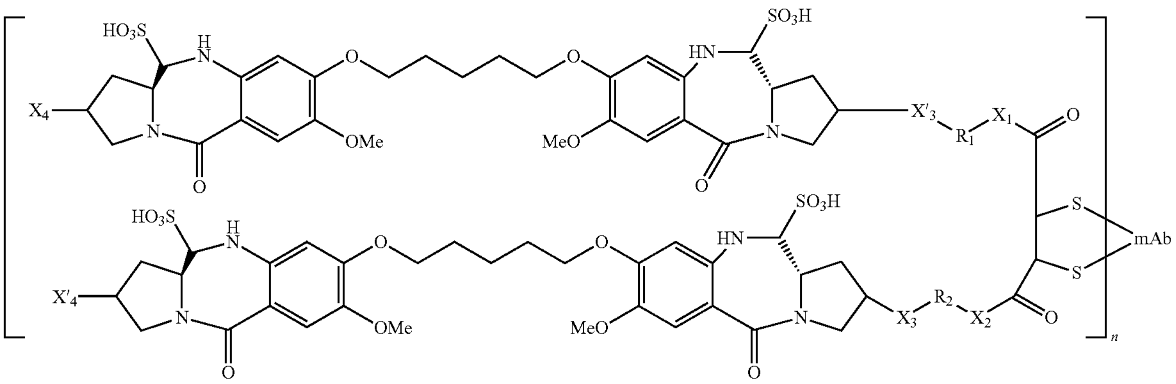

PB11

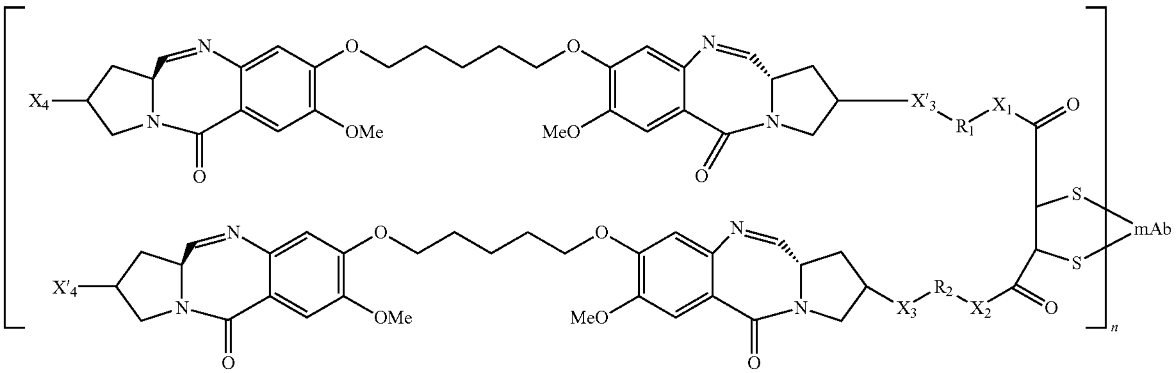

Wherein mAb is an antibody; n is 1~20; $X_3$ and $X'_3$ are independently $CH_2$, O, NH, NHC(O), NHC(O)NH, C(O), OC(O), $OC(O)(NR_3)$, $R_1$, $NHR_1$, $NR_1$, $C(O)R_1$ or absent; $X_4$ and $X'_4$ are independently $CH_2$, C(O), C(O)NH, C(O)N $(R_1)$, $R_1$, $NHR_1$, $NR_1$, $C(O)R_1$ or C(O)O; $X_1$, $X_2$, $R_1$, $R_2$ and $R_3$ are the same defined in Formula (I). In addition, $R_1$ and/or $R_2$ can be absent.

The drugs/cytotoxic agents used for conjugation via a bridge linker of the present patent can be any analogues and/or derivatives of drugs/molecules described in the present patent. One skilled in the art of drugs/cytotoxic agents will readily understand that each of the drugs/cytotoxic agents described herein can be modified in such a manner that the resulting compound still retains the specificity and/or activity of the starting compound. The skilled artisan will also understand that many of these compounds can be used in place of the drugs/cytotoxic agents described herein. Thus, the drugs/cytotoxic agents of the present invention include analogues and derivatives of the compounds described herein.

All references cited herein and in the examples that follow are expressly incorporated by reference in their entireties.

EXAMPLES

The invention is further described in the following examples, which are not intended to limit the scope of the invention. Cell lines described in the following examples were maintained in culture according to the conditions specified by the American Type Culture Collection (ATCC) or Deutsche Sammlung von Mikroorganismen and Zellkulturen GmbH, Braunschweig, Germany (DMSZ), or The Shanghai Cell Culture Institute of Chinese Academy of Science, unless otherwise specified. Cell culture reagents were obtained from Invitrogen Corp., unless otherwise specified. All anhydrous solvents were commercially obtained and stored in Sure-seal bottles under nitrogen. All other reagents and solvents were purchased as the highest grade available and used without further purification. The preparative HPLC separations were performed with Varain PreStar HPLC. NMR spectra were recorded on Varian Mercury 400 MHz Instrument. Chemical shifts (.delta.) are reported in parts per million (ppm) referenced to tetramethylsilane at 0.00 and coupling constants (J) are reported in Hz. The mass spectral data were acquired on a Waters Xevo QTOF mass spect equipped with Waters Acquity UPLC separations module and Acquity TUV detector.

Example 1 tert-Butyl 3-(2-(2-(2-hydroxyethoxy)ethoxy)ethoxy) propanoate (34)

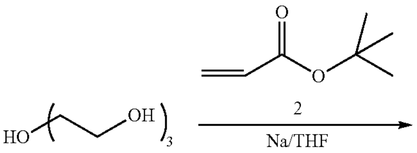

33

-continued

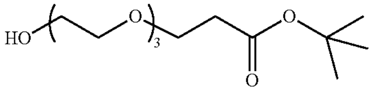

34

To 350 mL of anhydrous THF was added 80 mg (0.0025 mol) of sodium metal and triethylene glycol 2 (150.1 g, 1.00 mol) with stirring. After the sodium had completely dissolved, tert-butyl acrylate (24 mL, 0.33 mol) was added. The solution was stirred for 20 h at room temperature and neutralized with 8 mL of 1.0 M HCl. The solvent was removed in vacuo and the residue was suspended in brine (250 mL) and extracted with ethyl acetate (3×125 mL). The combined organic layers were washed with brine (100 mL) then water (100 mL), dried over sodium sulfate, and the solvent was removed. The resulting colorless oil was dried under vacuum to give 69.78 g (76% yields) of product 34. $^1$H NMR: 1.41 (s, 9H), 2.49 (t, 2H, J=6.4 Hz), 3.59-3.72 (m, 14H). ESI MS m/z-$C_{13}H_{25}O_6$ (M−H), cacld. 277.17, found 277.20.

Example 2 tert-Butyl 3-(2-(2-(2-(tosyloxy)ethoxy)ethoxy)ethoxy)propanoate (35)

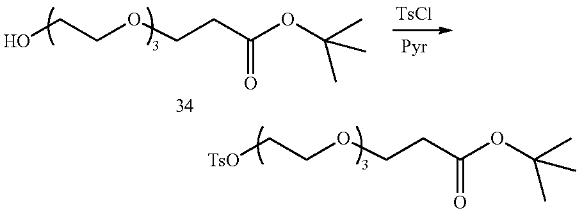

34

35

A solution of 34 (10.0 g, 35.95 mmol) in acetonitrile (50.0 mL) was treated with pyridine (20.0 mL). A solution of tosyl chloride (7.12 g, 37.3 mmol) in 50 mL acetonitrile was added dropwise via an addition funnel over 30 minutes. After 5 h TLC analysis revealed that the reaction was complete. The pyridine hydrochloride that had formed was filtered off and the solvent was removed. The residue was purified on silica gel by eluting from with 20% ethyl acetate in hexane to with neat ethyl acetate to give 11.2 g (76% yield) of compound 35. $^1$H NMR: 1.40 (s, 9H), 2.40 (s, 3H), 2.45 (t, 2H, J=6.4 Hz), 3.52-3.68 (m, 14H), 4.11 (t, 2H, J=4.8 Hz), 7.30 (d, 2H, J=8.0 Hz), 7.75 (d, 2H, J=8.0 Hz); ESI MS m/z+$C_{20}H_{33}O_8S$ (M+H), cacld. 433.18, found 433.30.

Example 3 tert-Butyl 3-(2-(2-(2-azidoethoxy)ethoxy)ethoxy)propanoate (36)

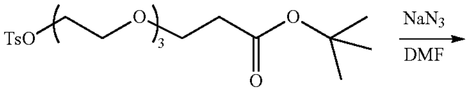

35

-continued

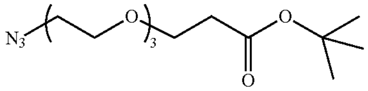

36

To 50 mL of DMF was added tert-butyl 3-(2-(2-(2-(tosyloxy)ethoxy)ethoxy)ethoxy)propanoate 35 (4.0 g, 9.25 mmol) and sodium azide (0.737 g, 11.3 mmol) with stirring. The reaction was heated to 80° C. After 4 h TLC analysis revealed that the reaction was complete. The reaction was cooled to room temperature and quenched with water (25 mL). The aqueous layer was separated and extracted into ethyl acetate (3×35 mL). The combined organic layers were dried over anhydrous magnesium sulfate, filtered, and the solvent removed in vacuo. The crude azide (about 90% pure by TLC) was used without further purification. $^1$H NMR ($CDCl_3$): 1.40 (s, 9H), 2.45 (t, 2H, J=6.4 Hz), 3.33 (t, 2H, J=5.2 Hz), 3.53-3.66 (m, 12H). ESI MS m/z+$C_{13}H_{26}N_3O_8$ (M+H), cacld. 304.18, found 304.20.

Example 4

13-Amino-4,7,10-trioxadodecanoic acid tert-butyl ester, 37; 13-Amino-bis(4,7,10-trioxadodecanoic acid tert-Butyl Ester), 38.

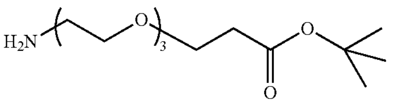

+

37

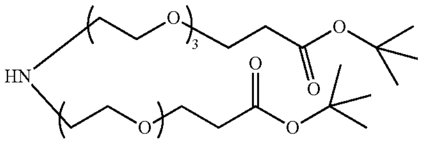

38

The crude azide material 36 (5.0 g, 14.84 mmol) was dissolved in ethanol (80 mL) and 300 mg of 10% Pd/C was added. The system was evacuated under vacuum and placed under 2 atm of hydrogen gas via hydrogenation reactor with vigorous stirring. The reaction was then stirred overnight at room temperature and TLC showed that the starting materials disappeared. The crude reaction was passed through a short pad of celite rinsing with ethanol. The solvent was removed and the amine purified on silica gel using a mixture of methanol (from 5% to 15%) and 1% triethylamine in methylene chloride as the eluant to give 13-amino-4,7,10- trioxadodecanoic acid tert-butyl ester 37 (1.83 g, 44% yield, ESI MS m/z+$C_{13}H_{27}NO_5$ (M+H), cacld. 278.19, found 278.30) and 13-amino-bis(4,7,10-trioxadodecanoic acid tert-butyl ester), 38 (2.58 g, 32% yield, ESI MS m/z+ $C_{26}H_{52}NO_{10}$ (M+H), cacld. 538.35, found 538.40).

Example 5

3-(2-(2-(2-aminoethoxy)ethoxy)ethoxy)propanoic acid, HCl salt, 39.

39

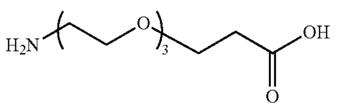

To 13-amino-4,7,10-trioxadodecanoic acid tert-butyl ester, 37 (0.80 g, 2.89 mmol) in 30 mL of dioxane was 10 ml of HCl (36%) with stirring. After 0.5 h TLC analysis revealed that the reaction was complete, the reaction mixture was evaporated, and co-evaporated with EtOH and EtOH/Toluene to form the title product in HCl salt (>90% pure, 0.640 g, 86% yield) without further purification. ESI MS m/z+$C_9H_{20}NO_5$ (M+H), cacld. 222.12, found 222.20.

Example 6

13-Amino-bis(4,7,10-trioxadodecanoic acid, HCl salt, 40.

40

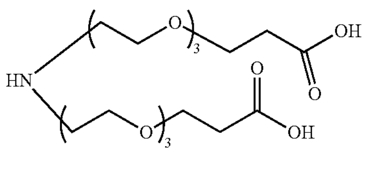

To 13-amino-bis(4,7,10-trioxadodecanoic acid tert-butyl ester), 38 (1.00 g, 1.85 mmol) in 30 mL of dioxane was 10 ml of HCl (36%) with stirring. After 0.5 h TLC analysis revealed that the reaction was complete, the reaction mixture was evaporated, and co-evaporated with EtOH and EtOH/Toluene to form the title product in HCl salt (>90% pure, 0.71 g, 91% yield) without further purification. ESI MS m/z+$C_{18}H_{36}NO_{10}$ (M+H), cacld. 426.22, found 426.20.

Example 7 bis(2,5-dioxopyrrolidin-1-yl) but-2-ynedioate, 9.

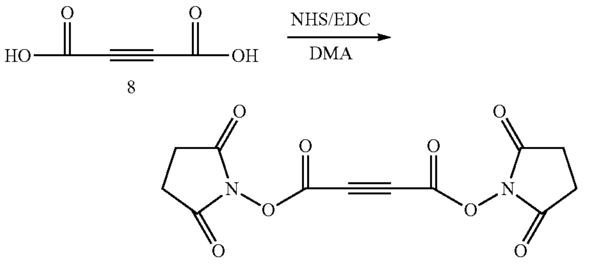

8

9

To but-2-ynedioic acid 8 (2.0 g, 17.54 mmol) in DMA (100 ml) was added NHS (5.0 g, 43.4 mmol) and EDC (12.0 g, 62.5 mmol). The mixture was stirred under dark overnight, evaporated and purified on $SiO_2$ column eluted with EtOAc/DCM (1:10) to afford the title compound 9 (4.10 g, 76% yield). ESI MS m/z+$C_{12}H_9N_2O_8$ (M+H), cacld. 309.03, found 309.20.

Example 8

4,7-dioxodec-5-ynedioic acid, 15.

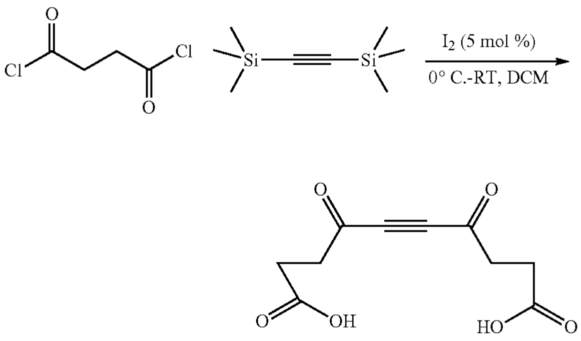

To a stirred solution of bis(trimethylsilyl)acetylene (5.0 g, 29.34 mmol) and iodine (0.37 g, 1.45 mmol) in dichloromethane (100 mL), was added succinyl chloride (18.11 g, 116.83 mmol) slowly in a dropwise manner at 0° C. After addition, the mixture was allowed to stir at room temperature until complete conversion as indicated by TLC (~2 h). The reaction mixture was quenched with water (15 mL) and extracted with dichloromethane (3×70 mL). The combined extracts were washed with 15% solution of sodium thiosulphate, dried over anhydrous $Na_2SO_4$, and concentrated in vacuo. The resulting product was purified by column chromatography on silica gel (100-200 mesh, aqueous form, from 5% to 10% of $H_2O$ in acetonitrile) to afford the pure title product (5.50 g, yield 85%). ESI MS m/z-$C_{10}H_9O_6$ (M-H), cacld. 226.05, found 226.10.

Example 9

(R,R,S,S,R,4R,4'R)-5,5'-(((4,7-dioxodec-5-ynedioyl) bis(azanediyl))bis(4-hydroxy-3,1-phenylene))bis(4-(2-((1R,3R)-1-acetoxy-3-((2S,3S)—N,3-dimethyl-2-((R)-1-methylpiperidine-2-carboxamido) pentanamido)-4-methylpentyl)thiazole-4-carboxamido)-2-methylpentanoic acid), 79

79

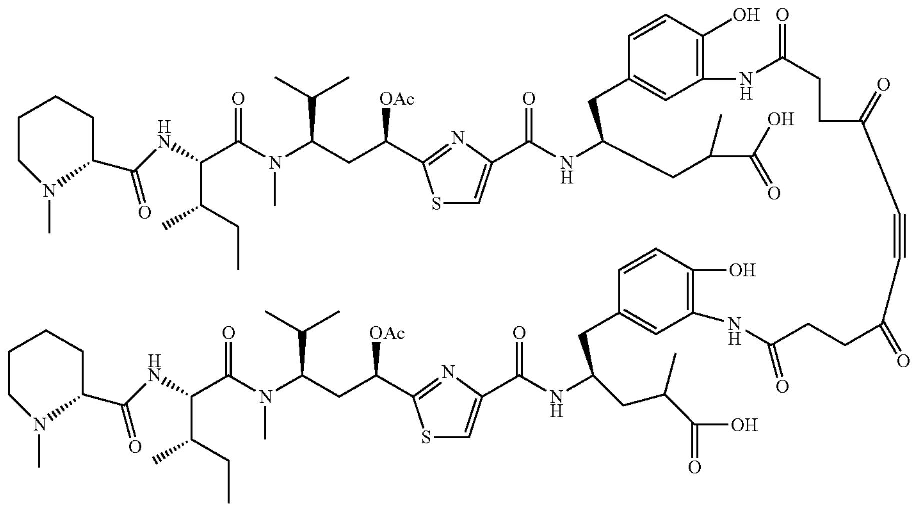

The compound 9 (25 mg, 0.081 mmol) in THF (3.0 ml) was added (4R)-4-(2-((1R,3R)-1-acetoxy-3-((2S,3S)-N,3-dimethyl-2-((R)-1-methylpiperidine-2-carboxamido)pentanamido)-4-methylpentyl)thiazole-4-carboxamido)-5-(3-amino-4-hydroxyphenyl)-2-methylpentanoic acid, 51 (Huang Y. et al, Med Chem. #44, 249th ACS National Meeting, Denver, Colo., Mar. 22~26, 2015; WO2014009774) (151 mg, 0.199 mmol) in THF (4.0 ml) and buffer (4 ml, 100 mM $Na_2HPO_4$, pH 7.0). After stirred at RT for 4 h, the mixture was concentrated and purified with C-18 preparative HPLC (250 mm×ID 20 mm), eluted with water/ethanol (90% water to 50% water in 55 min, v=15 ml/min). The fractions containing the product were pooled, concentrated and crystallized with EtOH/Hexane to afford the title compound (73 mg, 53% yield). ESI MS m/z+ $C_{86}H_{122}N_{12}N_aO_{20}S_2$ (M+Na), cacld. 1729.83, found 1730.10.

Example 10

14,17-dioxo-4,7,10,21,24,27-hexaoxa-13,18-diazatriacont-15-yne-1,30-dioic acid, 86.

86

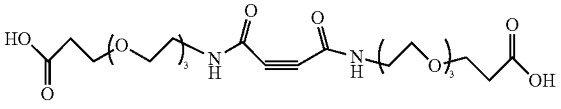

3-(2-(2-(2-Aminoethoxy)ethoxy)ethoxy)propanoic acid, HCl salt, 39 (601 mg, 2.33 mmol) in the mixture of THF (6 ml) and a buffer (150 mM $NaH_2PO_4$, pH 7.2, 4 ml) was added bis(2,5-dioxopyrrolidin-1-yl)but-2-ynedioate, 9 (350 mg, 1.13 mmol). After stirred at RT under dark for 4 h, the mixture was concentrated and purified with $SiO_2$ column, eluted with water/acetonitrile (1:9). The fractions containing the product were pooled and concentrated to afford the title compound (345 mg, 59% yield). ESI MS m/z-$C_{22}H_{36}N_2O_{12}$ (M−H), cacld. 519.22, found 519.30.

Example 11

13,18-bis(2-(2-(2-(2-carboxyethoxy)ethoxy)ethoxy) ethyl)-14,17-dioxo-4,7,10,21,24,27-hexaoxa-13,18-diazatriacont-15-yne-1,30-dioic acid, 87.

87

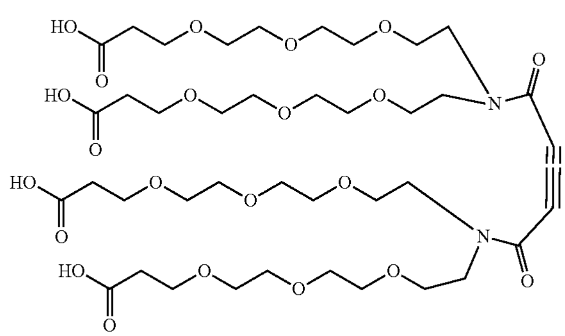

13-Amino-bis(4,7,10-trioxadodecanoic acid, HCl salt, 40 (650 mg, 1.40 mmol) in the mixture of THF (6 ml) and a buffer (150 mM $NaH_2PO_4$, pH 7.2, 4 ml) was added bis(2,5-dioxopyrrolidin-1-yl)but-2-ynedioate, 9 (190 mg, 0.61 mmol). After stirred at RT under dark for 4 h, the mixture was concentrated and purified with C-18 preparative HPLC (250 mm×ID 30 mm), eluted with water/ethanol (90% water to 50% water in 55 min, v=35 ml/min). The fractions containing the product were pooled and concentrated to afford the title compound (287 mg, 51% yield). ESI MS m/z-$C_{40}H_{67}N_2O_{22}$ (M−H), cacld. 927.42, found 928.30.

Example 12

Bis(2,5-dioxopyrrolidin-1-yl) 14,17-dioxo-4,7,10,21,24,27-hexaoxa-13,18-diazatriacont-15-yne-1,30-dioate, 88.

88

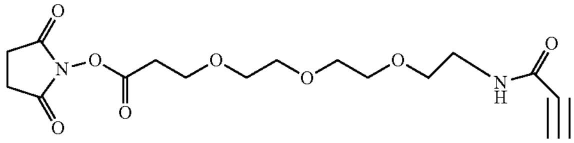

-continued

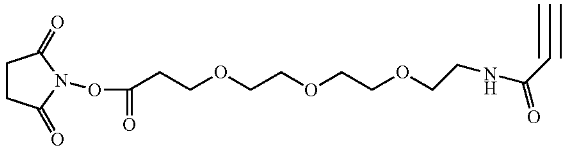

To 14,17-dioxo-4,7,10,21,24,27-hexaoxa-13,18-diazatriacont-15-yne-1,30-dioic acid, 86 (340 mg, 0.653 mmol) in DMA (6 ml) was added NHS (225 mg, 1.96 mmol) and EDC (401 mg, 2.08 mmol). The mixture was stirred under dark overnight, evaporated and purified on $SiO_2$ column eluted with EtOAc/DCM (5:1) to afford the title compound 88 (330 mg, 71% yield). ESI MS m/z+$C_{30}H_{43}N_4O_{16}$ (M+H), cacld. 715.26, found 715.20.

Example 13

Bis(2,5-dioxopyrrolidin-1-yl) 13,18-bis(2-(2-(2-(3-((2,5-dioxopyrrolidin-1-yl)oxy)-3-oxopropoxy)ethoxy)ethoxy)ethyl)-14,17-dioxo-4,7,10,21,24,27-hexaoxa-13,18-diazatriacont-15-yne-1,30-dioate, 89

89

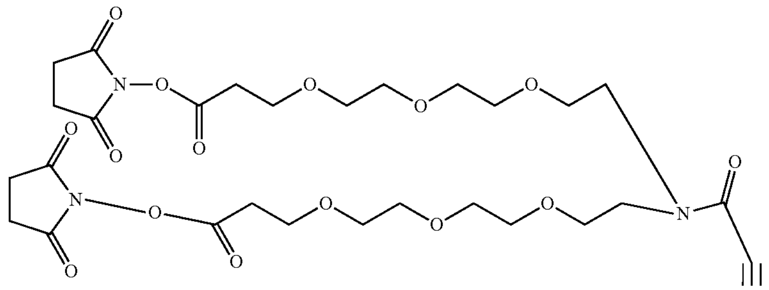

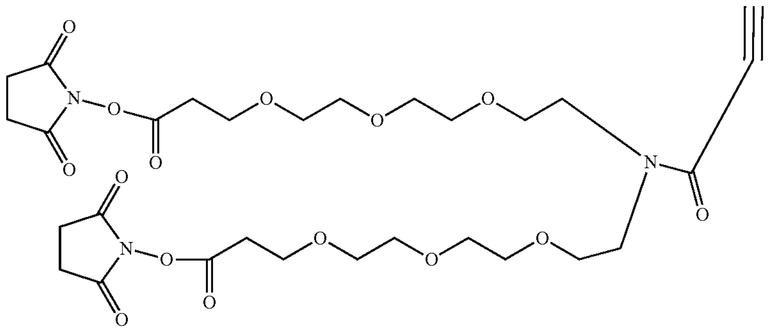

To 13,18-bis(2-(2-(2-(2-carboxyethoxy)ethoxy)ethoxy) ethyl)-14,17-dioxo-4,7,10,21,24,27-hexaoxa-13,18-diaza-triacont-15-yne-1,30-dioic acid, 87 (280 mg, 0.301 mmol) in DMA (6 ml) was added NHS (105.0 mg, 0.913 mmol) and EDC (200 mg, 1.04 mmol). The mixture was stirred under dark overnight, evaporated and purified on $SiO_2$ column eluted with EtOH/DCM (1:10~1:5) to afford the title compound 89 (249 mg, 63% yield). ESI MS m/z+$C_{56}H_{81}N_6O_{30}$ (M+H), cacld. 1317.49, found 1317.80.

Example 14

(R,R,S,S,R,4R,4'R)-5,5'-(((14,17-dioxo-4,7,10,21,24,27-hexaoxa-13,18-diazatriacont-15-yne-1,30-dioyl) bis(azanediyl))bis(4-hydroxy-3,1-phenylene))bis(4-(2-((1R,3R)-1-acetoxy-3-((2S,3S)-N,3-dimethyl-2-((R)-1-methylpiperidine-2-carboxamido) pentanamido)-4-methylpentyl)thiazole-4-carboxamido)-2-methylpentanoic acid), 90

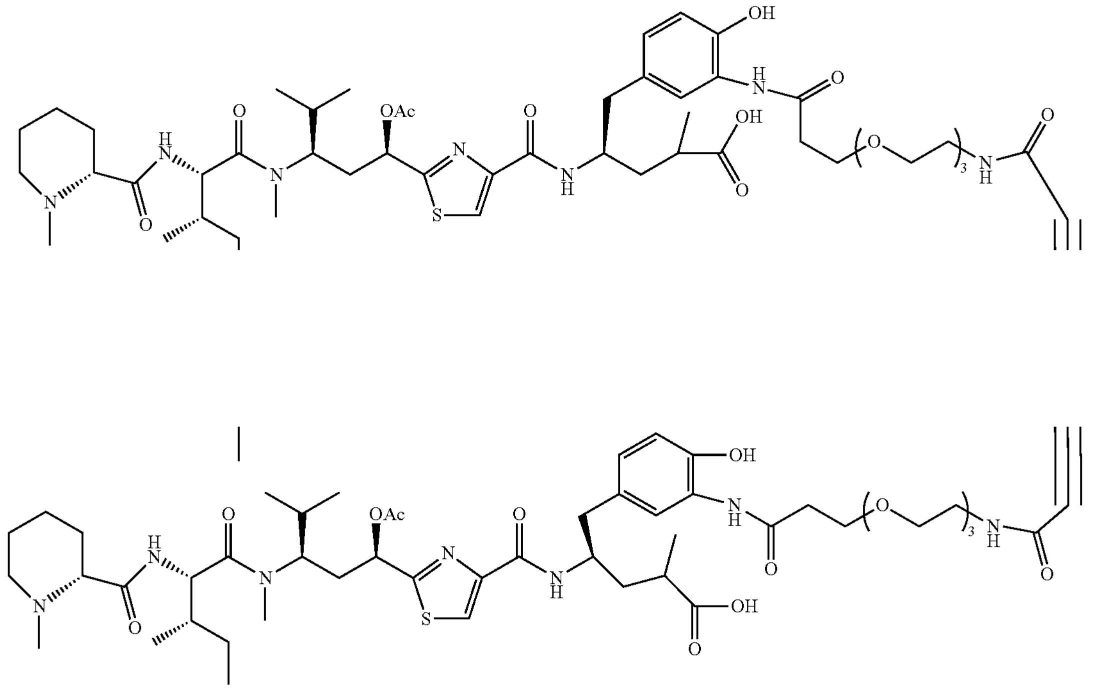

90

The compound 88 (30 mg, 0.042 mmol) in THF (3.0 ml) was added (4R)-4-(2-((1R,3R)-1-acetoxy-3-((2S,3S)-N,3-dimethyl-2-(((R)-1-methylpiperidine-2-carboxamido)pentanamido)-4-methylpentyl)thiazole-4-carboxamido)-5-(3-amino-4-hydroxyphenyl)-2-methylpentanoic acid, 51 (Huang Y. et al, Med Chem. #44, $249^{th}$ ACS National Meeting, Denver, Colo., Mar. 22~26, 2015; WO2014009774) (80 mg, 0.107 mmol) in THF (4.0 ml) and buffer (4 ml, 100 mM $Na_2HPO_4$, pH 7.0). After stirred at RT for 4 h, the mixture was concentrated and purified with C-18 preparative HPLC (250 mm×ID 20 mm), eluted with water/ethanol (95% water to 50% water in 55 min, v=15 ml/min). The fractions containing the product were pooled, concentrated and crystallized with EtOH/Hexane to afford the title compound (48 mg, 56% yield). ESI MS m/z-$C_{98}H_{147}N_{14}O_{26}S_2$ (M−H), cacld. 2000.01, found 2000.40.

Example 15

Conjugated Compound 90 to an Antibody for 91.

91

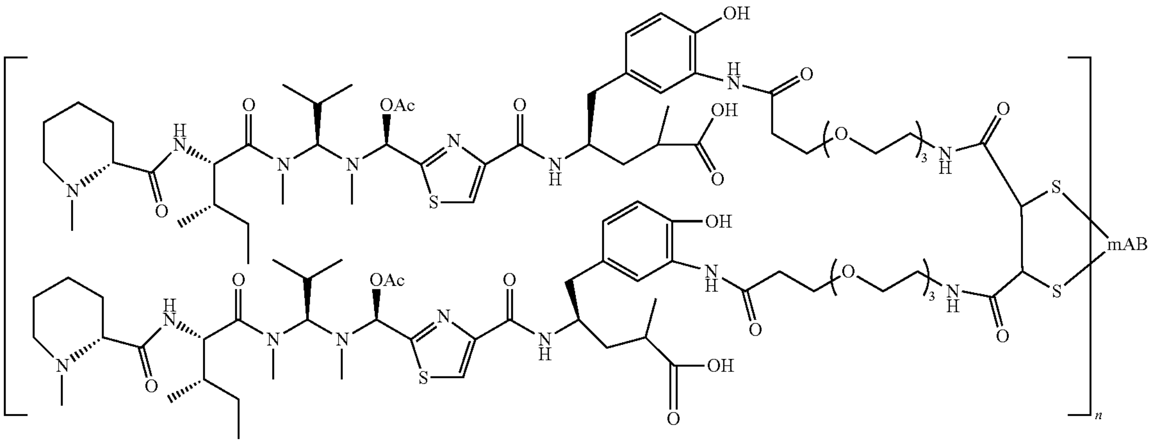

To a mixture of 2.0 mL of 10 mg/ml Herceptin in pH 6.0~8.0, were added of 0.70~2.0 mL PBS buffer of 100 mM $NaH_2PO_4$, pH 6.5~7.5 buffers, TCEP (28 μL, 20 mM in water) and the compound 90 (14 μL, 20 mM in DMA). The mixture was incubated at RT for 2~16 h, then DHAA (135 μL, 50 mM) was added in. After continuous incubation at RT overnight, the mixture was purified on G-25 column eluted with 100 mM $NaH_2PO_4$, 50 mM NaCl pH 6.0~7.5 buffer to afford 16.8~17.9 mg of the conjugate compound 91 (~87% yield) in 13.1~14.9 ml buffer. The drug/antibody ratio (DAR) was 4.0 (4.04), which was determined via UPLC-Qtof mass spectrum. It was 96~99% monomer analyzed by SEC HPLC (Tosoh Bioscience, Tskgel G3000SW, 7.8 mm ID×30 cm, 0.5 ml/min, 100 min) and a single band measured by SDS-PAGE gel.

Example 16

Compound 92 (Containing 4 Tubulysin Analogs Per Bridge Linker)

92

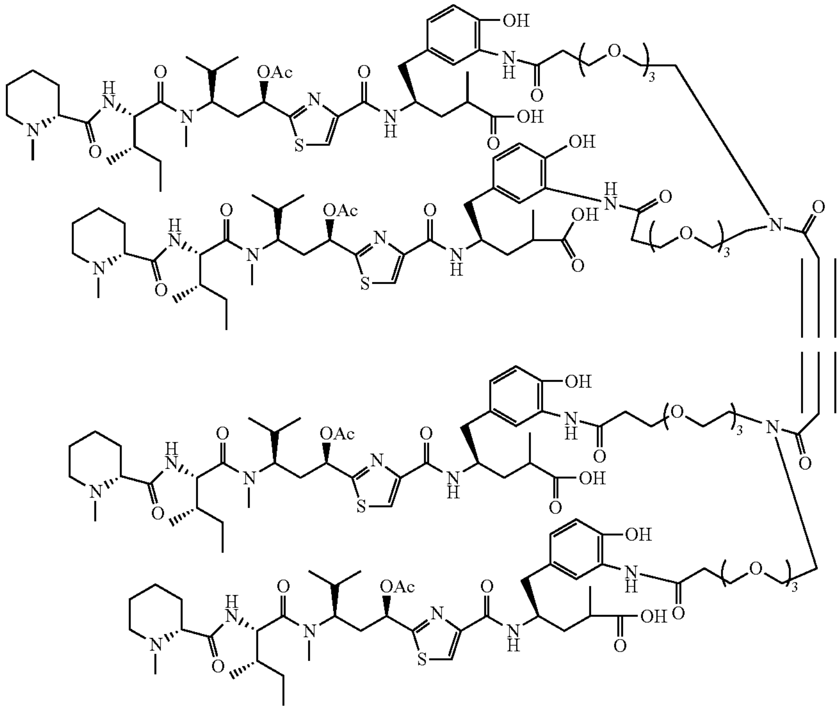

The compound 89 (35 mg, 0.026 mmol) in THF (3.0 ml) was added (4R)-4-(2-((1R,3R)-1-acetoxy-3-((2S,3S)-N,3-dimethyl-2-((R)-1-methylpiperidine-2-carboxamido)pentanamido)-4-methylpentyl)thiazole-4-carboxamido)-5-(3-amino-4-hydroxyphenyl)-2-methylpentanoic acid, 51 (Huang Y. et al, Med Chem. #44, 249$^{th}$ ACS National Meeting, Denver, Colo., Mar. 22~26, 2015; WO2014009774) (100.6 mg, 0.132 mmol) in THF (4.0 ml) and buffer (4 ml, 100 mM $Na_2HPO_4$, pH 7.0). After stirred at RT for 4 h, the mixture was concentrated and purified with C-18 preparative HPLC (250 mm×ID 20 mm), eluted with water/ethanol (95% water to 50% water in 50 min, v=15 ml/min). The fractions containing the product were pooled, concentrated and crystallized with EtOH/Hexane to afford the title compound 92 (47.6 mg, 47% yield). ESI MS m/z-$C_{192}H_{291}N_{26}O_{50}S_4$ (M−H), cacld. 3890.00, found 3890.30.

Example 17

Conjugated Compound 92 to an Antibody for 93

Example 18

In Vitro Cytotoxicity Evaluation of Conjugates 91 and 93 in Comparison with T-DM1

The cell lines used in the cytotoxicity assays were HL-60, a human promyelocytic leukemia cell line; NCI-N87, a human gastric carcinoma cell line; BT-474, a human invasive ductal carcinoma cell line; and SKOV3, a human ovarian carcinoma cell line. For HL-60, NCI-N87, and BT-474 cells, the cells were grown in RPMI-1640 with 10% FBS. For SKOV3 cells, the cells were grown in McCoy's 5A Medium with 10% FBS. To run the assay, the cells (180 μl, 6000 cells) were added to each well in a 96-well plate and incubated for 24 hours at 37° C. with 5% $CO_2$. Next, the cells were treated with test compounds (20 μl) at various concentrations in appropriate cell culture medium (total volume, 0.2 mL). The control wells contain cells and the medium but lack the test compounds. The plates were incubated for 120 hours at 37° C. with 5% $CO_2$. MTT (5 mg/ml) was then added to the wells (20 μl) and the plates

93

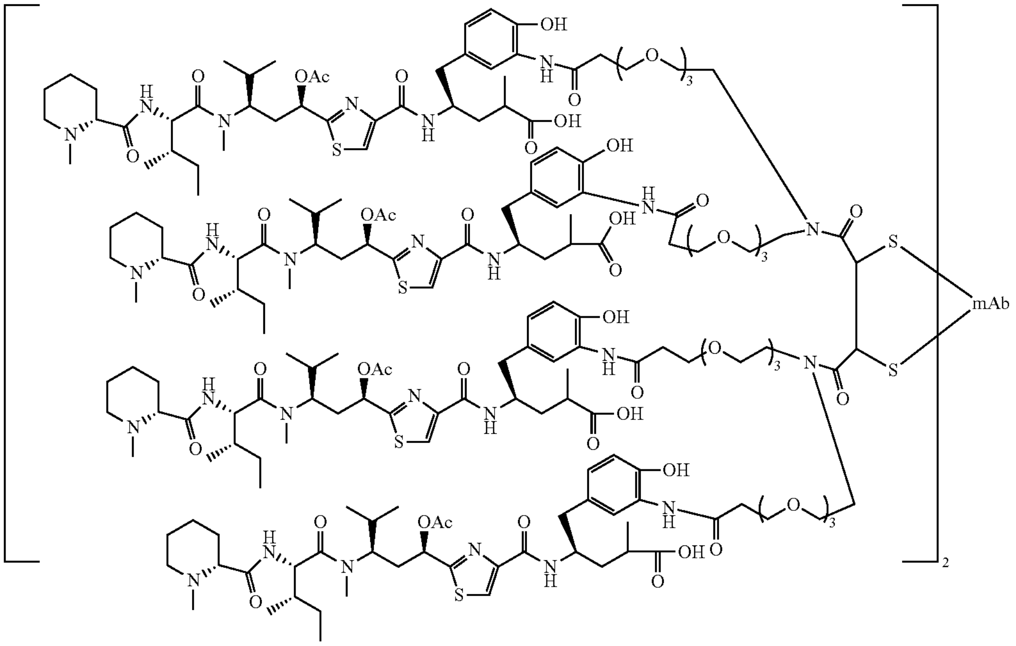

To a mixture of 2.0 mL of 10 mg/ml Herceptin in pH 6.0~8.0, were added of 0.70~2.0 mL PBS buffer of 100 mM $NaH_2PO_4$, pH 6.5~7.5 buffers, TCEP (28 μL, 20 mM in water) and the compound 92 (14 μL, 20 mM in DMA). The mixture was incubated at RT for 2~16 h, then DHAA (135 μL, 50 mM) was added in. After continuous incubation at RT overnight, the mixture was purified on G-25 column eluted with 100 mM $NaH_2PO_4$, 50 mM NaCl pH 6.0~7.5 buffer to afford 16.9~17.5 mg of the conjugate compound 92 (~85% yield) in 13.1~14.9 ml buffer. The drug/antibody ratio (DAR) was 8.0 (7.95), which was determined via UPLC-Qtof mass spectrum. It was 96~99% monomer analyzed by SEC HPLC (Tosoh Bioscience, Tskgel G3000SW, 7.8 mm ID×30 cm, 0.5 ml/min, 100 min) and a single band measured by SDS-PAGE gel.

were incubated for 1.5 hr at 37° C. The medium was carefully removed and DMSO (180 μl) was added afterward. After it was shaken for 15 min, the absorbance was measured at 490 nm and 570 nm with a reference filter of 620 nm. The inhibition % was calculated according to the following equation: inhibition %=[1-(assay-blank)/(control-blank)]×100.

The cytotoxicity results:

| $IC_{50}$ (nM) | N87 cell (Ag+) | SK-OV-3 cell (Ag+) | HL60 cell (Ag+) |
|---|---|---|---|
| Conjugate 91 | 0.108 nM | 0.089 nM | >20 nM |
| Conjugate 93 | 0.037 nM | 0.029 nM | >10 nM |
| T-DM1 | 0.270 nM | 0.191 nM | >15 nM |

Specificity of conjugate 91 for N87 cell was over 185 ($IC_{50}$>20/$IC_{50}$=0.108), and for SK-OV-3 cell was over 225; Specificity of conjugate 93 for N87 cell was over 270 ($IC_{50}$>10/$IC_{50}$=0.037), and for SK-OV-3 cell was over 344; Specificity of conjugate T-DM1 for N87 cell was over 55 ($IC_{50}$>15/$IC_{50}$=0.27), and for SK-OV-3 cell was over 78.

Both conjugate 91 and conjugate 93 were extremely more potent than the commercial conjugate T-DM1. The conjugate 93 having DAR=8 was three-fold more potent than conjugate 91 having DAR=4.

Example 19

Antitumor Activity In vivo

The in vivo efficacy of conjugates 91 and 93 along with T-DM1 were evaluated in a human gastric carcinoma N-87 cell line tumor xenograft models. Five-week-old female BALB/c Nude mice (24 animals) were inoculated subcutaneously in the area under the right shoulder with N-87 carcinoma cells ($5\times10^6$ cells/mouse) in 0.1 mL of serum-free medium. The tumors were grown for 8 days to an average size of 130 $mm^3$. The animals were then randomly divided into 4 groups (6 animals per group). The first group of mice served as the control group and was treated with the phosphate-buffered saline vehicle. The remaining three groups were treated with conjugates 91, 93 and T-DM1 respectively at dose of 5 mg/Kg administered intravenously. Three dimensions of the tumor were measured every 4 days and the tumor volumes were calculated using the formula tumor volume=½ (length×width×height). The weight of the animals was also measured at the same time. A mouse was sacri-sacrificed when any one of the following criteria was met: (1) loss of body weight of more than 20% from pretreatment weight, (2) tumor volume larger than 1500 $mm^3$, (3) too sick to reach food and water, or (4) skin necrosis. A mouse was considered to be tumor-free if no tumor was palpable.

Figure 11:
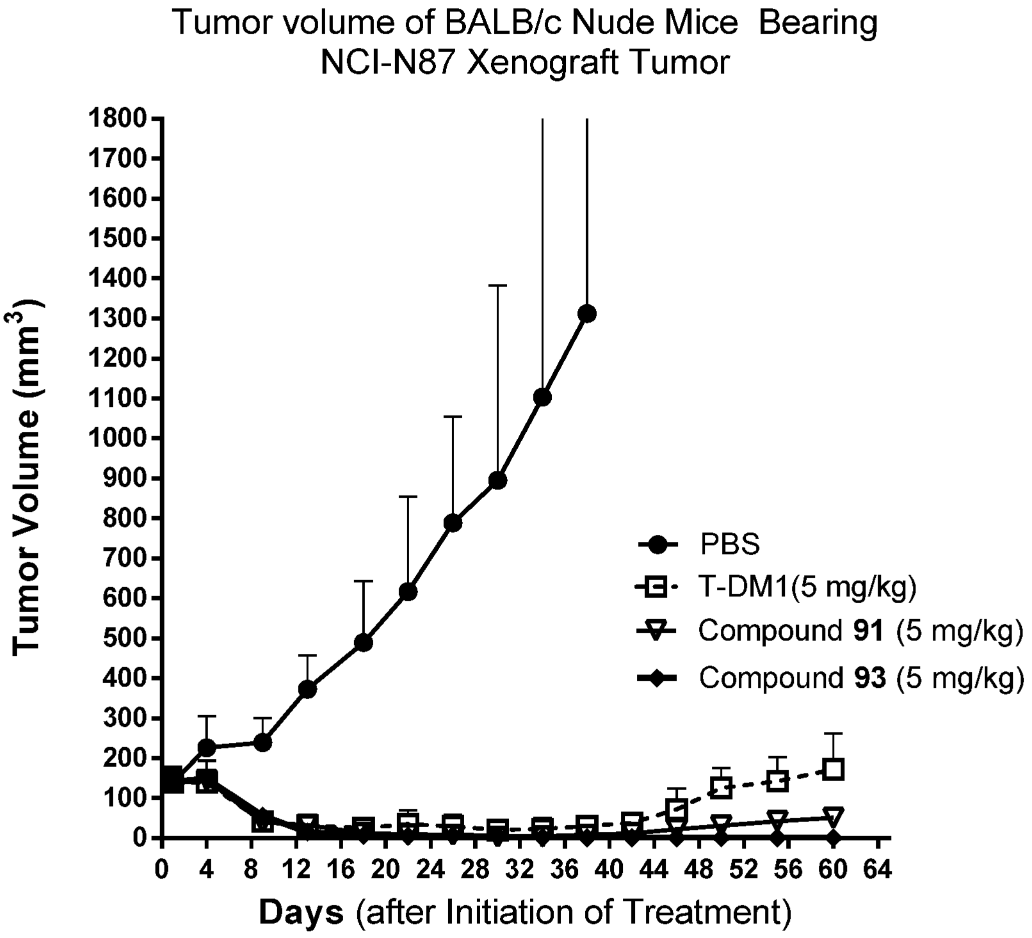
FIG. 11 shows the comparison of the anti-tumor effect of conjugate compounds 91 and 93 with T-DM1 using human gastric tumor N87 cell model at dosing, 5 mg/kg, i.v., one injection. Both compounds 91 and 93 were better than T-DM1: the compound 93 completely eradicated the tumor at day 14~18 till day 60 (the end of experiment). Compound 91 eradicated the tumor at day 14~22 until day 42~50 and inhibited the tumor growth till the end of the test. In contrast T-DM1 did not completely eliminate the tumor and only inhibited the tumor growth for 44 days.

The results were plotted in FIG. 11. All the three conjugates compounds did not cause the animal body weight loss. And the animals at control group were sacrificed at day 38 due to the tumor volume larger than 1500 $mm^3$ and all control animals were too sick. All 6/6 animals at the group of compound 93 had completely no tumor measurable at day 14~18 till day 60 (the end of experiment). All 6/6 animals at the group of Compound 91 group had no tumor measurable at day 14~22 and 2/6 animals had tumor growth (measurable) back at days 42 and 50. In contrast only 2/6 animals at the group of T-DM1 had no tumor measurable at days 14 and 22 until day 38 and 50.

The invention claimed is:

1. A cell-binding agent-drug conjugate compound of Formula (II)

(II)

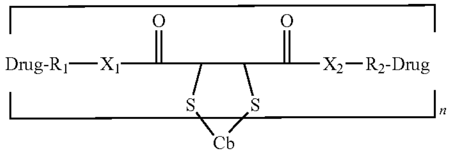

wherein:

Cb represents a cell-binding agent;

$Drug_1$ and $Drug_2$ are the same or different and represent cytotoxic agents;

n is 1~20;

$R_1$ and $R_2$ are the same or different, and are absent, a linear alkyl having from 1 to 6 carbon atoms; branched or cyclic alkyl having from 3 to 6 carbon atoms; linear, branched or cyclic alkenyl or alkynyl having from 2 to 6 carbon atoms; ester, ether, or amide having from 2 to 6 carbon atoms; or polyethyleneoxy unit of formula $(OCH_2CH_2)_p$, wherein p is an integer from 1 to about 1000, or a combination thereof; and $X_1$ and $X_2$ are independently NH, N($R_3$), O, S or $CH_2$; $R_3$ is H, a linear alkyl having from 1 to 6 carbon atoms; branched or cyclic alkyl having from 3 to 6 carbon atoms; linear, branched or cyclic alkenyl or alkynyl having from 2 to 6 carbon atoms; or esters, ether, amide having from 2 to 6 carbon atoms; or polyethyleneoxy unit of formula $(OCH_2CH_2)_p$, wherein p is an integer from 0 to about 1000, or a combination thereof, wherein the cell-binding agent is selected from the group consisting of an antibody, a protein, a vitamin, a peptide, a polymeric micelle, a liposome, a lipoprotein-based drug carrier, a nano-particle drug carrier, and a dendrimer, each of which optionally is coated with a cell-binding ligand, and a combination thereof, and wherein the cytotoxic agents are selected from the group consisting of:

1). chemotherapeutic agents consisting of:

a). alkylating agents consisting of: nitrogen mustards consisting of chlorambucil, chlornaphazine, cyclophosphamide, dacarbazine, estramustine, ifosfamide, mechlorethamine, mechlorethamine oxide hydrochloride, mannomustine, mitobronitol, melphalan, mitolactol, pipobroman, novembichin, phenesterine, prednimustine, thiotepa, trofosfamide, and uracil mustard; CC-1065 and adozelesin, carzelesin and bizelesin compounds thereof; duocarmycin compounds, KW-2189 and CBI-TMI; benzodiazepine dimers consisting of dimers of pyrrolobenzodiazepine or tomaymycin, indolinobenzodiazepines, imidazobenzothiadiazepines, and oxazolidinobenzodiazepines; nitrosoureas consisting of carmustine, lomustine, chlorozotocin, fotemustine, nimustine, and ranimustine; alkylsulphonates consisting of busulfan, treosulfan, improsulfan and piposulfan; triazenes; platinum containing compounds consisting of carboplatin, cisplatin, and oxaliplatin; aziridines consisting of benzodopa, carboquone, meturedopa, and uredopa; ethylenimines and methylamelamines consisting of altretamine, triethylenemelamine, trietylenephosphoramide, triethylenethiophosphaor-amide and trimethylolomelamine;

b). plant alkaloids consisting of: Vinca alkaloids consisting of vincristine, vinblastine, vindesine, vinorelbine, and navelbin; taxoids consisting of paclitaxel, docetaxol, Maytansinoids consisting of DM1, DM2, DM3, DM4, DM5, DM6, DM7, maytansine and ansamitocins, cryptophycins consisting of cryptophycin 1 and cryptophycin 8; epothilones, eleutherobin, discodermolide, bryostatins, dolostatins, auristatins, tubulysins, and cephalostatins; pancratistatin; sarcodictyin; and spongistatin;

c). DNA topoisomerase inhibitors consisting of: epipodophyllins consisting of 9-aminocamptothecin, camptothecin, crisnatol, daunomycin, etoposide, etoposide phosphate, irinotecan, mitoxantrone, novantrone, retinoic acids, teniposide, topotecan, and 9-nitrocamptothecin; mitomycins;

d). antimetabolites consisting of: anti-folate: DHFR inhibitors consisting of methotrexate, trimetrexate, denopterin, pteropterin, and aminopterin; IMP dehydrogenase inhibitors consisting of mycophenolic acid, tiazofurin, ribavirin, and EICAR; ribonucleotide reductase inhibitors consisting of hydroxyurea, and deferoxamine; pyrimidine compounds consisting of uracil compounds consisting of ancitabine, azacitidine, 6-azauridine, capecitabine, carmofur, cytarabine, dideoxyuridine, doxifluridine, enocitabine, 5-fluorouracil, floxuridine, and ratitrexed; cytosine compounds consisting of cytarabine, cytosine arabinoside, and fludarabine; Purine compounds consisting of azathioprine, fludarabine, mercaptopurine, thiamiprine, and thioguanine; folic acid replenisher;

e). hormonal therapies consisting of: receptor antagonists consisting of anti-estrogen consisting of: megestrol, raloxifene, and tamoxifen; LHRH agonists consisting of goscrclin, and leuprolide acetate; anti-androgens consisting of bicalutamide, flutamide, calusterone, dromostanolone propionate, epitiostanol, goserelin, leuprolide, mepitiostane, nilutamide, testolactone, and trilostane; retinoids/deltoids consisting of Vitamin D3 compounds consisting of CB 1093, EB 1089 KH 1060, cholecalciferol, and ergocalciferol; Photodynamic therapies consisting of verteporfin, phthalocyanine, photosensitizer Pc4, and demethoxy-hypocrellin A; cytokines consisting of interferon-alpha, interferon-gamma, tumor necrosis factor, and human proteins containing a TNF domain;

f). kinase inhibitors consisting of BIMW 2992, imatinib, gefitinib, pegaptanib, sorafenib, dasatinib, sunitinib, erlotinib, nilotinib, lapatinib, axitinib, pazopanib, vandetanib, E7080, mubritinib, ponatinib, bafetinib, bosutinib, cabozantinib, vismodegib, iniparib, ruxolitinib, CYT387, axitinib, tivozanib, sorafenib, bevacizumab, cetuximab, Trastuzumab, Ranibizumab, Panitumumab, and ispinesib;

g). antibiotics consisting of enediyne antibiotics consisting of calicheamicins consisting of calicheamicin $\gamma 1$, $\delta 1$, $\alpha 1$ and $\beta 1$; dynemicin consisting of dynemicin A and deoxydynemicin; esperamicin, kedarcidin, C-1027, maduropeptin, and neocarzinostatin chromophore, aclacinomysins, actinomycin, authramycin, azaserine, bleomycins, cactinomycin, carabicin, carminomycin, carzinophilin; chromomycins, dactinomycin, daunorubicin, detorubicin, 6-diazo-5-oxo-L-norleucine, doxorubicin, morpholino-doxorubicin, cyanomorpholino-doxorubicin, 2-pyrrolino-doxorubicin and deoxydoxorubicin, epirubicin, esorubicin, idarubicin, marcellomycin, nitomycins, mycophe-nolic acid, nogalamycin, olivomycins, peplomycin, potfiromycin, puromycin, quelamycin, rodorubicin, streptonigrin, streptozocin, tubercidin, ubenimex, zinostatin, and zorubicin;

h). Polyketides (acetogenins) consisting of bullatacin and bullatacinone; gemcitabine, epoxomicins, bortezomib, thalidomide, lenalidomide, pomalidomide, tosedostat, zybrestat, PLX4032, STA-9090, stimuvax, allovectin-7, Xegeva, Provenge, Yervoy, isoprenylation inhibitors, dopaminergic neurotoxins, cell cycle inhibitors, actinomycins consisting of actinomycin D, and dactinomycin, bleomycins consisting of bleomycin A2, bleomycin B2, and peplomycin, anthracyclines consisting of daunorubicin, doxorubicin, idarubicin, epirubicin, pirarubicin, zorubicin, mtoxantrone, MDR inhibitors, $Ca^{2+}$ ATPase inhibitors, histone deacetylase inhibitors consisting of vorinostat, romidepsin, panobinostat, valproic acid, mocetinostat, belinostat, PCI-24781, entinostat, SB939, resminostat, givinostat, AR-42, CUDC-101, sulforaphane, and trichostatin A; thapsigargin, celecoxib, glitazones, epigallocatechin gallate, disulfiram, salinosporamide A; anti-adrenals consisting of aminoglutethimide, mitotane, and trilostane; aceglatone; aldophosphamide glycoside; aminolevulinic acid; amsacrine; arabinoside, bestrabucil; bisantrene; edatraxate; defofamine; demecolcine; diaziquone; eflornithine, elfomithine; elliptinium acetate, etoglucid; gallium nitrate; gacytosine, hydroxyurea; ibandronate, lentinan; lonidamine; mitoguazone; mitoxantrone; mopidamol; nitracrine; pentostatin; phenamet; pirarubicin; podophyllinic acid; 2-ethylhydrazide; procarbazine; protein-bound polysaccharide; razoxane; rhizoxin; sizofiran; spirogermanium; tenuazonic acid; triaziquone; 2, 2',2"-trichlorotriethylamine; trichothecenes consisting of T-2 toxin, verrucarin A, roridin A and anguidine; urethane, siRNA, and antisense drugs;

2). anti-autoimmune disease agents consisting of: cyclosporine, cyclosporine A, aminocaproic acid, azathioprine, bromocriptine, chlorambucil, chloroquine, cyclophosphamide, corticosteroids consisting of amcinonide, betamethasone, budesonide, hydrocortisone, flunisolide, fluticasone propionate, fluocortolone danazol, dexamethasone, triamcinolone acetonide, and beclometasone dipropionate, DHEA, enanercept, hydroxychloroquine, infliximab, meloxicam, methotrexate, mofetil, mycophenylate, prednisone, sirolimus, and tacrolimus;

3). anti-infectious disease agents consisting of:

a). aminoglycosides consisting of: amikacin, astromicin, gentamicin consisting of netilmicin, sisomicin, and isepamicin, hygromycin B, kanamycin consisting of amikacin, arbekacin, bekanamycin, dibekacin, and tobramycin, neomycin consisting of framycetin, paromomycin, and ribostamycin, netilmicin, spectinomycin, streptomycin, tobramycin, verdamicin;

b). amphenicols consisting of azidamfenicol, chloramphenicol, florfenicol, and thiamphenicol;

c). ansamycins consisting of geldanamycin, and herbimycin;

d). carbapenems consisting of biapenem, doripenem, ertapenem, imipenem/cilastatin, meropenem, and panipenem;

e). cephems consisting of carbacephem, cefacetrile, cefaclor, cefradine, cefadroxil, cefalonium, cefaloridine, cefalotin or cefalothin, cefalexin, cefaloglycin, cefamandole, cefapirin, cefatrizine, cefazaflur, cefazedone, cefazolin, cefbuperazone, cefcapene, cefdaloxime, cefepime, cefminox, cefoxitin, cefprozil, cefroxadine, ceftezole, cefuroxime, cefixime, cefdinir, cefditoren, cefepime, cefetamet, cefmenoxime, cefodizime, cefonicid, cefoperazone, ceforanide, cefotaxime, cefotiam, cefozopran, cephalexin, cefpimizole, cefpiramide, cefpirome, cefpodoxime, cefprozil, cefquinome, cefsulodin, ceftazidime, cefteram, ceftibuten, ceftiolene, ceftizoxime, ceftobiprole, ceftriaxone, cefuroxime, cefuzonam, cephamycin consisting of cefoxitin, cefotetan, and cefmetazole, oxacephem consisting of flomoxef, and latamoxef;

f). glycopeptides consisting of bleomycin, vancomycin consisting of oritavancin, and telavancin, teicoplanin, and ramoplanin;

g). glycylcyclines;

h). $\beta$-lactamase inhibitors consisting of penam consisting of sulbactam, and tazobactam, and clavam;

i). lincosamides consisting of clindamycin, and lincomycin;

j). lipopeptides consisting of daptomycin, A54145, and calcium-dependent antibiotics;

k). macrolides consisting of azithromycin, cethromycin, clarithromycin, dirithromycin, erythromycin, flurithromycin, josamycin, ketolide consisting of telithromycin, and cethromycin, midecamycin, miocamycin, oleandomycin, rifamycins consisting of rifampicin, rifampin, rifabutin, and rifapentine, rokitamycin, roxithromycin, spectinomycin, spiramycin, tacrolimus, troleandomycin, and telithromycin;

l). monobac-tams consisting of aztreonam and tigemonam;

m). oxazolidinones;

n). penicillins consisting of: amoxicillin, ampicillin consisting of pivampicillin, hetacillin, bacampicillin, metampicillin, and talampicillin, azidocillin, azlocillin, benzylpenicillin, benzathine benzylpenicillin, benzathine phenoxymethylpenicillin, clometocillin, procaine benzylpenicillin, carbenicillin, cloxacillin, dicloxacillin, epicillin, flucloxacillin, mecillinam, mezlocillin, meticillin, nafcillin, oxacillin, penamecillin, penicillin, pheneticillin, phenoxymethylpenicillin, piperacillin, propicillin, sulbenicillin, temocillin, and ticarcillin;

o). polypeptides consisting of bacitracin, colistin, and polymyxin B;

p). quinolones consisting of alatrofloxacin, balofloxacin, ciprofloxacin, clinafloxacin, danofloxacin, difloxacin, enoxacin, enrofloxacin, floxin, garenoxacin, gatifloxacin, gemifloxacin, grepafloxacin, kano trovafloxacin, levofloxacin, lomefloxacin, marbofloxacin, moxifloxacin, nadifloxacin, norfloxacin, orbifloxacin, ofloxacin, pefloxacin, trovafloxacin, grepafloxacin, sitafloxacin, sparfloxacin, temafloxacin, tosufloxacin, and trovafloxacin;

q). streptogramins consisting of pristinamycin, quinupristin and dalfopristin;

r). sulfonamides consisting of mafenide, prontosil, sulfacetamide, sulfamethizole, sulfanilimide, sulfasalazine, sulfisoxazole, trimethoprim, and trimethoprim-sulfamethoxazole;

s). steroid antibacterials;

t). tetracyclines consisting of doxycycline, chlortetracycline, clomocycline, demeclocycline, lymecycline, meclocycline, metacycline, minocycline, oxytetracycline, penimepicycline, rolitetracycline, tetracycline, and glycylcyclines;

u). antibiotics consisting of annonacin, arsphenamine, bactoprenol inhibitors, DADAL/AR inhibitors, dictyostatin, discodermolide, eleutherobin, epothilone, ethambutol, etoposide, faropenem, fusidic acid, furazolidone, isoniazid, laulimalide, metronidazole, mupirocin, mycolactone, NAM synthesis inhibitors, nitrofurantoin, paclitaxel, platensimycin, pyrazinamide, quinupristin/dalfopristin, rifampicin (rifampin), tazobactam tinidazole, and uvaricin;

4). anti-viral drugs consisting of:

a). entry/fusion inhibitors consisting of aplaviroc, maraviroc, vicriviroc, gp41, PRO 140, and CD4;

b). integrase inhibitors consisting of raltegravir, elvitegravir, and globoidnan A;

c). maturation inhibitors consisting of bevirimat, and vivecon;

d). neuraminidase inhibitors consisting of oseltamivir, zanamivir, and peramivir;

e). nucleosides and nucleotides consisting of abacavir, aciclovir, adefovir, amdoxovir, apricitabine, brivudine, cidofovir, clevudine, dexelvucitabine, didanosine, elvucitabine, emtricitabine, entecavir, famciclovir, fluorouracil, 3'-fluoro-substituted 2',3'-dideoxynucleoside compounds, fomivirsen, ganciclovir, idoxuridine, lamivudine, 1-nucleosides consisting of β-1-thymidine and β-1-2'-deoxycytidine, penciclovir, racivir, ribavirin, stampidine, stavudine, taribavirin, telbivudine, tenofovir, trifluridine valaciclovir, valganciclovir, zalcitabine, and zidovudine;

f). non-nucleosides consisting of amantadine, ateviridine, capravirine, diarylpyrimidines, delavirdine, docosanol, emivirine, efavirenz, foscarnet, imiquimod, interferon alfa, loviride, lodenosine, methisazone, nevirapine, NOV-205, peginterferon alfa, podophyllotoxin, rifampicin, rimantadine, resiquimod, and tromantadine;

g). protease inhibitors consisting of amprenavir, atazanavir, boceprevir, darunavir, fosamprenavir, indinavir, lopinavir, nelfinavir, pleconaril, ritonavir, saquinavir, telaprevir, and tipranavir;

h). anti-virus drugs consisting of abzyme, arbidol, calanolide a, ceragenin, cyanovirin-n, diarylpyrimidines, epigallocatechin gallate, foscarnet, griffithsin, taribavirin, hydroxyurea, KP-1461, miltefosine, pleconaril, portmanteau inhibitors, ribavirin, and seliciclib;

5). a radioisotope selected from the group consisting of $^{3}H$, $^{11}C$, $^{14}C$, $^{18}F$, $^{32}P$, $^{35}S$, $^{64}Cu$, $^{68}Ga$, $^{86}Y$, $^{99}Tc$, $^{111}In$, $^{123}I$, $^{124}I$, $^{125}I$, $^{131}I$, $^{133}Xe$, $^{177}Lu$, $^{211}At$, and $^{213}Bi$;

6). a chromophore molecule, which is capable of absorbing a UV light, florescent light, IR light, near IR light, or visual light, and which is selected from the group consisting of xanthophores, erythrophores, iridophores, leucophores, melanophores, cyanophores, fluorophore molecules which are fluorescent chemical compounds re-emitting light upon light, visual phototransduction molecules, photophore molecules, luminescence molecules, luciferin compounds; non-protein organic fluorophores consisting of xanthene compounds consisting of fluorescein, rhodamine, Oregon green, eosin, and Texas red; cyanine compounds consisting of cyanine, indocarbocyanine, oxacarbocyanine, thiacarbocyanine, and merocyanine; squaraine compounds and ring-substituted squaraines consisting of Seta, SeTau, and Square dyes; naphthalene compounds consisting of dansyl and prodan compounds; coumarin compounds; oxadiazole compounds consisting of pyridyloxazole, nitrobenzoxadiazole and benzoxadiazole; anthracene compounds consisting of anthraquinones consisting of DRAQ5, DRAQ7 and CyTRAK Orange; pyrene compounds; oxazine compounds consisting of Nile red, Nile blue, cresyl violet, oxazine 170; acridine compounds consisting of proflavin, acridine orange, and acridine yellow; arylmethine compounds consisting of auramine, crystal violet, and malachite green; tetrapyrrole compounds consisting of porphin, phthalocyanine, and bilirubin; fluorophore compounds consisting of CF dye, DRAQ and CyTRAK probes, BODIPY, Alexa Fluor, DyLight Fluor, Atto and Tracy, FluoProbes, Abberior Dyes, DY and MegaStokes Dyes, Sulfo Cy dyes, HiLyte Fluor, Seta, SeTau and Square Dyes, Quasar and Cal Fluor dyes, SureLight Dyes, APC, APCXL, RPE, BPE, allophycocyanin, aminocoumarin, APC-Cy7 conjugates, BODIPY-FL, Cascade Blue, Cy2, Cy3, Cy3.5, Cy3B, Cy5, Cy5.5, Cy7, fluorescein, FluorX, hydroxycoumarin, Lissamine Rhodamine B, Lucifer yellow, methoxycoumarin, NBD, Pacific Blue, Pacific Orange, PE-Cy5 conjugates, PE-Cy7 conjugates, PerCP, R-Phycoerythrin, Red 613, Seta-555-Azide, Seta-555-DBCO, Seta-555-NHS, Seta-580-NHS, Seta-680-NHS, Seta-780-NHS, Seta-APC-780, Seta-PerCP-680, Seta-R-PE-670, SeTau-380-NHS, SeTau-405-Maleimide, SeTau-405-NHS, SeTau-425-NHS, SeTau-647-NHS, Texas Red, TRITC, TruRed, X-Rhodamine, 7-AAD, Acridine Orange, Chromomycin A3, CyTRAK Orange, DAPI, DRAQ5, DRAQ7, ethidium bromide, Hoechst33258, Hoechst33342, LDS 751, mithramycin, propidiumlodide, SYTOX Blue, SYTOX Green, SYTOX Orange, thiazole Orange, TO-PRO, cyanine monomer, TOTO-1, TO-PRO-1, TOTO-3, TO-PRO-3, YOSeta-1, YOYO-1; and 7). a pharmaceutically acceptable salt or acid of any of the above drugs.

2. The cell-binding agent-drug conjugate compound according to claim 1, wherein the cell-binding agent is an antibody.

3. The cell-binding agent-drug conjugate compound according to claim 1, wherein the fluorophores are selected from the group consisting of DCFH, DHR, Fluo-3, Fluo-4, Indo-1, SNARF, Allophycocyanin, AmCyan1, AsRed2, Azami Green, Azurite, B-phycoerythrin, Cerulean, CyPet, DsRed monomer, DsRed2, EBFP, EBFP2, ECFP, EGFP, Emerald, EYFP, GFP, GFP, GFP, GFP, GFP, GFP, GFP, GFPuv, HcRed1, J-Red, Katusha, Kusabira Orange, mCFP, mCherry, mCitrine, Midoriishi Cyan, mKate, mKeima-Red, mKO, mOrange, mPlum, mRaspberry, mRFP1, mStrawberry, mTFP1, mTurquoise2, P3, Peridinin Chlorophyll, R-phycoerythrin, T-Sapphire, TagCFP, TagGFP, TagRFP, TagYFP, tdTomato, Topaz, TurboFP602, TurboFP635, TurboGFP, TurboRFP, TurboYFP, Venus, Wild Type GFP, YPet, ZsGreen1, and ZsYellow1.

4. The cell-binding agent-drug conjugate compound according to claim 1, wherein $Drug_1$ and $Drug_2$ are a chromophore molecule.

5. The cell-binding agent-drug conjugate compound according to claim 1, wherein $Drug_1$ and $Drug_2$ are selected from the group consisting of tubulysins, calicheamicins, auristatins, maytansinoids, CC-1065 and adozelesin, carzelesin and bizelesin compounds thereof, daunorubicin and doxorubicin compounds, taxanoids, cryptophycins, epothilones, benzodiazepine dimers consisting of dimers of pyrrolobenzodiazepine, tomaymycin, anthramycin, indolinobenzodiazepines, imidazobenzothiadiazepines, and oxazolidinobenzodiazepines, calicheamicins and the enediyne antibiotics, actinomycin, azaserines, bleomycins, epirubicin, tamoxifen, idarubicin, dolastatins/auristatins consisting of monomethyl auristatin E, MMAE, MMAF auristatin PYE, auristatin TP, auristatins 2-AQ, 6-AQ, EB, and EFP, duocarmycins, thiotepa, vincristine, hemiasterlins, nazumamides, microginins, radiosumins, alterobactins, microsclerodermins, theonellamides, esperamicins, siRNA, nucleolytic enzymes, and pharmaceutically acceptable salts and acids of any of the above molecules.

6. The cell-binding agent-drug conjugate compound according to claim 1, wherein the cell-binding agent is selected from the group consisting of full-length antibodies consisting of polyclonal antibodies, monoclonal antibodies, dimers, multimers, and multispecific antibodies; a single chain antibody, an antibody fragment that binds to a target cell, a monoclonal antibody, a single chain monoclonal antibody, or a monoclonal antibody fragment that binds the target cell, a chimeric antibody, a chimeric antibody fragment that binds to the target cell, a domain antibody, a domain antibody fragment that binds to the target cell, a resurfaced antibody, a resurfaced single chain antibody, or a resurfaced antibody fragment that binds to the target cell, a humanized antibody or a resurfaced antibody, a humanized single chain antibody, or a humanized antibody fragment that binds to the target cell, anti-idiotypic antibodies, CDR's, diabody, triabody, miniantibody, small immune proteins, a lymphokine, a hormone, a vitamin, a growth factor, a colony stimulating factor, a nutrient-transport molecule, and large molecular weight proteins.

7. The cell-binding agent-drug conjugate compound according to claim 1, wherein the cell-binding agent is capable of targeting against a tumor cell, a virus infected cell, a microorganism infected cell, a parasite infected cell, an autoimmune disease cell, an activated tumor cells, a myeloid cell, an activated T-cell, an affecting B cell, or a melanocyte.

8. The cell-binding agent-drug conjugate compound according to claim 1, wherein the cell-binding agent is capable of targeting against any one of following antigens and receptors: CD3, CD4, CD5, CD6, CD7, CD8, CD9, CD10, CD11a, CD11b, CD11c, CD12w, CD14, CD15, CD16, CDw17, CD18, CD19, CD20, CD21, CD22, CD23, CD24, CD25, CD26, CD27, CD28, CD29, CD30, CD31, CD32, CD33, CD34, CD35, CD36, CD37, CD38, CD39, CD40, CD41, CD42, CD43, CD44, CD45, CD46, CD47, CD48, CD49b, CD49c, CD51, CD52, CD53, CD54, CD55, CD56, CD58, CD59, CD61, CD62E, CD62L, CD62P, CD63, CD66, CD68, CD69, CD70, CD72, CD74, CD79, CD79a, CD79b, CD80, CD81, CD82, CD83, CD86, CD87, CD88, CD89, CD90, CD91, CD95, CD96, CD98, CD100, CD103, CD105, CD106, CD109, CD117, CD120, CD125, CD126, CD127, CD133, CD134, CD135, CD138, CD141, CD142, CD143, CD144, CD147, CD151, CD147, CD152, CD154, CD156, CD158, CD163, CD166, CD168, CD174, CD180, CD184, CDw186, CD194, CD195, CD200, CD200a, CD200b, CD209, CD221, CD227, CD235a, CD240, CD262, CD271, CD274, CD276, CD303, CD304, CD309, CD326, 4-1BB, 5AC, 5T4, Adenocarcinoma antigen, AGS-5, AGS-22M6, activin receptor-like kinase 1, AFP, AKAP-4, ALK, Alpha intergrin, Alpha v beta6, amino-peptidase N, amyloid beta, androgen receptor, angiopoietin 2, angiopoietin 3, Annexin A1, Anthrax toxin protective antigen, anti-transferrin receptor, AOC3, B7-H3, *Bacillus anthracis* anthrax, BAFF, B-lymphoma cell, bcr-abl, Bombesin, BORIS, C5, C242 antigen, CA125, CA-IX, CALLA, CanAg, Canis lupus familiaris IL31, Carbonic anhydrase IX, Cardiac myosin, CCL11, CCR4, CCR5, CD3E, CEA, CEACAM3, CEACAM5, CFD, Ch4D5, Cholecystokinin 2, CLDN18, Clumping factor A, CRIPTO, FCSF1R, CSF2, CTLA4, CTAA16.88 tumor antigen, CXCR4, C-X-C chemokine receptor type4, cyclic ADP ribose hydrolase, Cyclin B1, CYP1B1, Cytomegalovirus, Cytomegalovirus glycoprotein B, Dabigatran, DLL3, DPP4, DR5, *E. coli* shiga toxin type-1, *E. coli* shiga toxin type-2, ED-B, EGFL7, EGFR, EGFRII, EGFRvIII, Endoglin, endothelin B receptor, endotoxin, EpCAM, EphA2, Episialin, ERBB2, ERBB3, ERG, *Escherichia coli*, ETV6-AML, FAP, FCGR1, alpha-Fetoprotein, Fibrin II, beta chain, Fibronectin extra domain-B, FOLR, folate receptor alpha, folate hydrolase, Fos-related antigen 1.F protein of respiratory syncytial virus, Frizzled receptor, Fucosyl GM1, GD2 ganglioside, G-28, GD3 idiotype, GloboH, Glypican 3, N-glycolylneuraminic acid, GM3, GMCSF receptor a-chain, growth differentiation factor 8, GP100, GPNMB, GUCY2C, heat shock proteins, hemagglutinin, hepatitis B surface antigen, hepatitis B virus, HER1, HER2, HER2/neu, HER3, IgG4, HGF/SF, HHGFR, HIV-1, histone complex, HLA-DR, HLA-DR10, HLA-D RB , HMWMAA, human chorionic gonadotropin, HNGF, human scatter factor receptor kinase, HPV E6/E7, Hsp90, hTERT, ICAM-1, Idiotype, IGF1R, IGHE, IFN-γ, Influenza hemagglutinin, IgE, IgE Fc region, IGHE, IL-1, IL-2 receptor, IL-4, IL-5, IL-6, IL-6R, IL-9, IL-10, IL-12, IL-13, IL-17, IL-17A, IL-20, IL-22, IL-23, IL31RA, ILGF2, Integrins, interferon gamma-induced protein, ITGA2, ITGB2, KIR2D, LCK, Le, Legumain, Lewis-Y antigen, LFA-1, LHRH, LINGO-1,lipoteichoic acid, LIV1A, LMP2, LTA, MAD-CT-1, MAD-CT-2, MAGE-1, MAGE-2, MAGE-3, MAGE A1, MAGE A3, MAGE 4, MART1, MCP-1, MIF, MS4A1, MSLN, MUC1, MUC1-KLH, MUC 16, MCP1, Mel anA/MART1, ML-IAP, MPG, MS4A1, MYCN, myelin-associated glycoprotein, myostatin, NA17, NARP-1, NCA-90, Nectin-4, NGF, neural apoptosis-regulated proteinase 1, NOGO-A, Notch receptor, Nucleolin, Neu oncogene product, NY-BR-1, NY-ESO-1, OX-40, OxLDL, OY-TES1, P21, p53 nonmutant, P97, Page4, PAP, paratope of anti-(N-glycolylneuraminic acid), PAX3, PAX5, PCSK9, PDCD1, PDGF-Rα, PDGFR-β, PDL-1, PLAC1, PLAP-like testicular alkaline phosphatase, platelet-derived growth factor receptor beta, phosphate-sodium co-transporter, PMEL 17, polysialic acid, proteinase3, prostatic carcinoma, PS, prostatic carcinoma cells, pseudomonas aeruginosa, PSMA, PSA, PSCA, rabies virus glycoprotein, RHD, Rhesus factor, RANKL, RhoC, Ras mutant, RGS5, ROBO4, respiratory syncytial virus, RON, sarcoma translocation breakpoints, SART3, sclerostin, SLAMF7, selectin P, SDC1, sLe(a), somatomedin C, SIP, somatostatin, sperm protein 17, SSX2, STEAP1, STEAP2, STn, TAG-72, survivin, T-cell receptor, T cell transmembrane protein, TEM1, TENB2, Tenascin C , TGF-α, TGF-β, TGF-β1, TGF-β2, Tie, Tie2, TIM-1, Tn, TNF, TNF-α, TNFRSF8, TNFRSF10B, TNFRSF13B, TPBG, TRAIL-R1, tumor-associated calcium signal transducer 2, tumor specific glycosylation of MUC1, TWEAK receptor, TYRP1, TRP-2, tyrosinase, VCAM-1, VEGF, VEGF-A, VEGF-2, VEGFR-1, VEGFR2, or vimentin, WT1, XAGE 1, or cells expressing any insulin growth factor receptors, or any epidermal growth factor receptors.

9. The cell-binding agent-drug conjugate compound according to claim 7, wherein the tumor cell is selected from the group consisting of lymphoma cells, myeloma cells, renal cells, breast cancer cells, prostate cancer cells, ovarian cancer cells, colorectal cancer cells, gastric cancer cells, squamous cancer cells, small-cell lung cancer cells, none small-cell lung cancer cells, testicular cancer cells, and cells that grow and divide at an unregulated, quickened pace to cause cancers.

10. The cell-binding agent-drug conjugate compound according to claim 1, wherein $R_1$ or $R_2$ is selected from the group consisting of 6-maleimidocaproyl, maleimido propanoyl, valine-citrulline, alanine-phenylalanine, lysine-phenylalanine, p-aminobenzyloxycarbonyl, 4-thio-pentanoate, 4-(N-maleimidomethyl)cyclo-hexane-1-carboxylate, 4-thio-butyrate, maleimidoethyl, 4-thio-2-hydroxysulfonyl-butyrate, pyridinyl-dithiol, alkoxy amino, ethyleneoxy, 4-methyl-4-dithio-pentanoic, azido, alkynyl, dithio, peptides, and (4-acetyl)aminobenzoate.

11. The cell-binding agent-drug conjugate compound of claim 1, wherein the conjugate compound of Formula (II) is selected from the group consisting of structures of T01, T02, T03, T04, T05, T06 and T07 as following:

T01

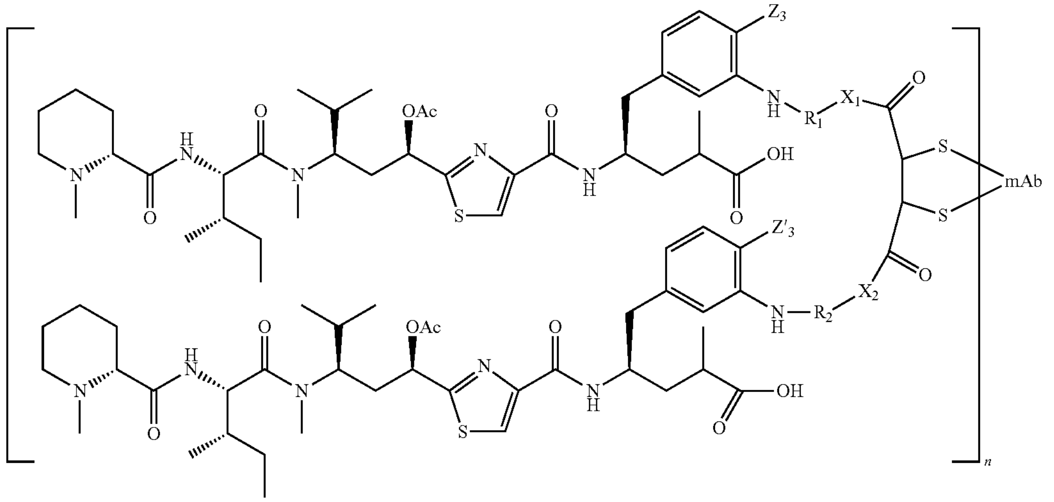

-continued
T02
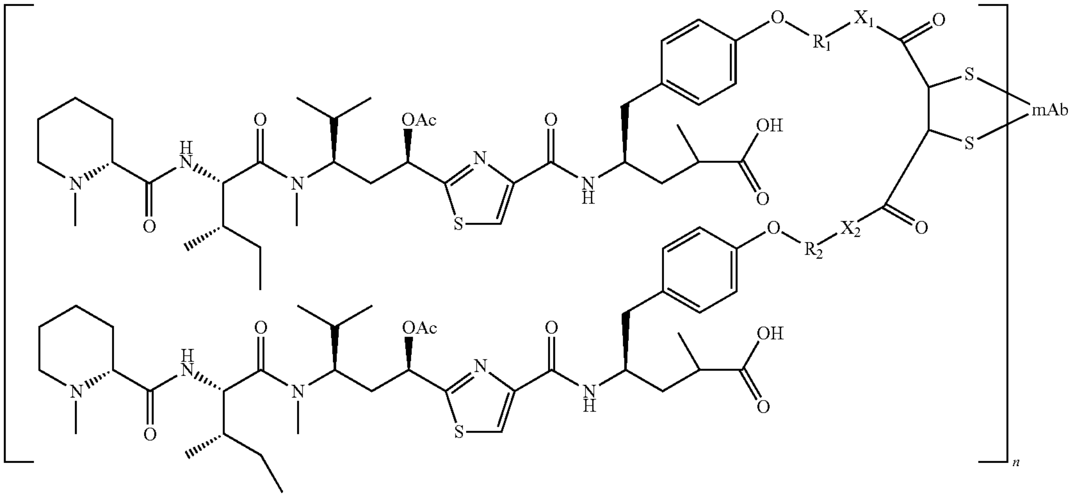
T03
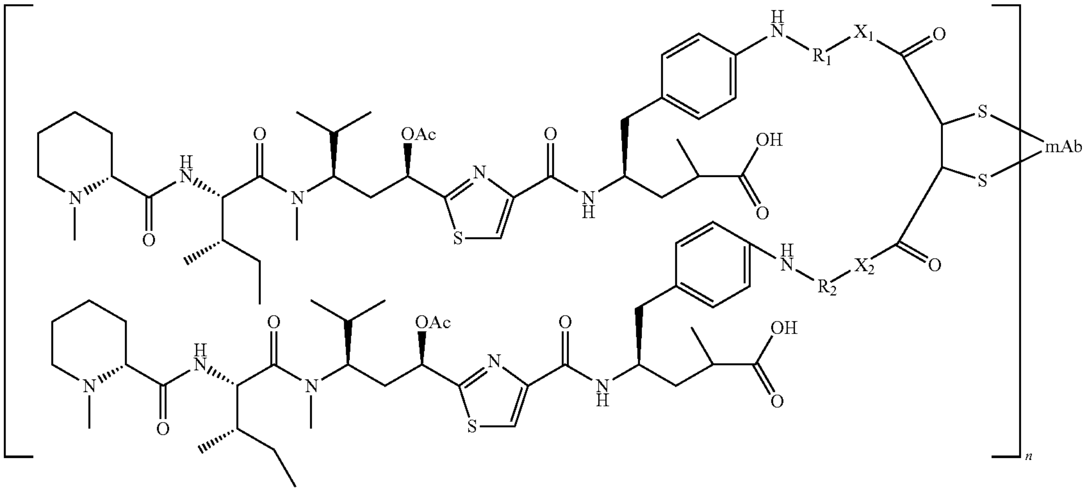
T04
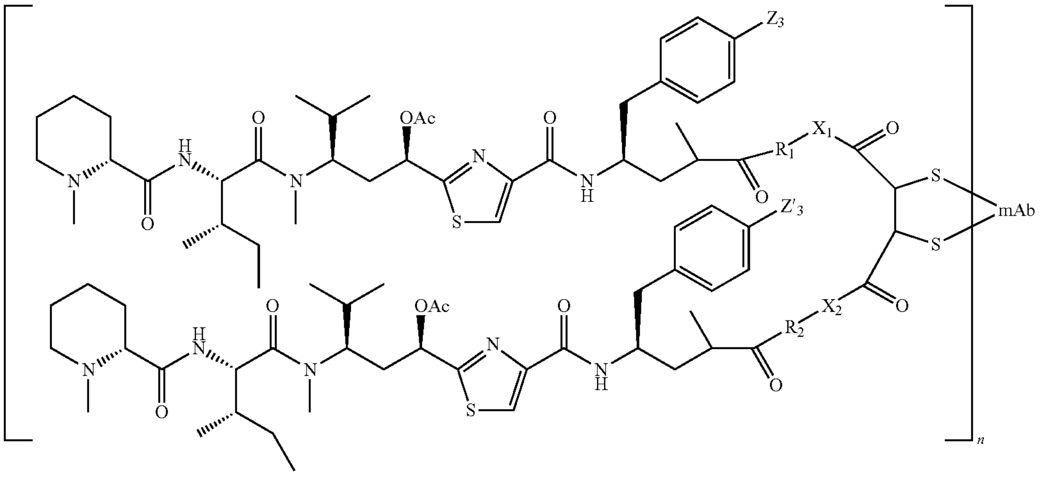

-continued
T05
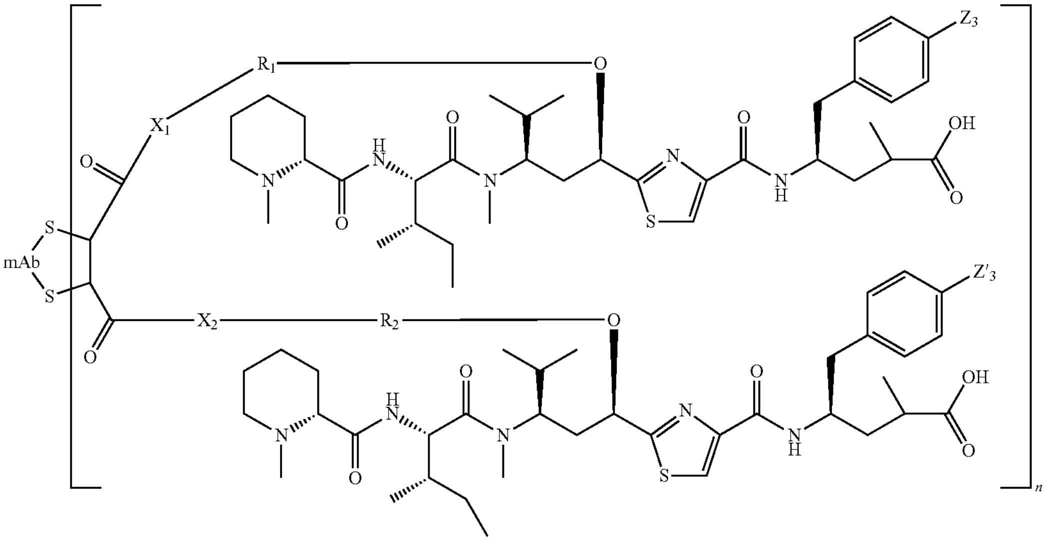
T06
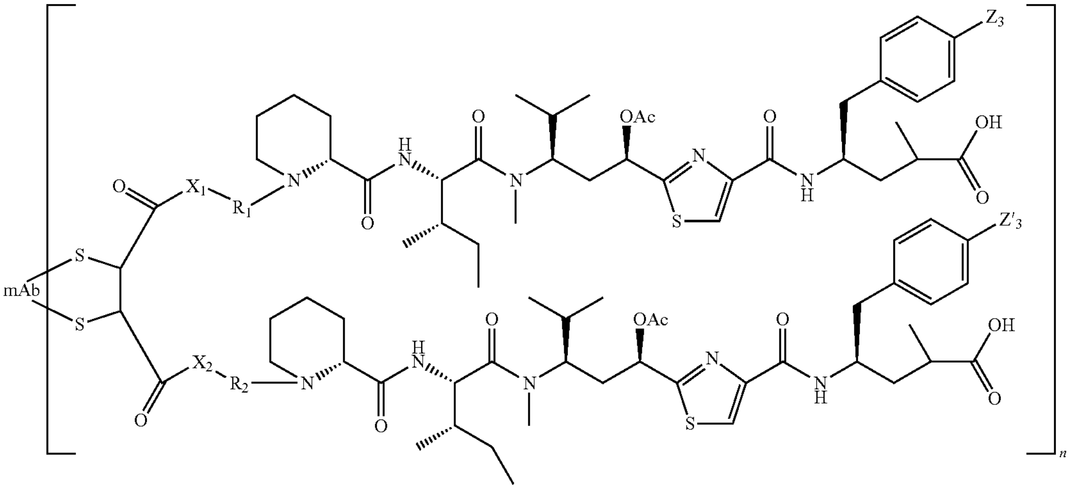
T07
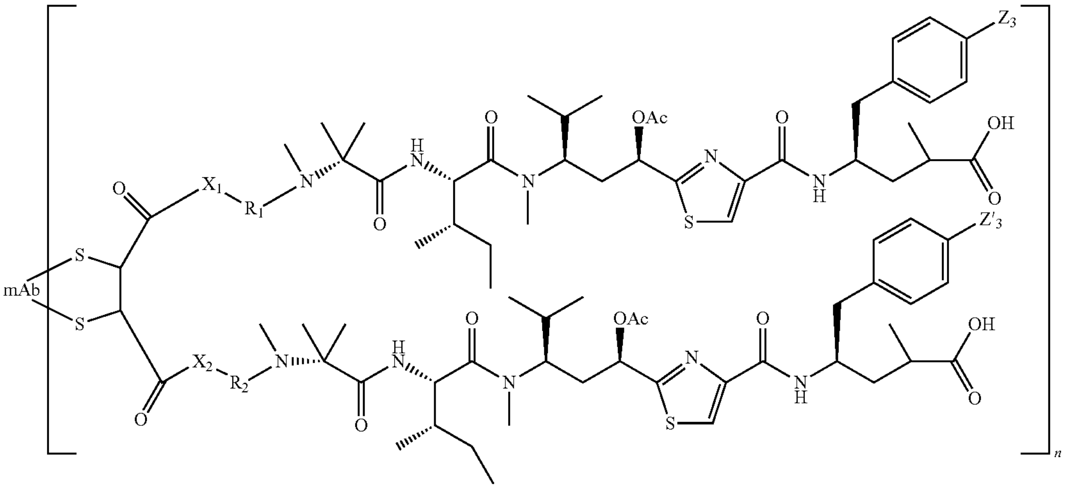
wherein mAb is an antibody; $Z_3$ and $Z'_3$ are independently H, $OP(O)(OM_1)(OM_2)$, $OCH_2OP(O)(OM_1)(OM_2)$, $OSO_3M_1$, $R_1$, or O-glycoside comprising glucoside, galactoside, mannoside, glucuronoside, alloside, and fructoside, NH-glycoside, S-glycoside or $CH_2$-glycoside; $M_1$ and $M_2$ are independently H, Na, K, Ca, Mg, $NH_4$, $NR_1R_2R_3$; n is 1~20.

12. The cell-binding agent-drug conjugate compound of claim 1, wherein the conjugate compound of Formula (II) has a structure of C01 as following:

C01

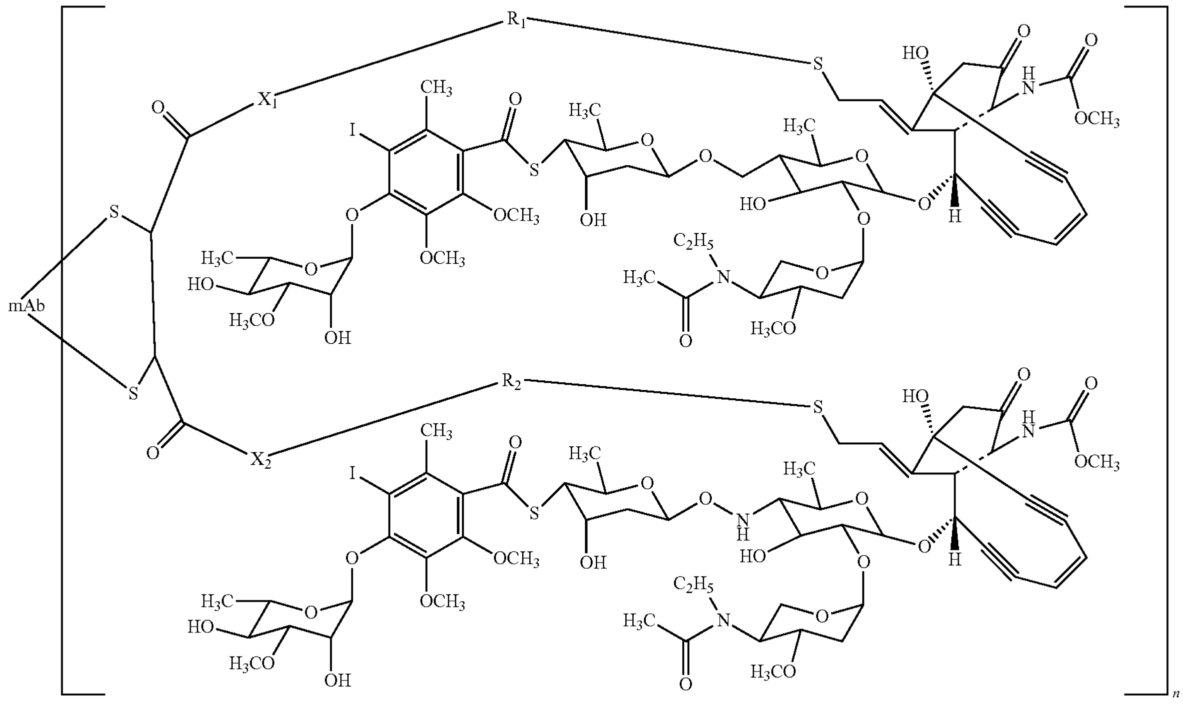

wherein mAb is an antibody; n is 1~20.

13. The cell-binding agent-drug conjugate compound of claim 1, wherein the conjugate compound of Formula (II) has a structure of M01 as following:

14. The cell-binding agent-drug conjugate compound of claim 1, wherein the conjugate compound of Formula (II) is selected from the group consisting of structures of Tx01, Tx02 and Tx03 as following:

M01

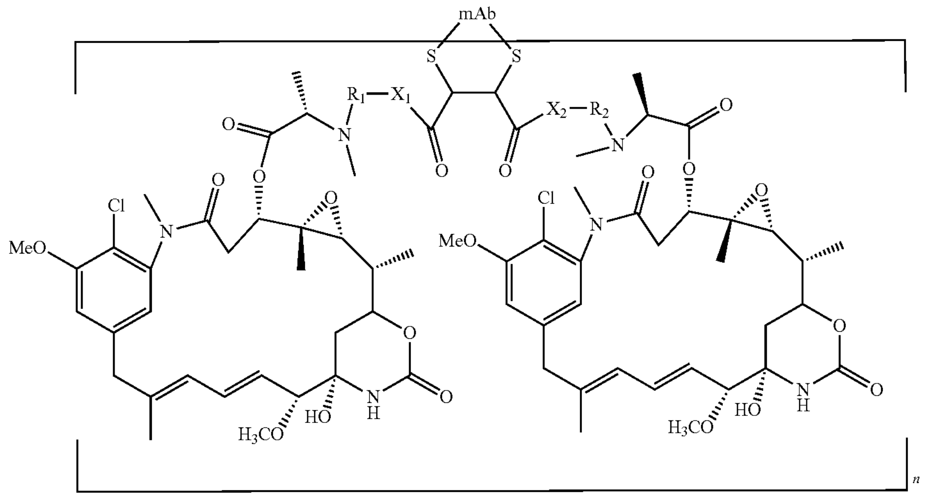

wherein mAb is an antibody; n is 1~20.

Tx01
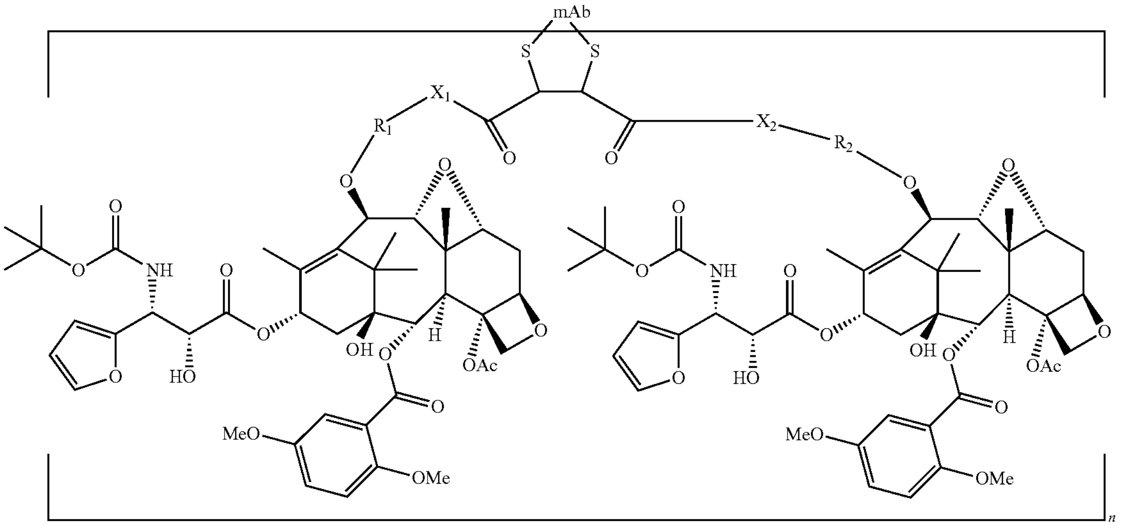
Tx02
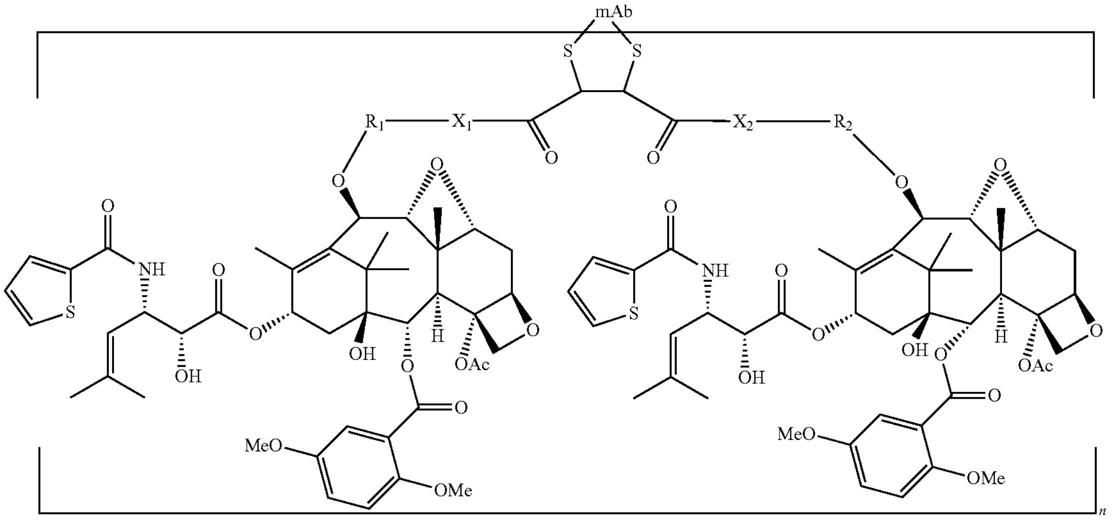
Tx03
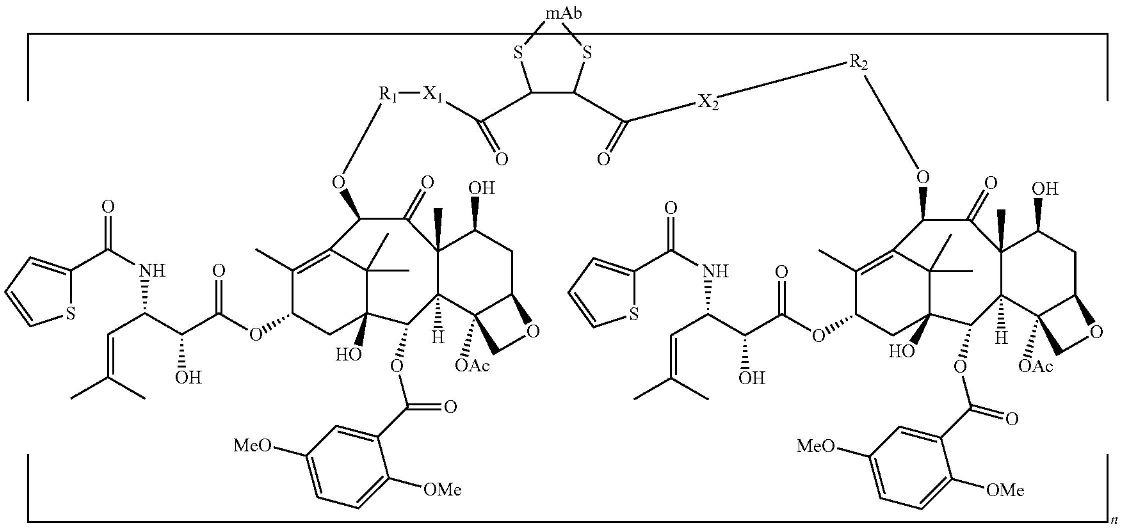
wherein mAb is an antibody; n is 1~20.

15. The cell-binding agent-drug conjugate compound of claim 1, wherein the conjugate compound of Formula (II) is selected from the group consisting of structures of CC01, CC02, and CC03 as following:

CC01

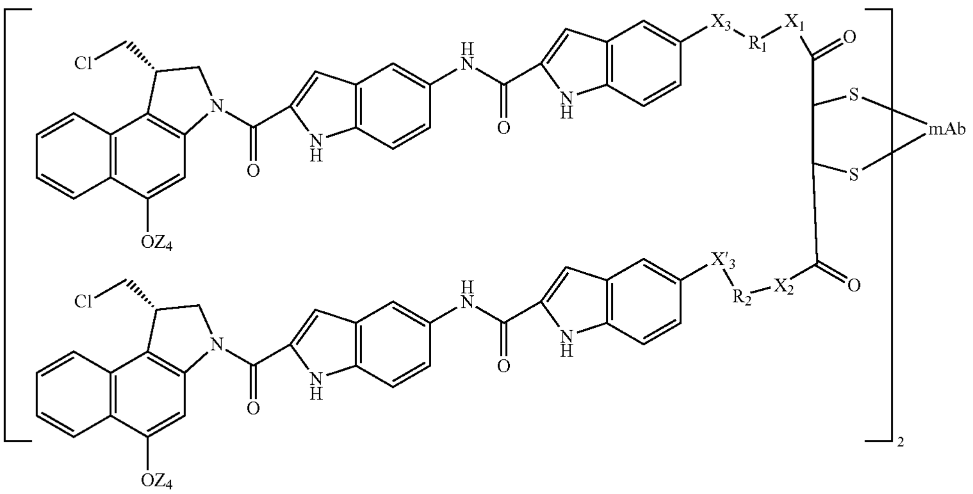

CC02

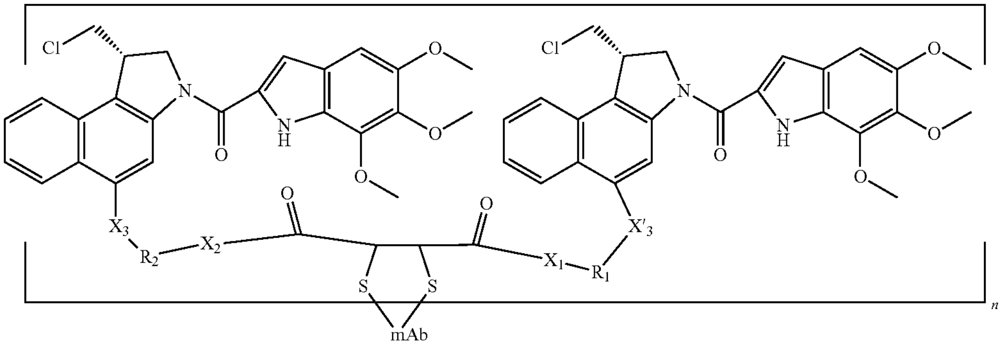

CC03

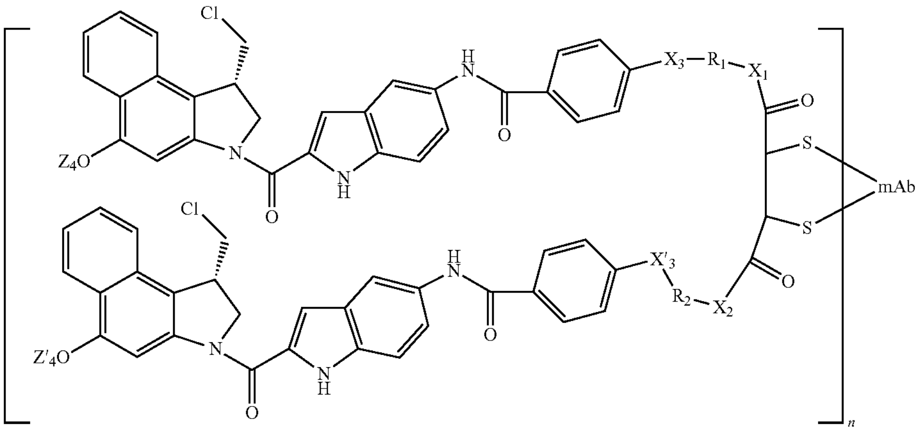

wherein mAb is an antibody; n is 1~20; $Z_4$ and $Z'_4$ are independently H, $PO(OM_1)(OM_2)$, $CH_2PO(OM_1)(OM_2)$, $SO_3M_1$, $CH_3N(CH_2CH_2)_2NC(O)$—, $O(CH_2CH_2)_2NC(O)$—, $R_1$, or glycoside; $X_3$ and $X'_3$ are independently O, NH, NHC(O), OC(O), —C(O)O, $R_1$, or absent.

16. The cell-binding agent-drug conjugate compound of claim 1, wherein the conjugate compound of Formula (II) is selected from the group consisting of structures of Da01, Da02, Da03 and Da04 as following:

Da01
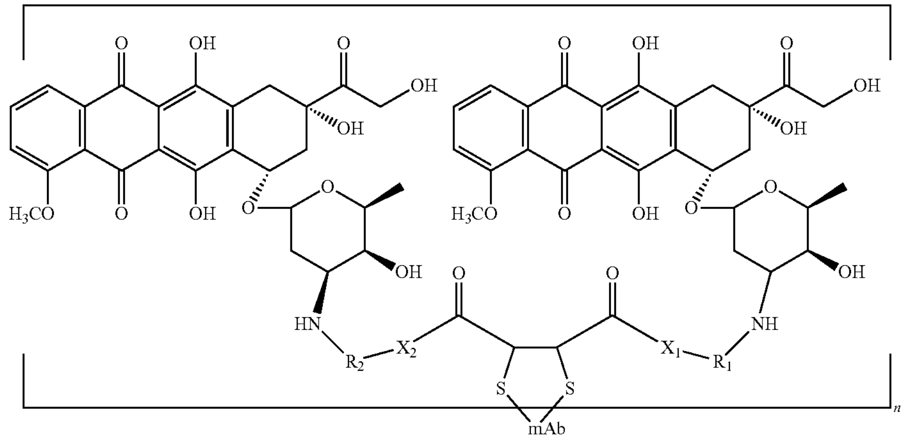
Da02
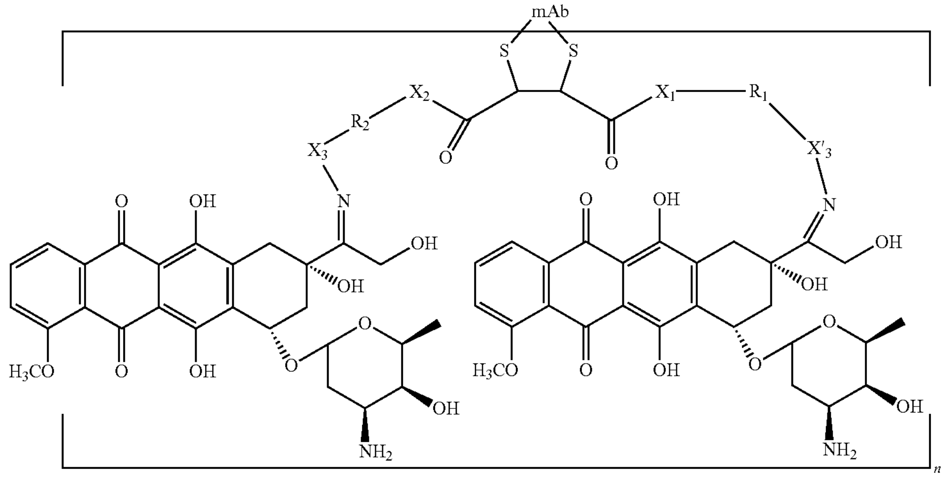
Da03
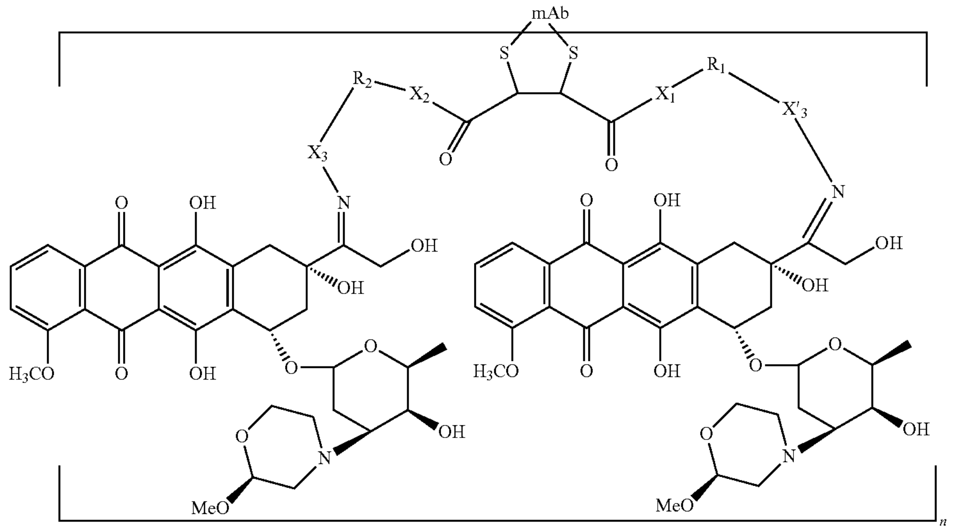

-continued
Da04
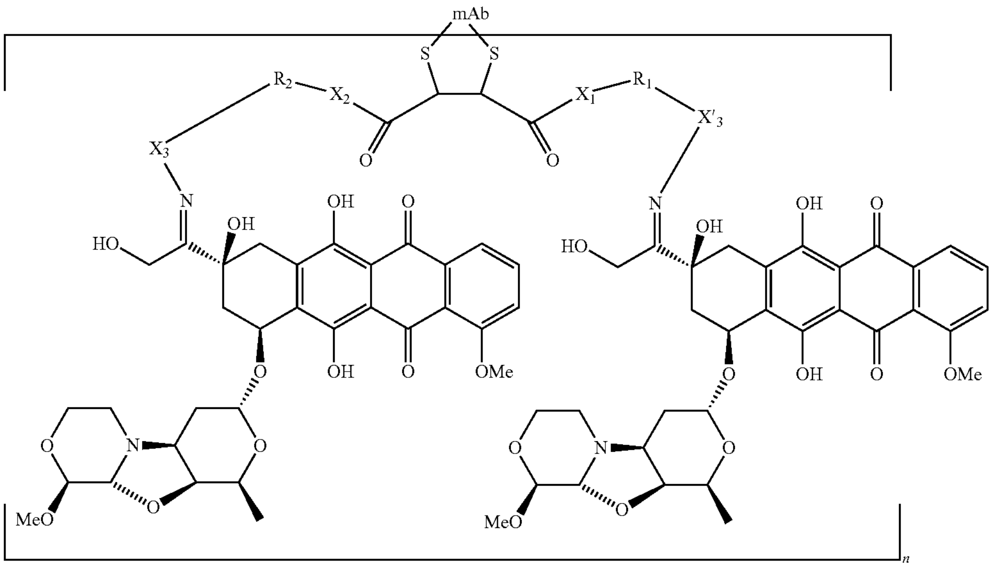
wherein mAb is an antibody; n is 1~20; $X_3$ and $X'_3$ are independently H, O, NH, NHC(O), NHC(O)NH, C(O), $R_1$, or OC(O).
17. The cell-binding agent-drug conjugate compound of claim 1, wherein the conjugate compound of Formula (II) is selected from the group consisting of structures of Au01, Au02, Au03, Au04, and Au05 as following:
Au01
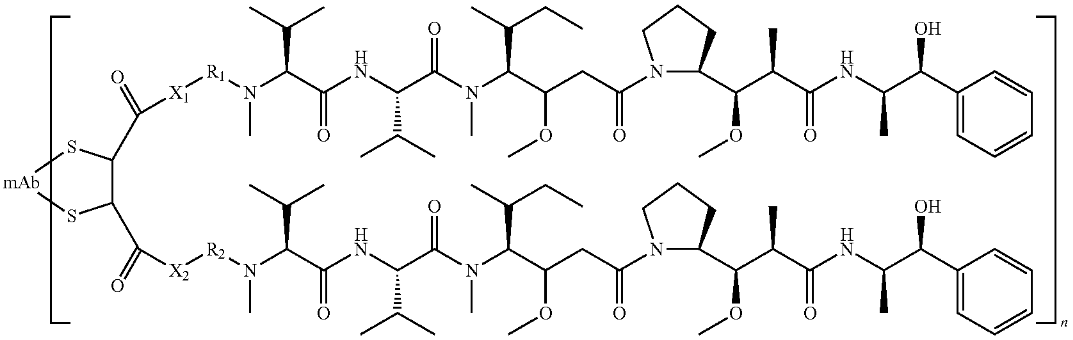
Au02
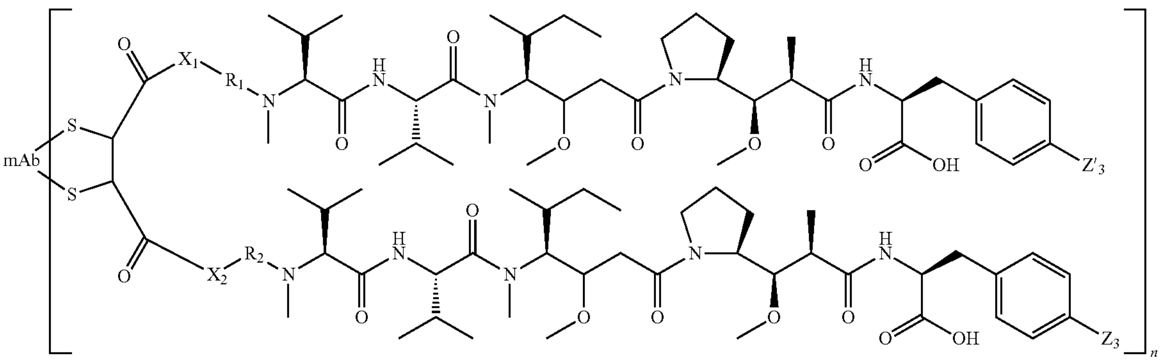

-continued

Au03

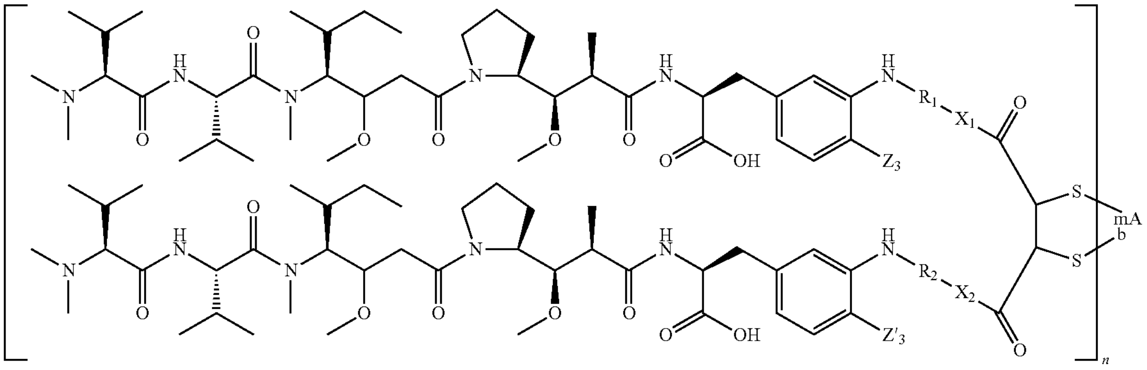

Au04

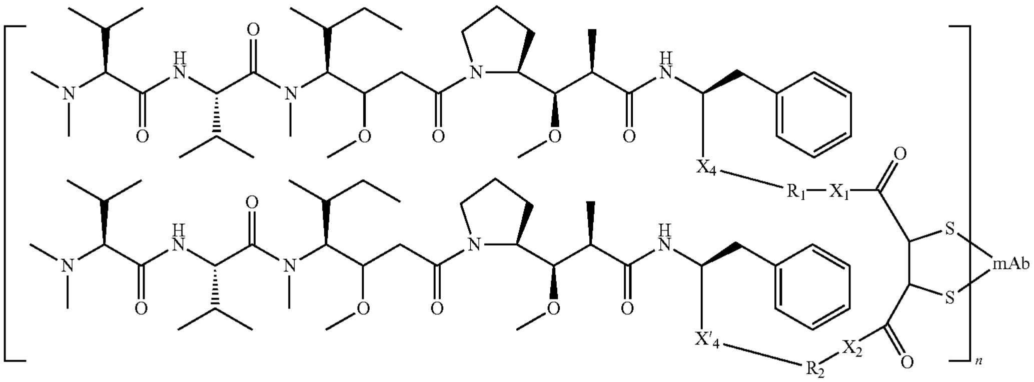

Au05

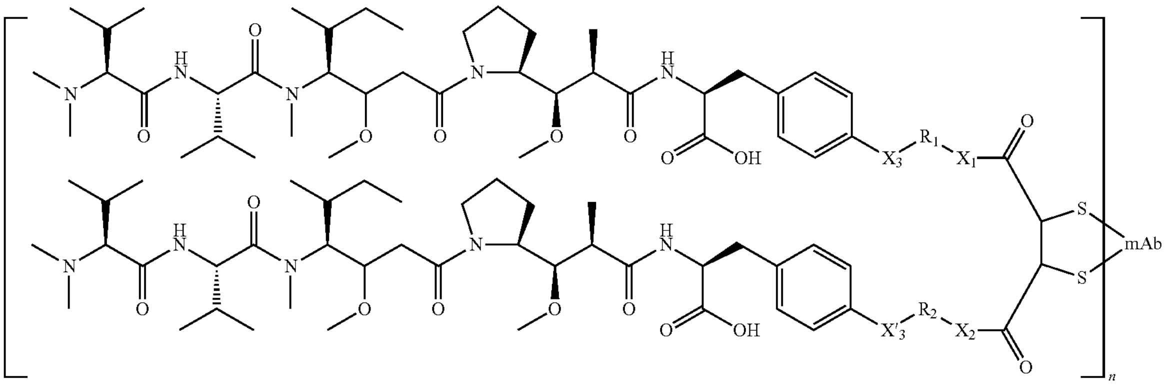

wherein mAb is an antibody; n is 1~20; $X_3$ and $X'_3$ are independently $CH_2$, O, NH, NHC(O), NHC(O)NH, C(O), OC(O) $R_1$, or absent; $X_4$ and $X'_4$ are independently $CH_2$, C(O), C(O)NH, $C(O)N(R_1)$, $R_1$, $NHR_1$, $NR_1$, $C(O)R_1$ or C(O)O; $Z_3$ and $Z'_3$ are independently H, $R_1$, $OP(O)(OM_1)(OM_2)$, $NHR_1$, $OCH_2OP(O)(OM_1)(OM_2)$, $OSO_3M_1$, or O-glycoside selected from the group consisting of glucoside, galactoside, mannoside, glucuronoside, alloside, and fructoside, NH-glycoside, S-glycoside, or $CH_2$-glycoside.

18. The cell-binding agent-drug conjugate compound of claim 1, wherein the conjugate compound of Formula (II) is selected from the group consisting of PB01, PB02, PB03, PB04, PB05, PB06, PB07, PB08, PB09, PB10 and PB11 as following:

PB01
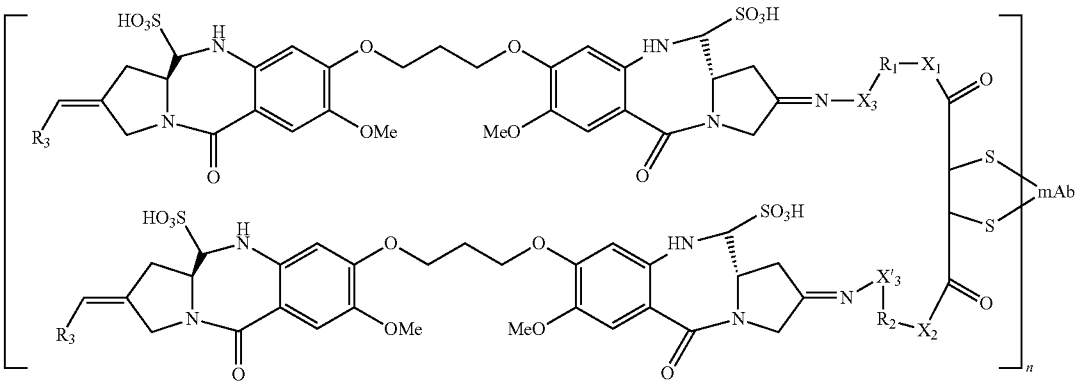
PB02
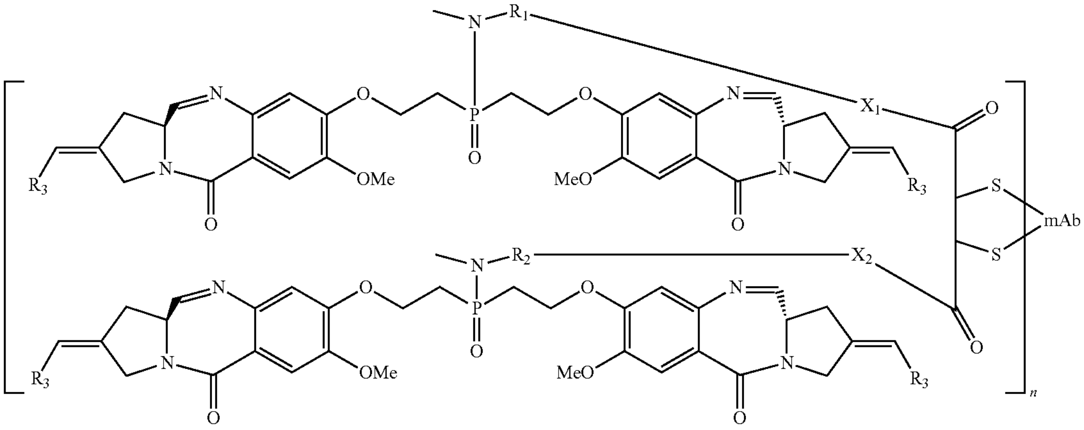
PB03
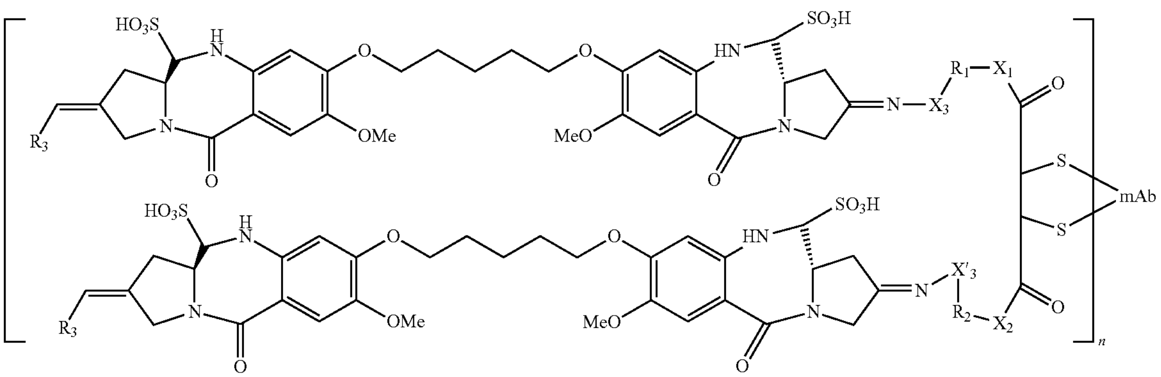
PB04
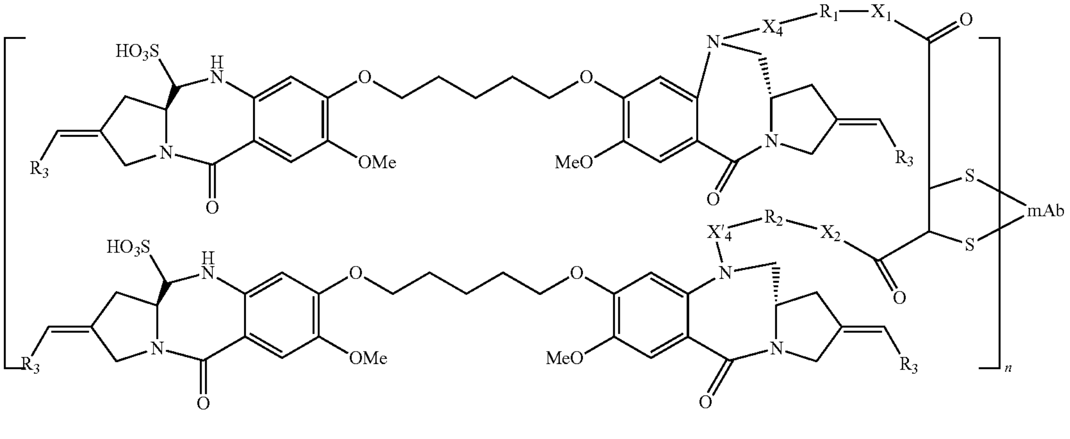

-continued
PB05
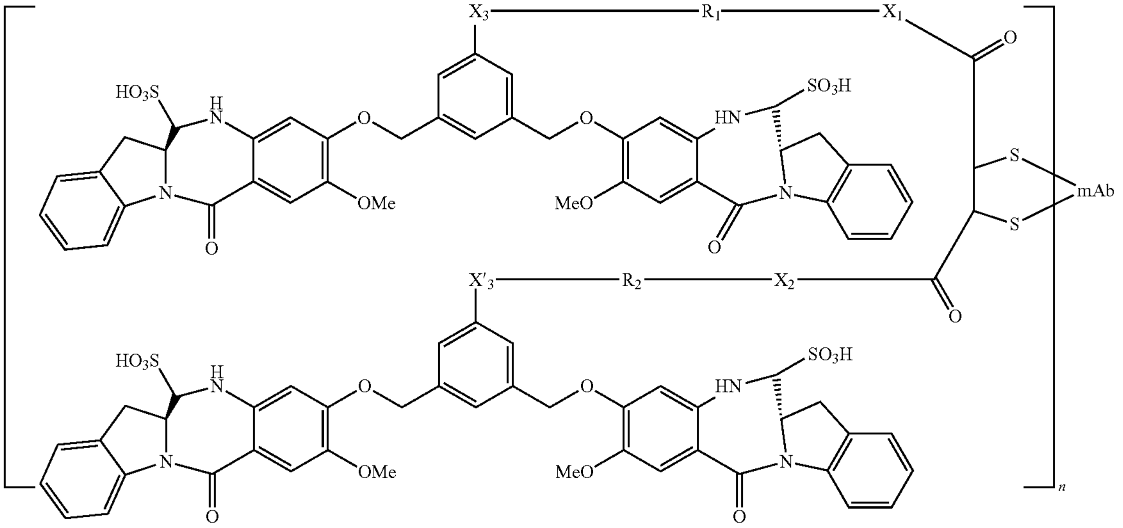
PB06
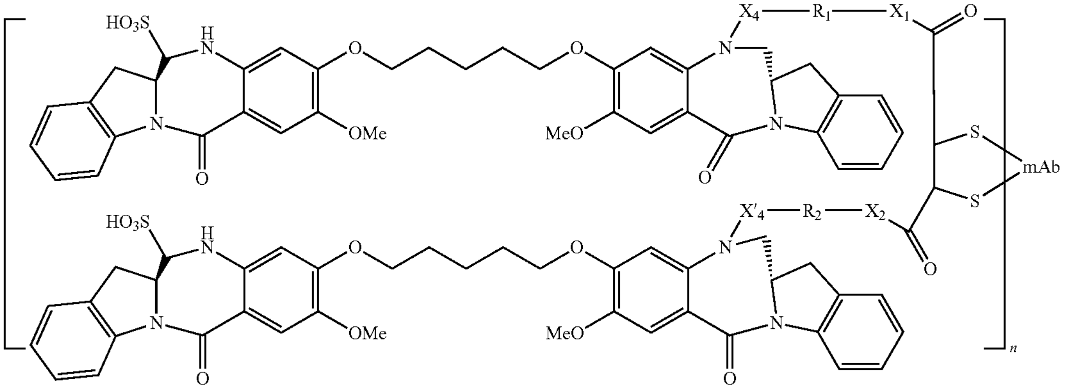
PB07
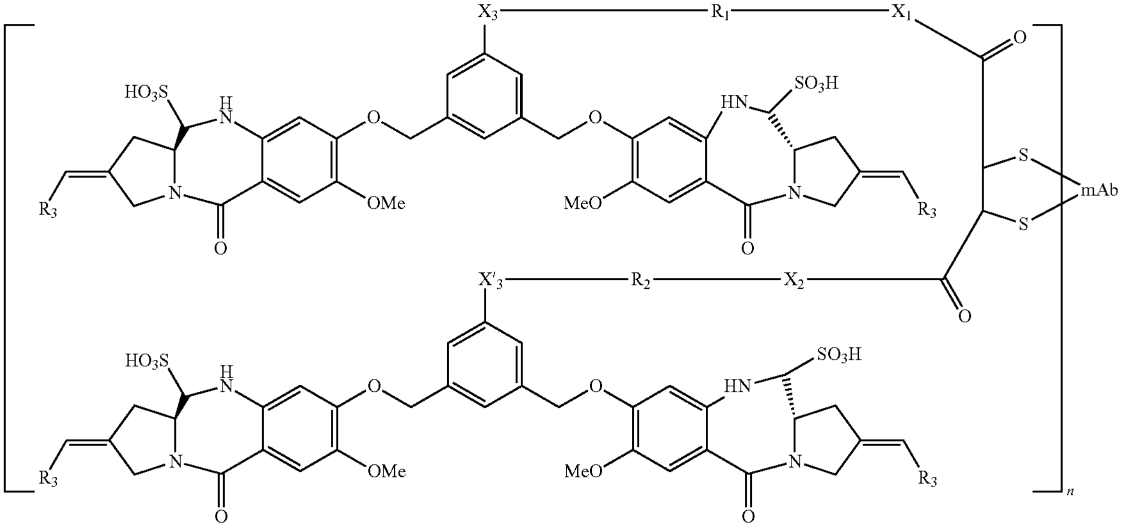

-continued
PB08
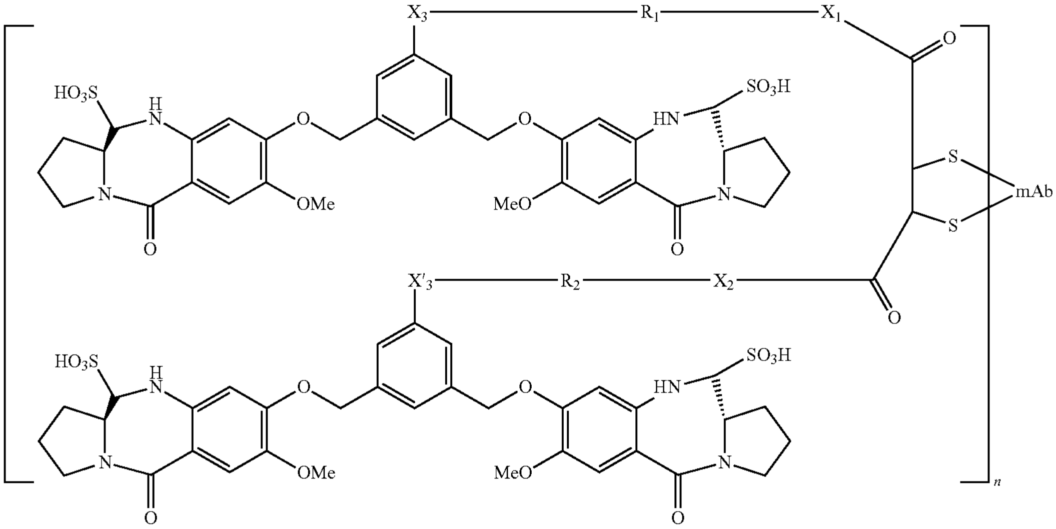
PB09
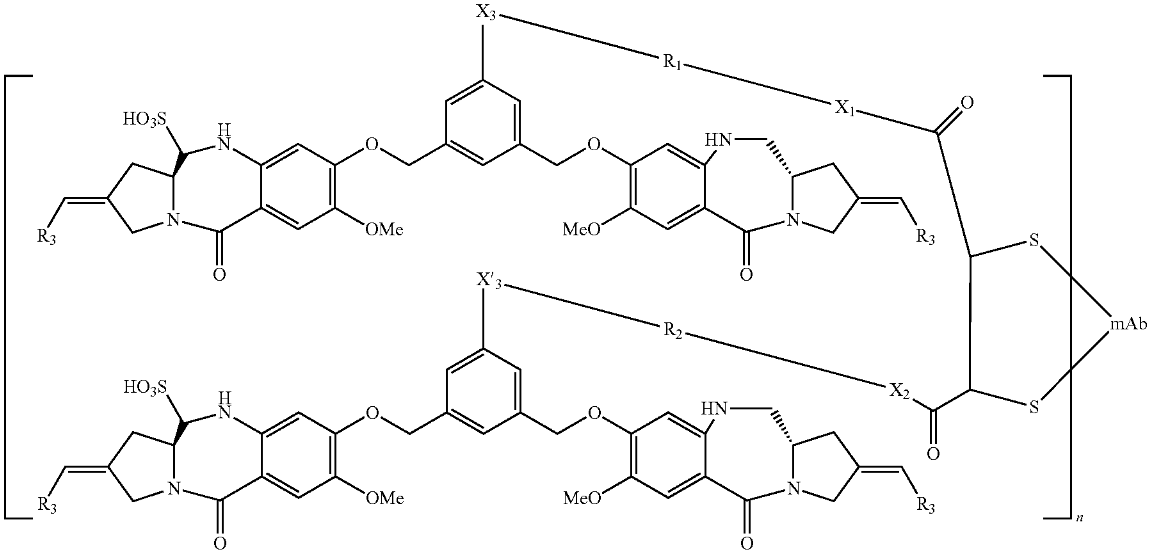
PB10
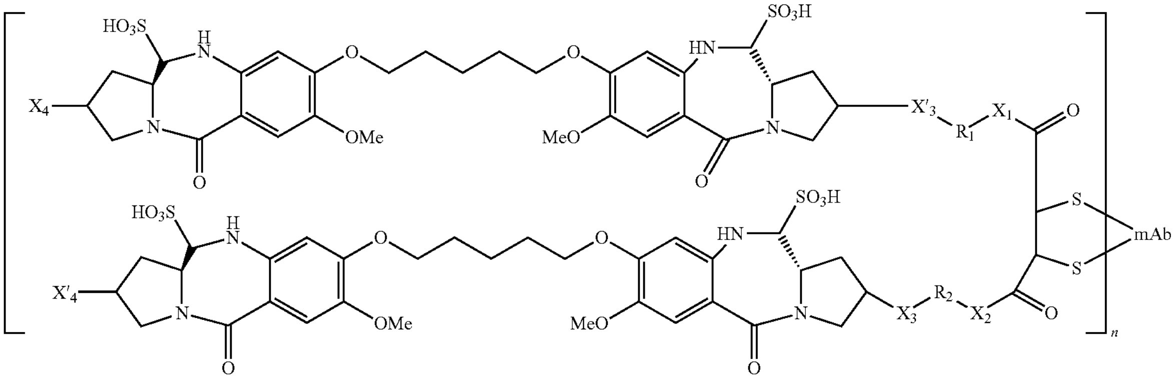

-continued

PB11

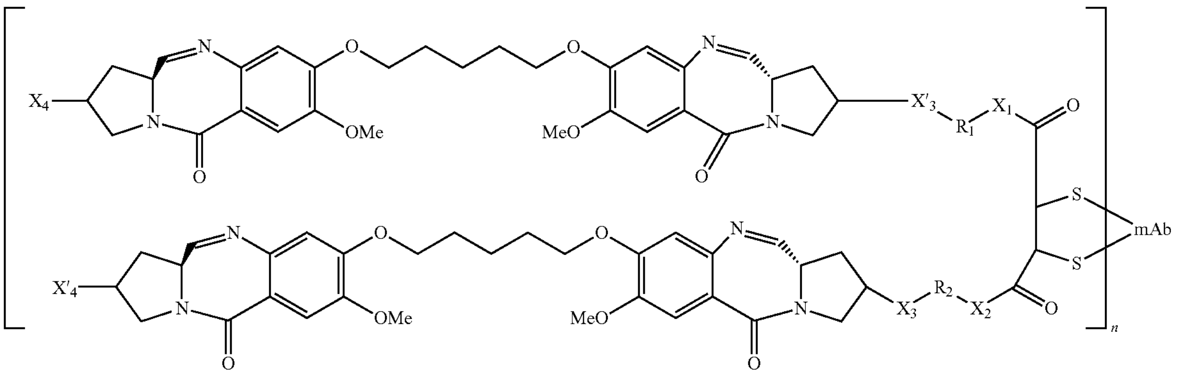

wherein mAb is an antibody; n is 1~20; $X_3$ and $X'_3$ are independently $CH_2$, O, NH, NHC(O), NHC(O)NH, C(O), OC(O), $OC(O)(NR_3)$, $R_1$, $NHR_1$, $NR_1$ $C(O)R_1$ or absent; $X_4$ and $X'_4$ are independently $CH_2$, C(O), C(O)NH, $C(O)N(R_1)$, $R_1$, $NHR_1$, $NR_1$, $C(O)R_1$ or C(O)O.

19. The cell-binding agent-drug conjugate compound of claim 1, having in vitro, in vivo or ex vivo cell killing activity.

20. The cell-binding agent-drug conjugate compound of claim 1, wherein $R_1$ or $R_2$ comprises a peptide of 1~20 units of natural or unnatural amino acids, a p-aminobenzyl unit, a 6-maleimidocaproyl unit, a disulfide unit, a thioether unit, a hydrozone unit, a triazole unit, or an alkoxime unit.

21. The cell-binding agent-drug conjugate compound of claim 1, wherein $R_1$ or $R_2$ is cleavable by a protease.

22. A pharmaceutical composition comprising a therapeutically effective amount of the cell-binding agent-drug conjugate compound of claim 1, and a pharmaceutically acceptable salt, carrier, diluent, or excipient therefor.

23. A method of treating gastric cancer, ovarian cancer, or leukemia comprising administering to a patient in need thereof the pharmaceutical composition of claim 22.

24. The method of claim 23, further comprising administering concurrently to the patient a synergistically effective amount of a therapeutic agent of a chemotherapeutic agent, radiation therapy, immunotherapy agent, autoimmune disorder agent, or anti-infectious agent.

25. The method according to claim 24, wherein the therapeutic agent comprises abatacept, abiraterone acetate, acetaminophen /hydrocodone, adalimumab, afatinib dimaleate, alemtuzumab, alitretinoin, ado-trastuzumab emtansine, amphetamine mixed salts or amphetamine/dextroamphetamine, anastrozole, aripiprazole, atazanavir, atezolizumab, atorvastatin, axitinib, belinostat, bevacizumab, cabazitaxel, cabozantinib, bexarotene, blinatumomab, bortezomib, bosutinib, brentuximab vedotin, budesonide, budesonide/formoterol, buprenorphine, capecitabine, carfilzomib, celecoxib, ceritinib, cetuximab, ciclosporin, cinacalcet, crizotinib, dabigatran, dabrafenib, darbepoetin alfa, darunavir, imatinib mesylate, dasatinib, denileukin diftitox, denosumab, depakote, dexlansoprazole, dexmethylphenidate, dinutuximab, doxycycline, duloxetine, emtricitabine/rilpivirine/tenofovir disoproxil fumarate, emtricitabine/tenofovir/efavirenz, enoxaparin, enzalutamide, epoetin alfa, erlotinib, esomeprazole, eszopiclone, etanercept, everolimus, exemestane, everolimus, ezetimibe, ezetimibe/simvastatin, fenofibrate, filgrastim, fingolimod, fluticasone propionate, fluticasone/salmeterol, fulvestrant, gefitinib, glatiramer, goserelin acetate, imatinib, ibritumomab tiuxetan, ibrutinib, idelalisib, infliximab, insulin aspart, insulin detemir, insulin glargine, insulin lispro, interferon beta la, interferon beta lb, lapatinib, ipilimumab, ipratropium bromide/salbutamol, lanreotide acetate, lenaliomide, lenvatinib mesylate, letrozole, levothyroxine, levothyroxine, lidocaine, linezolid, liraglutide, lisdexamfetamine, MEDI4736, memantine, methylphenidate, metoprolol, modafinil, mometasone, nilotinib, nivolumab, ofatumumab, obinutuzumab, olaparib, olmesartan, olmesartan/hydrochlorothiazide, omalizumab, Omega-3 fatty acid ethyl ester, oseltamivir, oxycodone, palbociclib, palivizumab, panitumumab, panobinostat, pazopanib, pembrolizumab, pemetrexed, pertuzumab, pneumococcal conjugate vaccine, pomalidomide, pregabalin, quetiapine, rabeprazole, radium 223 chloride, raloxifene, raltegravir, ramucirumab, ranibizumab, regorafenib, rituximab, rivaroxaban, romidepsin, rosuvastatin, ruxolitinib phosphate, salbutamol, sevelamer, sildenafil, siltuximab, sitagliptin, sitagliptin/metformin, solifenacin, sorafenib, sunitinib, tadalafil, tamoxifen, telaprevir, temsirolimus, tenofovir/emtricitabine, testosterone gel, thalidomide, tiotropium bromide, toremifene, trametinib, trastuzumab, tretinoin, ustekinumab, valsartan, vandetanib, vemurafenib, vorinostat, ziv-aflibercept, zostavax, or a pharmaceutically acceptable salt thereof.

26. A method for detecting, monitoring, or studying interactions or functions of a cell-binding agent-drug conjugate compound with a targeted cell comprising utilizing the cell-binding agent-drug conjugate compound of claim 4.

27. The pharmaceutical composition of claim 22, further comprising a synergistically effective amount of a therapeutic agent of a chemotherapeutic agent, radiation therapy, immunotherapy agent, autoimmune disorder agent, or anti-infectious agent.

* * * * *